US012714295B2

(12) United States Patent
Sato et al.

(10) Patent No.: US 12,714,295 B2
(45) Date of Patent: Aug. 25, 2026

(54) OVERTUBE FOR ENDOSCOPE

(71) Applicant: OLYMPUS CORPORATION, Tokyo (JP)

(72) Inventors: Hideyuki Sato, Hachioji (JP); Arimasa Sugimoto, Hachioji (JP); Jun Wakasone, Wako (JP); Ryu Kubo, Hachioji (JP); Tatsuya Higuchi, Chofu (JP)

(73) Assignee: OLYMPUS CORPORATION, Tokyo (JP)

(*) Notice: Subject to any disclaimer, the term of this patent is extended or adjusted under 35 U.S.C. 154(b) by 346 days.

(21) Appl. No.: 18/371,670

(22) Filed: Sep. 22, 2023

(65) Prior Publication Data

US 2024/0016372 A1 Jan. 18, 2024

Related U.S. Application Data

(63) Continuation of application No. PCT/JP2021/013897, filed on Mar. 31, 2021.

(51) Int. Cl.
*A61B 1/00* (2006.01)
*A61B 1/01* (2006.01)

(52) U.S. Cl.
CPC .................................... *A61B 1/01* (2013.01)

(58) Field of Classification Search
CPC ... A61B 1/01; A61B 1/00135; A61B 1/00142; A61B 1/015; A61B 1/00082; A61B 1/0137; A61B 1/00151; A61B 1/00147
See application file for complete search history.

(56) References Cited

U.S. PATENT DOCUMENTS

| | | | | |
|---|---|---|---|---|
| 2007/0276181 | A1* | 11/2007 | Terliuc | A61B 1/041 600/106 |
| 2008/0228034 | A1 | 9/2008 | Fujikura | |
| 2009/0287045 | A1 | 11/2009 | Mitelberg et al. | |

(Continued)

FOREIGN PATENT DOCUMENTS

| | | | |
|---|---|---|---|
| JP | 2005-168990 | A | 6/2005 |
| JP | 2005-261857 | A | 9/2005 |
| JP | 2007-521907 | A | 8/2007 |

(Continued)

OTHER PUBLICATIONS

International Search Report dated Jun. 29, 2021 received in PCT/JP2021/013897.

*Primary Examiner* — Timothy J Neal
(74) *Attorney, Agent, or Firm* — Scully, Scott, Murphy & Presser, P.C.

(57) ABSTRACT

An overtube for an endoscope includes: a tube body having a main lumen through which the endoscope is inserted and an air-supply lumen through which gas flows; a fixing balloon provided on an outer peripheral surface of a distal end of the tube body, expandable outward from the outer peripheral surface and contractible toward the outer peripheral surface; an air supply device configured to send the gas to the air-supply lumen; and an airtight valve unit having a tubular portion communicating with the main lumen at a rear end of the tube body, the airtight valve unit closing the gap between the endoscope inserted through the tubular portion into the main lumen and an inner peripheral surface of the tubular portion.

15 Claims, 91 Drawing Sheets

(56) References Cited

U.S. PATENT DOCUMENTS

2015/0105621 A1* 4/2015 Farhadi .............. A61B 1/00135
600/115

FOREIGN PATENT DOCUMENTS

| | | | |
|---|---|---|---|
| JP | 2007-268147 | A | 10/2007 |
| JP | 2008-220775 | A | 9/2008 |
| JP | 2011-010950 | A | 1/2011 |
| JP | 2011-056187 | A | 3/2011 |
| JP | 2013-244192 | A | 12/2013 |
| WO | 2005/074377 | A2 | 8/2005 |

* cited by examiner

AIR DELIVERY DEVICE
110
111
111a
PUMP
pa
111b
FIRST CHECK VALVE
111f
OPENING
111c
SECOND CHECK VALVE
111e
SECOND PIPELINE SWITCHING UNIT
pc
pb
111d
FIRST PIPELINE SWITCHING UNIT
pd
112
PRESSURE GAUGE
113
RELIEF VALVE
110a

AIR DELIVERY DEVICE
210
211
211a
PUMP
211b
FIRST CHECK VALVE
O (211f)
OPENING
211c
SECOND CHECK VALVE
SW2 (211e)
SECOND PIPELINE SWITCHING UNIT
SW1 (211d)
FIRST PIPELINE SWITCHING UNIT
212a
P1
P2
DIAPHRAGM UNIT
P3
213
RELIEF VALVE
210a 210
211
211a
PUMP
211b
FIRST CHECK VALVE
O (211g)
OPENING
211c
SECOND CHECK VALVE
SW2 (211d)
SECOND PIPELINE SWITCHING UNIT
SW1 (211e)
FIRST PIPELINE SWITCHING UNIT
212a
P1
P2
DIAPHRAGM UNIT
P3
213
RELIEF VALVE
AIR DELIVERY DEVICE
210a 210
211
211a
PUMP
211b
FIRST CHECK VALVE
211c
SECOND CHECK VALVE
211g
FIRST OPENING
211h
211f
SECOND OPENING
211d (211g)
211e (211f)
212a
P1
DIAPHRAGM UNIT
P2
P3
213
RELIEF VALVE
AIR DELIVERY DEVICE
210a 210A
211
211a
PUMP
211b
FIRST CHECK VALVE
211c
SECOND CHECK VALVE
211g
FIRST OPENING
211h
211f
SECOND OPENING
212a
P1
213
RELIEF VALVE
P4
DIAMETER EXPANDING UNIT
AIR DELIVERY DEVICE
P3
210a 210B
211
211a
PUMP
211b
FIRST CHECK VALVE
211c
SECOND CHECK VALVE
211g
FIRST OPENING
211h
211f
SECOND OPENING
212a
217
PRESSURE ADJUSTMENT UNIT
P5
P1
212B
218
P2
DIAPHRAGM UNIT
213
RELIEF VALVE
P3
AIR DELIVERY DEVICE
210a

AIR DELIVERY DEVICE
210C
211
211a
PUMP
211b
FIRST CHECK VALVE
211c
SECOND CHECK VALVE
211g
FIRST OPENING
211h
211f
SECOND OPENING
212a
219
PRESSURE INDICATOR
P5
P1
212C
218
P2
DIAPHRAGM UNIT
213
RELIEF VALVE
P3
210a

AIR DELIVERY DEVICE
210D
211
211a
PUMP
211b
FIRST CHECK VALVE
211c
SECOND CHECK VALVE
211g
FIRST OPENING
211h
211f
SECOND OPENING
212a
219D
PRESSURE INDICATOR
P6
DIAMETER EXPANDING UNIT
P7
213
RELIEF VALVE
P8
210a 319 (319A, 319B, 319C, 319D,
319E, 319F, 319H, 319I,
319J, 319K, 319L)
211a
221
211
216
218
310
215
F69
F69
9
7
6
5
301
2
3
4

OVERTUBE FOR ENDOSCOPE

CROSS-REFERENCE TO RELATED APPLICATIONS

The present application is a continuation application based on PCT Patent Application No. PCT/JP2021/013897, filed on Mar. 31, 2021, the entire content of which is hereby incorporated by reference.

BACKGROUND

Technical Field

The present invention relates to an overtube for endoscope.

Description of the Background

An overtube for an endoscope used during treatment using an endoscope is known. The overtube for an endoscope is used for the purpose of curbing contact and sliding between living tissue and an endoscope when the endoscope is moved forward and backward and rotated within a patient's body. Since an inner circumferential surface of the overtube for an endoscope has less sliding resistance with respect to an outer circumference of the endoscope than living tissue, the endoscope can be moved forward and backward and rotated more smoothly. Thus, the endoscope can be operated accurately and easily.

The overtube for an endoscope includes a main tube through which the endoscope is inserted, a fixing balloon that expands and contracts outward of the main tube at a distal end portion of the main tube, and an air supply device that supplies air to the fixing balloon (refer to Japanese Unexamined Patent Application, First Publication No. 2007-268147 (Patent Document 1)).

The overtube for an endoscope is often inserted into the body using the endoscope as a guide after the endoscope has been inserted into the body in advance. In this case, for example, when the endoscope is inserted into a tube having a large bent portion such as an intestinal tract, the endoscope and an inner wall of the tube come into contact at the bent portion of the tube. In this state, when the overtube for an endoscope is inserted using the endoscope as a guide, a distal end of the overtube for an endoscope is pushed into a contact portion between the endoscope and the inner wall of the tube, and thus, a part of the inner wall of the tube may be caught up between the overtube for an endoscope and a side surface of the endoscope.

The overtube described in Patent Document 1 has openings of uniform size in a longitudinal direction, and has uniform flexibility in the longitudinal direction. Therefore, the inner wall of the tube is likely to be caught up.

Since the overtube described in Patent Document 1 cannot close an insertion port at a proximal end that is disposed outside the body, liquid or gas in the body tends to flow backward from the insertion port to the outside of the body. When the liquid or gas from the body flows backward, there is a possibility that the treatment cannot be carried out smoothly.

In the overtube described in Patent Document 1, when a first balloon reaches a second pressure or higher, the second balloon expands, and thus a pressure of the first balloon is relaxed. Thus, it is possible to curb, to some extent, an outer diameter becoming too large due to excessive pressure being applied to the first balloon.

However, when an amount of air supply suddenly increases, the pressure in the first balloon temporarily suddenly increases. Therefore, the air supply device in the medical equipment described in Patent Document 1 needs to be equipped with an expensive control device for controlling the amount of air supply.

As described above, the overtube described in Patent Document 1 may impose a load on the patient during treatment or may make smooth operation of the endoscope difficult.

There is a strong demand for an overtube for an endoscope that reduces a load on a patient and enables smooth operation of the endoscope.

SUMMARY

The present invention provides an overtube for an endoscope that reduces a load on a patient and enables smooth operation of the endoscope.

An overtube for endoscope according to an aspect of the present invention includes: a tube body having a main lumen through which the endoscope is inserted and an air-supply lumen through which gas flows; a fixing balloon provided on an outer peripheral surface of a distal end of the tube body, expandable outward from the outer peripheral surface and contractible toward the outer peripheral surface; an air supply device configured to send the gas to the air-supply lumen; and an airtight valve unit having a tubular portion communicating with the main lumen at a rear end of the tube body, the airtight valve unit closing the gap between the endoscope inserted through the tubular portion into the main lumen and an inner peripheral surface of the tubular portion.

According to the above aspect, it is possible to provide an overtube for an endoscope that reduces a load on a patient and enables smooth operation of the endoscope.

BRIEF DESCRIPTION OF DRAWINGS

FIG. 121 is a cross-sectional view along line F121-F121 in FIG. 120.

FIG. 122 is a cross-sectional view along line F122-F122 in FIG. 120.

FIG. 123 is a cross-sectional view along line F123-F123 in FIG. 121.

FIG. 124 is a cross-sectional view showing an example of a method for using the overtube for an endoscope according to the eighth embodiment of the present invention.

FIG. 125 is a cross-sectional view showing an example of the method for using the overtube for an endoscope according to the eighth embodiment of the present invention.

FIG. 126 is a cross-sectional view showing an example of the method for using the overtube for an endoscope according to the eighth embodiment of the present invention.

FIG. 127 is a cross-sectional view showing an example of the method for using the overtube for an endoscope according to the eighth embodiment of the present invention.

FIG. 128 is a cross-sectional view showing an example of the method for using the overtube for an endoscope according to the eighth embodiment of the present invention.

EMBODIMENTS

Figure 1:
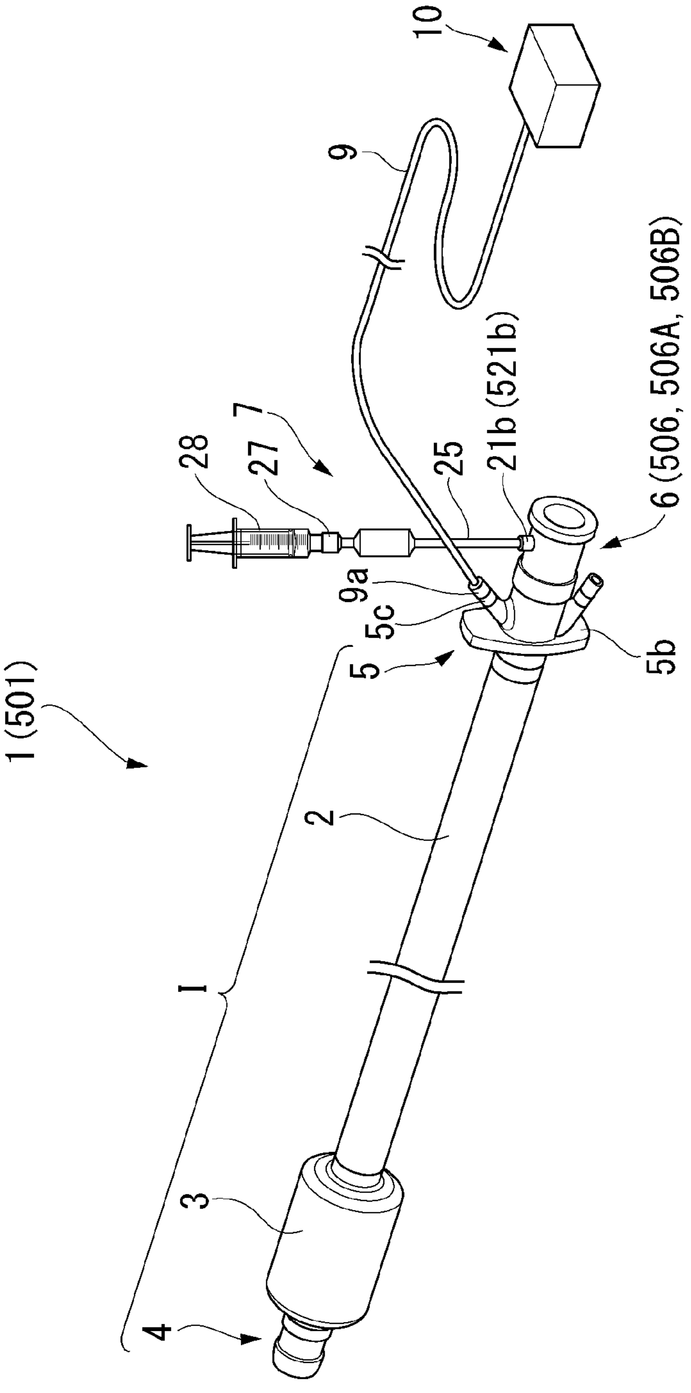
FIG. 1 is a schematic perspective view showing an example of an overtube for an endoscope according to a first embodiment of the present invention.

Hereinafter, embodiments of the present invention are described with reference to the accompanying drawings. In all the drawings, even when the embodiments are different, the same or corresponding members are denoted by the same reference numerals, and common descriptions will be omitted.

First Embodiment

An overtube for an endoscope according to a first embodiment of the present invention will be described.

FIG. 1 is a schematic perspective view showing an example of the overtube for an endoscope according to the first embodiment of the present invention.

The overtube 1 shown in FIG. 1 is an example of the overtube for an endoscope according to this embodiment.

The overtube 1 includes a main tube 2 (a tube main body), a fixing balloon 3, a distal end tip 4, a grip portion 5, an airtight valve unit 6, an airtight valve operation tube 7, and an air supply device 10.

The overtube 1 is a long member that is inserted into a patient's body and allows an endoscope to pass therethrough. The distal end tip 4, the fixing balloon 3, and the main tube 2 are disposed in this order from a distal end to a proximal end in an insertion direction of the overtube 1.

Hereinafter, for each of components of the overtube 1, based on an arrangement in a longitudinal direction in a state in which they are assembled into the overtube 1, an end near the distal end of the overtube 1 may be referred to as a distal end, and an end near the proximal end of the overtube 1 may be referred to as a proximal end. A portion of each of the components closer to the distal end may be referred to as a distal end portion, and a portion thereof closer to the proximal end may be referred to as a proximal end portion.

Unless otherwise specified, the distal end portion may or may not include the distal end. Similarly, the proximal end portion may or may not include the proximal end.

The distal end tip 4, the fixing balloon 3, and the main tube 2 form an insertion portion 1 of the overtube 1 that is inserted into the body. The fixing balloon 3 is operated by an operator to be in a diameter-expanded stale and a diameter-contracted state. FIG. 1 shows the fixing balloon 3 in the diameter-expanded state. When the insertion portion 1 is inserted into the body, the fixing balloon 3 is in the diameter-contracted state. In the diameter-contracted state, the fixing balloon 3 is in a folded state and is close to the main tube 2. Thus, an outer diameter of the fixing balloon 3 is reduced to approximately the same size as an outer diameter of the main tube 2.

In the overtube 1, the proximal end portion of the main tube 2, the airtight valve unit 6, the airtight valve operation tube 7, and the air supply device 10 are disposed outside the patient's body.

An insertion place of the overtube 1 is not particularly limited as long as it is inside the patient's body. The overtube 1 is particularly suitable for use in inserting an endoscope into an organ with many bent places, such as the intestine. An example in which the overtube 1 is inserted into the intestinal tract will be described below.

An example of an endoscope inserted through the overtube 1 will be described.

Figure 2:
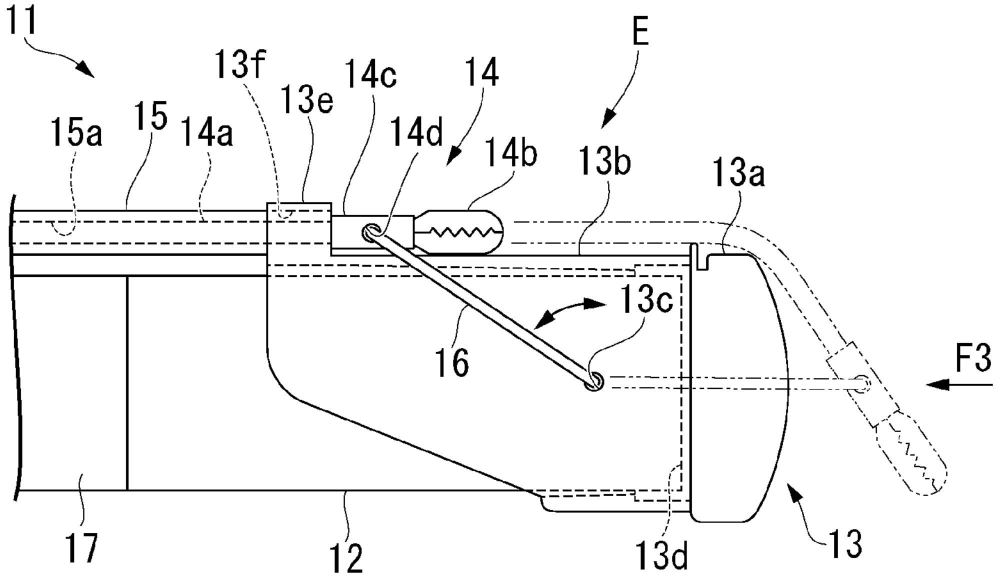
FIG. 2 is a schematic front view showing an example of an endoscope inserted into the overtube for an endoscope according to the first embodiment of the present invention.
Figure 3:
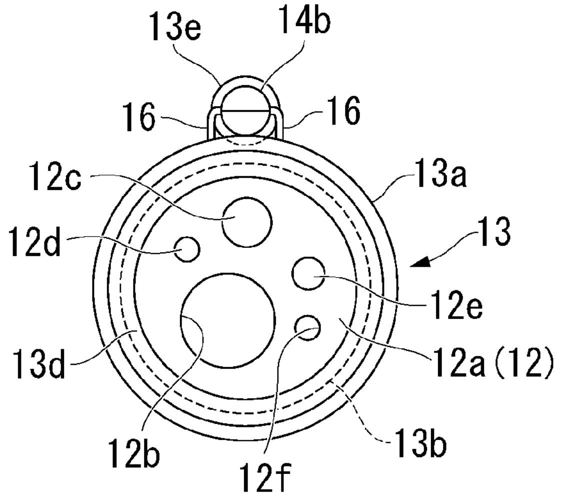
FIG. 3 is a side view seen from F3 in FIG. 2.

FIG. 2 is a schematic front view showing an example of the endoscope inserted into the overtube for an endoscope according to the first embodiment of the invention. FIG. 3 is a side view seen from F3 in FIG. 2.

As FIG. 2 shows a configuration at the distal end portion, the endoscope 11 has a distal end portion 12 and an endoscopic treatment tool E.

The distal end portion 12 is provided at a distal end of the insertion portion of the endoscope 11 that is inserted into the patient's body. The distal end portion 12 has a hard cylindrical shape. A proximal end of the distal end portion 12 is connected to a distal end of a curved portion 17 in the insertion portion. For example, the curved portion 17 has a plurality of joint rings connected to each other, and can be bent in an up-down direction and a right-left direction by pulling an operating wire extending in a longitudinal direction of the insertion portion along the joint rings. A proximal end of the curved portion 17 is connected to a distal end of a flexible tube portion in the insertion portion. An operating part that performs various operations in the endoscope 11 is connected to a proximal end of the flexible tube portion. For example, the operating part can operate a bending direction and an amount of bending of the curved portion 17.

As shown in FIG. 3, a tubular treatment tool channel **12*b* through which the treatment tool is inserted and a nozzle 12*f* through which a fluid can pass open in a distal end surface 12*a* of the distal end portion 12**.

The treatment tool channel **12*b* is inserted through the insertion portion. A proximal end portion of the treatment tool channel 12*b*** is connected to a forceps port into which the treatment tool is inserted.

The nozzle **12*f* is inserted through the insertion portion. A proximal end portion of the nozzle 12*f*** is connected to a fluid supply port that supplies a fluid.

A distal end surface of an imaging lens **12*c* that acquires an image in front of the distal end portion 12, and a light emission surface of each of light guides 12*d* and 12*e* that illuminate the front of the distal end portion 12 are disposed on the distal end surface 12*a***.

As shown in FIG. 2, the endoscopic treatment tool E includes a gripping device 14 and an endoscope cap 13 that supports the gripping device 14 and is mounted on the distal end portion 12.

The gripping device 14 includes a long flexible elongated member **14*a*, a gripping portion 14*b* that is connected to a distal end of the elongated member 14*a* and grips a living tissue, and a connector 14*c* provided on the proximal end side of the gripping portion 14*b***.

The elongated member **14*a* is, for example, a coil sheath. The gripping portion 14*b* has a pair of gripping pieces that can be opened and closed and can grasp a living tissue between the pair of gripping pieces. The connector 14*c* is provided, for example, between the elongated member 14*a* and the gripping portion 14*b*, and has a through hole 14*d* that passes therethrough in a direction orthogonal to the longitudinal direction of the elongated member 14*a***.

The endoscope cap 13 includes a hood portion **13*b*, a cap portion 13*a*, a channel tube 15, and a connecting member 16**.

Hereinafter, in the description of the endoscope cap 13, the up-down direction and the right-left direction may be used. Each of the up-down direction and the right-left direction is a radial direction of the hood portion **13*b*. A direction in which a longitudinal axis of the hood portion 13*b* and a longitudinal axis of the channel tube 15 are lined up is the up-down direction. The right-left direction is orthogonal to the up-down direction and an axial direction of the distal end portion 12. The up-down direction and the right-left direction of the endoscope cap 13 may correspond to an up-down direction and a right-left direction in an operation of the curved portion 17 of the endoscope 11**, respectively.

The hood portion **13*b* has a substantially cylindrical shape and is mounted on an outer circumferential surface of the distal end portion 12. An abutting portion 13*d* which abuts on the distal end surface 12*a* of the distal end portion 12 protrudes toward the center at an inner circumferential portion on the distal end side of the hood portion 13*b*. As shown in FIG. 3, when seen from the distal end side of the distal end portion 12, the abutting portion 13*d* forms a circular opening that opens outward from the treatment tool channel 12*b*, the imaging lens 12*c*, and the light guides 12*d* and 12*e***.

The hood portion **13*b* is fitted to the outer circumferential surface of the distal end portion 12, and is fixed to the distal end portion 12 in which a state in which the abutting portion 13*d* is in contact with the distal end surface 12*a*. The hood portion 13*b* may be fixed to the distal end portion 12 by friction between the inner circumferential surface of the hood portion 13*b* and the outer circumferential surface of the distal end portion 12. The hood portion 13*b* may be fixed to the distal end portion 12 by a fixing tape or an adhesive interposed between the inner circumferential surface of the hood portion 13*b* and the outer circumferential surface of the distal end portion 12**.

The hood portion **13*b* has a pair of support holes 13*c* for supporting the connecting member 16. The pair of support holes 13*c* are provided at positions spaced apart from each other in a circumferential direction of the hood portion 13*b* and facing each other in the right-left direction. Each of the support holes 13*c* passes through the hood portion 13*b* from the outer circumferential surface to the inner circumferential surface of the hood portion 13*b*** in the radial direction.

Each of the support holes **13*c* is formed on the proximal end side of the hood portion 13*b* with respect to the abutting portion 13*d*, and is located on the distal end side of the hood portion 13***b* with respect to a distal end of the channel tube 15 which will be described below.

A convex portion 13*e* through which a fixing hole 13*f* passes in the longitudinal direction of the hood portion 13*b* is formed on a proximal end portion of the hood portion 13*b*.

The cap portion 13*a* is a substantially annular member coaxial with the hood portion 13*b*, and protrudes from the distal end of the hood portion 13*b* in the longitudinal direction of the hood portion 13*b*. A dimension of the cap portion 13*a* in the longitudinal direction is such that a focal length of the imaging lens 12*c* is short, and a focal position of the imaging lens 12*c* is disposed near the distal end of the cap portion 13*a*. In an example of a design of the endoscope 11, the focal length of the imaging lens 12*c* is 10 mm, and a length of the cap portion 13*a* is 5 mm.

The channel tube 15 is a long member through which the elongated member 14*a* is inserted. The channel tube 15 extends substantially parallel to the longitudinal direction of the hood portion 13*b*. A channel 15*a* that is a through hole through which the elongated member 14*a* can move forward and backward extends in the longitudinal direction inside the channel tube 15.

A distal end portion of the channel tube 15 is fixed to the abutting portion 13*d* while being inserted through the fixing hole 13*f* formed in the convex portion 13*e*. A method for fixing the channel tube 15 may be adhesive bonding or heat fusion.

The connecting member 16 is supported by the hood portion 13*b* and connects the hood portion 13*b* to the gripping device 14. The connecting member 16 is an elongated linear member such as a thread. The connecting member 16 is preferably a member that is flexible and has little or no stretch in the longitudinal direction, such as a soft thread. The connecting member 16 may be a wire instead of a thread.

The connecting member 16 is disposed outside the hood portion 13*b* and extends between the pair of support holes 13*c* via the through hole 14*d* of the connector 14*c*.

Both end portions of the connecting member 16 are inserted into the support hole 13*c* from the outside toward the inside. The both end portions of the connecting member 16 disposed in the hood portion 13*b* are locked to the support holes 13*c* from the inside of the hood portion 13*b* in a state in which they are prevented from slipping off, for example, by knots formed at both ends.

Thus, the connecting member 16 is swingably supported with respect to the hood portion 13*b* with the pair of support holes 13*c* as fulcrums.

The gripping portion 14*b* is moved between a maximum retracted position shown by a solid line in FIG. 1 and a lowered position shown by a two-dot chain line by pushing and pulling the elongated member 14*a* in the longitudinal direction.

The maximum retracted position is a position in which the gripping portion 14*b* or the connector 14*c* abuts the distal end of the channel tube 15 and is prevented from moving toward the proximal end side.

When the elongated member 14*a* is extruded forward in the longitudinal direction from the maximum retracted position, the connector 14*c* together with the connecting member 16 swings from the upper side to the lower side with the support hole 13*c* as a fulcrum. Thus, the gripping portion 14*b* moves to the lowered position in which the gripping portion 14*b* is lowered from the upper side to the lower side in front of the cap portion 13*a*.

The lowered position changes in a range in the up-down direction in front of the distal end portion 12 according to an extrusion length of the elongated member 14*a*. Therefore, by appropriately changing the extrusion length of the elongated member 14*a*, the gripping portion 14*b* can be brought closer to an affected area that requires treatment.

When the gripping portion 14*b* moves to a position in which the living tissue can be gripped, the living tissue of the affected area can be gripped by opening and closing the gripping portion 14*b*.

When the elongated member 14*a* is pulled rearward in the longitudinal direction, the gripping portion 14*b* rises in the manner opposite to that described above and returns from the lowered position to the maximum retracted position.

When the gripping portion 14*b* moves toward the maximum retracted position in a state in which the gripping portion 14*b* grips the living tissue, the living tissue gripped by the gripping portion 14*b* is lifted upward.

Further, when the gripping portion 14*b* approaches the maximum retracted position, the living tissue approaches the distal end portion 12. Since the cap portion 13*a* protrudes from the distal end portion 12, the living tissue does not come closer to the distal end surface 12*a* than an amount of protrusion of the cap portion 13*a*. Therefore, the living tissue that has been lifted and approaches the distal end surface 12*a* while being away from the distal end surface 12*a* can be observed within a visual field of the imaging lens 12*c*.

In this state, for example, the lifted living tissue can be excised in front of the distal end surface 12*a* by letting out a treatment tool such as a high-frequency knife from the treatment tool channel 12*b*. For example, when the living tissue is a diseased tissue, the diseased tissue can be exfoliated or completely excised with a treatment tool such as an electric scalpel.

As shown in FIG. 3, since the endoscope 1I has the convex portion 13*e* that protrudes outward in the radial direction from the cap portion 13*a* having a substantially circular shape, the overtube 1 through which the endoscope 1I is inserted needs to have an inner diameter larger than the sum of an outer diameter of the endoscope cap 13 and a height of the convex portion 3*e* when seen in the axial direction of the distal end portion 12.

Now, the description of the overtube 1 will be returned to.

Figure 4:
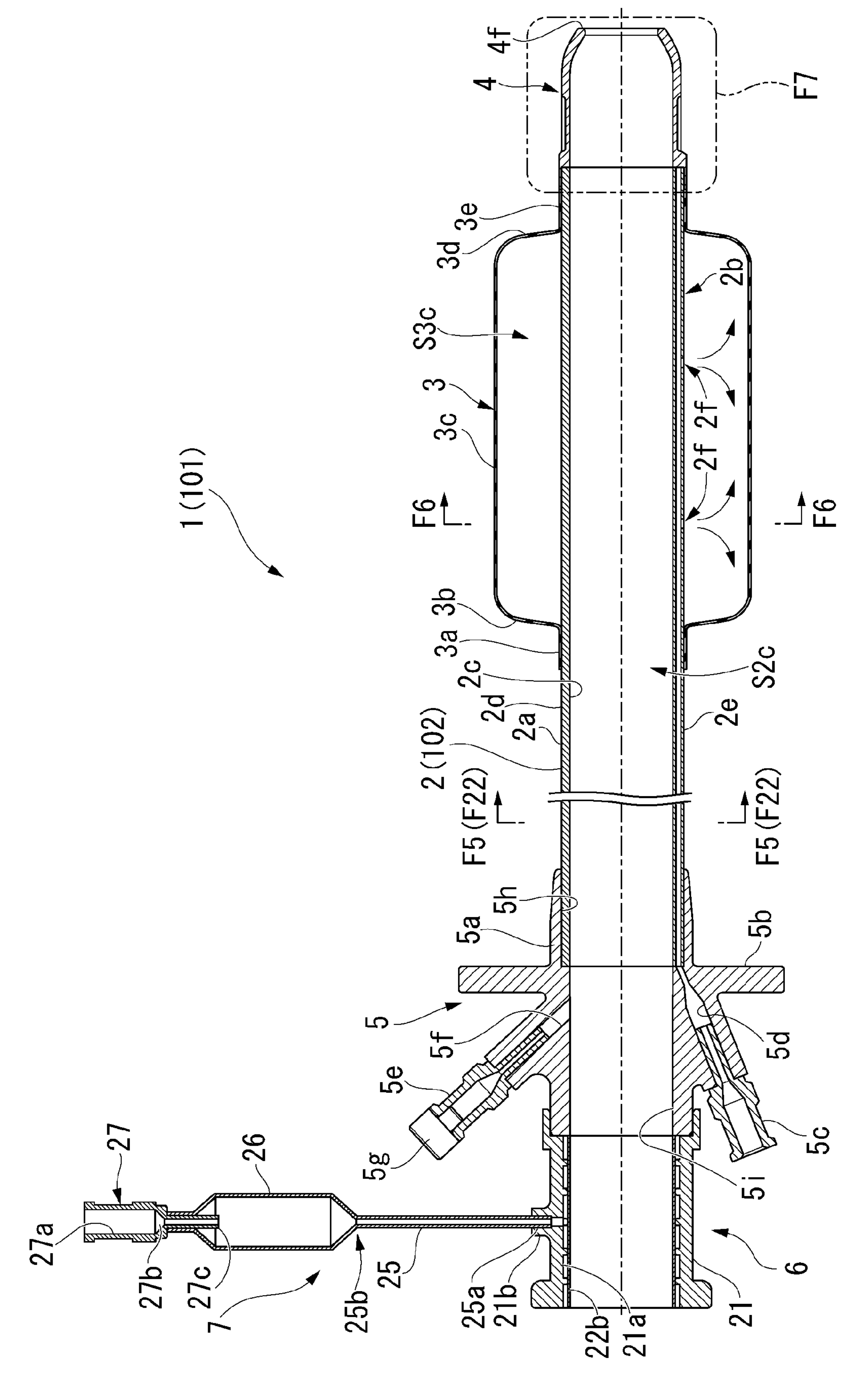
FIG. 4 is a schematic cross-sectional view showing an example of the overtube for an endoscope according to the first embodiment of the present invention.
Figure 5:
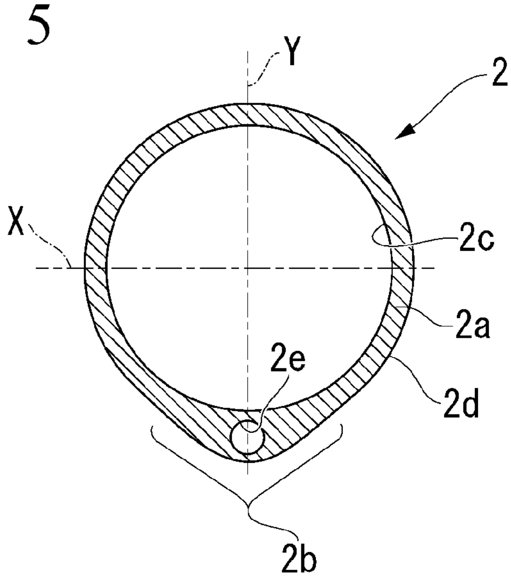
FIG. 5 is a cross-sectional view taken along line F5-F5 in FIG. 4.
Figure 6:
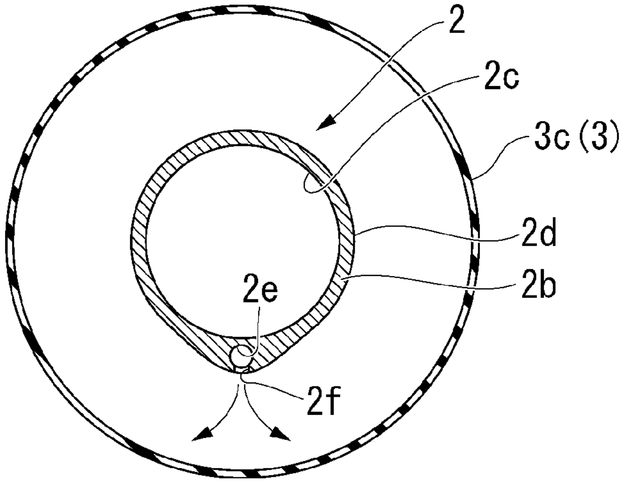
FIG. 6 is a cross-sectional view taken along line F6-F6 in FIG. 4.

FIG. 4 is a schematic cross-sectional view showing an example of the overtube for an endoscope according to the first embodiment of the present invention. FIG. 5 is a cross-sectional view taken along line F5-F5 in FIG. 4. FIG. 6 is a cross-sectional view taken along line F6-F6 in FIG. 4.

As shown in FIG. 4, the distal end tip 4 is connected to a distal end of the main tube 2, and the grip portion 5 is connected to a proximal end thereof. The fixing balloon 3 is fixed to an outer circumference of the main tube 2 near the distal end tip 4. However, FIG. 4 shows a state in which the fixing balloon 3 is in the diameter-expanded state.

A length of the main tube 2 is a length required for a site into which the endoscope 11 is inserted.

As shown in FIG. 5, the main tube 2 is a multi-lumen tube in which a first lumen 2*c* (a main lumen) and a second lumen 2*e* (an air supply lumen) are formed in the longitudinal direction.

The first lumen 2*c* is a circular hole having an inner diameter through which the endoscope 11 can be inserted. The first lumen 2*c* passes through the main tube 2 in the longitudinal direction. The first lumen 2*c* is surrounded by a tube wall 2*a* (a constant thickness portion) having a constant thickness.

The second lumen 2*e* is an air supply lumen for circulating air supplied from the air supply device 10 to the fixing balloon 3. An inner diameter of the second lumen 2*e* is smaller than an inner diameter of the first lumen 2*c*. The inner diameter of the second lumen 2*e* may be, for example, 0.5 mm or more and 3.0 mm or less, although it depends on a material of the main tube 2.

The second lumen 2*e* is adjacent to the first lumen 2*c* in the radial direction and extends in parallel to the second lumen 2*e* in the longitudinal direction of the first lumen 2*c*.

The second lumen 2*e* extends in the longitudinal direction of the first lumen 2*c* at a thick portion 2*b* in which a portion of the tube wall 2*a* protrudes outward in the radial direction.

Therefore, an outer circumferential surface 2*d* of the main tube 2 is formed by the tube wall 2*a* surrounding the first lumen 2*c* and the thick portion 2*b* that bulges outward in the radial direction from the tube wall 2*a*. A cross-sectional shape of the outer circumferential surface 2*d* is approximately circular with the thick portion 2*b* protruding from the circular tube wall 2*a*.

The outer circumferential surface 2*d* forming a top portion of the thick portion 2*b* in a protruding direction is a smooth curved surface that is convex outward. A thickness of the thick portion 2*b* gradually approaches a thickness of the tube wall 2*a* as it goes away from the top portion in the circumferential direction. The outer circumferential surface 2*d* forming a connecting portion between the thick portion 2*b* and the tube wall 2*a* is a curved surface that smoothly connects with the outer circumferential surface 2*d* of the tube wall 2*a*.

With such a configuration, bending rigidity of the main tube 2 is minimized with respect to an axis Y passing through the center of the thick portion 2*b* and the center of the first lumen 2*c*, and is maximized with respect to an axis X that is orthogonal to the axis Y at the center of the first lumen 2*c*.

As shown in FIG. 4, the second lumen 2*e* extends from the proximal end of the main tube 2 (a left end in FIG. 4) to near the distal end of the main tube 2 (a right end in FIG. 4). The proximal end of the second lumen 2*e* is open, while the distal end is closed.

An opening 2*f* communicating with the inside of the second lumen 2*e* passes through the outer circumferential surface 2*d* of the thick portion 2*b* surrounded by the fixing balloon 3.

The number of openings 2*f* is not particularly limited as long as it is one or more. In the example shown in FIG. 3, they are formed at two locations separated in the longitudinal direction of the main tube 2.

A material of the main tube 2 has flexibility. The main tube 2 can bend according to a curvature of the body when it is inserted into the body.

For example, the material of the main tube 2 may be silicone rubber with a rubber hardness (Shore A) of A70. In this case, the thickness of the tube wall 2*a* may be 1.25 mm.

In this case, when the inner diameter of the second lumen 2*e* is 17.5 mm, the maximum thickness of the thick portion 2*b* may be 1.5 mm or more and 5 mm or less.

As shown in FIG. 4, the fixing balloon 3 is disposed on the outer circumferential surface 2*d* at the distal end portion of the main tube 2 so as to surround the opening 2*f*.

The fixing balloon 3 is made of a thin elastic elastomer, and a diameter thereof can expand and contract in the radial direction. The fixing balloon 3 has a cylindrical shape as a whole in the diameter-expanded state. The fixing balloon 3 can be folded in the circumferential direction in the diameter-contracted state.

Hereinafter, unless otherwise specified, a shape of the fixing balloon 3 in the diameter-expanded state in which tension is not generated will be described.

The fixing balloon 3 has a first cylindrical portion 3*a*, a first diameter-expanded portion 3*b*, a second cylindrical portion 3*c*, a second diameter-expanded portion 3*d*, and a third cylindrical portion 3*e* in this order from the proximal end toward the distal end of the fixing balloon 3.

The first cylindrical portion 3*a* has an inner diameter that is fitted to the outer circumferential surface 2*d* of the main tube 2 from the outside, and is airtightly fixed to the outer circumferential surface 2*d*. A method for fixing the first cylindrical portion 3*a* is not particularly limited as long as airtightness is maintained. For example, the first cylindrical portion 3*a* may be fixed to the outer circumferential surface 2*d* by adhesion, heat fusion, or the like.

The first diameter-expanded portion 3*b* has a tubular shape that is connected to the distal end of the first cylindrical portion 3*a* and extends from the distal end of the first cylindrical portion 3*a* toward the distal end of the overtube 1. A diameter of the first diameter-expanded portion 3*b* gradually increases from a diameter of the first cylindrical portion 3*a* as it goes from the proximal end to the distal end of the first diameter-expanded portion 3*b*.

The second cylindrical portion 3*c* has a cylindrical shape that smoothly connects to the distal end of the first diameter-expanded portion 3*b* and extends from the distal end of the first diameter-expanded portion 3*b* toward the distal end of the overtube 1. An outer diameter of the second cylindrical portion 3*c* has a constant value that is smaller than an inner diameter of an indwelling site in the body, such as the intestinal tract, in the diameter-expanded state in which tension is not generated. However, as will be described below, when it is expanded by supplying air, it can be expanded to a diameter larger than the inner diameter of the indwelling site.

As shown in FIGS. 4 and 6, the second cylindrical portion 3*c* is disposed substantially concentrically with the first lumen 2*c* at a position in which each of the openings 2*f* is surrounded from the outside in the radial direction.

As shown in FIG. 4, the second diameter-expanded portion 3*d* has a tubular shape that is connected to the distal end of the second cylindrical portion 3*c* and extends from the distal end of the second cylindrical portion 3*c* toward the distal end of the overtube 1. A diameter of the second diameter-expanded portion 3*d* gradually decreases from the diameter of the second diameter-expanded portion 3*d* as it goes from the proximal end to the distal end of the first diameter-expanded portion 3*b*. Therefore, the diameter of the second diameter-expanded portion 3*d* gradually increases from the distal end to the proximal end of the second diameter-expanded portion 3*d*.

The third cylindrical portion 3*e* is connected to the distal end of the second diameter-expanded portion 3*d*. Like the first cylindrical portion 3*a*, the third cylindrical portion 3*e* has an inner diameter that fits onto the outer circumferential surface 2*d* of the main tube 2 from the outside, and is airtightly fixed to the outer circumferential surface 2*d*.

In the example shown in FIG. 4, the third cylindrical portion 3*e* is fixed at a position in which the distal end of the third cylindrical portion 3*e* is close to the distal end of the main tube 2.

A material of the fixing balloon 3 is not particularly limited as long as it can be expanded or contracted to a required size by a pressure of air supplied between the main tube 2 and the fixing balloon 3.

For example, the material of the fixing balloon 3 may be silicone rubber having a rubber hardness (Shore A) of A15 or more and A30 or less. In this case, a thickness of the fixing balloon 3 may be, for example, 0.15 mm or more and 0.3 mm or less.

In the diameter-expanded state of the fixing balloon 3, a space S3*c* surrounded by the outer circumferential surface 2*d* of the main tube 2 and the inner circumferential surfaces of the first diameter-expanded portion 3*b*, the second cylindrical portion 3*c*, and the second diameter-expanded portion 3*d* in the fixing balloon 3 communicates with the second lumen 2*e* through each of the openings 2*f*. The space S3*c* is separated from a space S2*c* formed inside the first lumen 2*c* by the main tube 2, and thus does not communicate with the space S2*c*.

The distal end tip 4 is connected to the distal end of the main tube 2. The distal end tip 4 has flexibility. The distal end tip 4 as a whole is a tubular member coaxial with the first lumen 2*c* of the main tube 2.

Figure 7:
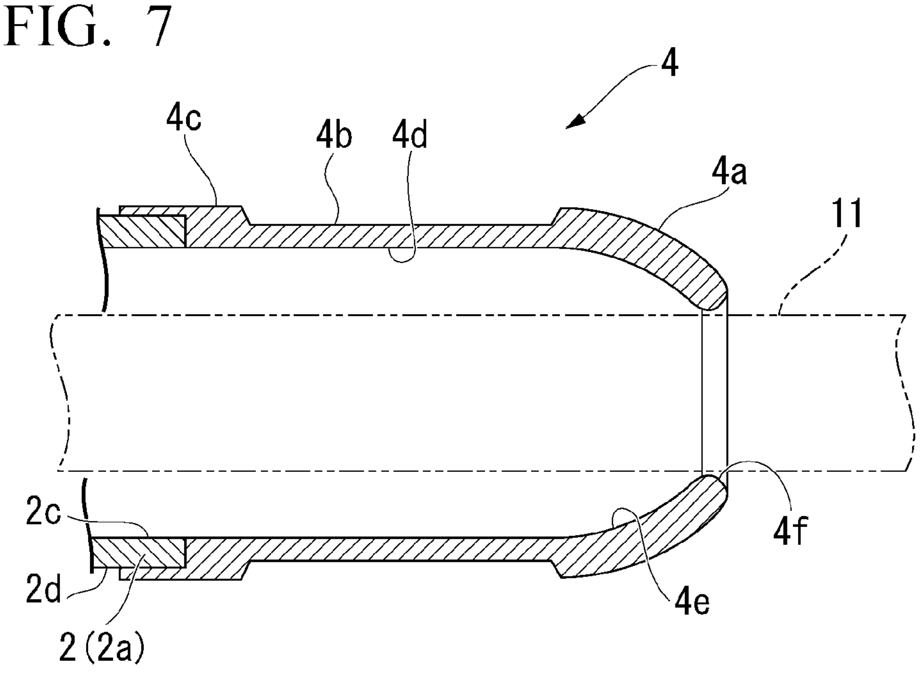
FIG. 7 is an enlarged view of an F7 portion in FIG. 4.

Referring to FIG. 7, a detailed shape of the distal end tip 4 will be described.

FIG. 7 is an enlarged view of an F7 portion in FIG. 4.

The distal end tip 4 has a connecting portion 4*c*, a second tube portion 4*b*, and a first tube portion 4*a* in this order from the proximal end toward the distal end of the distal end tip 4.

The connecting portion 4*c* has a substantially circular ring shape connected to the main tube 2. A proximal end portion of the connecting portion 4*c* is fitted to the outer circumferential surface 2*d* of the main tube 2 from the outside and is fixed to the distal end of the main tube 2. Therefore, an outer diameter of the connecting portion 4*c* is slightly larger than an outer diameter of the outer circumferential surface 2*d* of the main tube 2.

A method for fixing the connecting portion 4*c* is not particularly limited. For example, the connecting portion 4*c* may be fixed to the main tube 2 by, for example, adhesive, heat welding, or the like.

The second lumen 2*e* at the distal end portion of the main tube 2 may be closed by fixing the connecting portion 4*c*. However, the connecting portion 4*c* may be fixed to the main tube 2 in a state in which the second lumen 2*e* is closed by injecting an adhesive or the like into the distal end portion of the second lumen 2*e*.

The second tube portion 4*b* is a tubular body having lower rigidity than the main tube 2. A shape of the second tube portion 4*b* is not particularly limited as long as the endoscope 11 can be inserted therein and the second tube portion 4*b* has lower rigidity than the connecting portion 4*c*.

The first tube portion 4*a* extends from the distal end of the second tube portion 4*b*. The first tube portion 4*a* is a tubular body having higher rigidity than the second tube portion 4*b*, and a distal end opening 4*f* passes through the distal end thereof.

A diameter of the distal end opening 4*f* is smaller than that of a second inner circumferential surface 4*d*, and is large enough to allow the endoscope 11 to be inserted therethrough. For example, the first tube portion 4*a* has an annular shape of which a diameter gradually decreases from the proximal end toward the distal end of the first tube portion 4*a*.

The detailed shape and material of the distal end tip 4 are not particularly limited as long as they satisfy the following Equations (1a) and (1b) at the same time.

[Math 1]

$$K1 > K2 \quad (1a)$$

$$K3 > K2 \quad (1b)$$

Here, K1 is a rigidity of the first tube portion 4*a*, K2 is a rigidity of the second tube portion 4*b*, and K3 is a rigidity of the main tube 2. The rigidity here refers to bending rigidity.

In the example shown in FIG. 7, the second tube portion 4*b* has a cylindrical shape having an inner diameter substantially the same as that of the first lumen 2*c* of the main tube 2 and an outer diameter smaller than that of the outer circumferential surface 2*d* of the main tube 2.

In the example shown in FIG. 7, the first tube portion 4*a* is formed to be thicker than the second tube portion 4*b*. A first inner circumferential surface 4*e* which is an inner circumferential surface of the first tube portion 4*a* is a curved surface of which a diameter gradually decreases from the proximal end toward the distal end of the first tube portion 4*a*.

In the example shown in FIG. 7, the rigidity of the second tube portion 4*b* is made lower than the rigidity of the first tube portion 4*a* by changing the thickness.

In the example shown in FIG. 7, although the thickness of each of the second tube portion 4*b* and the first tube portion 4*a* is constant, the second tube portion 4*b* and the first tube portion 4*a* may have appropriate cross-sectional shapes having different cross-sectional secondary moments. For example, a projection, groove, or the like that extends in the longitudinal direction may be formed on at least one of the second tube portion 4*b* and the first tube portion 4*a*.

For example, the second tube portion 4*b* may be formed in a bellows shape with lower rigidity than the first tube portion 4*a*.

A material of the distal end tip 4 may be a silicone resin. For example, the material of the distal end tip 4 may be silicone rubber with a rubber hardness (Shore A) of A40. In this case, for example, the thickness of the second tube portion 4*b* may be 1 mm, and the thickness of the first tube portion 4*a* may be 2 mm.

As shown in FIG. 4, the grip portion 5 includes a tubular portion 5*a*, a stopper 5*b*, a first luer connector 5*c*, a first conduit 5*d*, a second luer connector 5*e*, a second conduit 5*f*, and a cap 5*g*.

The stopper 5*b* can be used by an operator to support the proximal end of the main tube 2 outside the patient's body and to operate insertion and extraction of the overtube 1.

The tubular portion 5*a* has a substantially cylindrical shape coaxial with the first lumen 2*c* of the main tube 2. A fitting hole 5*h* into which the outer circumferential surface 2*d* of the main tube 2 is fitted from the outside is formed in the distal end portion of the tubular portion 5*a*. The proximal end portion of the main tube 2 is fixed in the fitting hole 5*h* in a state in which the proximal end portion of the main tube 2 is inserted therein.

A method for fixing the main tube 2 is not particularly limited as long as it is airtight. For example, the main tube 2 may be fixed into the fitting hole 5*h* by adhesive, heat fusion, or the like.

An inner circumferential surface 5*i* which is a cylindrical surface having the same diameter as the first lumen 2*c* passes through the proximal end portion of the tubular portion 5*a* in the longitudinal direction. A distal end of the inner circumferential surface 5*i* is smoothly connected to the first lumen 2*c*.

The stopper 5*b* protrudes outward in the radial direction from an outer circumferential portion of the tubular portion 5*a*. A protruding position of the stopper 5*b* is equal to a position of the proximal end of the main tube 2 in the longitudinal direction. The stopper 5*b* protrudes upward and downward in the drawing. An exterior of the stopper 5*b* seen in the longitudinal direction is, for example, a substantially elliptical plate that is long in the up-down direction in the drawing (refer to FIG. 1).

The stopper 5*b* is provided, for example, for the purpose of preventing a portion of the overtube 1 on the proximal end side of the stopper 5*b* from entering the lumen when the overtube 1 is inserted into the patient's lumen. Therefore, the stopper 5*b* is formed to a size that cannot be inserted into the lumen. For example, when the overtube 1 is used by being inserted into the large intestine, the stopper 5*b* is formed to be larger than a size of the anus. In this case, it is more preferable that the size of the stopper 5*b* in the longitudinal direction does not enter a circle with a diameter of 55 mm or less centered on the center of the tubular portion 5*a*.

The first luer connector 5*c* is a luer lock type connector. The first luer connector 5*c* is mounted on the outer circumferential portion of the tubular portion 5*a* on the rear side of the stopper 5*b* in the grip portion 5. The first conduit 5*d* that communicates with the first luer connector 5*c* and the second lumen 2*e* of the main tube 2 fixed to the fitting hole 5*h* is formed in the tubular portion 5*a*.

As shown in FIG. 1, an air flow tube 9 (an air supply tube) of the air supply device 10 which will be described below is detachably connected to the first luer connector 5*c*.

As shown in FIG. 4, the second luer connector 5*e* is a luer lock type connector. The second luer connector 5*e* is mounted on the outer circumferential portion of the tubular portion 5*a* on the side opposite to the first luer connector 5*c* with the tubular portion 5*a* interposed therebetween. The second conduit 5*f* that communicates with the first luer connector 5*c* and opens to the inner circumferential surface 5*i* is formed inside the tubular portion 5*a*.

For example, a syringe can be detachably connected to the second luer connector 5*e*. For example, friction between the endoscope and the main tube 2 can be reduced by injecting sterilized water or medical lubricant from the syringe through the second luer connector 5*e* into the first lumen 2*c*.

In the example shown in FIG. 4, since the syringe is not connected, the cap 5*g* that airtightly closes an opening of the second luer connector 5*e* is mounted. Thus, the second conduit 5*f* is closed.

Next, the airtight valve unit 6 will be described.

Figure 8:
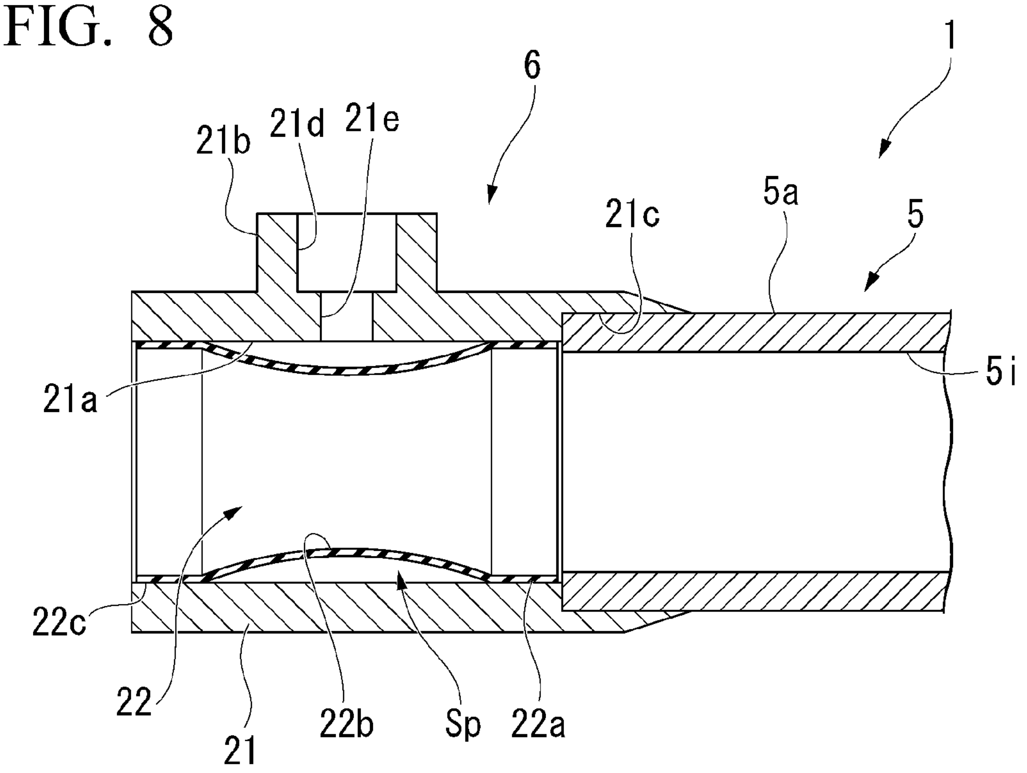
FIG. 8 is a schematic cross-sectional view showing an example of an airtight valve unit in the overtube for an endoscope according to the first embodiment of the present invention.
Figure 9:
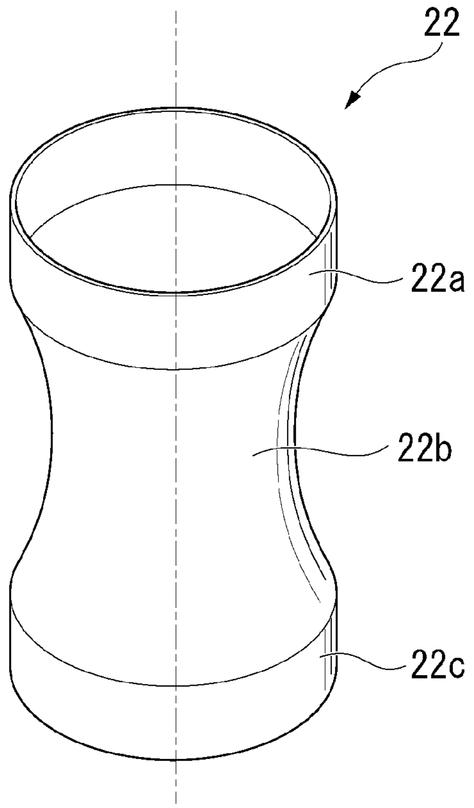
FIG. 9 is a schematic perspective view showing an example of an airtight balloon of the airtight valve unit in the overtube for an endoscope according to the first embodiment of the present invention.

FIG. 8 is a schematic cross-sectional view showing an example of the airtight valve unit in the overtube for an endoscope according to the first embodiment of the present invention. FIG. 9 is a schematic perspective view showing an example of an airtight balloon of the airtight valve unit in the overtube for an endoscope according to the first embodiment of the present invention.

The airtight valve unit 6 airtightly seals the outer circumferential portion of the endoscope 11 at the proximal end portion of the insertion portion 1 in a state in which the endoscope 11 is inserted through the first lumen 2*c* of the main tube 2.

As shown in FIG. 8, the airtight valve unit 6 has a cylinder frame portion 21 (a tubular portion) and an airtight balloon 22.

The cylinder frame portion 21 is a substantially cylindrical body.

A fitting hole 21*c* into which the proximal end portion of the tubular portion 5*a* of the grip portion 5 is fitted from the outside is formed on the distal end side of the cylinder frame portion 21.

An inner circumferential surface 21*a* forming a circular hole extending in the longitudinal direction of the grip portion 5 extends to the proximal end of the cylinder frame portion 21 at a lower portion of the fitting hole 21*c* on the left side in the drawing. A diameter of the inner circumferential surface 21*a* is slightly larger than a diameter of the inner circumferential surface 5*i* of the tubular portion 5*a*.

The proximal end of the tubular portion 5*a* is inserted into the fitting hole 21*c*, and is joined to the fitting hole 21*c* in a state in which the proximal end of the tubular portion 5*a* is in contact with the lower portion of the fitting hole 21*c*.

A tubular connection port 21*b* protrudes from an outer circumferential surface of the cylinder frame portion 21.

Inside the connection port 21*b*, a connection hole 21*d* and a through hole 21*e* are formed in this order from the outside in the radial direction of the cylinder frame portion 21 toward the inside.

The connection hole 21*d* is a concave portion for connecting an operation tube main body 25 which will be described below.

The through hole 21*e* allows an opening of the operation tube main body 25 connected to the connection hole 21*d* to communicate with a space inside the inner circumferential surface 21*a*.

A material of the cylinder frame portion 21 is not particularly limited. For example, the material of the cylinder frame portion 21 may include a resin, a metal, silicone rubber, and the like.

The airtight balloon 22 is a tubular member made of the same material as the fixing balloon 3.

The airtight balloon 22 has a first joint portion 22*a*, a middle portion 22*b*, and a second joint portion 22*c*.

The first joint portion 22*a* and the second joint portion 22*c* are respectively formed at the distal end and the proximal end of the airtight balloon 22. Each of the first joint portion 22*a* and the second joint portion 22*c* has an annular shape that can be joined to the inner circumferential surface 21*a* of the cylinder frame portion 21. In the example shown in FIG. 8, since the inner circumferential surface 21*a* is a cylindrical surface, each of the first joint portion 22*a* and the second joint portion 22*c* has an annular shape having the same outer diameter.

The middle portion 22*b* is connected to the proximal end of the first joint portion 22*a* and the distal end of the second joint portion 22*c*, and connects the first joint portion 22*a* and the second joint portion 22*c* over the entire circumference.

An outer diameter of the middle portion 22*b* is smaller than outer diameters of the first joint portion 22*a* and the second joint portion 22*c*, at least in part. In this embodiment, the outer diameter of the middle portion 22*b* decreases from the proximal end of the first joint portion 22*a* toward the rear, becomes the minimum at a center portion thereof in the axial direction, and increases from the center portion toward the second joint portion 22*c* located at the rear. As shown in FIG. 9, central axes of the first joint portion 22*a*, the middle portion 22*b*, and the second joint portion 22*c* are coaxial with each other.

As shown in FIG. 8, the airtight balloon 22 is inserted inside the inner circumferential surface 21*a* of the cylinder frame portion 21, and is joined to the inner circumferential surface 21*a* at the first joint portion 22*a* and the second joint portion 22*c*. A length of the airtight balloon 22 in the axial direction is not particularly limited, but in the example shown in FIG. 8, it is equivalent to a length of the inner circumferential surface 21*a* in the axial direction.

A method for joining the airtight balloon 22 is not particularly limited. For example, the airtight balloon 22 may be joined to the inner circumferential surface 21*a* by adhesion.

In a state in which the airtight balloon 22 is joined to the inner circumferential surface 21*a*, a space Sp is formed between the inner circumferential surface 21*a* and the middle portion 22*b*. The middle portion 22*b* covers the through hole 21*e* in the radial direction. Therefore, the space Sp communicates with the connection hole 21*d* of the connection port 21*b* through the through hole 21*e*.

As a material of the airtight balloon 22, an appropriate elastic elastomer is used. For example, a material that is the same as that of the fixing balloon 3 may be used as the material of the airtight balloon 22.

When a fluid is supplied into the space Sp or suctioned out from the space Sp through the connection port 21*b*, a shape of the middle portion 22*b* changes according to an internal pressure of the space Sp. The fluid supplied to the space Sp may be either gas or liquid as long as it can apply pressure that can change the shape of the middle portion 22*b*.

In this embodiment, a gas is supplied to the space Sp. A type of the gas is not particularly limited. For example, it is more preferable to use air as the gas in that the middle portion 22*b* can form a state in which the middle portion 22*b* protrudes inward by opening the space Sp to the atmosphere.

When the gas is supplied into the space Sp, the middle portion 22*b* forms a shape that bulges inside the inner circumferential surface 21*a* according to the internal pressure of the space Sp. For example, when more gas is supplied than a volume of the space Sp when the airtight balloon 22 is mounted, the internal pressure of the space Sp increases and the middle portion 22*b* expands. Thus, the volume of the space Sp increases. The expanded middle portion 22*b* reduces a space inside the airtight balloon 22 in the radial direction. For this reason, the inner diameter of the middle portion 22*b* maintains a minimum state at the center in the axial direction and decreases overall.

When the gas is suctioned out from the space Sp, the diameter of the middle portion 22*b* expands according to the decrease in the internal pressure of the space Sp. When the gas becomes less than the volume of the space Sp when the airtight balloon 22 is mounted, the middle portion 22*b* is pressed toward the inner circumferential surface 21*a*. When the whole gas is suctioned out from the space Sp, the middle portion 22*b* receives atmospheric pressure from inside the airtight balloon 22 and expands in diameter, and the middle portion 22*b* sticks to the inner circumferential surface 21*a*. Thus, a conduit having an inner diameter substantially the same as that of the inner circumferential surface 21*a* is formed inside the airtight balloon 22. FIG. 4 shows a state in which the gas in the space Sp has been suctioned out.

As shown in FIG. 4, the airtight valve operation tube 7 includes an operation tube main body 25, a pressure adjustment balloon 26, and a cock 27.

The operation tube main body 25 circulates gas to be taken into and out of the space Sp. A first end portion 25*a* of the operation tube main body 25 is connected to the connection port 21*b*. The pressure adjustment balloon 26 is connected to a second end portion 25*b* on the side opposite to the first end portion 25*a*.

The pressure adjustment balloon 26 communicates with the space Sp through the operation tube main body 25. The pressure adjustment balloon 26 does not expand until the pressure in the space Sp reaches a predetermined value, and expands after the pressure reaches the predetermined value. Thus, it is possible to adjust the pressure in the space Sp. Details of an action of the pressure adjustment balloon 26 in this embodiment will be described together with a motion of the overtube 1.

A shape and material of the pressure adjustment balloon 26 are not particularly limited as long as the pressure can be adjusted as described below. In the example shown in FIG. 4, the pressure adjustment balloon 26 has a substantially cylindrical shape and is made of silicone rubber.

The cock 27 is connected to the pressure adjustment balloon 26.

The cock 27 is a tube member through which a gas can flow. The cock 27 includes a connection hole 27*a*, a valve 27*b*, and an opening 27*c*.

The connection hole 27*a* detachably connects, for example, a gas moving device such as a syringe or a pump. In the example shown in FIG. 1, a syringe 28 is mounted in the cock 27 as the gas moving device.

As shown in FIG. 4, the valve 27*b* opens to allow the gas to flow when the gas moving device is connected to the connection hole 27*a*, and is closed to prevent the gas from flowing out of the connection hole 27*a* when the gas moving device is disconnected from the connection hole 27*a*.

The opening 27*c* opens into the pressure adjustment balloon 26 and allows the inside of the pressure adjustment balloon 26 and a flow path inside the cock 27 to communicate with each other.

As shown in FIG. 1, the air supply device 10 mainly supplies air for expanding the diameter of the fixing balloon 3. In this embodiment, the supplied air can also be suctioned into the air supply device 10 by appropriately switching a flow path within the air supply device 10.

The air supply device 10 has the air flow tube 9 that circulates air to the second lumen 2*e* of the main tube 2.

The air flow tube 9 communicates with an internal flow path of the air supply device 10 that supplies and takes in air, and extends outward from a casing of the air supply device 10. The air flow tube 9 forms an air flow path between the second lumen 2*e* and the internal flow path of the air supply device 10.

A connector 9*a* that is detachably connected to the first luer connector 5*c* of the grip portion 5 is provided at the distal end portion of the air flow tube 9 in an extending direction.

When the connector 9*a* is connected to the first luer connector 5*c*, the second lumen 2*e* and the internal flow path of the air supply device 10 are communicated with each other through the air flow tube 9.

An inner diameter of the conduit of the air flow tube 9 may be, for example, 2.0 mm or more and 5 mm or less.

The air supply device 10 has a pump for supplying air. A type of the pump is not particularly limited. For example, the pump may be an electric pump or a manual pump.

When the pump is an electric pump, it may be equipped with a pressure control circuit. A pressure control method is not particularly limited.

The air supply device 10 includes a relief valve that discharges the air to the outside when the pressure of the supplied air exceeds a certain value so that a supply pressure of the air does not exceed an allowable value of the internal pressure of the fixing balloon 3.

The air supply device 10 is capable of supplying air through the air flow tube 9 and suctioning air from the air flow tube 9. A configuration for switching between supply and suction is not particularly limited.

For example, the air supply device 10 may include a switching valve that selectively switches between a flow path between an air supply port of the pump and the air flow tube 9 and a flow path between an air suctioning port of the pump and the air flow tube 9, and a switching valve control part that controls an operation of the switching valve.

For example, the air supply device 10 may include a pump that can switch between air supply and air suction at an opening connected to the air flow tube 9.

Next, an operation of the airtight valve unit 6 will be described. In the operation of the overtube 1 and the endoscope 11, when the subject of operation is not limited to the operator, the subject of operation is referred to as an "operator or assistant." In the following, the "operator or assistant" may be referred to as "the operator or the like."

Figure 10:
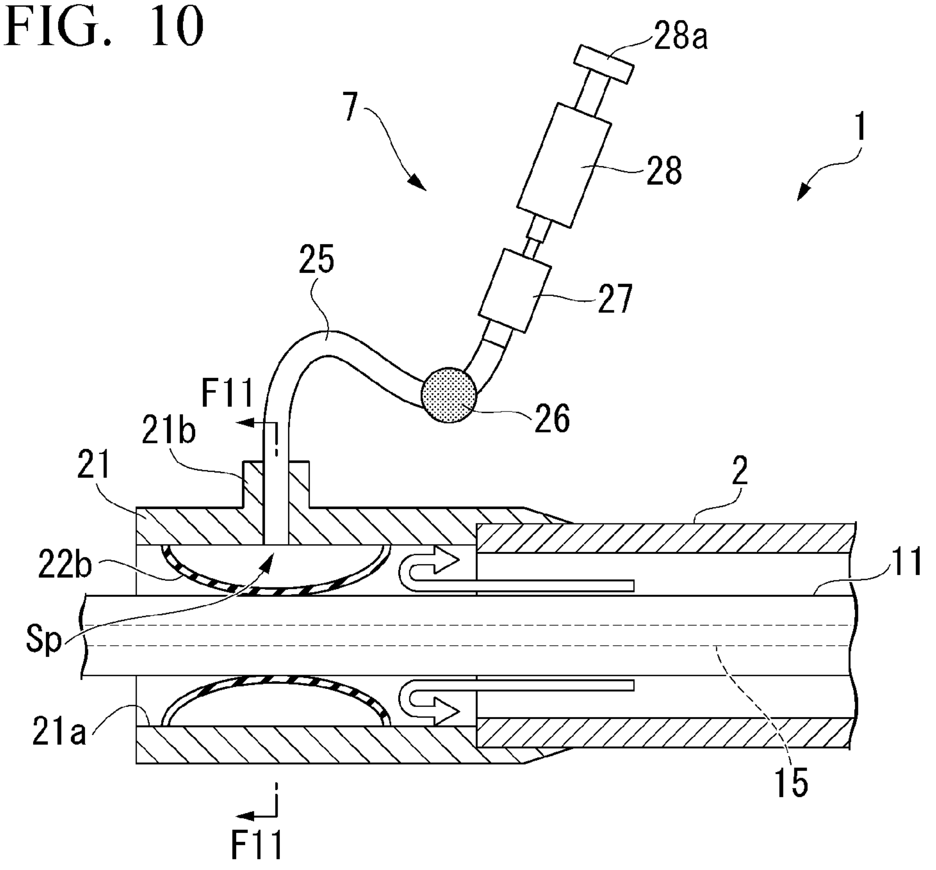
FIG. 10 is an explanatory diagram of an operation of the airtight valve unit in the overtube for an endoscope according to the first embodiment of the present invention.
Figure 11:
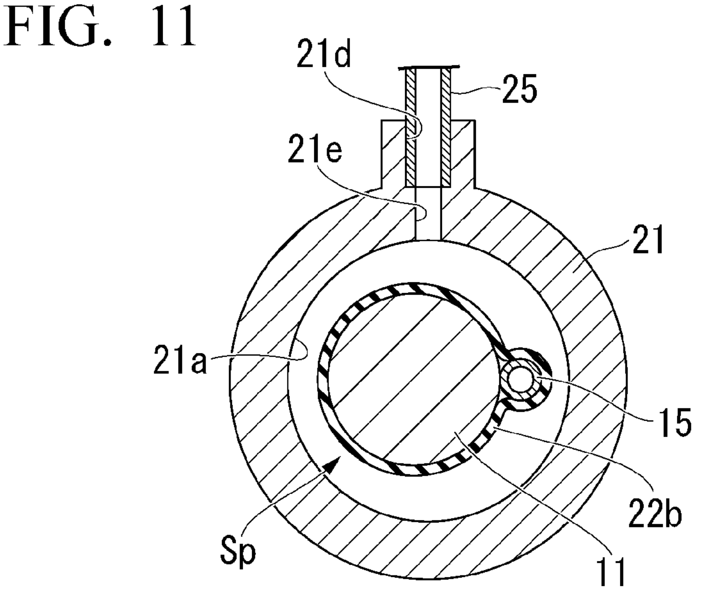
FIG. 11 is a cross-sectional view taken along line F11-F11 in FIG. 10.

FIG. 10 is an explanatory diagram of the operation of the airtight valve unit in the overtube for an endoscope according to the first embodiment of the present invention. FIG. 11 is a cross-sectional view taken along line F11-F11 in FIG. 10. In FIG. 11, illustration of an internal structure of the endoscope 11 is omitted for simplification.

As shown in FIG. 10, the syringe 28 is mounted in the cock 27.

When the operator or the like pulls a plunger 28*a* of the syringe 28, the gas in the space Sp is suctioned and moves inside the syringe 28. The inside of the space Sp becomes negative pressure. As a result, as shown in FIG. 4, the middle portion 22*b* is in close contact with the inner surface of the cylinder frame portion 21, and an inner diameter of a portion at which the middle portion 22*b* is disposed is expanded to a size equivalent to the inner diameter of the inner circumferential surface 5*i* of the grip portion 5 and the first lumen 2*c* of the endoscope 11. This state is referred to as an open state of the airtight valve unit 6.

When the airtight valve unit 6 is in the open state, an inner diameter of a portion inside the middle portion 22*b* is larger than the outer diameter of the endoscope 11 in which the endoscope cap 13 is mounted and which has the gripping device 14 and the channel tube 15. Therefore, when the airtight valve unit 6 is in the open state, the endoscope 11 can be smoothly inserted inside the middle portion 22*b*. At the time of insertion, the endoscope 11 is not in contact with the middle portion 22*b*, or even when it is in contact, only a part of the exterior thereof is in contact with the middle portion 22*b*. Therefore, the endoscope 11 does not receive insertion resistance from the middle portion 22*b*, or even when it does, the insertion resistance is small.

Similarly, the endoscope 11 can be inserted inside the inner circumferential surface 5*i* of the grip portion 5 and the first lumen 2*c* of the main tube 2 with low insertion resistance.

When the distal end of the endoscope 11 reaches the distal end opening 4*f* in the distal end tip 4, the endoscope 11 protrudes forward of the distal end tip 4 through the distal end opening 4*f*, as shown in FIG. 7.

At this time, since the distal end opening 4*f* is close to the endoscope 11 along the outer circumferential portion thereof, living tissue, body fluid, or the like in front of the distal end tip 4 are difficult to enter into the distal end tip 4.

As shown in FIG. 10, after the endoscope cap 13 passes through the inside of the cylinder frame portion 21, the operator or the like operates the plunger 28*a* to move the gas in the syringe 28 to the space Sp. Thus, the negative pressure in the space Sp is released, and the middle portion 22*b* bulges inward in the radial direction.

As shown in FIG. 11, the operator or the like supplies gas to the space Sp until the middle portion 22*b* is in contact with the entire circumference of the outer circumferential portion of the endoscope 11. Thus, the gap between the outer circumferential portion of the endoscope 11 and the middle portion 22*b* is closed. This state is referred to as a closed state of the airtight valve unit 6.

In the closed state, since the middle portion 22*b* is in close contact with the entire outer circumference of the endoscope 11, the endoscope 11 is held approximately at the center of the inner circumferential surface 21*a*. Therefore, in the vicinity of the middle portion 22*b*, only a sliding resistance load with respect to the middle portion 22*b* acts on the endoscope 11.

When the insertion resistance of the endoscope 11 does not become too large, the operator or the like may press the plunger 28*a* to form the closed state so that gas is supplied until the internal pressure of the space Sp becomes higher than atmospheric pressure. In this case, a tension due to expansion from a natural state is generated at at least the middle portion 22*b*.

Here, an example of a relationship between the amount of air supply from the syringe 28 (a volume of air supply) and the internal pressure of the space Sp will be described.

Figure 12:
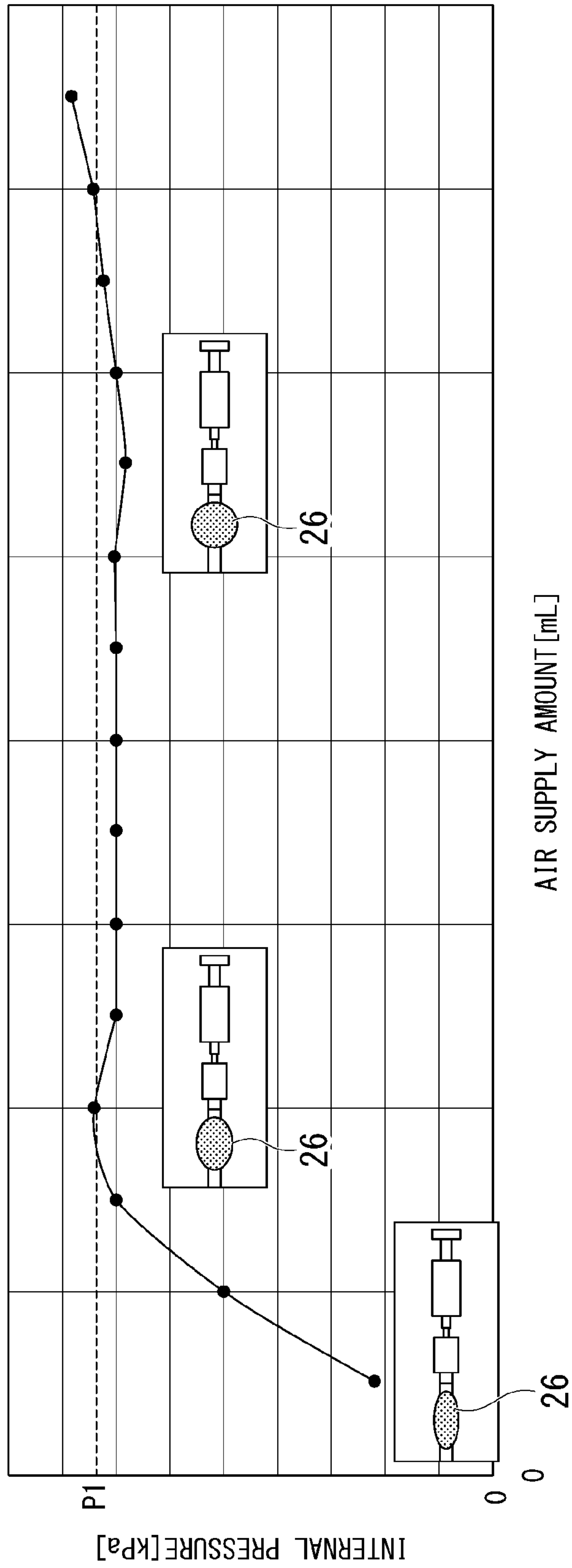
FIG. 12 is a graph showing an example of a relationship between an amount of air supply from a gas moving device and an internal pressure of the airtight balloon in the overtube for an endoscope according to the first embodiment of the present invention.

FIG. 12 is a graph showing the relationship between the amount of air supply from the gas moving device and the internal pressure of the airtight balloon in the overtube for an endoscope according to the first embodiment of the present invention. In FIG. 12, a horizontal axis represents the amount of air supply [mL], and a vertical axis represents the internal pressure [kPa] of the space Sp.

However, FIG. 12 is an example in which the gas supplied from the syringe 28 is air.

As shown in FIG. 12, until the internal pressure of the space Sp reaches a predetermined value P1, the pressure adjustment balloon 26 does not expand, and the airtight balloon 22 expands. When the internal pressure reaches a predetermined value P1, expansion of the pressure adjustment balloon 26 begins. Then, the pressure adjustment balloon 26 is expanded by air supply from the syringe 28, and an increase in the internal pressure of the space Sp is curbed. As a result, an internal pressure value of the space Sp is maintained within a predetermined range around P1 in a certain range of the amount of air supply until the pressure adjustment balloon 26 reaches expansion limit, and is prevented from increasing excessively.

In the overtube 1, the internal pressure value of the space Sp can be maintained within a predetermined range without the operator or the like performing detailed operations of the syringe 28, and thus the operation is simple.

However, a mechanism for adjusting the pressure inside the space Sp is not limited to the pressure adjustment balloon 26. For example, instead of the pressure adjustment balloon 26, an adjustment valve that opens at a predetermined internal pressure to release air supplied from the syringe 28 may be provided.

Next, an operation when the overtube 1 according to this embodiment is used will be described.

In the following, an example in which the endoscope 11 is a large intestine endoscope, and ESD (endoscopic submucosal dissection) is performed in the large intestine using an endoscope system that combines the overtube 1 and the endoscope 11 will be described.

A length of the insertion portion 1 of the overtube 1 is approximately a length from the anus to a treatment site, and is shorter than the insertion portion of the endoscope 11.

For example, when the overtube 1 is inserted after the endoscope 11 is inserted, it is more preferable to insert the endoscope 11 close to the treatment site before the overtube 1 is inserted into the body. In this case, the insertion portion of the endoscope 11 needs to be able to protrude from the distal end of the overtube 1 to some extent.

For example, it is more preferable that the length of the insertion portion 1 is 50 cm to 70 cm shorter than the insertion portion of the endoscope 11.

For example, when the insertion portion 1 is 70 cm shorter than the insertion portion of the endoscope 11, and the length from the anus to the treatment site is less than 70 cm, only the endoscope 11 can be disposed near the treatment site in a state in which the overtube 1 is disposed outside the patient's body.

Preferably, a minimum inner diameter of the middle portion 22*b* of the airtight balloon 22 is slightly smaller than an outer diameter of the insertion portion. Here, the minimum inner diameter of the middle portion 22*b* is a minimum inner diameter when the middle portion 22*b* protrudes most toward the center in a state in which no tension is generated in the middle portion 22*b*.

Figure 13:
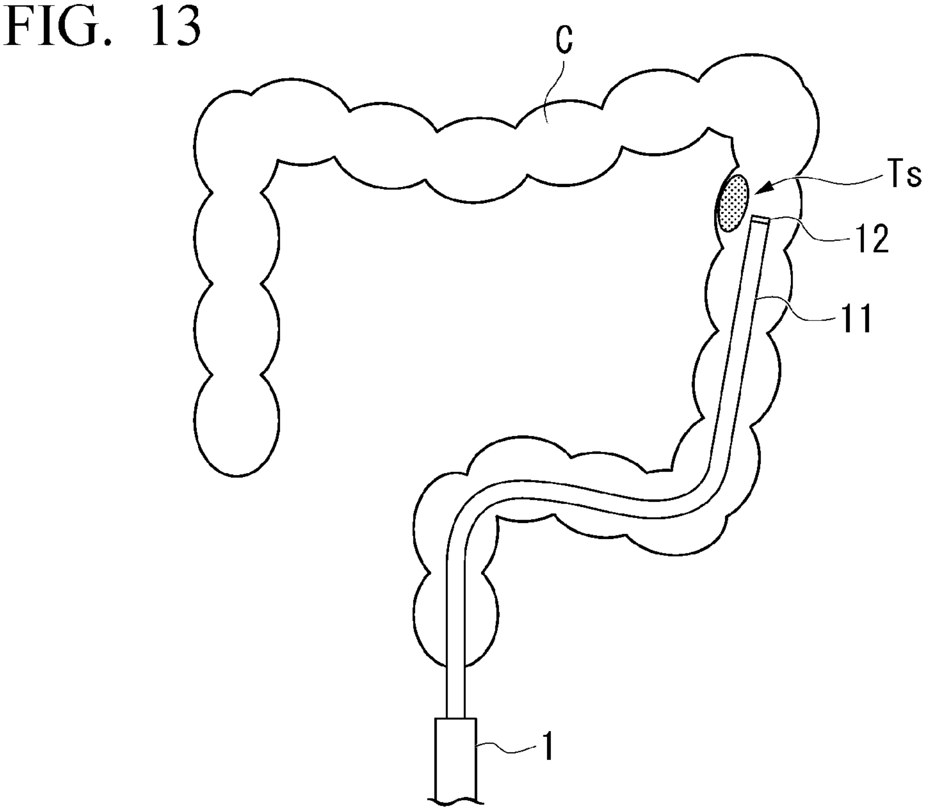
FIG. 13 is a schematic diagram showing an example of a method for using the overtube for an endoscope according to the first embodiment of the present invention.
Figure 14:
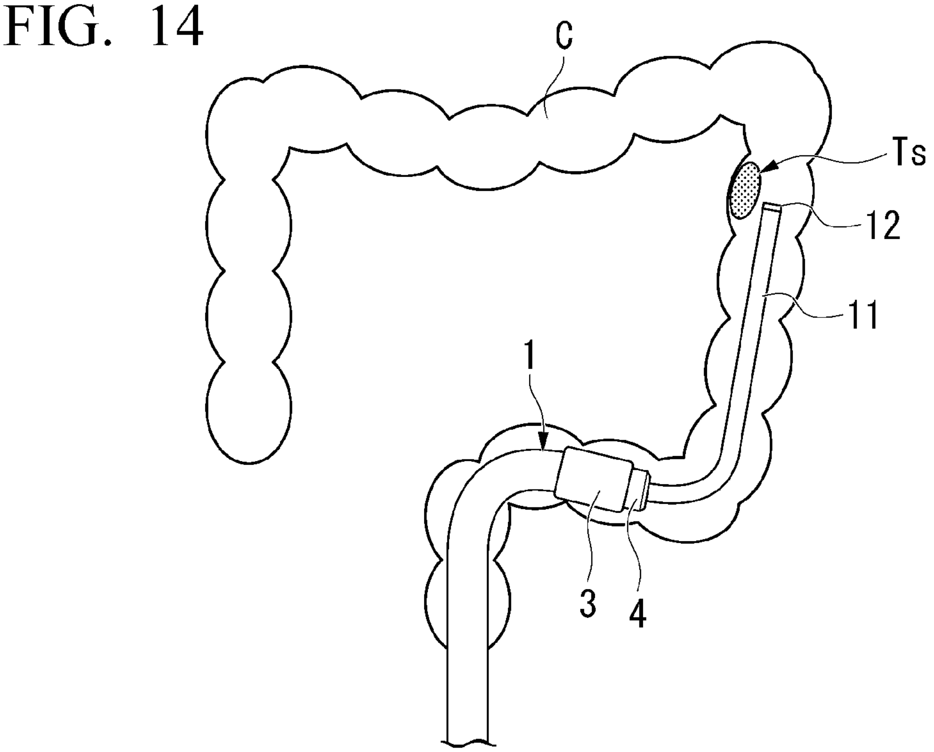
FIG. 14 is a schematic diagram showing the example of the method for using the overtube for an endoscope according to the first embodiment of the present invention.
Figure 15:
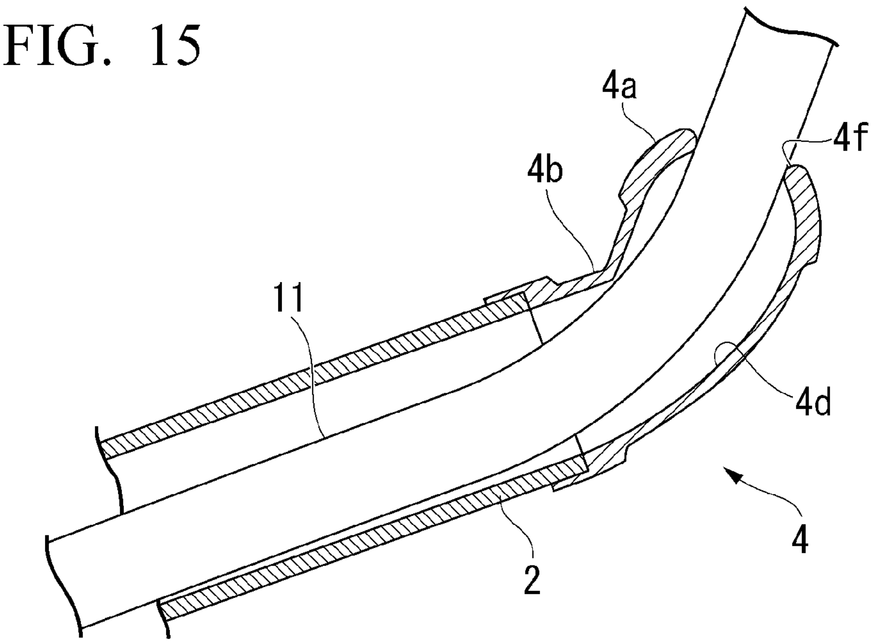
FIG. 15 is a schematic cross-sectional view showing an action of a distal end tip in the overtube for an endoscope according to the first embodiment of the present invention.

FIGS. 13 and 14 are schematic diagrams showing an example of a method for using the overtube for an endoscope according to the first embodiment of the present invention. FIG. 15 is a schematic cross-sectional view showing an action of the distal end tip in the overtube for an endoscope according to the first embodiment of the present invention.

Figure 16:
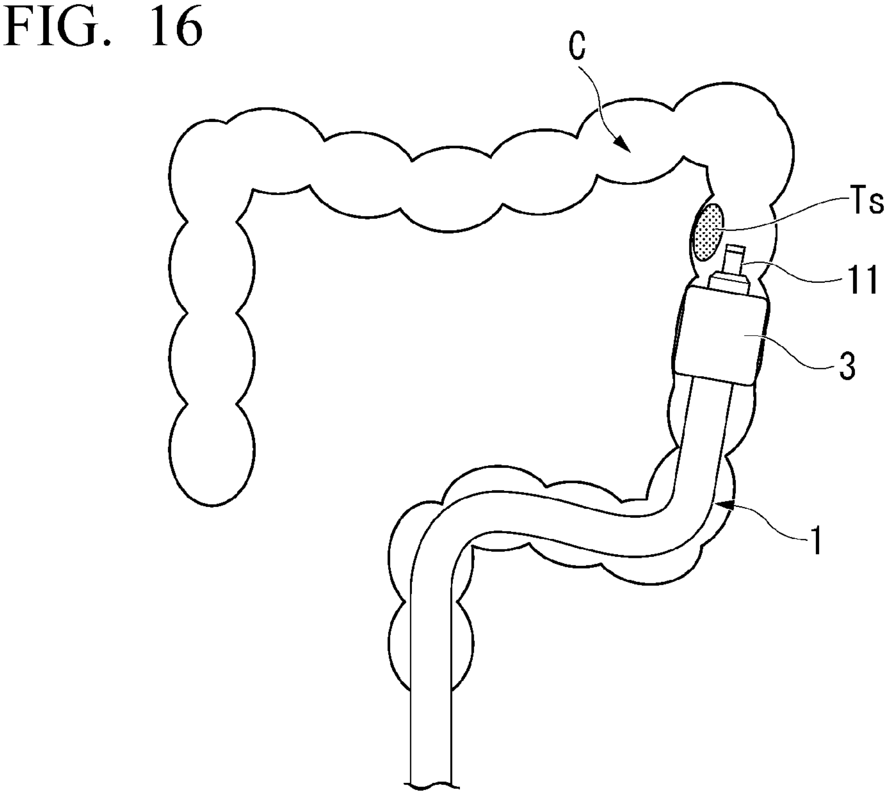
FIG. 16 is a schematic diagram showing an example of the method for using the overtube for an endoscope according to the first embodiment of the present invention.

FIG. 16 is a schematic diagram showing an example of the method for using the overtube for an endoscope according to the first embodiment of the present invention.

However, in FIGS. 13 to 16, for ease of viewing, detailed shapes of the endoscope cap 13, the gripping device 14, the channel tube 15, and the like of the endoscope 11 are omitted.

First, the overtube 1 is prepared.

In the prepared overtube 1, the gas in the space S3*c* inside the fixing balloon 3 is suctioned out by the air supply device 10. Therefore, the fixing balloon 3 is folded and close to the outer circumferential surface 2*d* of the main tube 2. Thus, the outer diameter of the overtube 1 at a portion at which the fixing balloon 3 is provided is reduced to approximately the same diameter as the outer diameter of the main tube 2 in which the fixing balloon 3 is not provided. This state is hereinafter referred to as a diameter-contracted state of the fixing balloon 3.

In the prepared overtube 1, the insertion portion of the endoscope 11 can be inserted into the cylinder frame portion 21 with low resistance. In the following, an example in which the gas supplied to the space Sp is air will be described.

For example, when the gas supplied to the space Sp is air, the air in the space Sp is suctioned to form the open state, or the middle portion 22*b* is made to protrude in a state in which no tension is generated.

Thus, a generally cylindrical space in which the endoscope 11 can move forward and backward without much resistance is formed inside the cylinder frame portion 21.

For example, in order to bring the space Sp to atmospheric pressure, the valve 27*b* is opened by mounting the syringe 28 with the plunger 28*a* removed in the cock 27. Therefore, the space Sp communicates with the outside, and the inside of the space Sp becomes atmospheric pressure. Then, when the syringe 28 is removed from the cock 27, the valve 27*b* is closed and the space Sp is maintained at atmospheric pressure.

Then, the operator inserts the distal end of the endoscope 11 into the cylinder frame portion 21 of the overtube 1. Then, the insertion portion of the endoscope 11 passes through the inner circumferential surface 5*i* of the grip portion 5, the first lumen 2*c* of the main tube 2, and the inside of the distal end tip 4, and thus the insertion portion of the endoscope 11 extends from the distal end opening 4*f* of the distal end tip 4.

Then, as shown in FIG. 13, the operator places the overtube 1 outside the patient's body and inserts the insertion portion of the endoscope 11 protruding from the overtube 1 into the large intestine C though the anus. Since the large intestine C is curved, the operator inserts the insertion portion while checking the inside of the large intestine C using images obtained by the endoscope 11. After the treatment site Ts appears in the image acquired by the endoscope 11, the operator stops inserting the endoscope 11.

Then, as shown in FIG. 14, the operator inserts the overtube 1 into the large intestine C from the anus along the insertion portion of the endoscope 11. At this time, the middle portion 22*b* of the airtight valve unit 6 (not shown) is brought into close contact with the outer circumferential portion of the endoscope 11.

For example, when ESD is performed only with a treatment tool that is inserted through the treatment tool channel 12*b* of the endoscope 11, the endoscope cap 13 can be removed from endoscope 11 along with the gripping device 14 and the channel tube 15.

In this case, when the minimum inner diameter of the middle portion 22*b* of the airtight balloon 22 is equal to or less than the outer diameter of the main tube 2 of the endoscope 11, a part of the middle portion 22*b* comes into contact with the outer circumferential surface of the main tube 2 over the entire circumference only by inserting the endoscope, and thus the gap between the overtube 1 and the endoscope 11 is closed. Furthermore, when a difference between the minimum inner diameter of the middle portion 22*b* and the outer diameter of the main tube 2 does not become too large, a contact area between the middle portion 22*b* and the outer circumferential surface of the main tube 2 will not become too large, and thus sliding resistance during relative movement between the endoscope 11 and the overtube 1 is reduced.

In this case, when the space Sp of the airtight balloon 22 is at atmospheric pressure, there is no need to supply any more air into the space Sp.

However, ESD may be performed using the gripping device 14 in addition to the treatment tool inserted through the treatment tool channel 12*b*. For example, the endoscope cap 13 is mounted on the distal end portion 12 of the endoscope 11, and the gripping device 14 and the channel tube 15 are disposed in the longitudinal direction of the main tube 2.

In this case, since an outer diameter of a portion of the endoscope 11 on which the endoscope cap 13 is mounted increases, it may become difficult to insert the endoscope into the overtube 1 in a state in which the middle portion 22*b* protruded.

According to this embodiment, the operator or the like mounts the syringe 28 in the cock 27 and suctions air out of the space Sp, and thus the middle portion 22*b* is in the open state. Thus, the portion on which the endoscope cap 13 is mounted can be smoothly inserted through the cylinder frame portion 21.

After the endoscope cap 13 is inserted, the operator or the like can increase the internal pressure of the space Sp by operating the plunger 28*a* of the syringe 28 mounted in the cock 27 to supply air to the space Sp.

Thus, the middle portion 22*b* is in close contact with a side surface of the insertion portion of the endoscope 11 on which the channel tube 15 is disposed on the outer circumferential surface (refer to FIG. 11), and a gap between the inside of the cylinder frame portion 21 and the side surface of the insertion portion of the endoscope 11 is closed.

At that time, since the pressure adjustment balloon 26 is provided in the air flow path, even when the amount of air supply by the plunger 28*a* increases to some extent, the internal pressure of the space Sp is maintained at a value close to the predetermined value P1, as shown in FIG. 12. Thus, since the internal pressure of the space Sp is restricted, even when relative movement occurs between the overtube 1 and the endoscope 11, the sliding resistance does not exceed a certain value. As a result, the overtube 1 can be smoothly inserted while airtightness of the airtight valve unit 6 is maintained.

As shown in FIG. 14, the large intestine C is an organ with many curved portions. As an overtube according to the related art moves along the bent endoscope, the overtube that cannot follow bends easily deviates from the central axis of the endoscope. In this case, it is known that since a large gap is created between the opening of the overtube and the side surface of the endoscope, the inner wall of the large intestine C may be caught in the gap.

As shown in FIG. 15, in the overtube 1 according to this embodiment, the distal end tip 4 is provided at the distal end.

The distal end of the distal end tip 4 is formed with the first tube portion 4*a* of which a diameter is reduced from the proximal end toward the distal end. Therefore, since the distal end opening 4*f* is close to the outer circumferential surface of the endoscope 11, the gap with the outer circumferential surface of the endoscope 11 is reduced.

Furthermore, the second tube portion 4*b* having lower rigidity than the first tube portion 4*a* extends from the proximal end of the first tube portion 4*a*.

Therefore, when the distal end tip 4 passes through a bent portion of the endoscope 11 that is bent to follow the shape of the large intestine C, the second tube portion 4*b* is deformed before the first tube portion 4*a*. Thus, the shape of the first tube portion 4*a*, particularly the distal end opening 4*f* is maintained in a shape that is close to the outer circumferential surface of the endoscope 11. That is, a gap between the distal end opening 4*f* and the side surface of the endoscope 11 can be prevented from being excessively expanded outside the bend of the endoscope 11 by curbing the deformation of the distal end opening 4*f*. Therefore, when the overtube 1 is inserted into the large intestine C, it is possible to prevent the inner wall of the large intestine C from being caught in the gap between the overtube 1 and the outer circumferential surface of the endoscope 11.

In the example shown in FIG. 13, since the treatment site Ts is located at a position near the anus, the overtube 1 is located outside the body when the endoscope 11 is stopped.

When the treatment site Ts is located far from the anus, the operator may insert the overtube 1 into the large intestine C before the distal end portion 12 of the endoscope 11 reaches the treatment site Ts. In this case, the operator may alternately advance the endoscope 11 and the overtube 1 while checking the position of the distal end portion 12 using the image of the endoscope 11, and thus the distal end portion 12 may move closer to the treatment site Ts.

When the distal end of the overtube 1 reaches the vicinity of the distal end portion 12 of the endoscope 11 disposed near the treatment site Ts, the operator operates the air supply device 10 to supply air to the fixing balloon 3 via the air flow tube 9 and the second lumen 2*e* and to expand the fixing balloon 3.

As shown in FIG. 16, when the fixing balloon 3 is sufficiently expanded, the fixing balloon 3 comes into contact with the inner wall of the large intestine C. Thus, the overtube 1 is fixed to the extent that it does not easily move relative to the large intestine C.

The operator performs ESD on the treatment site Ts using the treatment tool protruded from the endoscope 11. When the endoscope cap 13 is mounted, the gripping device 14 inserted through the channel tube 15 can lift and hold the mucous membrane at the treatment site Ts.

Then, the submucosal layer below the tumor at the treatment site Ts can be separated using a high-frequency knife or the like protruded from the treatment tool channel 12*b* of the endoscope 11.

During such ESD treatment, liquid, gas, or the like in the large intestine C may enter the overtube 1 from the distal end of the overtube 1.

In this embodiment, as shown in FIG. 10, since the airtight balloon 22 closes a gap between the outer circumferential surfaces of the endoscope 11 and the channel tube 15 and the cylinder frame portion 21 inside the cylinder frame portion 21, airtightness and liquid tightness are maintained. Thus, liquid, gas, or the like in the large intestine C are prevented from leaking from the cylinder frame portion 21.

When all necessary measures for ESD are completed, the operator operates the air supply device 10 to suction the air out of the fixing balloon 3 and to reduce the diameter of the fixing balloon 3. Then, the operator pulls out the endoscope 11 and channel tube 15 from the anus.

In this way, ESD using the overtube 1 is completed.

As described above, since the overtube 1 according to this embodiment includes the airtight balloon 22 in which the middle portion 22*b* protrudes to the inner surface of the cylinder frame portion 21, airtightness and liquid tightness between the overtube 1 and the inserted endoscope and the like can be ensured with a small amount of gas supply.

The insertion portion of the endoscope 11 for the large intestine described above is longer than that of the endoscope for the upper gastrointestinal tract.

Furthermore, since the large intestine has a complicated meandering structure, when the treatment site is in the ascending colon, there may be multiple sites having a large curvature before reaching the treatment site. In this case, like the endoscope 11, the overtube 1 is also greatly curved, and frictional resistance when the endoscope 11 is moved forward and backward relative to the overtube 1 is much greater than that in the endoscope for the upper gastrointestinal tract.

In such a situation, when the friction between the endoscope 11 and the airtight balloon 22 for ensuring airtightness and liquid tightness increases, it becomes difficult to move the endoscope 11 forward and backward smoothly.

The overtube 1 according to this embodiment can ensure airtightness and liquid tightness with the endoscope 11 inserted with a small amount of gas supply, and can also ensure airtightness and liquid tightness by appropriately setting dimensions without gas supply.

ESD in the large intestine C is more difficult than ESD in the stomach. The above-described method for stabilizing a position of the endoscope 11 in the large intestine C using the overtube 1 and combining the endoscope cap 13 is effective in simplifying ESD in the large intestine C.

On the other hand, when the shape and dimension of the airtight balloon 22 are set according to the outer diameter when the endoscope cap 13 is mounted, the gap between the airtight balloon 22 and the insertion portion of the endoscope 11 after the distal end portion 12 passes through the base increases. As a result, the amount of gas required to close the gap increases, the internal pressure of the airtight balloon 22 also increases, and the friction between the endoscope 11 and the airtight balloon 22 increases.

The airtight balloon 22 in this embodiment can bring the middle portion 22*b* into close contact with the inner surface of the cylinder frame portion 21 by creating a negative pressure in the space Sp. Therefore, regardless of an initial shape of the middle portion 22*b*, the distal end portion 12 with the endoscope cap 13 mounted can easily pass through. Furthermore, even when the channel tube 15 is disposed on the outer circumferential portion and a non-circular cross-sectional shape is formed, airtightness and liquid tightness can be ensured with a small amount of gas supply by releasing the negative pressure after the endoscope cap 13 passes through.

As described above, according to the overtube 1 according to the first embodiment, it is possible to provide an overtube for an endoscope that reduces a load on a patient and allows a smooth operation of the endoscope.

The first embodiment described above may be implemented with various modifications.

In the first embodiment, the example in which the air supply device 10 supplies air has been described. However, the air supply device 10 may supply a gas different from air to the fixing balloon 3 instead of air by providing a gas supply source different from air.

In the first embodiment, the example in which the airtight valve unit 6 is in the open state when the endoscope 11 with the endoscope cap 13 mounted is inserted has been described. However, the inner diameter of the middle portion 22*b* may be appropriately adjusted according to the outer diameter and exterior of the endoscope 1 through which the airtight valve unit 6 is inserted. For example, when the endoscope 11 can be inserted even if the airtight valve unit 6 is not in the open state and the middle portion 22*b* is expanded inward, the endoscope 11 may be inserted while the airtight valve unit 6 is not in the open state.

In the first embodiment, the example in which the operation tube main body 25 is connected to the connection port 21*b* has been described, but the operation tube main body 25 may be detachably connected to the connection port 21*b*.

The shape of the middle portion 22*b* of the airtight balloon 22 in the first embodiment is an example, and is not limited to the shape described above. For example, the middle portion 22*b* may have two or more protruding portions that protrude radially inward in the axial direction.

For example, the inner circumferential surface of the airtight balloon 22 may be coated with a hydrophilic coating.

In the first embodiment, the example in which the airtight valve unit 6 adjusts the internal pressure of the space Sp with the pressure adjustment balloon 26 has been described. However, the mechanism for adjusting the internal pressure of the space Sp is not limited to the pressure adjustment balloon 26. For example, instead of the pressure adjustment balloon 26, a relief valve that releases air to the outside when the pressure exceeds a predetermined value may be provided.

In the first embodiment, the example in which the rigidity of the first tube portion 4*a* and the rigidity of the second tube portion 4*b* are made different by making the thicknesses of the first tube portion 4*a* and the second tube portion 4*b* in the distal end tip 4 different from each other has been described. The configuration is not limited thereto as long as the rigidity is different.

For example, the rigidity of the thick portion 2*b* may be lowered than that of the first tube portion 4*a* by adopting a bellows structure as the second tube portion 4*b*.

For example, even when the thicknesses of the first tube portion 4*a* and the second tube portion 4*b* are the same, the first tube portion 4*a* and the second tube portion 4*b* may have different rigidities by making rigidity of each material of the first tube portion 4*a* and the second tube portion 4*b* different from each other.

The distal end tip 4 in the first embodiment may satisfy the following Equation (1c) in addition to Equations (1a) and (1b).

[Math 2]

$$K3 > K1 \tag{1c}$$

In this case, since the rigidity K3 of the first tube portion 4*a* is greater than the rigidity K1 of the main tube 2, buckling of the main tube 2 can be curbed when the overtube 1 is pushed into the large intestine C using the endoscope 11 as a guide.

In the first embodiment, the example in which the distal end tip 4 is fixed to the distal end of the main tube 2 has been described. However, the distal end tip 4 may be made of the same material as the main tube 2.

In the first embodiment, the example in which the pressure adjustment balloon 26 is provided at the second end portion 25*b* of the operation tube main body 25 has been described. However, the pressure adjustment balloon 26 may be provided between the first end portion 25*a* and the second end portion of the channel tube 15.

In the first embodiment, the example in which the air flow tube 9 of the air supply device 10 is connected to the first luer connector 5*c* has been described. However, an appropriate connection tube may be interposed between the first luer connector 5*c* and the air flow tube 9.

As described above, the first lumen 2*c* is an example of the main lumen through which the endoscope is inserted. The second lumen 2*e* is an example of the air supply lumen through which gas flows. The main tube 2 is an example of the tube main body. The cylinder frame portion 21 is an example of the tubular portion that communicates with the main lumen at the proximal end portion of the tube main body.

The fixing balloon 3 is an example of the fixing balloon that is provided on the outer circumferential surface of the distal end of the tube main body and is expandable outward of the outer circumferential surface and contractible toward the outer circumferential surface.

The air supply device 10 is an example of the air supply device that delivers gas to the air supply lumen.

The airtight valve unit 6 is an example of the airtight valve unit that has a tubular portion that communicates with the main lumen at the proximal end of the tube main body, and closes the gap between the endoscope inserted through the tubular portion into the main lumen and the inner circumferential surface of the tubular portion.

Second Embodiment

An overtube for an endoscope according to a second embodiment of the present invention will be described.

Figure 17:
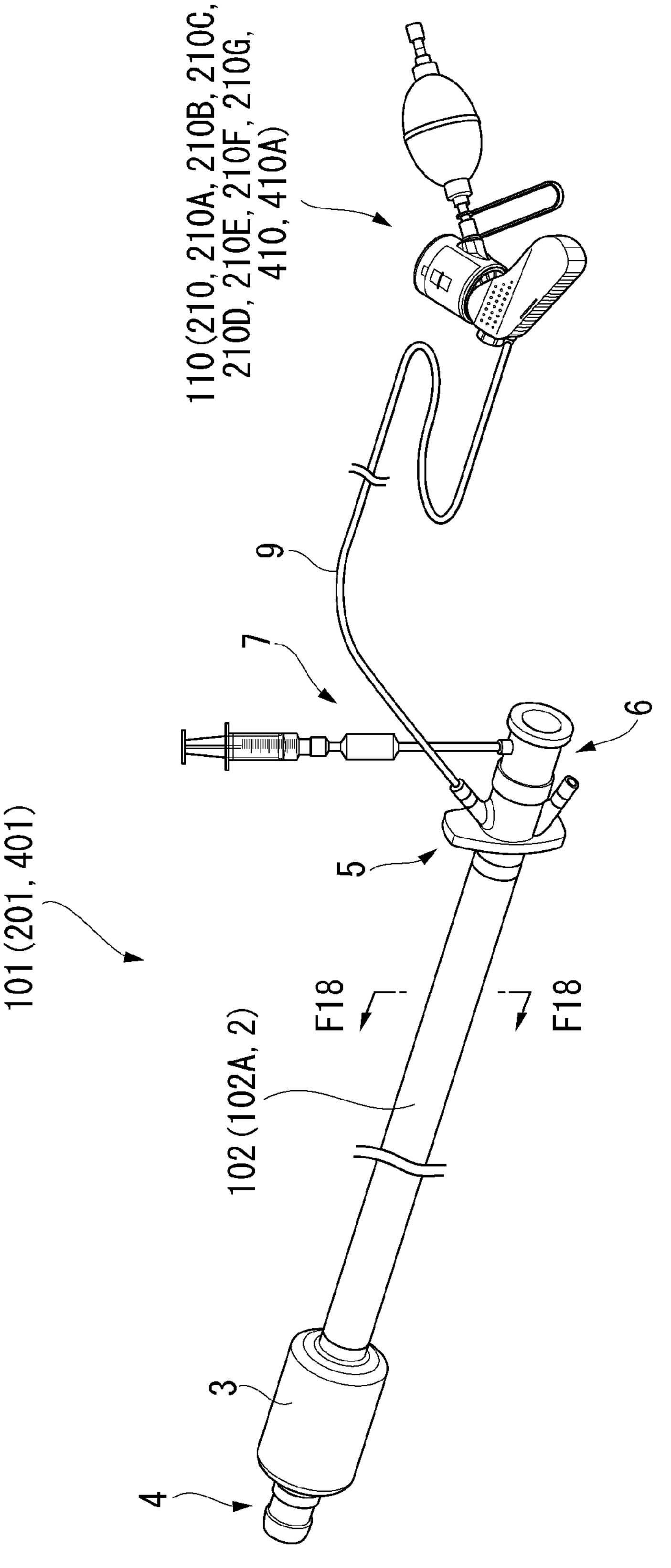
FIG. 17 is a schematic perspective view showing an example of an overtube for an endoscope according to a second embodiment of the present invention.

FIG. 17 is a schematic perspective view showing an example of the overtube for an endoscope according to the second embodiment of the present invention.

The overtube 101 shown in FIG. 17 is an example of the overtube for an endoscope according to this embodiment.

The overtube 101 includes a main tube 102 (a tube main body) and an air supply device 110 instead of the main tube 2 and the air supply device 10 of the overtube 1 according to the first embodiment. In the following, differences from the first embodiment will be mainly described.

Figure 18:
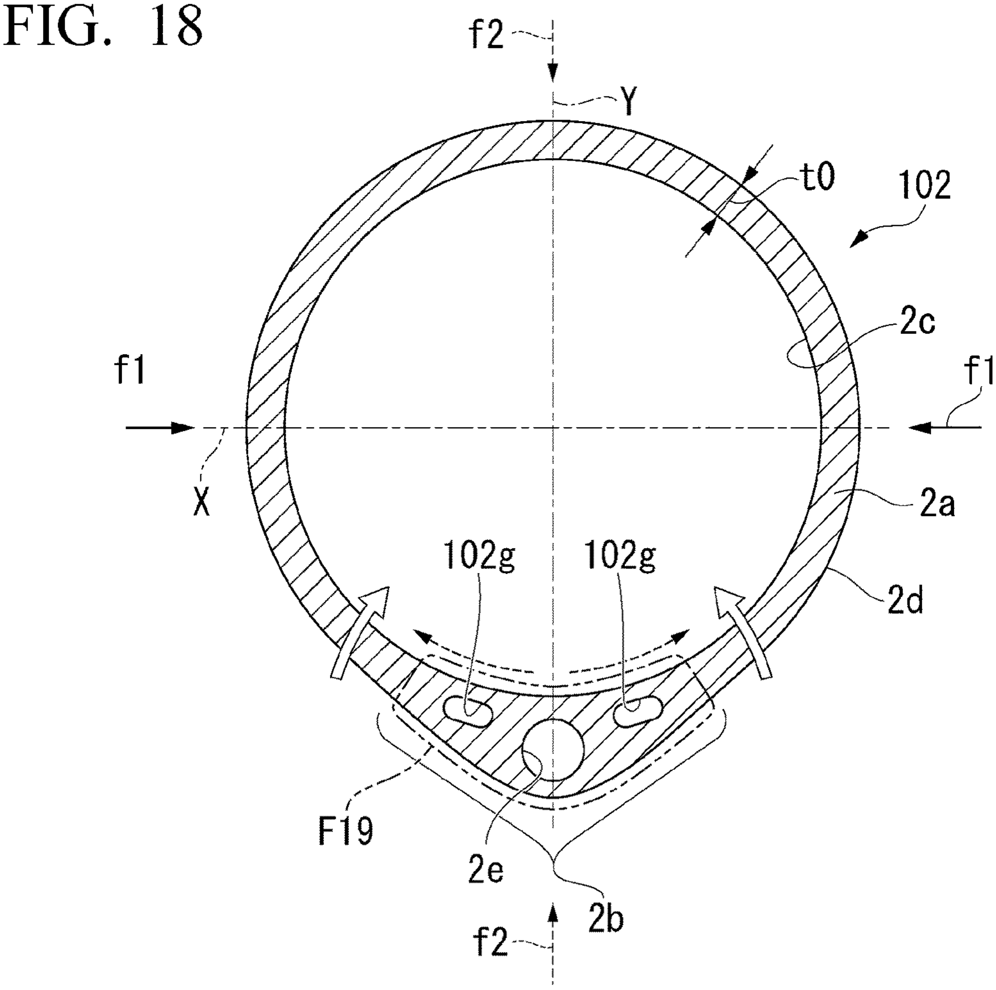
FIG. 18 is a cross-sectional view taken along line F19-F19 in FIG. 17.
Figure 19:
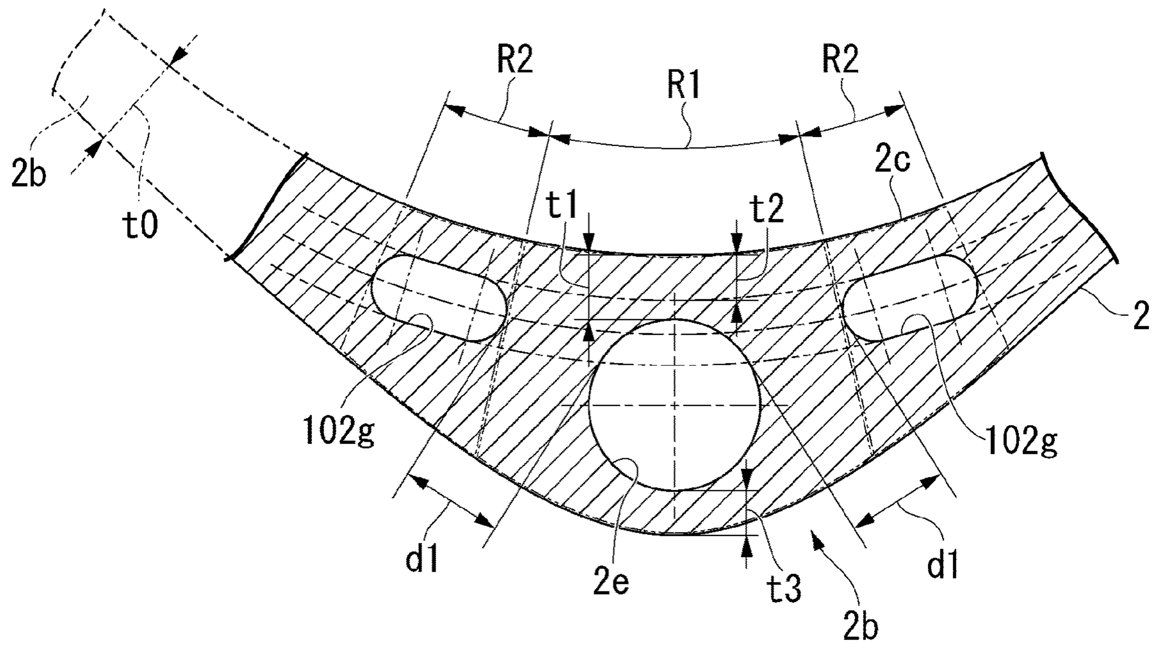
FIG. 19 is an enlarged view of an F19 portion in FIG. 18.
Figure 20:
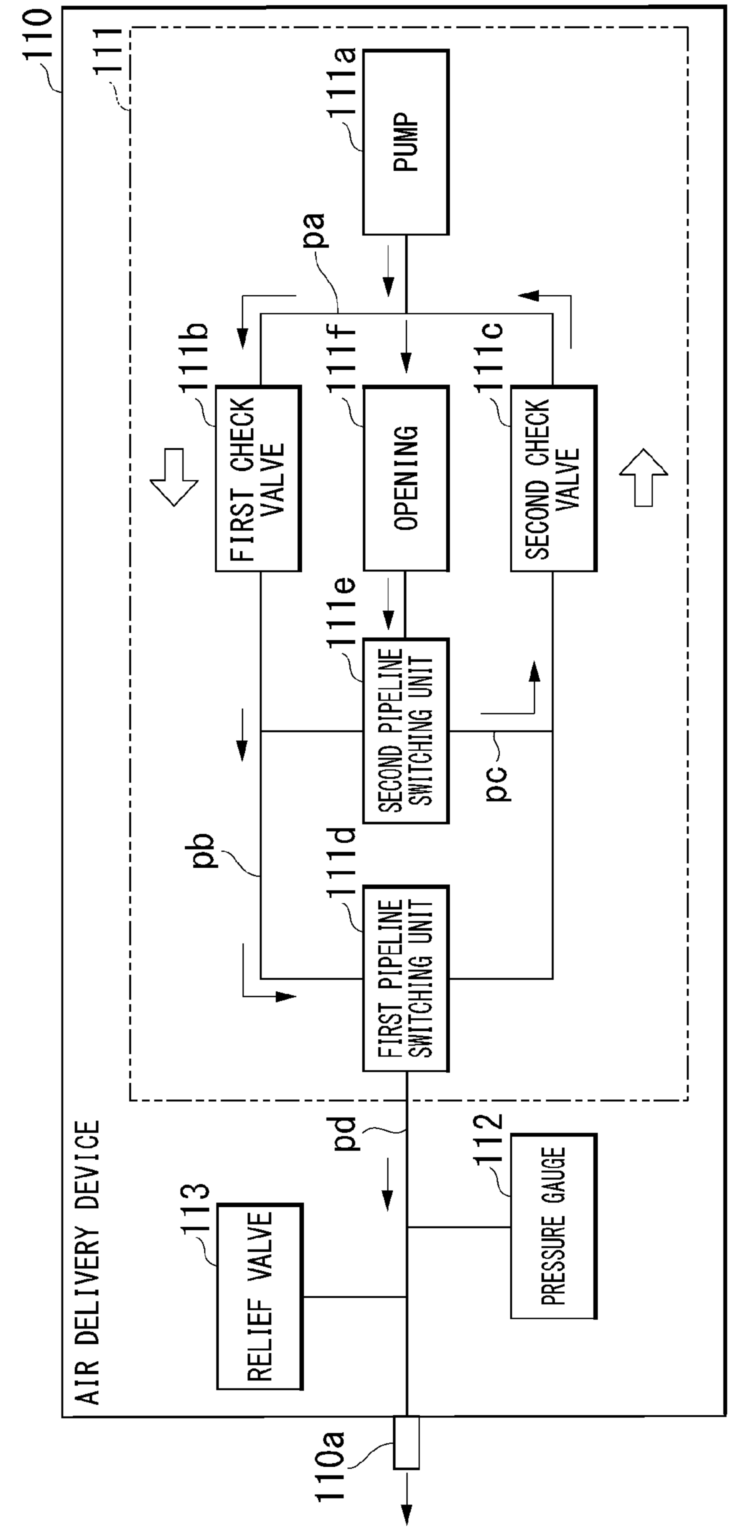
FIG. 20 is a block diagram showing an example of an air supply device in the overtube for an endoscope according to the second embodiment of the present invention.

FIG. 18 is a cross-sectional view taken along line F19-F19 in FIG. 17. FIG. 19 is an enlarged view of an F19 portion in FIG. 18.

As shown in FIG. 18, in the main tube 102 of this embodiment, a third lumen 102*g* (a dummy lumen) is further formed in the main tube 2.

In the following description of the main tube 102, in a cross section orthogonal to the longitudinal direction of the main tube 2, a direction along the circular inner circumferential surface of the first lumen 2*c* is referred to as a circumferential direction, and a direction orthogonal to the circumferential direction and along the diameter of the inner circumferential surface of the first lumen 2*c* is referred to as a radial direction. In the radial direction, a direction toward the center of the first lumen 2*c* may be referred to as an inward side in the radial direction, and a direction away from the center may be referred to as an outward side in the radial direction.

The third lumen 102*g* passes through the main tube 102 in the longitudinal direction. However, the third lumen 102*g* is a dummy hole formed for the purpose of adjusting the rigidity of the thick portion 2*b*. Since no fluid flows inside the third lumen 102*g*, a tube for causing a fluid to flow out is not connected to the third lumen 102*g*.

In this embodiment, an opening at the distal end of the third lumen 102*g* in the longitudinal direction is closed by a connecting portion with the distal end tip 4. An opening at the proximal end of the third lumen 102*g* in the longitudinal direction is closed by a connecting portion with the grip portion 5.

The third lumen 102*g* is formed in the thick portion 2*b* at a position close to the second lumen 2*e*. The third lumen 102*g* extends parallel to the second lumen 2*e*.

The number of third lumens 102*g* is not particularly limited. In the example shown in FIG. 18, they are formed at two locations facing each other in the circumferential direction with the second lumen 2*e* interposed therebetween.

In this case, since the third lumen 102*g* is formed near both sides of the second lumen 2*e* in the circumferential direction, even when an external force acts on any end portion of the thick portion 2*b* in the circumferential direction, the external force is less likely to be transmitted to the second lumen 2*e*, and thus a cross-sectional shape of the second lumen 2*e* can be easily maintained.

A cross-sectional shape of each of the third lumens 102*g* in a direction orthogonal to the longitudinal direction of the main tube 102 (hereinafter, simply referred to as a cross-sectional shape) is not particularly limited as long as it is a shape that can reduce the rigidity of the thick portion 2*b* at a portion away from the second lumen 2*e*.

The cross-sectional shapes of the third lumens 102*g* may be different from each other.

In the example shown in FIG. 18, each of the third lumens 102*g* is formed in a position and shape that are line-symmetrical with respect to the axis Y passing through the center of the second lumen 2*e*.

For example, a cross-sectional shape of the third lumen 102*g* may be a circle, an ellipse, an oval, a polygon, or the like. When the third lumen 102*g* is such a hole, since a substantial thickness of the thick portion 2*b* in which the third lumen 102*g* is formed is reduced, the third lumen 102*g* is easily collapsed when an external force such as a compressive force is applied, and the rigidity thereof is lowered.

For example, in the example shown in FIG. 18, the cross-sectional shape of each of the third lumens 102*g* is an oval that is elongated in the circumferential direction.

An example of a relative positional relationship between the second lumen 2*e* and each of the third lumens 102*g* will be described with reference to FIG. 19.

Each of the third lumens 102*g* is formed at a position closer to the first lumen 2*c* in the radial direction. A distance between the inner circumferential surface of the third lumen 102*g* closer to the first lumen 2*c* and the inner circumferential surface of the first lumen 2*c* is t2. Assuming that the thickness of the tube wall 2*a* is t0, t2 may be half or less of t0.

Although the distance between the radially outward inner circumferential surface of the third lumen 102*g* and the outer circumferential surface of the thick portion 2*b* is not particularly limited, in the example shown in FIG. 19, it is longer than t2. Therefore, the third lumen 102*g* is formed closer to the first lumen 2*c* than the center of the thick portion 2*b* in the radial direction.

On the other hand, a distance between the inner circumferential surface of the second lumen 2*e* closer to the first lumen 2*c* and the inner circumferential surface of the first lumen 2*c* is t1 which is longer than t2.

A distance between the radially outward inner circumferential surface of the second lumen 2*e* and the outer circumferential surface of the thick portion 2*b* is t3 which is less than or equal to t1. Therefore, the second lumen 2*e* is formed in the center of the thick portion 2*b* in the radial direction or slightly outward in the radial direction.

A distance between the inner circumferential surface of the third lumen 102*g* and the inner circumferential surface of the second lumen 2*e* is d1. d1 is more preferably longer than t2, and is t1 or more in the example shown in FIG. 19.

For example, when the material of the main tube 102 is silicone rubber with a rubber hardness (Shore A) of A60 to A80, and the inner diameter of the first lumen 2*c* is 13.8 mm, and t0 is 1.2 mm, and the maximum thickness of the thick portion 2*b* is 3.1 mm, and when the diameter of the second lumen 2*e* is 1.9 mm, and t1 is 0.7 mm, and t3 is 0.3 mm, the following dimension can be exemplified as a suitable dimension for the third lumen 102*g*.

t2 is 0.5 mm, a length of the third lumen 102*g* in the circumferential direction is 1.54 mm or more and 2 mm or less, a width of the third lumen 102*g* in the radial direction is 0.7 mm, and d1 is 1.3 mm.

According to such a configuration, a first region R1 and a second region R2 are formed side by side in the circumferential direction in the thick portion 2*b*.

The first region R1 is a region that includes the second lumen 2*e* and is sandwiched between the third lumens 102*g* in the circumferential direction.

The second region R2 is a region that is formed in a length range of the third lumen 102*g* in the circumferential direction and of which rigidity is lower than that of the first region R1. The second region R2 has lower rigidity than the tube wall 2*a*.

Next, the air supply device 110 will be described.

Figure 21:
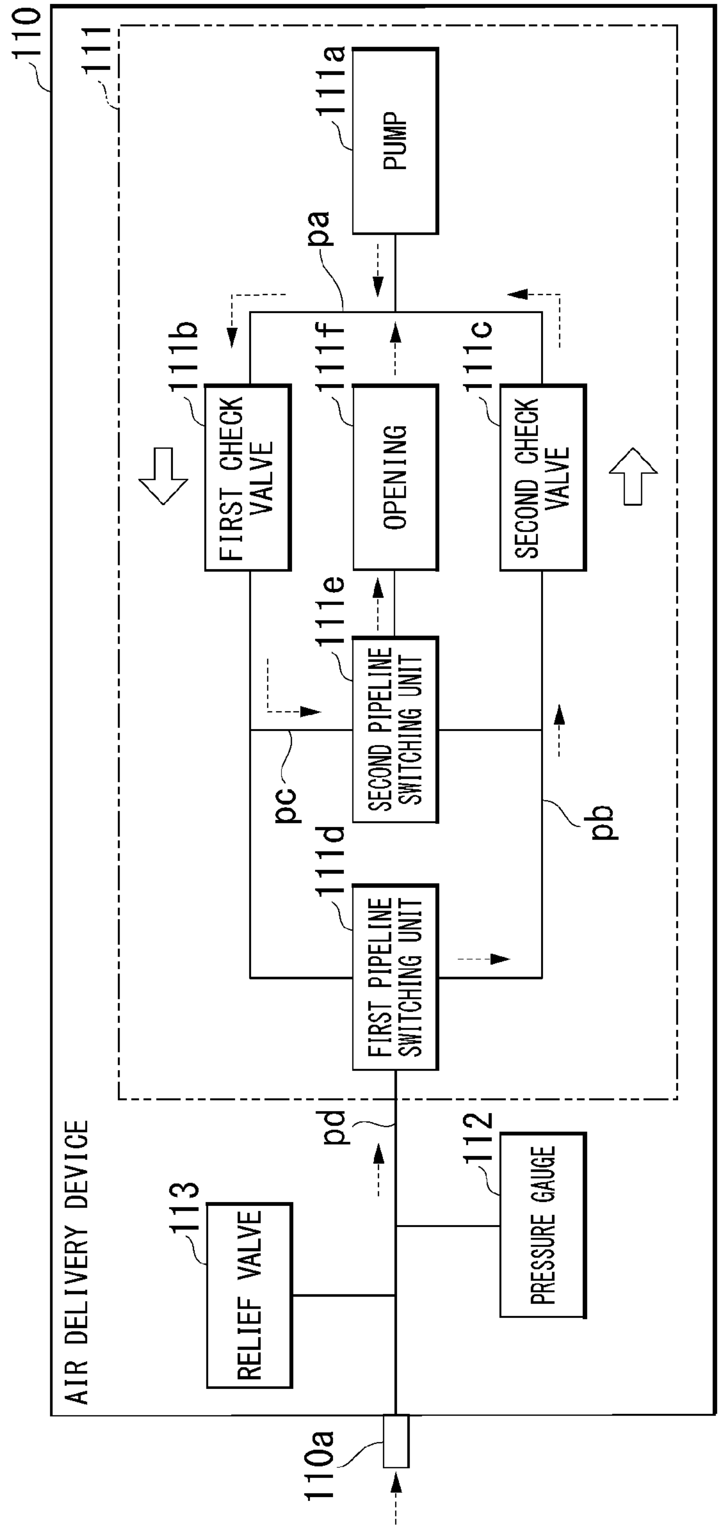
FIG. 21 is a block diagram showing a flow during air suction of the air supply device in the overtube for an endoscope according to the second embodiment of the present invention.
Figure 24:
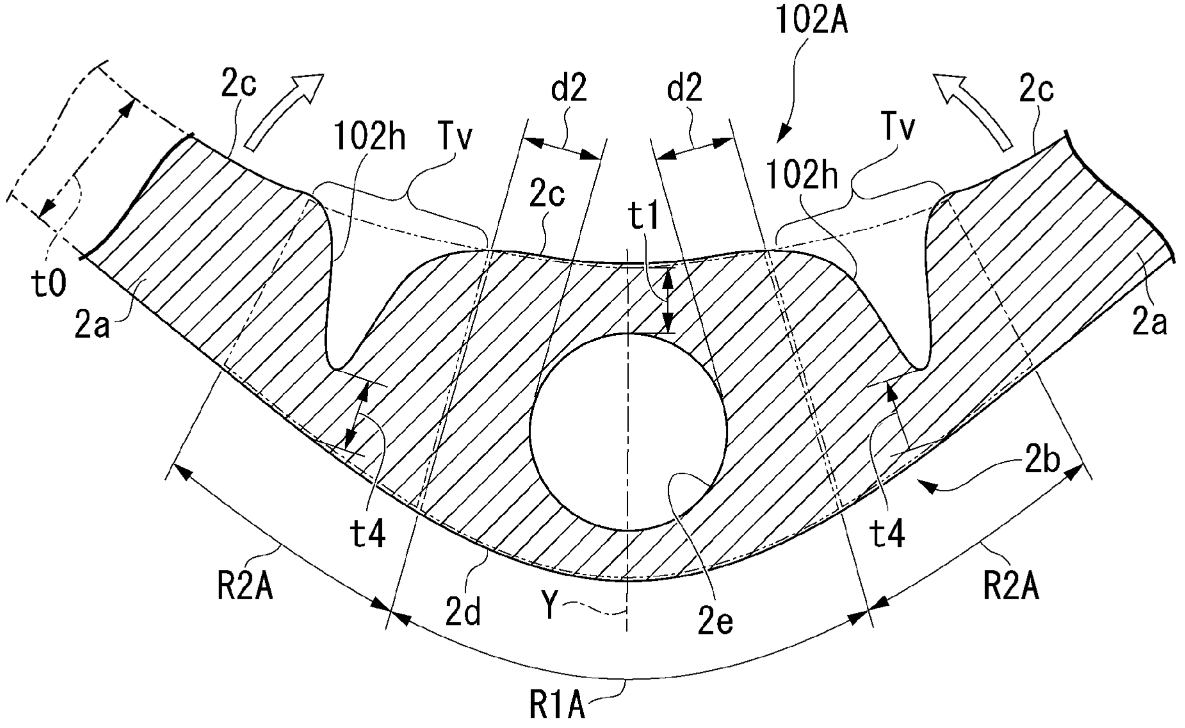
FIG. 24 is a schematic cross-sectional view showing a main portion of a main tube that can be used in the overtube for an endoscope according to the second embodiment of the present invention.

FIG. 24 is a block diagram showing an example of the air supply device in the overtube for an endoscope according to the second embodiment of the present invention. FIG. 21 is a block diagram showing a flow during air suction in the air supply device in the overtube for an endoscope according to the second embodiment of the present invention.

As shown in FIG. 24, the air supply device 110 has an air supply mechanism 111, a pressure gauge 112 and a relief valve 113.

The air supply device 110 includes a connection tube 110*a* to which the air flow tube 9 is connected. The connection tube 110*a* allows an air flow path in the air flow tube 9 and an air flow path in the air supply device 110 to communicate with each other.

The air supply mechanism 111 includes a pump 111*a*, a first check valve 111*b*, a second check valve 111*c*, a first conduit switching part 111*d*, a second conduit switching part 111*e*, and an opening 111*f*.

The pump 111*a* forms a flow of air in a conduit within the air supply mechanism 111. A type of the pump 111*a* is not particularly limited. For example, the pump 111*a* may be an electric pump or a manual pump. Examples of the manual pump include a rubber bulb pump, a diaphragm pump, a bellows tube pump, a syringe pump, and the like.

The first check valve 111*b* and the second check valve 111*c* are provided at both end portions of an air supply path pa through which air is supplied by the pump 111*a*, and restrict the flow of air in one direction at both end portions of the air supply path pa. Thus, a flow from the second check valve 111*c* to the first check valve 111*b* is formed in the air supply path pa.

The first check valve 111*b* and the second check valve 111*c* are connected to each other via a conduit pb in which the first conduit switching part 111*d* is disposed and a conduit pc in which the second conduit switching part 111*e* is disposed.

The first check valve 111*b* allows the air in the air supply path pa to pass toward the conduits pb and pc, and blocks the flow of air from the conduits pb and pc to the air supply path pa.

The second check valve 111*c* allows the air flowing through the conduits pb and pc to pass toward the air supply path pa, and blocks the flow of air from the air supply path pa toward the conduits pb and pc.

A conduit pd that communicates with the connection tube 110*a* is connected to the first conduit switching part 111*d*. The first conduit switching part 111*d* selectively switches between a conduit in which the conduit pb communicates with the conduit pd but does not communicate with the second check valve 111*c*, and a conduit in which the conduit pb does not communicate with the conduit pd but communicates with the second check valve 111*c*.

For example, a switching device such as a flow path switching valve may be used as the first conduit switching part 111*d*. When the conduits connected to each other can be manually switched, it is not necessary to use a switching device as the first conduit switching part 111*d*.

The second conduit switching part 111*e* communicates with the opening 111*f* that opens air to the outside of the air supply mechanism 111. The second conduit switching part 111*e* selectively switches between a conduit in which the conduit pc communicates with the second check valve 111*c* but does not communicate with the first check valve 111*b* and a conduit in which the conduit pc does not communicate with the second check valve 111*c* but communicates with the first check valve 111*b*.

For example, a switching device such as a flow path switching valve may be used as the second conduit switching part 111*e*. When the conduits connected to each other can be manually switched, it is not necessary to use a switching device as the second conduit switching part 111*e*.

As shown in FIG. 24, in the case of a state in which the conduit pd communicates with the first check valve 111*b* due to the first conduit switching part 111*d*, and the conduit pc communicates with the second check valve 111*e* due to the second conduit switching part 111*e*, an air flow path through which air is suctioned from the opening 111*f* by the air supply from the pump 111*a*, and the air is supplied from the conduit pd through the connection tube 110*a* is formed (refer to a solid line arrow).

As shown in FIG. 21, in the case of a state in which the conduit pd communicates with the second check valve 111*c* due to the first conduit switching part 111*d*, and the conduit pc communicates with the first check valve 111*b* due to the second conduit switching part 111*e*, an air flow path through which air is suctioned from the conduit pd via the connection tube 110*a* by air supply of the pump 111*a*, and the air is supplied from the opening 111*f* is formed (refer to a broken line arrow).

The pressure gauge 112 and the relief valve 113 are provided in this order in the conduit pd that is directed from the first conduit switching part 111*d* to the connection tube 110*a*.

The pressure gauge 112 measures a pressure of air in the conduit pd and displays a magnitude of the pressure. The pressure gauge 112 may be able to display the magnitude of pressure numerically, but the display method is not limited to numerical display. For example, the pressure display on the pressure gauge 112 may be able to visually display an absolute value of the pressure or an amount of relative deviation from a reference value.

The relief valve 113 discharges the air flowing through the conduit pd to the outside when the pressure of air in the conduit pd exceeds a predetermined allowable pressure value. Thus, the pressure of air in the conduit pd is kept below the allowable pressure value.

The allowable pressure value is set to a value in which the fixing balloon 3 communicating with the conduit pd via the air flow tube 9 and the second lumen 2*e* does not excessively expand. An allowable size of the fixing balloon 3 is predetermined according to the lumen into which the overtube 101 is inserted.

According to the air supply device 110, since the first conduit switching part 111*d* and the second conduit switching part 111*e* are provided, it is possible to selectively switch between air supply to the air flow tube 9 and air suction from the air flow tube 9 using the pump 111*a* that supplies air in one direction. In the case of air supply, the opening 111*f* functions as an air suctioning port for suctioning air from the outside. In the case of suctioning air, the opening 111*f* functions as a discharge port for discharging the suctioned air to the outside.

The air supply device 110 has the pressure gauge 112. Thus, the operator can expand and contract the fixing balloon 3 while checking whether the pressure of the air supplied to the fixing balloon 3 is appropriate.

The air supply device 110 has a relief valve 113. Thus, even when the operator performs an air supply operation that exceeds the allowable pressure value, an increase in the pressure of the fixing balloon 3 can be curbed to the allowable value or less.

Since the air supply device 110 is provided in the main tube 102, the operator can perform the treatment smoothly.

Next, the operation of the overtube 101 will be described focusing on differences from the first embodiment.

According to the overtube 101 according to this embodiment, the air inside the fixing balloon 3 is supplied and suctioned by the air supply device 110 instead of the air supply device 10. Therefore, like the overtube 1 according to the first embodiment, the overtube 101 can be used for various treatments and surgeries using the endoscope 11 by being inserted into the patient's body and fixed therein.

In particular, in this embodiment, a main tube 102 is used instead of the main tube 2. Hereinafter, the action of this embodiment will be described focusing on the action of the main tube 102.

Like the overtube 1, the overtube 101 may be used by being inserted into the lumen having a bent portion in the patient's body.

For example, as in the main tube 2 shown in FIG. 5, when the thick portion 2*b* is provided and the second lumen 2*e* is formed in the thick portion 2*b*, the overtube 1 passing through the bent portion is bent according to the bent shape of the lumen, and thus a bending load acts on the main tube 2 passing through the bent portion.

When the main tube 2 is bent at a large bending angle, it may not be able to maintain a cross-sectional shape shown in FIG. 5. For example, the tube wall 2*a* may be deformed by being collapsed in the radial direction. In this case, since the endoscope 11 is inserted into the first lumen 2*c*, a cross-sectional area approximately equal to the outer diameter of the endoscope 11 is secured.

However, when the second lumen 2*e* is collapsed, the air supply to the fixing balloon 3 is interrupted, which may impede the expansion and contraction operation of the fixing balloon 3.

The inventor conducted extensive research on how the main tube 2 is collapsed, found that when the main tube 2 is subjected to bending, the main tube 2 rotates so that the axis Y shown in FIG. 5 approaches a neutral plane of bend and is likely to be collapsed toward the axis Y, and thus arrived at the present invention.

As shown in FIG. 18, like the main tube 2, the bending rigidity of the main tube 102 is minimized with respect to the axis Y passing through the center of the thick portion 2*b* and the center of the first lumen 2*c*, and is maximized with respect to the axis X orthogonal to the axis Y at the center of the first lumen 2*c*.

In this case, when it is subjected to bending so that the axis X is the neutral plane of the bend, it should be collapsed in a direction of an arrow f2, but since the bending rigidity around axis X is greater than the bending rigidity around axis Y, work required for bending around axis X is also great. On the other hand, the main tube 102 is long and is inserted with less restriction from the lumen and the endoscope 11. Apart of the main tube 102 is readily rotatable around a central axis in the longitudinal direction. Thus, when it is subjected to bending around the axis X, the main tube 102 rotates in a more bendable direction, and the neutral plane of the bend gradually approaches the axis Y.

Figure 22:
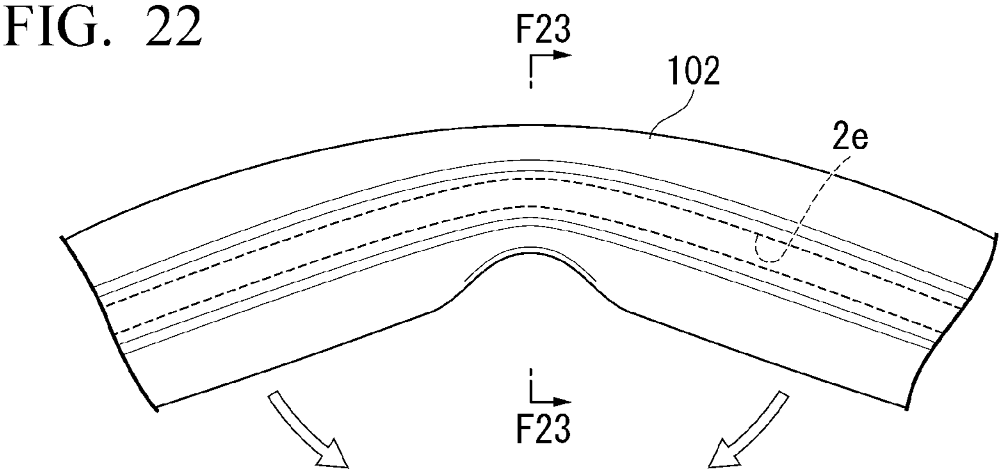
FIG. 22 is a schematic perspective view showing a bent state of the overtube for an endoscope according to the second embodiment of the present invention.
Figure 23:
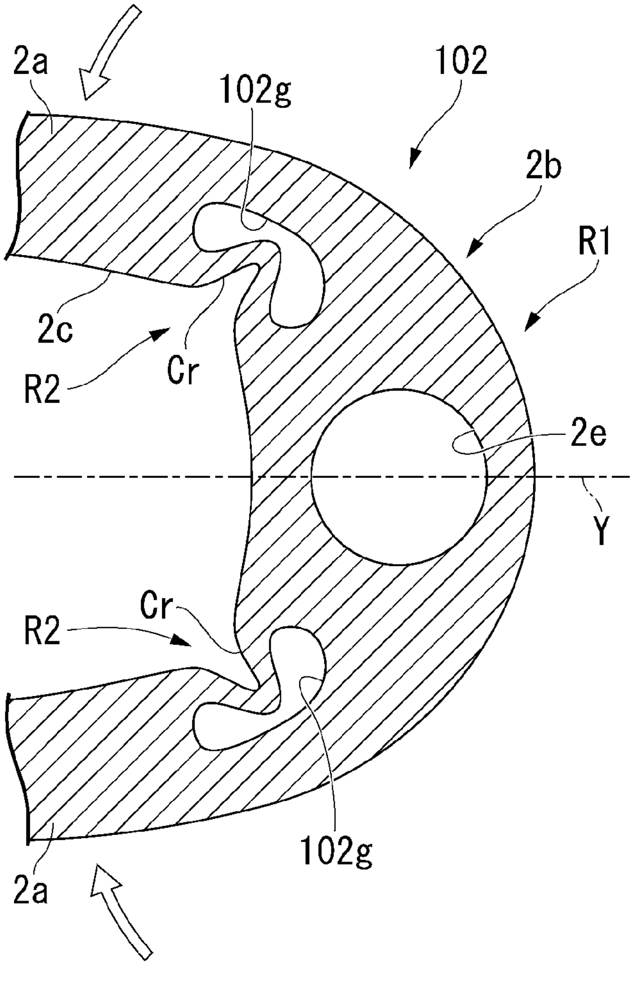
FIG. 23 is a cross-sectional view taken along line F23-F23 in FIG. 22.

FIG. 22 is a schematic perspective view showing a bent state of the overtube for an endoscope according to the second embodiment of the present invention. FIG. 23 is a cross-sectional view taken along line F23-F23 in FIG. 22.

FIG. 22 shows a state in which the main tube 102 rotates and the thick portion 2*b* moves along the neutral plane of the bend when it is subjected to bending indicated by a white arrow.

Within the bend, the tube wall 2*a* is kinked and a large dent is created.

In this way, when the main tube 102 rotates, the rigidity of the thick portion 2*b* has little effect on bending deformation, and thus the main tube 102 can be easily bent with a low load.

In order to curb a deformation of the cross-sectional shape of the second lumen 2*e* in the main tube 102 bent in this way, the second lumen 2*e* should be made difficult to be deformed when it is collapsed in the direction of the arrow f1.

FIG. 23 shows an example of a cross section in the vicinity of the second lumen 2*e* when the tube wall 2*a* is collapsed in this way.

In this embodiment, the third lumens 102*g* are formed on both sides of the second lumen 2*e* interposed therebetween in the circumferential direction. When the tube wall 2*a* is collapsed in a direction approaching the axis Y, stress is concentrated at a portion in which the rigidity is reduced due to the third lumen 102*g*. Thus, the third lumen 102*g* is collapsed in the radial direction, and the tube wall 2*a* is bent around the third lumen 102*g*. For example, a folding groove Cr extending outward in the radial direction is formed on the inner circumferential surface of the first lumen 2*c* facing the third lumen 102*g*.

In this way, the distortion due to the external force of bending is absorbed by the deformation of the thick portion 2*b* around the third lumen 102*g*. As a result, compared to a case in which the third lumen 102*g* is formed and the second region R2 with low rigidity is not present, since the stress around the second lumen 2*e* is relaxed, the deformation of the second lumen 2*e* is curbed.

Therefore, even when the main tube 102 is bent inside the lumen, there is no possibility that the second lumen 2*e* will be collapsed, making it difficult for the air to flow, or that the conduit will be closed.

Thus, even when the main tube 102 is inserted into the lumen with a bent portion, the operator can expand and contract the fixing balloon 3 without any problem.

For example, it is possible to prevent a fixing position of the overtube 101 from becoming unstable due to the inability to expand the fixing balloon 3 to an appropriate outer diameter. Thus, surgery using the endoscope 11 can be performed smoothly.

For example, it is possible to prevent the fixing balloon 3 from being unable to be sufficiently contracted in diameter during insertion and removal, thereby preventing a load from being applied to the patient during insertion and removal.

As described above, the overtube 101 according to the second embodiment is the same as the overtube 1 except that it includes the main tube 102 and the air supply device 110 instead of the main tube 2 and the air supply device 10 of the overtube 1 according to the first embodiment. Therefore, as in the first embodiment, it is possible to provide an overtube for an endoscope that reduces a load on the patient and allows a smooth operation of the endoscope.

In particular, according to this embodiment, since the main tube 102 is provided, even when the main tube 102 is inserted into the lumen having a bent portion, the operator can expand and contract the fixing balloon 3 without any problem.

The tube wall 2*a* is an example of a constant thickness portion having a constant thickness in the circumferential direction of the main tube 102.

The thick portion 2*b* is an example of a thick portion in which an air supply lumen is formed and a thickness defined by a distance between the outer circumferential surface and the inner circumferential surface in the radial direction is greater than a thickness of the constant thickness portion.

The main tube 102 is an example of a tube main body having the constant thickness portion and a thick portion.

The first region R1 is an example of a first region that is formed on the thick portion and includes the air supply lumen. The second region R2 is an example of a second region that is adjacent to the first region in the circumferential direction and has lower rigidity than both the first region and the constant thickness portion.

The third lumen 102*g* is an example of a dummy lumen which is a hole that is formed in the second region, extends in the axial direction along an extending direction of the air supply lumen, and cannot supply air to the fixing balloon or cannot suction air from the fixing balloon.

In the thick portion 2*b* of the main tube 102, a minimum thickness in the radial direction of a portion sandwiched between the dummy lumen and the main lumen is thinner than a minimum thickness in the radial direction of a portion sandwiched between the air supply lumen and the main lumen.

The air flow tube 9 is an example of an air supply tube that extends from the air supply device 110.

The second lumen 2*e* communicates with the air supply tube, and the third lumen 102*g* does not communicate with the air supply tube.

The second embodiment described above may be implemented with various modifications.

For example, the main tube used for the overtube 101 is not limited to the main tube 102. For example, in the main tube 102, the second region R2 is formed by providing the third lumen 102*g*, but the method for forming the second region R2 is not limited thereto.

FIG. 24 is a schematic cross-sectional view showing a main portion of a main tube that can be used for the overtube for an endoscope according to the second embodiment of the present invention.

The main tube 102A (the tube main body) shown in FIG. 24 can be used in place of the main tube 102 in the overtube 101.

The main tube 102A has a groove 102*h* formed in place of the third lumen 102*g* in the main tube 102.

In the following, differences from the second embodiment will be mainly described.

The groove 102*h* is a V-shaped groove that extends radially outward from the inner circumferential surface of the first lumen 2*c*. A groove width in the circumferential direction in the groove 102*h* decreases radially outward from the inner circumferential surface of the first lumen 2*c*. The groove 102*h* has a similar cross-sectional shape that extends in the longitudinal direction of the main tube 102A.

The groove 102*h* forms a thickness changing portion Tv in which the thickness of the thick portion 2*b* gradually decreases, reaches a minimum value, and then increases in the circumferential direction. The minimum thickness in the thickness changing portion Tv is a distance t4 from the groove bottom of the groove 102*h* to the outer circumferential surface 2*d*, t4 is shorter than t0.

Although a position of each of the grooves 102*h* may be different in distance from the second lumen 2*e*, in the example shown in FIG. 24, the position is line-symmetrical with respect to the axis Y.

A length in the circumferential direction between the position of the groove 102*h* in the first lumen 2*c* and the inner circumferential surface of the second lumen 2*e* is d2. More preferably, d2 is greater than or equal to t1.

According to such a configuration, the second lumen 2*e* is sandwiched between the grooves 102*h* on both sides in the circumferential direction. Thus, a first region R1A and a second region R2A are formed on the thick portion 2*b*.

The first region R1A is a region that includes the second lumen 2*e* and is sandwiched between two thickness changing portions in the circumferential direction.

The second region R2A is a region that is formed in a range of the maximum groove width of the groove 102*h* in the circumferential direction and has reduced rigidity compared to the first region R1A. The second region R2A also has lower rigidity than the tube wall 2*a*.

The action of the main tube 102A will be described.

Figure 25:
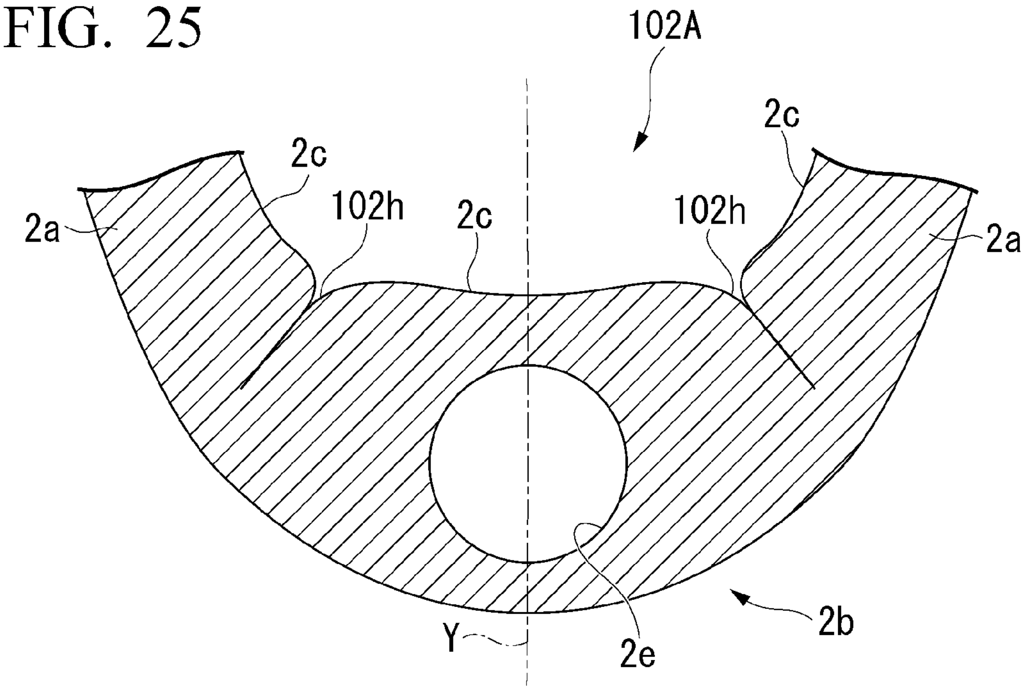
FIG. 25 is a schematic cross-sectional view showing a bent state of the main tube shown in FIG. 24.

FIG. 25 is a schematic cross-sectional view showing a state in which the main tube shown in FIG. 24 is bent.

As in the main tube 102, a case in which the main tube 102A is subjected to bending and is collapsed toward the axis Y will be described.

As shown in FIG. 25, when the tube wall 2*a* is collapsed toward the axis Y, the groove width of each of the grooves 102*h* decreases. In the example shown in FIG. 25, inner surfaces of the grooves 102*h* are in contact with each other.

Each of the tube walls 2*a* adjacent to the groove 102*h* bends around the groove bottom of the groove 102*h* with a light load until the groove 102*h* is closed. Therefore, the groove 102*h* has a function of a hinge for rotating the tube wall 2*a*.

The stress in the vicinity of each of the grooves 102*h* hardly increases until the groove inner surfaces of the grooves 102*h* come into contact with each other.

Therefore, deformation in the vicinity of the second lumen 2*e* can be curbed by setting a groove angle of the groove 102*h* to an appropriate size according to an amount of collapse of the tube wall 2*a*.

As described above, since the main tube 102A has the groove 102*h* instead of the third lumen 102*g*, the second region R2A with low rigidity is formed, like the second region R2. Thus, compared to a case in which the second region R2A with low rigidity due to the formation of the groove 102*h* is not present, the stress around the second lumen 2*e* is relaxed, and thus deformation of the second lumen 2*e* is curbed.

As a result, the main tube 102A has the same action as the main tube 102.

In the description of the second embodiment, the example in which the third lumen 102*g* is provided at the thick portion 2*b* has been described. However, as long as the rigidity in the second region R2 does not decrease too much, the third lumen 102*g* may be provided in a region over both the tube wall 2*a* and the thick portion 2*b*, or in a region of the tube wall 2*a*. The same applies to the groove 102*h* of the modified example.

In the description of the second embodiment, the example in which the second region R2 is formed on both sides of the first region R1 in the circumferential direction has been described. However, even when there is only one second region R2, if the deformation of the second lumen 2*e* is curbed within a necessary range, there may be only one second region R2.

The second region R2A in the modified example is also similar to the second region R2.

The main tube 102A is an example of a tube main body including the constant thickness portion having a constant thickness in the circumferential direction surrounding the main lumen and the thick portion in which an air supply lumen is formed and of which a thickness defined by the distance between the outer circumferential surface and the inner circumferential surface in the radial direction is larger than the thickness of the constant thickness portion.

The first region R1A is an example of a first region formed on the thick portion and including the air supply lumen.

The second region R2A is an example of a second region that is adjacent to the first region in the circumferential direction and has lower rigidity than both the first region and the constant thickness portion.

The thickness changing portion Tv formed in the second region R2A is an example of a thickness changing portion that is recessed radially outward from the inner circumferential surface of the main lumen and of which a thickness changes.

Third Embodiment

An overtube for an endoscope according to a third embodiment of the present invention will be described.

An overtube 201 shown in FIG. 17 is an example of an overtube for an endoscope according to this embodiment.

The overtube 201 includes an air supply device 210 instead of the air supply device 10 of the overtube 1 according to the first embodiment.

In the following, differences from the first embodiment will be mainly described.

Figure 26:
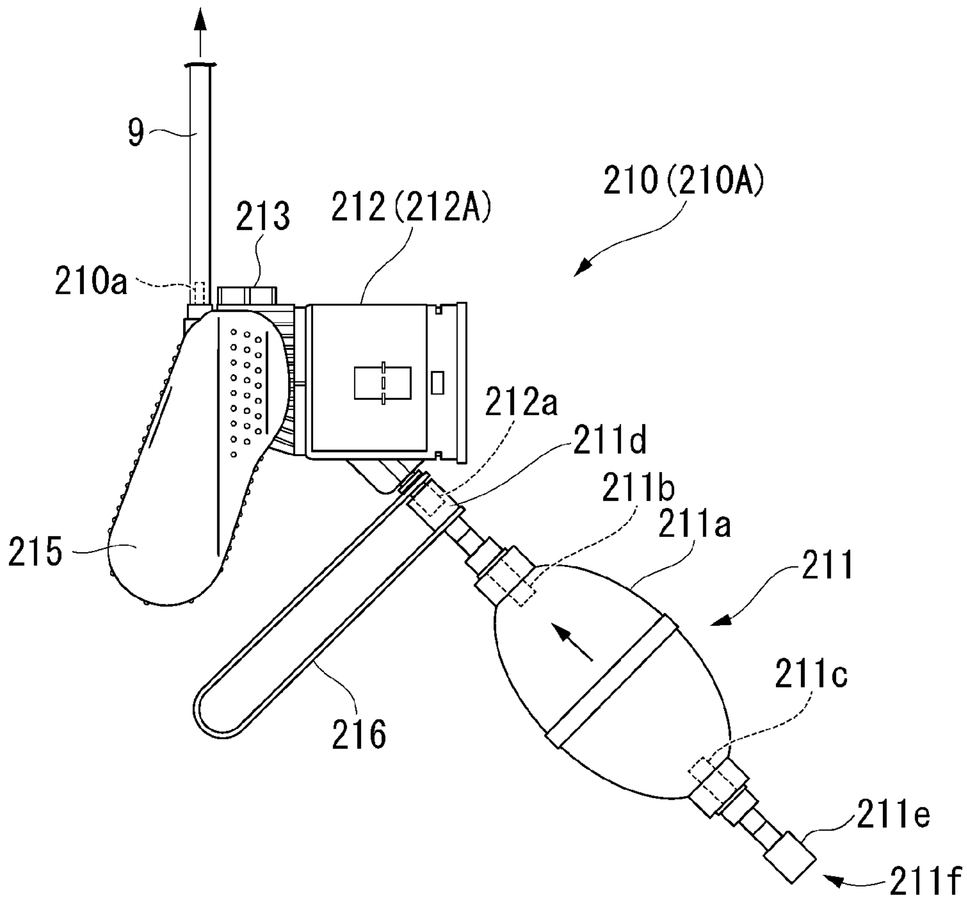
FIG. 26 is a schematic front view showing an air supply device in an overtube for an endoscope according to a third embodiment of the present invention.
Figure 27:
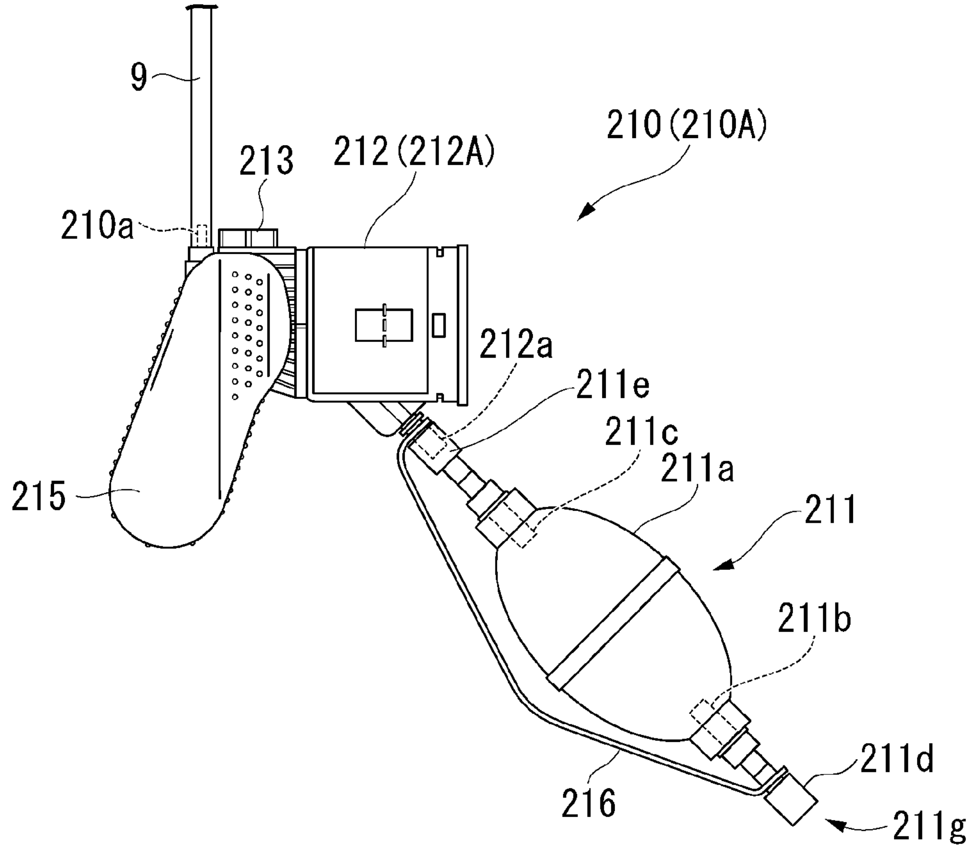
FIG. 27 is a schematic front view showing arrangement of the air supply device in the overtube for an endoscope according to the third embodiment of the present invention during air suction.

FIG. 26 is a schematic front view showing the air supply device in the overtube for an endoscope according to the third embodiment of the present invention. FIG. 27 is a schematic front view showing the arrangement of the air supply device during the air suction.

As shown in FIG. 26, the air supply device 210 includes a manual air supply mechanism 211, a main body portion 212, and a connecting band 216.

An appropriate configuration for manually supplying and suctioning air is used as the manual air supply mechanism 211. For example, the manual air supply mechanism 211 includes a pump 211*a* (a manual pump), a first check valve 211*b*, a second check valve 211*c*, a first connection portion 211*d* (a pump-side connector, a first connector) and a second connection portion 211*e* (a pump-side connector, a second connector).

The pump 211*a* is not particularly limited as long as it is a manual pump that sends gas. For example, the pump 211*a* may be a rubber bulb pump, a diaphragm pump, a bellows tube pump, a syringe pump, or the like. In the example shown in FIG. 26, the pump 211*a* is a rubber bulb pump. In this case, the pump 211*a* is formed of an egg-shaped or rugby ball-shaped rubber ball. Tubular portions through which air flows are formed at both end portions of the pump 211*a* in the longitudinal direction.

The first check valve 211*b* and the second check valve 211*c* are respectively disposed in the tubular portions.

In the tubular portion in which the first check valve 211*b* is disposed, a first opening 211*g* (refer to FIG. 27) that communicates with the inside of the pump 211*a* when the first check valve 211*b* is opened is formed outside the first check valve 211*b*.

In the tubular portion in which the second check valve 211*c* is disposed, a second opening 211*f* (refer to FIG. 26) that communicates with the inside of the pump 211*a* when the second check valve 211*c* is opened is formed outside the second check valve 211*c*.

The first check valve 211*b* causes the air inside the pump 211*a* to flow to the outside through the opening of the tubular portion in which the first check valve 211*b* is disposed, and prevents external air from entering the inside through the opening of the tubular portion.

The second check valve 211*c* causes the air outside the pump 211*a* to flow to the inside through the opening of the tubular portion in which the second check valve 211*c* is disposed, and prevents the internal air from flowing out of the opening of the tubular portion.

The first connection portion 211*d* is provided outside the first opening 211*g* (refer to FIG. 27) in the tubular portion in which the first check valve 211*b* is disposed. The first connection portion 211*d* is detachably connected to a connection tube 212*a* in the main body portion 212 which will be described below.

A connection structure between the first connection portion 211*d* and the connection tube 212*a* is not particularly limited as long as they can be connected detachably. For example, a luer lock type connector may be used as the first connection portion 211*d*. For example, when the connection tube 212*a* is a female luer lock type, a male luer lock type connector is used as the first connection portion 211*d*.

The second connection portion 211*e* is provided outside the second opening 211*f* (refer to FIG. 27) in the tubular portion in which the second check valve 211*c* is disposed. The second connection portion 211*e* is detachably connected to the connection tube 212*a*. For example, as in the first connection portion 211*d*, a luer lock type connector may be used as the second connection portion 211*e*.

The main body portion 212 is a casing in which a flow path through which air flows is formed.

The main body portion 212 includes a connection tube 212*a* (a main body-side connector), an air supply tube 210*a*, a relief valve 213, and a grip 215 (a gripping portion).

The connection tube 212*a* protrudes outside the casing of the main body portion 212. The connection tube 212*a* allows the manual air supply mechanism 211 to be attached to and detached from the first connection portion 211*d* and the second connection portion 211*e*. The inside of the connection tube 212*a* communicates with the manual air supply mechanism 211 when either the first connection portion 211*d* or the second connection portion 211*e* is mounted.

The air supply tube 210*a* protrudes to the outside of the casing of the main body portion 212. A flow path through which air supplied from the manual air supply mechanism 211 flows is formed between the air supply tube 210*a* and the connection tube 212*a* inside the casing of the main body portion 212.

The air supply tube 210*a* is connected to the air flow tube 9 and communicates with a flow path inside the air flow tube 9.

The relief valve 213 is disposed on the outer circumferential portion of the casing of the main body portion 212. The relief valve 213 is the same as the relief valve 113 in the first embodiment, except that it is provided on a flow path between the connection tube 212*a* and the air supply tube 210*a*. Details of the flow path between the connection tube 212*a* and the air supply tube 210*a* will be described below.

The grip 215 protrudes from the outer circumferential portion of the main body portion 212. A shape of the grip 215 is not particularly limited as long as a user can grip the main body portion 212.

A connection state of the manual air supply mechanism 211 with respect to the main body portion 212 is a first connection state in which the first connection portion 211*d* shown in FIG. 26 is connected to the connection tube 212*a*, and a second connection state in which the second connection portion 211*e* shown in FIG. 27 is connected to the connection tube 212*a*.

The operator can manually switch between the first connection state and the second connection state. For example, to switch the first connection state to the second connection state, the operator unlocks the first connection portion 211*d* and removes the first connection portion 211*d* from the connection tube 212*a*. The operator changes a direction of the manual air supply mechanism 211, connects the second connection portion 211*e* to the connection tube 212*a*, and locks the second connection portion 211*e*. Switching from the second connection state to the first connection state is performed by performing a reverse operation.

In the first connection state, air supplied from the first opening 211*g* flows into the connection tube 212*a* by the operator operating the pump 211*a*.

In the second connection state, air suctioned by the operator's operation of the pump 211*a* flows into the second opening 211*f* from the connection tube 212*a*.

Therefore, also in the air supply tube 210*a* communicating with the connection tube 212*a*, a direction in which air flows is changed according to the connection state of the manual air supply mechanism 211.

The connecting band 216 connects the main body portion 212 to the manual air supply mechanism 211 so as not to impede movement and posture change of the manual air supply mechanism 211 necessary for switching the connection state of the manual air supply mechanism 211.

For example, the connecting band 216 is made of a flexible resin. A mounting position of the connecting band 216 on the main body portion 212 and the manual air supply mechanism 211 is not particularly limited as long as the movement and posture change of the manual air supply mechanism 211 are not hindered. In the example shown in FIG. 26, the connecting band 216 is rotatably mounted on the outer circumferential portion of the connection tube 212*a* of the main body portion 212 and on the outside of the tubular portion between the first connection portion 211*d* and the pump 211*a*.

As shown in FIG. 27, a length of the connecting band 216 is sufficiently longer than a length from the first connection portion 211*d* to the second connection portion 211*e* of the manual air supply mechanism 211.

A functional configuration of the air supply device 210 will be described with reference to FIGS. 28 and 29.

Figure 28:
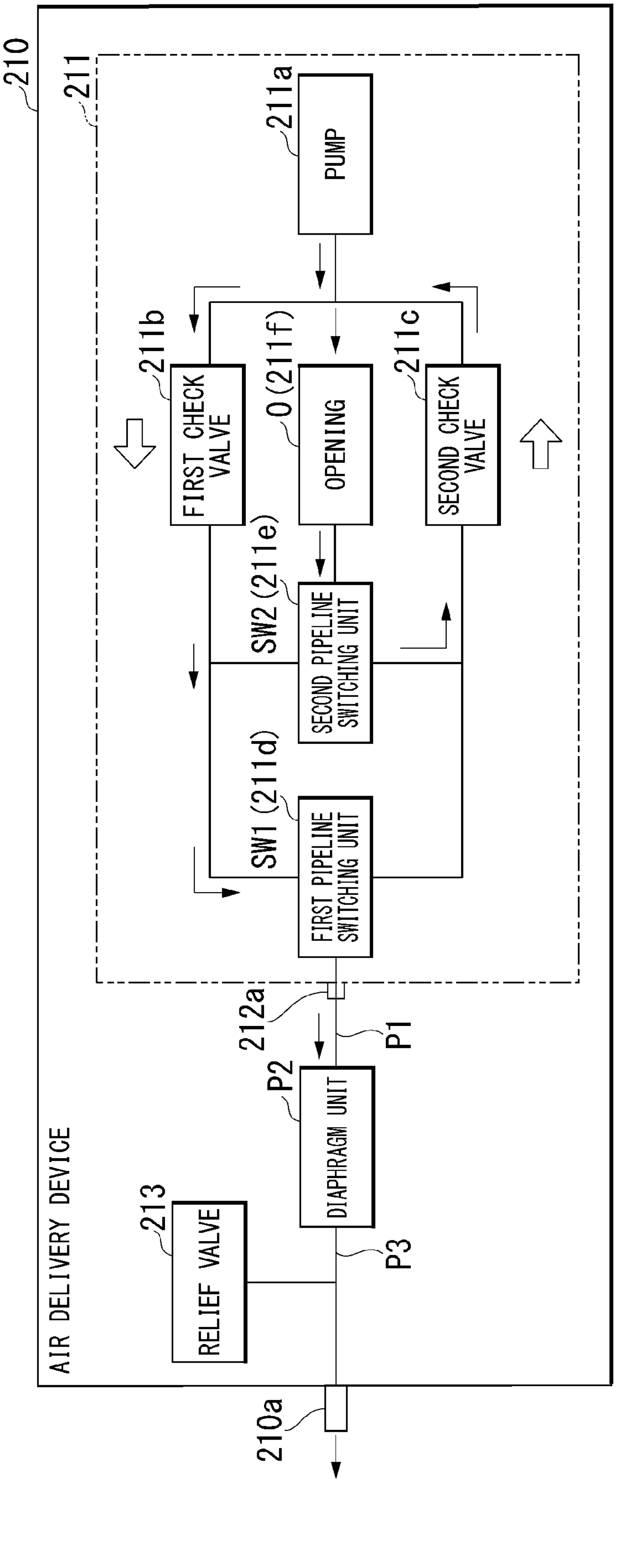
FIG. 28 is a block diagram showing an example of the air supply device in the overtube for an endoscope according to the third embodiment of the present invention.

FIG. 28 is a block diagram showing an example of the air supply device in the overtube for an endoscope according to the third embodiment of the present invention. FIG. 29 is a block diagram showing a flow during air suction in the air supply device.

As shown in FIG. 28, the air supply device 210 includes the above-described manual air supply mechanism 211, relief valve 213, and air supply tube 210*a*, instead of the air supply mechanism 111, the relief valve 113, and the connection tube 110*a* of the air supply mechanism 111 in the first embodiment. The air flow tube 9 similar to that in the first embodiment is connected to the air supply tube 210*a* (refer to FIG. 27).

As shown in FIG. 28, the manual air supply mechanism 211 includes a pump 211*a*, a first check valve 211*b*, a second check valve 211*c*, a first conduit switching part SW1, a second conduit switching part SW2, and an opening O, instead of the pump 111*a*, the first check valve 111*b*, the second check valve 111*c*, the first conduit switching part 111*d*, the second conduit switching part 111*e*, and the opening 111*f*.

Like the first conduit switching part 111*d*, the first conduit switching part SW1 may use a flow path switching valve or the like, but in the example shown in FIGS. 26 and 27, the conduits to be switched are manually attached and detached.

Therefore, in the first connection state, as shown in FIG. 28, the first conduit switching part SW1 and the second conduit switching part SW2 correspond to the first connection portion 211*d* and the second connection portion 211*e*, respectively. In this case, the opening O corresponds to the second opening 211*f*.

Figure 29:
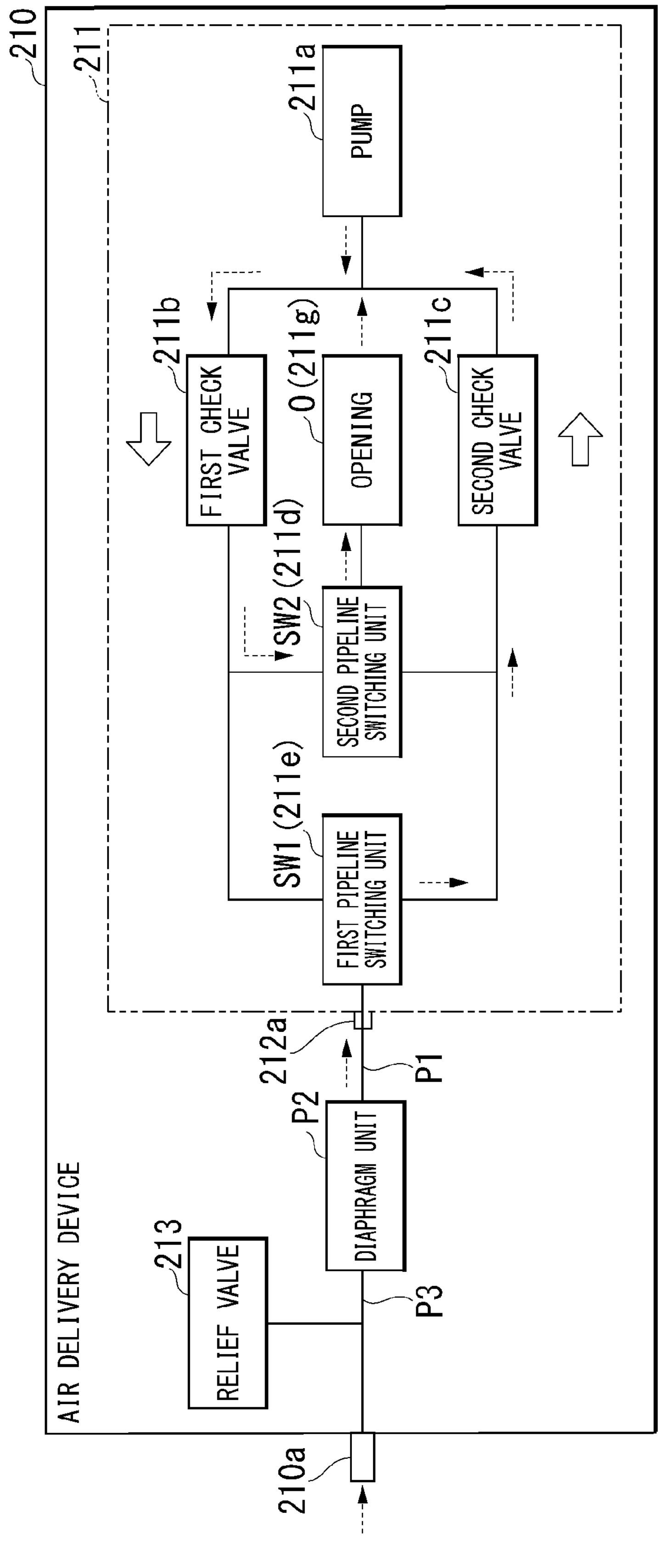
FIG. 29 is a block diagram showing a flow during air suction of the air supply device in the overtube for an endoscope according to the third embodiment of the present invention.

Similarly, in the second connection state, as shown in FIG. 29, the first conduit switching part SW1 and the second conduit switching part SW2 correspond to the second connection portion 211*e* and the first connection portion 211*d*, respectively. In this case, the opening O corresponds to the first opening 211*g*.

In the manual air supply mechanism 211 in the first connection state, as indicated by a solid line in FIG. 28, an air flow that is the same as in the air supply device 10 of the first embodiment is formed, and air is supplied to the connection tube 212*a*.

In the manual air supply mechanism 211 in the second connection state, as indicated by the dashed line in FIG. 29, an air flow that is the same as in the air supply device 10 of the first embodiment is formed, and air is suctioned through the connection tube 212*a*.

As shown in FIG. 28, a first conduit P1, a throttle portion P2, and a second conduit P3 are disposed in this order from the connection tube 212*a* toward the air supply tube 210*a* between the connection tube 212*a* and the air supply tube 210*a*.

The first conduit P1 circulates air between the connection tube 212*a* and the throttle portion P2.

The throttle portion P2 is provided for the purpose of reducing the pressure of the air supplied from the first conduit P1. The configuration of the throttle portion P2 is not particularly limited as long as the pressure of the air after passing through the throttle portion P2 can be reduced by reducing a flow path cross-sectional area. For example, the throttle portion P2 may be formed of a tubular portion in which a tube having a smaller flow path cross-sectional area than the first conduit P1 extends. For example, the throttle portion P2 may be formed by an orifice plate in which an orifice that protrudes inward from a tube wall of the first conduit P1 and is smaller than the flow path cross-sectional area of the first conduit P1 is formed in the conduit of the first conduit P1. For example, the throttle portion P2 may be formed of a porous body of which an opening area as a whole is smaller than the flow path cross-sectional area of the first conduit P1.

The second conduit P3 is formed by a tube having a flow path cross-sectional area larger than a flow path cross-sectional area at the throttle portion P2. In this embodiment, the second conduit P3 extends to the proximal end of the second lumen 2*e* by the air flow tube 9 connected to the air supply tube 210*a*.

The relief valve 213 is connected to the second conduit P3 between the air supply tube 210*a* and the throttle portion P2.

The relief valve 213 is the same as the relief valve 113 in the second embodiment, except that it is provided in the second conduit P3. Therefore, when the pressure of the air in the second conduit P3 becomes higher than an allowable value, the air is exhausted from the relief valve 213 to the outside of the main body portion 212 (refer to FIG. 27).

Figure 30:
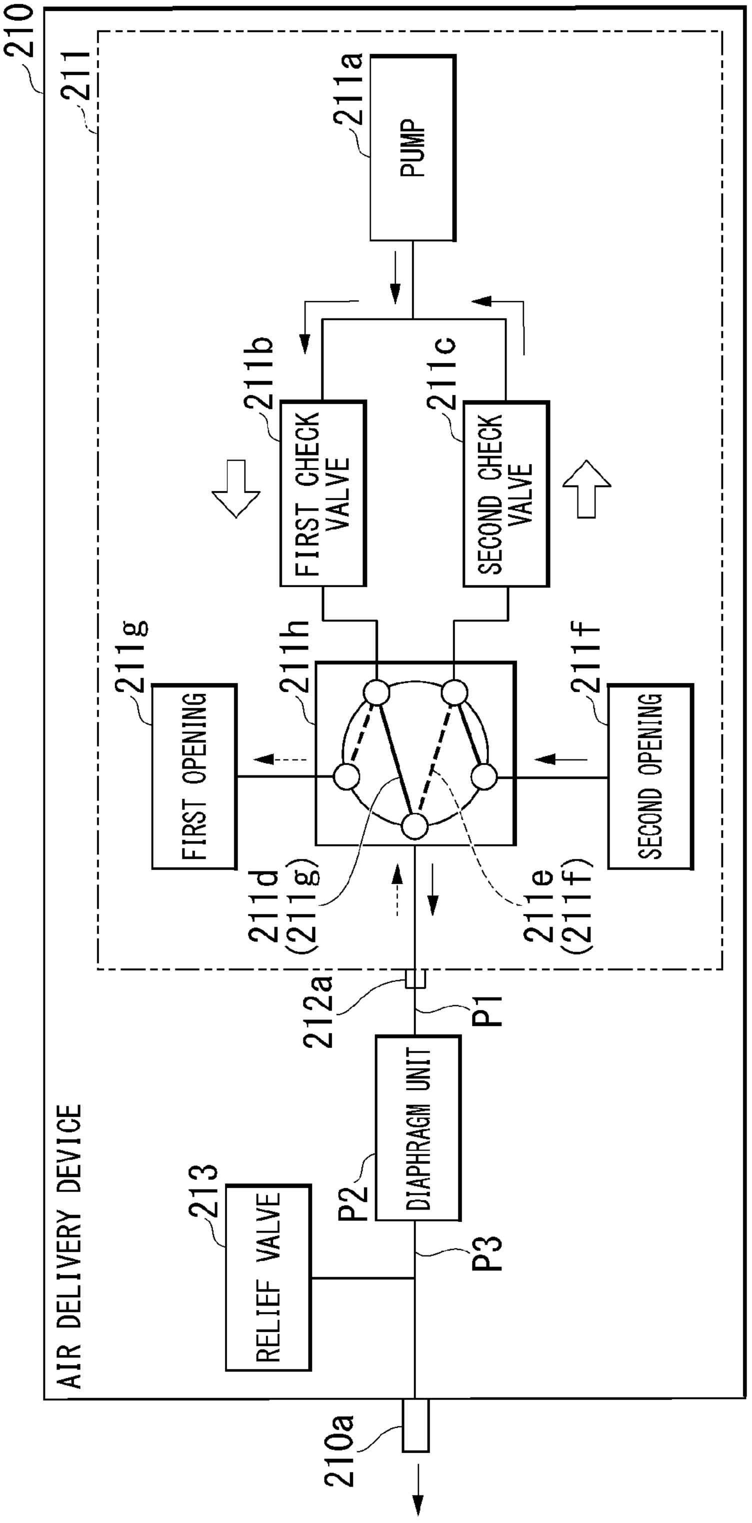
FIG. 30 is a block diagram showing an example of the air supply device in the overtube for an endoscope according to the third embodiment of the present invention.

The functional configuration of the air supply device 210 shown in FIGS. 26 and 27 can also be indicated by a block diagram as shown in FIG. 30.

FIG. 30 is a block diagram showing an example of the air supply device in the overtube for an endoscope according to the third embodiment of the present invention.

As shown in FIG. 30, the manual air supply mechanism 211 includes a conduit switching part 211*h* instead of the first conduit switching part SW1 and the second conduit switching part SW2.

The conduit switching part 211*h* forms the first connection state when air is being supplied as indicated by a black line. Thus, the first connection portion 211*d* is connected to the connection tube 212*a*, and the connection tube 212*a* communicates with the first opening 211*g*. At this time, external air is suctioned in from the second opening 211*f*.

The conduit switching part 211*h* forms the second connection state during air suction as indicated by a broken line. Thus, the second connection portion 211*e* is connected to the connection tube 212*a*, the connection tube 212*a* communicates with the second opening 21I f, and the air suctioned from the first opening 211*g* is exhausted to the outside.

In this embodiment, the function of the conduit switching part 211*h* is realized manually. However, the conduit switching part 211*h* may be replaced with a switching device such as a flow path switching valve.

The air supply device 210 communicates with the fixing balloon 3 via the air flow tube 9 and the second lumen 2*e*, as in the first embodiment. Thus, the operator can supply air to the fixing balloon 3 and can suction air from the fixing balloon 3 by appropriately switching the manual air supply mechanism 211 between the first connection state and the second connection state. Therefore, as in the first embodiment, the operator can expand and contract the fixing balloon 3.

The action of this embodiment will be described with a focus on the action of the throttle portion P2 in the air supply device 210.

First, a problem of air supply in a manual pump will be described with reference to FIGS. 31 and 32.

Figure 31:
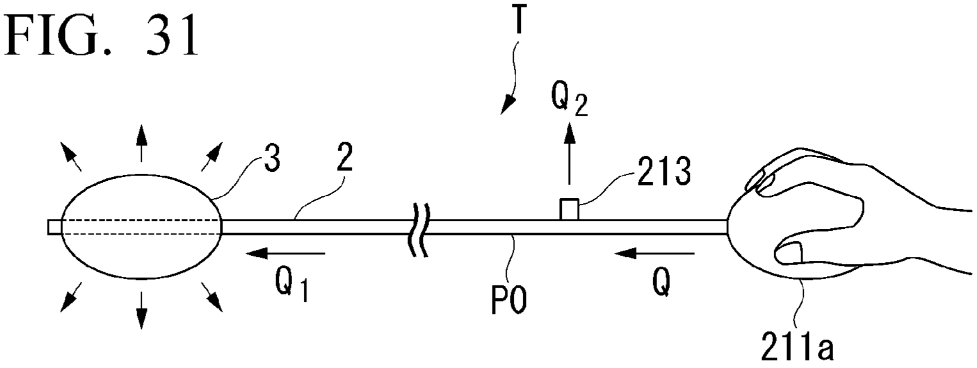
FIG. 31 is a schematic diagram showing an action of a relief valve in a manual pump

FIG. 31 is a schematic diagram showing an action of a relief valve in the manual pump. However, in FIG. 31, illustration of the air flow tube 9 is omitted for simplification.

Figure 32:
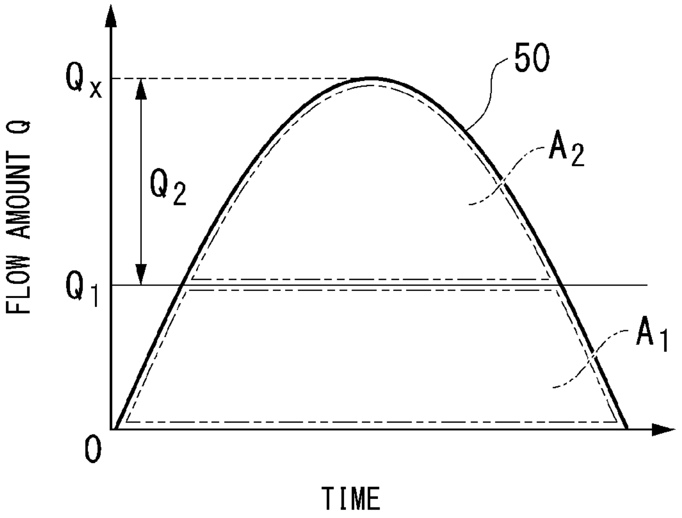
FIG. 32 is a graph showing an example of a relationship between a flow rate of air supplied by the manual pump and an amount of loss leaking from the relief valve.

FIG. 32 is a graph showing an example of a relationship between a flow rate of air supplied by the manual pump and an amount of loss leaking from the relief valve. In FIG. 32, a horizontal axis represents time, and a vertical axis represents the flow rate of air supplied from the manual pump.

In the overtube T shown in FIG. 31, the throttle portion P2 is removed from the overtube 201. Furthermore, the overtube T includes a conduit P0 having a constant flow path cross-sectional area, instead of the first conduit P1 and the second conduit P3.

It is assumed that the flow rate of air supplied to the conduit P0 by operating the pump 211*a* is Q. As shown in FIG. 32, when the operator presses the pump 211*a*, the flow rate Q increases over time, reaches the maximum value Qx, and then gradually decreases, as shown by a curve 50. When a volume change of the pump 211*a* ceases, the flow rate Q becomes zero. When a diameter of the fixing balloon 3 does not expand to a required size with this operation, the operator removes his/her hand from the pump 211*a*, suctions air into the pump 211*a*, and then repeats the same operation.

The maximum value Q, of the flow rate Q and the time required for the flow rate Q to reach the maximum value Q, depend on a pressing force and pressing speed of the operator. In order to quickly perform a treatment, the operator often presses the pump 211*a* to quickly increase the flow rate. Thus, for example, it is assumed that in the conduit P0, the flow rate reaches an allowable pressure of the relief valve 213 when the flow rate is equal to or higher than $Q_1$ ($Q_1<Q_x$). In this case, a flow rate $Q_2$ ($=Q-Q_1$) exceeding Q1 in the flow rate Q is exhausted from the relief valve 213 to the outside.

In this case, air at a flow rate Q1 is supplied to the inside of the fixing balloon 3 with which the conduit P0 communicates through the air flow tube 9 and the second lumen 2*e* (not shown) in the main tube 2.

Therefore, a volume $A_1$ of air supplied to the fixing balloon 3 by one pressing operation becomes a value obtained by integrating the curve 50 within a range less than Q1, as shown in FIG. 32. Similarly, a loss volume $A_2$ of the air exhausted from the relief valve 213 is a value obtained by integrating the curve 50 within a range equal to or greater than $Q_1$.

This means that as the loss volume $A_2$ with respect to the volume $A_1$ increases, air supply efficiency of the air supply device of the overtube T is lowered. When the air supply efficiency is low, the operator will have to operate the pump 211*a* for a longer time in order to expand the fixing balloon 3 to a required outer diameter, and thus working time required to perform the treatment is increased.

As described above, in the manual pump, when the operator strongly or quickly operates the pump 211*a*, operation time for expanding the diameter of the fixing balloon 3 may rather be lengthened.

In this embodiment, in view of these problems, the throttle portion P2 is provided in the air supply device 210. Thus, the operator is allowed to perform mom efficient air supply operation.

When the throttle portion P2 is formed between the first conduit P1 and the second conduit P3, even when the operator strongly presses the pump 211*a*, the flow rate of air flowing into the second conduit P3 is reduced by the throttle portion P2 provided on the upstream side of the relief valve 213. Thus, the pressure inside the second conduit P3 including the air flow tube 9 decreases. As a result, an amount of loss of air in the relief valve 213 is also reduced.

Furthermore, since flow path resistance increases due to the throttle portion P2, the flow rate cannot be increased unless the operator presses the pump 211*a* more strongly than in a case in which the throttle portion P2 is not present. The magnitude of flow rate resistance is transmitted to the operator operating the pump 211*a* as a sense of resistance. This sense of resistance also has an effect of making the operator relax the pressing force.

According to this embodiment, since it is possible to expand the diameter of the fixing balloon 3 with a smaller amount of loss of air than the case in which the throttle portion P2 is not present by providing the throttle portion P2, the time required for the operator to operate the pump 211*a* is reduced.

Next, conditions for a shape suitable for the throttle portion P2 will be described.

Figure 33:
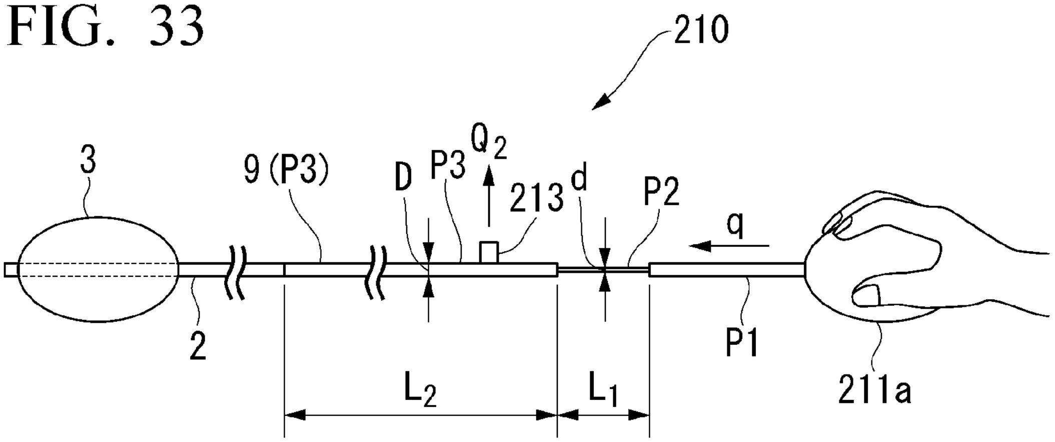
FIG. 33 is a schematic diagram showing a flow path shape of the air supply device in the overtube for an endoscope according to the third embodiment of the present invention.

FIG. 33 is a schematic diagram showing a flow path shape of the air supply device in the overtube for an endoscope according to the third embodiment of the present invention.

The shape of the first conduit P1 is a cylinder with an inner diameter of D [mm].

The shape of the throttle portion P2 is a cylindrical flow path with an inner diameter of d [mm] and a length of $L_1$ [mm]. For example, when the throttle portion P2 is not cylindrical shape, a diameter of a circle having the same cross-sectional area is used as d. For example, when the throttle portion P2 is a square with a side length of s, $2\times s/\sqrt{\pi}$ is used as d. For example, when the throttle portion P2 is formed of a porous body, $2\times r\times\sqrt{N}$ is used as d, wherein r is an average radius of holes in a cross section orthogonal to the flow path, and N is the number of holes.

The shape of the second conduit P3 is a cylindrical flow path with an inner diameter of D [mm]. The same applies to the inner diameter of the air flow tube 9 that connects to the air supply tube 210*a* and forms a part of the second conduit P3. Hereinafter, the entire length of the second conduit P3 including the air flow tube 9 will be indicated by $L_2$ [mm].

A flow rate when the first conduit P1 and the second conduit P3 are directly connected without the throttle portion P2 (hereinafter, referred to as a case without the throttle portion) is indicated by q [L/min], and a flow rate when the throttle portion P2 is present is indicated by q' [L/min].

It has been experimentally found that in the case without the throttle portion P2, a pressure $P_1$ in the first conduit P1 and a pressure P3 in the second conduit P3 follow the Darcy-Weisbach equation. $P_1$ and $P_3$ are equal to each other and are indicated by the following Equation (3a).

[Math 3]

$$P_1 = P_3 = \frac{12.38}{1000} \cdot \frac{L_2}{D^4} q \qquad (3a)$$

Assuming that the flow rate when the throttle portion P2 is present is q', a pressure $P_1'$ in the first conduit P1 and a pressure $P_3'$ in the second conduit P3 are indicated by the following Equations (3b) and (3c), respectively.

[Math 4]

$$P_1' = \frac{12.38}{1000} \cdot \left(\frac{L_2}{D^4} + \frac{L_1}{d^4}\right) q' \qquad (3b)$$

$$P_3' = \frac{12.38}{1000} \cdot \frac{L_2}{D^4} q' \qquad (3c)$$

Assuming that $P_1$ and $P_1'$ are input pressures by the pump 211*a*, and $P_1$ and $P_1'$ are equal to each other, the condition under which a pressure $P_3'$ in the second conduit P3 after passing through the throttle portion P2 is less than 90% of the pressure $P_1'$ in the first conduit P1 is the following Equation (3d).

Here, "less than 90%" is an example in consideration of practicality. It is preferable to set the pressure P3' to less than 90% of the pressure $P_1'$ because the amount of loss of air exhausted from the relief valve 213 can be reduced.

However, when the pressure P3' is too low, a speed of diameter expansion of the fixing balloon 3 may become too slow. More preferably, the pressure $P_3'$ is determined so that the speed of diameter expansion of the fixing balloon 3 becomes an appropriate value within a range of less than 90%. For example, the pressure $P_3'$ may be 80% or more of $P_1'$, more preferably 50% or more.

For example, the pressure $P_3'$ may be set to be less than 80%, less than 70%, or the like of the pressure $P_1'$ to determine the condition of the throttle portion P2.

[Math 5]

$$P_3' < 0.9P_1 = 0.9P_1' \qquad (3d)$$

When Equations (3b) and (3c) are substituted into Equation (3d) and rearranged, the following Equation (3e) is obtained.

[Math 6]

$$\frac{L_1}{d^4} > \frac{1}{9} \cdot \frac{L_2}{D^4} \qquad (3e)$$

In this embodiment, in the case in which the shapes of the throttle portion P2 and the second conduit P3 satisfies the condition of Equation (3e), when the pump 211*a* is operated to supply air, the pressure in the second conduit P3 on the downstream side of the throttle portion P2 can be made less than 90% of the pressure on the upstream side of the throttle portion P2. Thus, the amount of loss of air exhausted from the relief valve 213 communicating with the second conduit P3 on the downstream side of the throttle portion P2 is reduced.

In order to rewrite Equation (3e) under the condition that the pressure is less than X %, a coefficient "1/9" in Equation (3e) should be replaced with "1/(0.1×X)."

The overtube 201 of this embodiment is the same as the overtube 1 except that it includes the air supply device 210 instead of the air supply device 10 of the overtube 1 according to the first embodiment. Therefore, as in the first embodiment, it is possible to provide an overtube for an endoscope that reduces the load on the patient and allows a smooth operation of the endoscope.

In particular, according to this embodiment, the air supply device 210 has the manual air supply mechanism 211, and the air supply device 210 has the throttle portion P2. Thus, since the diameter of the fixing balloon 3 can be expanded with a smaller amount of loss of air than the case without the throttle portion P2, the time required for the operator to operate the pump 211*a* is reduced.

The first conduit P1 in the air supply device 210 is an example of a first conduit through which gas sent from the pump 211*a*, which is an example of a manual pump, flows.

The throttle portion P2 in the air supply device 210 is an example of a constricted portion that is connected to the first conduit and has a flow path cross-sectional area that is smaller than the flow path cross-sectional area of the first conduit.

The second conduit P3 in the air supply device 210 is an example of a second conduit that has a flow path cross-sectional area larger than the flow path cross-sectional area of the throttle portion and allows gas flowing through the throttle portion to flow toward the fixing balloon.

The relief valve 213 is an example of a relief valve that is provided in the second conduit and exhausts gas from the second conduit when the pressure in the second conduit exceeds a certain value.

First Modified Example

A modified example (a first modified example) of the air supply device used in place of the air supply device 210 in the overtube 201 according to the third embodiment will be described.

As shown in FIG. 17, an air supply device 210A of this modified example can be used in place of the air supply device 210 of the overtube 201.

As shown in FIG. 26, the air supply device 210A has a main body portion 212A instead of the main body portion 212 of the air supply device 210.

The main body portion 212A is different from the main body portion 212 in the configuration of the flow path from the connection tube 212*a* to the air supply tube 210*a*. In the following, differences from the third embodiment will be mainly described.

Figure 34:
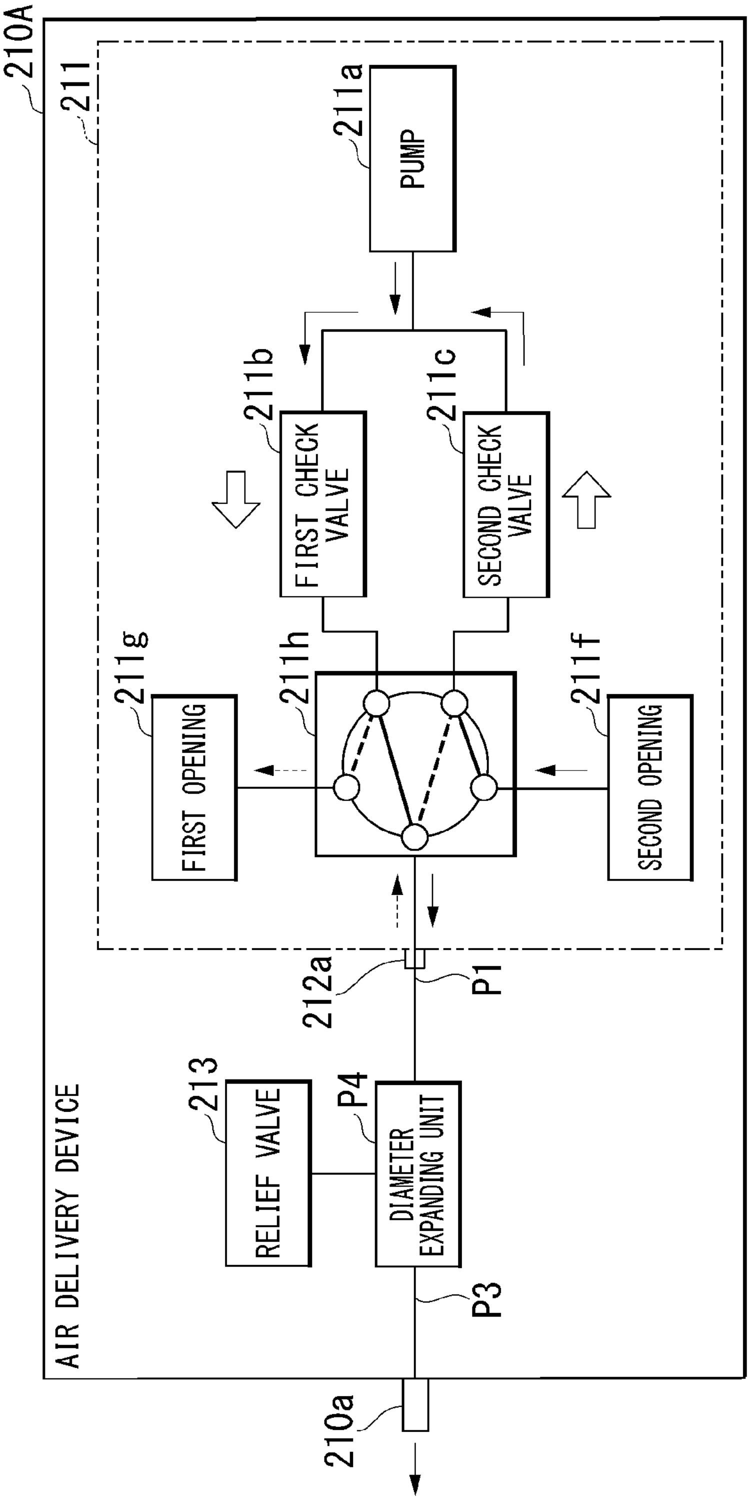
FIG. 34 is a block diagram showing a modified example (a first modified example) of the air supply device used in the overtube for an endoscope according to the third embodiment of the present invention.
Figure 35:
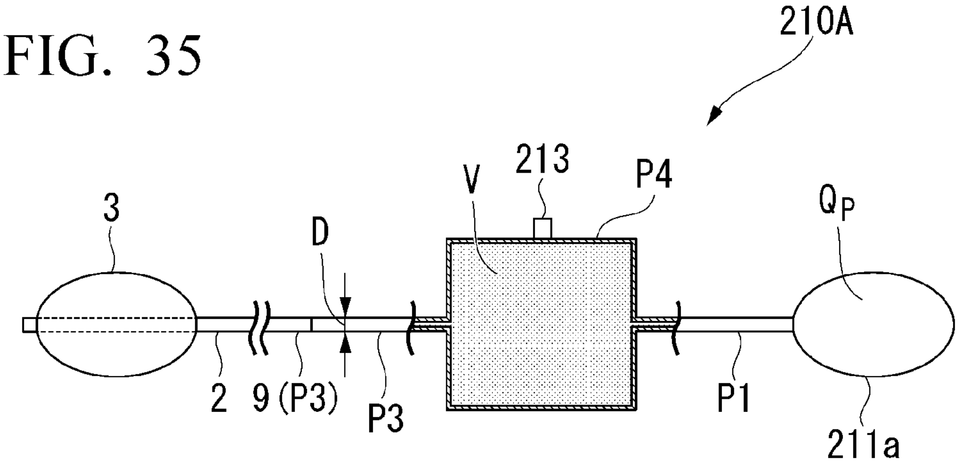
FIG. 35 is a schematic diagram showing a flow path shape of the modified example (the first modified example) of the air supply device.

FIG. 34 is a block diagram showing the modified example (the first modified example) of the air supply device used in the overtube for an endoscope according to the third embodiment of the present invention. FIG. 35 is a schematic diagram showing a flow path shape of the modified example (the first modified example) of the air supply device.

As shown in FIG. 34, the air supply device 210A has a diameter-expanded portion P4 instead of the throttle portion P2. However, the relief valve 213 in this modified example is disposed in the diameter-expanded portion P4.

The diameter-expanded portion P4 is provided for the purpose of reducing the pressure of air supplied from the first conduit P1. The diameter-expanded portion P4 is a casing having a flow path cross-sectional area larger than the flow path cross-sectional area of each of the first conduit P1 and the second conduit P3. The flow path cross-sectional area of the diameter-expanded portion P4 is an area of a cross section orthogonal to a flow direction of air from the first conduit P1 to the second conduit P3.

The shape of the diameter-expanded portion P4 is not particularly limited as long as the pressure of the air in the diameter-expanded portion P4 can be reduced more than the pressure of the first conduit P1.

For example, the diameter-expanded portion P4 may be formed of a tubular portion having a larger flow path cross-sectional area than that of the first conduit P1. For example, the diameter-expanded portion P4 may have a box shape with a cross-sectional area larger than the inner diameter of the first conduit P1.

The diameter-expanded portion P4 shown in FIG. 35 is schematically shaped like a box with a volume of V. A shape of the flow path cross section in the diameter-expanded portion P4 is not particularly limited. The shape of the flow path cross section of the diameter-expanded portion P4 may be circular, elliptical, rectangular, polygonal, or the like.

The action of this modified example will be described with a focus on the effect of the diameter-expanded portion P4 in the air supply device 210A.

In this modified example, the diameter-expanded portion P4 is provided in the air supply device 210A is, and the relief valve 213 is disposed in the diameter-expanded portion P4, thereby allowing the operator to perform more efficient air supply operation.

When the diameter-expanded portion P4 is formed between the first conduit P1 and the second conduit P3, since the flow path cross-sectional area is widened at the diameter-expanded portion P4, the pressure is lower in the diameter-expanded portion P4 than in the first conduit P1. Thus, when the flow rate by the operator's operation is the same, the time required for the pressure in the diameter-expanded portion P4 to reach the allowable pressure exhausted from the relief valve 213 disposed in the diameter-expanded portion P4 is extended.

Therefore, the internal pressure of the diameter-expanded portion P4 increases without air being exhausted, and during this period, the air continues to flow in the first conduit P1 to some extent.

Thus, the amount of loss of air exhausted from the relief valve 213 is reduced.

Next, conditions for a suitable shape for the diameter-expanded portion P4 will be described. A unit system in Equation of this modified example is not particularly limited.

The shape of each of the first conduit P1 and the second conduit P3 is cylindrical with an inner diameter of D, as in the third embodiment.

A volume of the diameter-expanded portion P4 is V. A pressure before the pressure of the diameter-expanded portion P4 increases due to the air supply from the pump 211*a* to the diameter-expanded portion P4 is set to P. When a pressure when air with a volume $Q_P$ flows into the diameter-expanded portion P4 from the pump 211*a* is P', the following Equation (3f) can be obtained from the Boyle-Charles law. Here, it is assumed that air does not flow out of the diameter-expanded portion P4 when air flows in.

For example, the volume $Q_P$ may be the maximum amount of air supply of the pump 211*a* in one operation. For example, the volume $Q_P$ can be the maximum air supply volume in the pump 211*a*. In this case, P' is the pressure inside the diameter-expanded portion P4 at the time of maximum air supply in one operation.

[Math 7]

$$P' = P\left(1 + \frac{Q_P}{V}\right) \tag{3f}$$

When a cylindrical tube having an inner diameter that is the same as that of the second conduit P3 is disposed instead of the diameter-expanded portion P4, a volume V' per unit length of the cylindrical tube is indicated by the following Equation (3g).

[Math 8]

$$V' = \frac{\pi D^2}{4} \tag{3g}$$

When the pressure when air with a volume $Q_P$ flows into the cylindrical tube from the pump 211*a* is P", the following Equation (3h) is obtained based on the same assumption as in the calculation of P.

[Math 9]

$$P'' = P\left(1 + \frac{4Q_P}{\pi D^2}\right) \tag{3h}$$

The condition for the pressure P' of the diameter-expanded portion P4 to be less than 90% of the pressure P" without the diameter-expanded portion P4 is the following Equation (3i).

Here. "less than 90%" is an example in consideration of practicality. It is preferable to set the pressure P' to less than 90% of the pressure P" because the amount of loss of air exhausted from the relief valve 213 can be reduced.

However, when the pressure P' is too low, the speed of diameter expansion of the fixing balloon 3 may become too slow. It is more preferable that the pressure P' is determined so that the speed of diameter expansion of the fixing balloon 3 becomes an appropriate value within a range of less than 90%. For example, the pressure P' may be 80% or more of P", more preferably 50% or more.

At the same time, the speed of diameter expansion of the fixing balloon 3 can be maintained as much as possible.

For example, the conditions for the diameter-expanded portion P4 may be determined so that the pressure P' is less than 80%, less than 70%, or the like of the pressure P".

[Math 10]

$$P' < 0.9P'' \tag{3i}$$

When Equations (3f) and (3h) are substituted into Equation (3i) and rearranged, the following Equation (3j) is obtained.

[Math 11]

$$\frac{Q_P}{V} < \frac{3.6Q_P}{\pi D^2} - 0.1 \tag{3j}$$

In this modified example, when the shapes of the diameter-expanded portion P4 and the first conduit P1 satisfy the condition of Equation (3e), the pressure inside the diameter-expanded portion P4 can be made less than 90% of the pressure inside the first conduit P1 when the pump 211*a* is operated to supply air. Thus, the amount of loss of air exhausted from the relief valve 213 is reduced.

The overtube 201 having the air supply device 210A of this modified example is the same as the overtube 201, except that it includes the air supply device 210A instead of the air supply device 210 of the overtube 201 according to the third embodiment. Therefore, according to this modified example, as in the third embodiment, it is possible to provide an overtube for an endoscope that reduces the load on the patient and allows a smooth operation of the endoscope.

In particular, according to this modified example, the air supply device 210A has the diameter-expanded portion P4 in which the relief valve 213 is provided.

Thus, since the diameter of the fixing balloon 3 can be expanded with a smaller amount of loss of air than in the case in which the diameter-expanded portion P4 is not present, the time for the operator to operate the pump 211*a* is reduced.

The diameter-expanded portion P4 in the air supply device 210A is an example of a diameter-expanded portion that is connected to the first conduit and has a flow path cross-sectional area larger than the flow path cross-sectional area of the first conduit.

The relief valve 213 in the air supply device 210A is an example of a relief valve that is provided in the diameter-expanded portion and exhausts gas from the diameter-expanded portion when the pressure in the diameter-expanded portion exceeds a certain value.

The second conduit P3 in the air supply device 210A is an example of a second conduit that has a flow path cross-sectional area smaller than that of the diameter-expanded portion and allows the gas flowing through the diameter-expanded portion to flow toward the fixing balloon.

Second Modified Example

A modified example (a second modified example) of the air supply device used in place of the air supply device 210 in the overtube 201 of the third embodiment will be described.

As shown in FIG. 17, an air supply device 210B of this modified example can be used in place of the air supply device 210 of the overtube 201.

Figure 36:
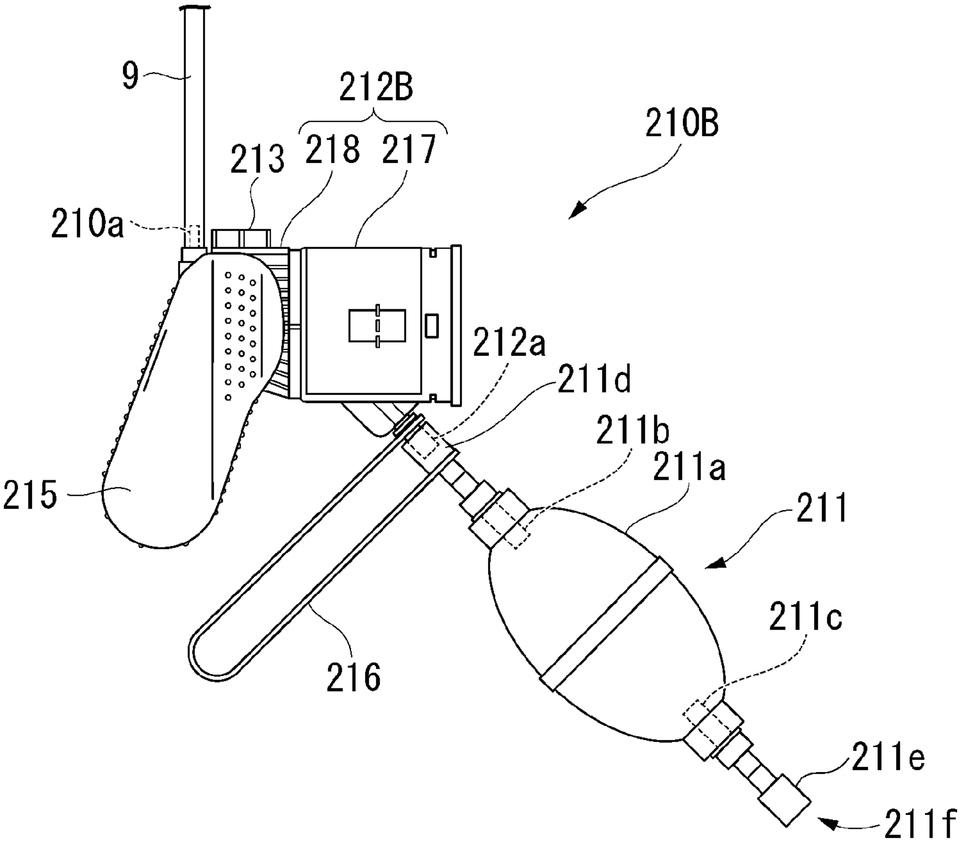
FIG. 36 is a schematic front view showing a modified example (a second modified example) of the air supply device used in the overtube for an endoscope according to the third embodiment of the present invention.

FIG. 36 is a schematic front view showing the modified example (the second modified example) of the air supply device used in the overtube for an endoscope according to the third embodiment of the present invention.

As shown in FIG. 36, the air supply device 210B includes a main body portion 212B instead of the main body portion 212 of the air supply device 210.

The main body portion 212B includes a pressure adjustment part 217 and a casing 218 between the connection tube 212*a* and the air supply tube 210*a*.

The grip 215 in this modified example is formed in the casing 218.

Like the manual air supply mechanism 211 in the second embodiment, the manual air supply mechanism 211 in this modified example can switch between the first connection state and the second connection state with respect to the connection tube 212*a* of the main body portion 212B.

In the following, differences from the third embodiment will be mainly described.

Figure 37:
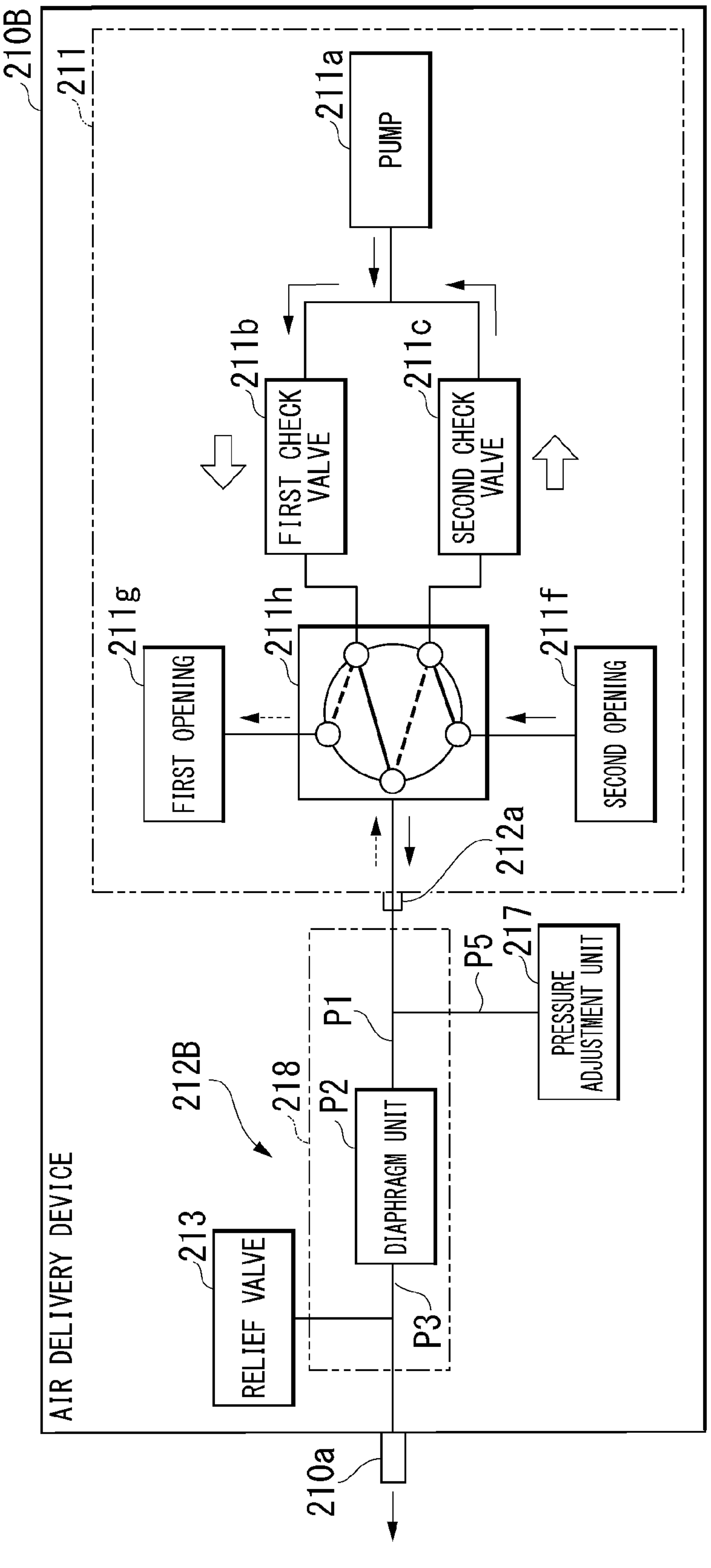
FIG. 37 is a block diagram showing the modified example (the second modified example) of the air supply device used in the overtube for an endoscope according to the third embodiment of the present invention.
Figure 38:
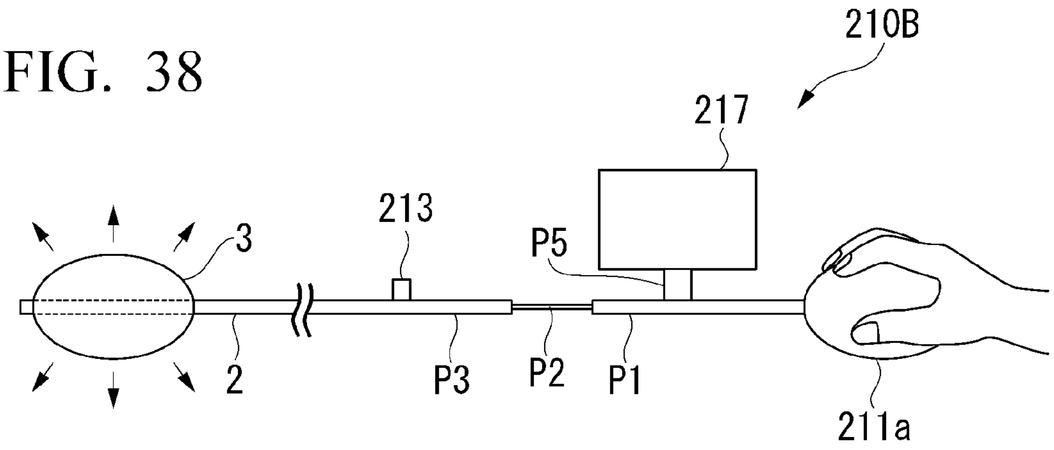
FIG. 38 is a schematic diagram showing a flow path shape of the modified example (the second modified example) of the air supply device.

FIG. 37 is a block diagram showing the modified example (the second modified example) of the air supply device used in the overtube for an endoscope according to the third embodiment of the present invention. FIG. 38 is a schematic diagram showing a flow path shape of the modified example (the second modified example) of the air supply device. However, in FIG. 38, illustration of the air flow tube 9 is omitted for simplicity (the same applies to FIGS. 39 to 40 below).

As shown in FIG. 37, the air supply device 210B has the throttle portion P2 and the relief valve 213 that are the same as those in the third embodiment.

The throttle portion P2 in this modified example is disposed inside the casing 218.

The relief valve 213 in this modified example communicates with the second conduit P3 inside the casing 218.

As schematically shown in FIG. 38, the pressure adjustment part 217 communicates with the first conduit P1 through the third conduit P5.

The pressure adjustment part 217 branches the air supplied from the pump 211*a* through the first conduit P1 and stores the air therein without discharging the air to the outside. Thus, an increase in pressure in the first conduit P1 is alleviated, and the pressure of the air flowing into the second conduit P3 through the throttle portion P2 is also alleviated.

The configuration of the pressure adjustment part 217 is not particularly limited as long as the increase in pressure in the first conduit P1 can be alleviated by storing air inside the pressure adjustment part 217.

For example, the pressure adjustment part 217 may be configured to form a storage space for storing air supplied to the first conduit P1.

For example, the pressure adjustment part 217 may be formed of a box, a container, or the like that forms a storage space having a certain volume. In this case, as air flows into the pressure adjustment part 217, the internal pressure of the first conduit P1 and the internal pressure of the pressure adjustment part 217 increase. However, since the volume into which air flows is as large as the pressure adjustment part 217, the increase in pressure in the first conduit P1 is reduced compared to a case in which the pressure adjustment part 217 is not provided.

As the volume of the pressure adjustment part 217 becomes larger, the increase in pressure in the first conduit P1 is alleviated.

When the internal pressure of the pressure adjustment part 217 increases to some extent and exceeds the flow path resistance of the throttle portion P2, the air stored in the pressure adjustment part 217 returns to the first conduit P1 through the third conduit P5 and is pushed out toward the fixing balloon 3 through the throttle portion P2.

For example, the pressure adjustment part 217 may be configured to form a storage space of which a volume changes according to the pressure in the first conduit P1. Examples of the pressure adjustment part 217 of which the volume changes include a syringe, a bellows tube, and a bag of which a volume changes by deformation according to the internal pressure.

The pressure adjustment part 217 of which the volume changes may be formed of an elastic body that expands and contracts according to the pressure.

The pressure adjustment part 217 of which the volume changes may include an elastic member that applies an elastic force that resists a volume change.

Figure 39:
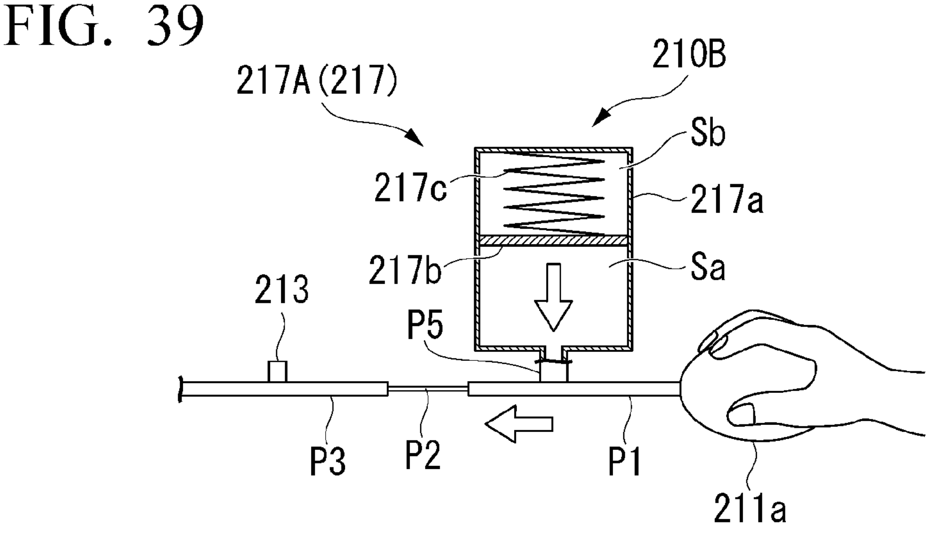
FIG. 39 is a schematic diagram showing an example of the modified example (the second modified example) of the air supply device.

FIG. 39 is a schematic diagram showing an example of the modified example (the second modified example) of the air supply device.

A pressure adjustment part 217A shown in FIG. 39 is an example of the pressure adjustment part 217 of which the volume changes.

The pressure adjustment part 217A includes a cylindrical portion 217*a*, a piston 217*b*, and a spring 217*c*.

The cylindrical portion 217*a* is, for example, a cylinder, a rectangular tube, or the like that is elongated in one direction. The third conduit P5 communicates with an end portion of the cylindrical portion 217*a* in the longitudinal direction.

The piston 217*b* is movable in the longitudinal direction of the cylindrical portion 217*a* inside the cylindrical portion 217*a*. The piston 217*b* divides the cylindrical portion 217*a* in the longitudinal direction into a first space Sa and a second space Sb. The cylindrical portion 217*a* slides on the inner surface of the cylindrical portion 217*a* in an airtight manner, and is movable in the longitudinal direction.

The opening of the third conduit P5 faces the first space Sa.

The spring 217*c* is disposed in the second space Sb, and elastically connects the end portion of the cylindrical portion 217*a* in the longitudinal direction in the second space Sb and the piston 217*b*.

The spring 217*c* biases the piston 217*b* against the pressure in the first space Sa.

According to the pressure adjustment part 217A, when the pump 211*a* is operated and air is supplied to the first conduit P1, more air flows to the third conduit P5 which has a lower flow path resistance than the throttle portion P2.

The air that has flowed into the first space Sa from the third conduit P5 flows into the first space Sa until the pressure reaches a balance with a biasing force of the spring 217*c*. The air that has flowed into the first space Sa is biased by the spring 217*c* through the piston 217*b*.

When the supply of air by the pump 211*a* ends, and a flow rate of the air flowing through the first conduit P1 decreases, the piston 217*b* moves toward the third conduit P5 according to the biasing force from the spring 217*c*. Thus, the air in the first space Sa is pushed out of the third conduit P5. Therefore, the air stored in the first space Sa returns to the first conduit P1 through the third conduit P5. Thus, the stored air is supplied to the fixing balloon 3 without loss.

The first space Sa is an example of a storage space of which a volume can be changed in the pressure adjustment part 217A.

Figure 40:
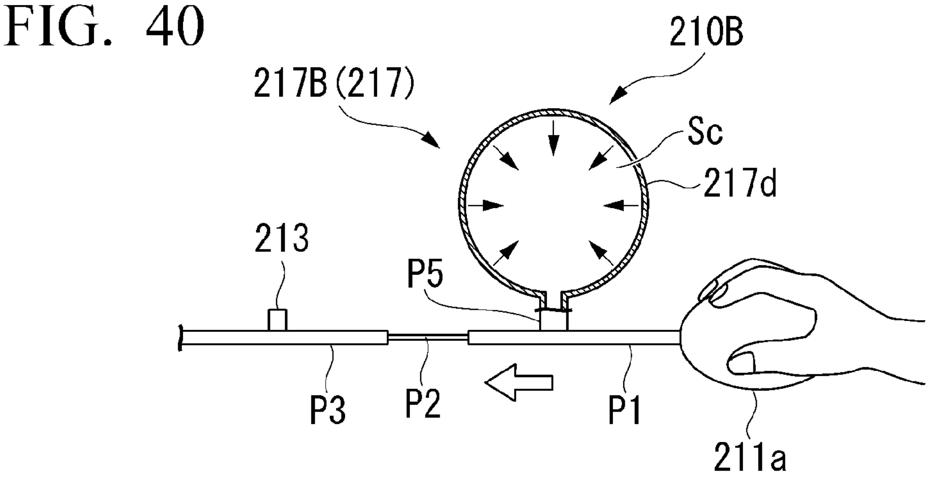
FIG. 40 is a schematic diagram showing an example of the modified example (the second modified example) of the air supply device.

FIG. 40 is a schematic diagram showing an example of the modified example (the second modified example) of the air supply device.

A pressure adjustment part 217B shown in FIG. 40 is an example of a pressure adjustment part 217 of which a volume changes.

The pressure adjustment part 217B includes a balloon 217*d* instead of the cylindrical portion 217*a*, the piston 217*b*, and the spring 217*c* of the pressure adjustment part 217A.

The balloon 217*d* is formed of a bag-shaped elastomer having one opening that communicates with the third conduit P5. As a material of the balloon 217*d*, an elastomer having appropriate elasticity that can expand and contract according to the pressure of the air in the first conduit P1 is used.

According to the pressure adjustment part 217B, when the pump 211*a* is operated and air is supplied to the first conduit P1, the air flowing toward the third conduit P5 flows into the inside. An internal space Sc of the pressure adjustment part 217B expands according to the pressure of the air.

The air that has flowed into the internal space Sc flows into the internal space Sc until it reaches a pressure that balances with a tension of the balloon 217*d*. The air that has flowed into the internal space Sc is biased from the balloon 217*d*.

When the supply of air by the pump 211*a* ends, and the flow rate of the air flowing through the first conduit P1 decreases, the air in the internal space Sc is pushed out of the third conduit P5 according to the biasing force from the balloon 217*d*. Therefore, as in the pressure adjustment part 217A, the air stored in the internal space Sc returns to the first conduit P1 through the third conduit P5. Thus, the stored air is supplied to the fixing balloon 3 without loss.

The internal space Sc is an example of a storage space of which a volume can be changed in the pressure adjustment part 217B.

The configuration of the pressure adjustment parts 217A and 217B may be included in devices such as pressure gauges and pressure indicators that display pressure, for example. In this case, as the pressure adjustment part 217, a device such as a pressure gauge or a pressure indicator may be used.

Next, an example of an air supply operation using the air supply device 210B will be described, focusing on the action of the pressure adjustment part 217.

FIGS. 41 to 44 are explanatory diagrams of the operation of the modified example (the second modified example) of the air supply device.

However, in FIGS. 41 to 44, illustration of the air flow tube 9 is omitted for simplification.

Figure 41:
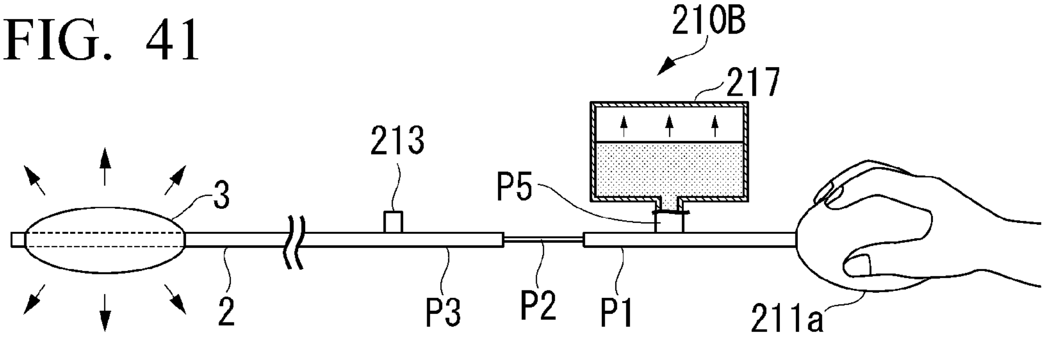
FIG. 41 is an explanatory diagram of an operation of the modified example (the second modified example) of the air supply device.

As shown in FIG. 41, when the operator starts pushing the pump 211*a*, some of the air supplied to the first conduit P1 is supplied to the inside of the fixing balloon 3 via the throttle portion P2, the second conduit P3, the air flow tube 9 (not shown), and the second lumen 2*e* in the main tube 2.

The air other than the supplied air branches to the pressure adjustment part 217 through the third conduit P5. Therefore, even when the operator presses the pump 211*a* sharply or strongly, excessive air will not flow into the throttle portion P2. In FIG. 41, an amount of inflow of air is schematically shown by a shaded portion. An illustrated white portion does not mean a vacuum, but schematically shows a state in which air can easily flow in.

For example, when the pressure adjustment part 217 is formed of a bag or a balloon, an initial volume of the pressure adjustment part 217 is close to 0, and air can easily flow in as long as the pressure exceeds the atmospheric pressure outside the pressure adjustment part 217.

For example, when the pressure adjustment part 217 is formed of a box having a constant volume, the pressure increases in proportion to the amount of inflow. However, when the volume of the pressure adjustment part 217 is made sufficiently large, the gradient of pressure increase can be reduced.

The throttle portion P2 in this modified example has the action of alleviating the pressure increase in the second conduit P3 on the downstream side, as in the throttle portion P2 in the third embodiment. In this modified example, the pressure increase in the second conduit P3 is further curbed together with a pressure relief effect of the diameter-expanded portion P4.

Thus, even when the operator presses the pump 211*a* sharply or strongly, the air in the second conduit P3 is less likely to be exhausted from the relief valve 213.

When the pressure adjustment part 217 is formed of a pressure gauge or a pressure indicator, the operator can adjust the amount of air to be supplied by looking at the pressure displayed by the pressure adjustment part 217 during the air supply operation. Also in this respect, air is difficult to be exhausted from the relief valve 213.

Air efficiently flows into the fixing balloon 3, and the fixing balloon 3 expands.

Figure 42:
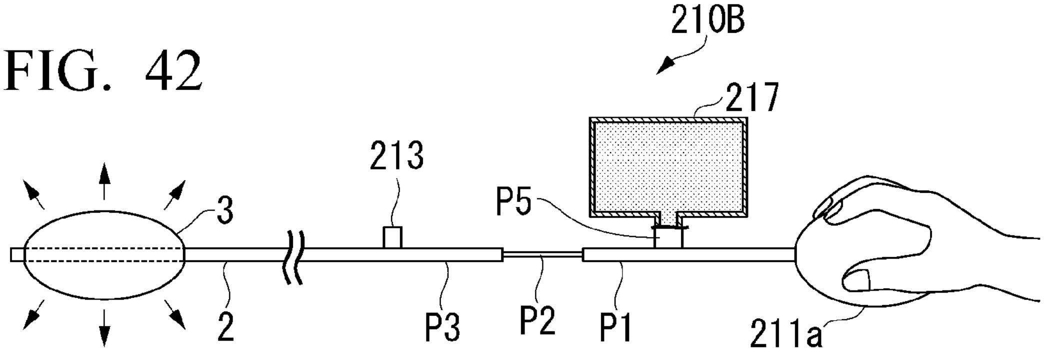
FIG. 42 is an explanatory diagram of the operation of the modified example (the second modified example) of the air supply device.

As shown by the shaded portion in FIG. 42, when air flows into the pressure adjustment part 217 to some extent, the internal pressure of the pressure adjustment part 217 gradually increases. Thus, the resistance that the operator receives from the pump 211*a* gradually increases.

The operator can recognize that air has been sufficiently supplied to the fixing balloon 3 since he/she encounters large resistance after the air is supplied for a certain amount of time.

Figure 43:
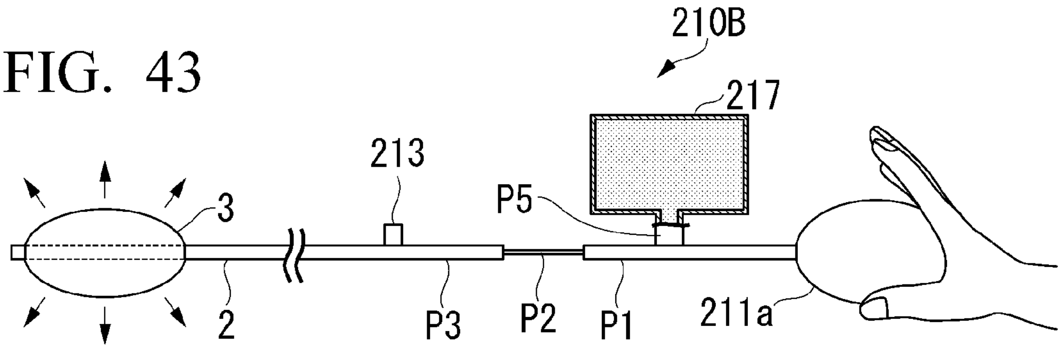
FIG. 43 is an explanatory diagram of the operation of the modified example (the second modified example) of the air supply device.

Thus, the operator removes his/her hand front the pump 211*a* to stop air supply (refer to FIG. 43). Even when the operator does not stop the air supply, if the pressure in the second conduit P3 exceeds the allowable pressure, the air will be exhausted front the relief valve 213, and thus the fixing balloon 3 is not expanded excessively. In this case, the air supply resistance is maintained at a constant high level, and thus the operator stops the air supply without too much delay.

When the air supply is stopped, the increase in the amount of air in the air flow path in the overtube 201 having the air supply device 210B is stopped.

Since the internal pressure of the pressure adjustment part 217 has increased to some extent at the time of stopping, the air in the pressure adjustment part 217 flows into the fixing balloon 3 even after the stopping according to the internal pressure at the time of stopping. Therefore, even when the air supply is stopped in a state in which an amount of diameter expansion of the fixing balloon 3 is small, insufficient air is supplied to the fixing balloon 3 within a range of the volume of the pressure adjustment part 217.

When the pressure adjustment part 217 has a configuration in which the air therein can be biased, as in the pressure adjustment parts 217A and 217B, the air inside the pressure adjustment part 217 can more easily move to the fixing balloon 3 more quickly.

Figure 44:
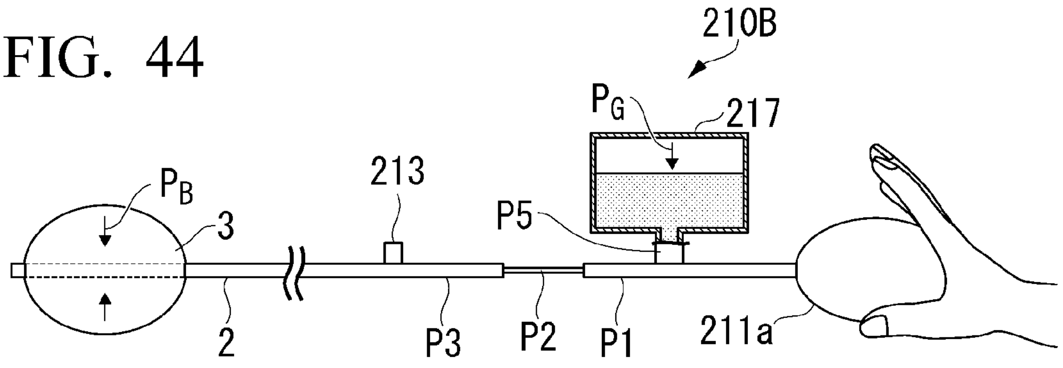
FIG. 44 is an explanatory diagram of the operation of the modified example (the second modified example) of the air supply device.

As shown in FIG. 44, when the air moves until a pressure PH in the fixing balloon 3 and a pressure P, in the pressure adjustment part 217 are balanced, a pressure equilibrium state is formed in the overtube 201.

In this way, the diameter expansion operation of the fixing balloon 3 is completed.

When the diameter of the fixing balloon 3 is reduced, the air in the fixing balloon 3 is suctioned by the manual air supply mechanism 211.

Like the manual air supply mechanism 211 in the second embodiment, the manual air supply mechanism 211 of this modified example is capable of rapidly suctioning air by operating the pump 211*a* after the connection state of the manual air supply mechanism 211 is switched to the second connection state.

When air remains in the pressure adjustment part 217 during the suctioning of air, the air in the pressure adjustment part 217 is also suctioned together with the air in the fixing balloon 3.

For example, when the air in the pressure adjustment part 217 is biased, as in the pressure adjustment parts 217A and 217B, the time required for suctioning air is further shortened. In this case, the operator can perform an air suctioning operation more quickly and easily.

The overtube 201 having the air supply device 210B of this modified example is the same as the overtube 201, except that it includes the air supply device 210B instead of the air supply device 210 of the overtube 201 according to the third embodiment. Therefore, according to this modified example, as in the third embodiment, it is possible to provide an overtube for an endoscope that reduces the load on the patient and allows a smooth operation of the endoscope.

In particular, according to this modified example, the air supply device 210B further includes a pressure adjustment part 217 in addition to the air supply device 210.

Thus, compared to the air supply device 210, the increase in pressure on the downstream side of the throttle portion P2 can be further curbed. As a result, since the diameter of the fixing balloon 3 can be expanded with a small amount of loss of air, the time required for the operator to operate the pump 211*a* is reduced.

The pressure adjustment parts 217, 217A, and 217B in the air supply device 210B are examples of a pressure indicator that is connected to a first conduit, has a flow path having a flow path cross-sectional area that is larger than the flow path cross-sectional area of the first conduit, and displays the pressure of the first conduit.

Each of the internal space in the pressure adjustment part 217, the first space Sa in the pressure adjustment part 217A, and the internal space Sc in the pressure adjustment part 217B forms a flow path through which air flows, and has a flow path cross-sectional area larger than that of the first conduit P1.

Third Modified Example

A modified example (a third modified example) of the air supply device used instead of the air supply device 210 in the overtube 201 of the third embodiment will be described.

As shown in FIG. 17, an air supply device 210C of this modified example can be used in place of the air supply device 210 of the overtube 201.

Figure 45:
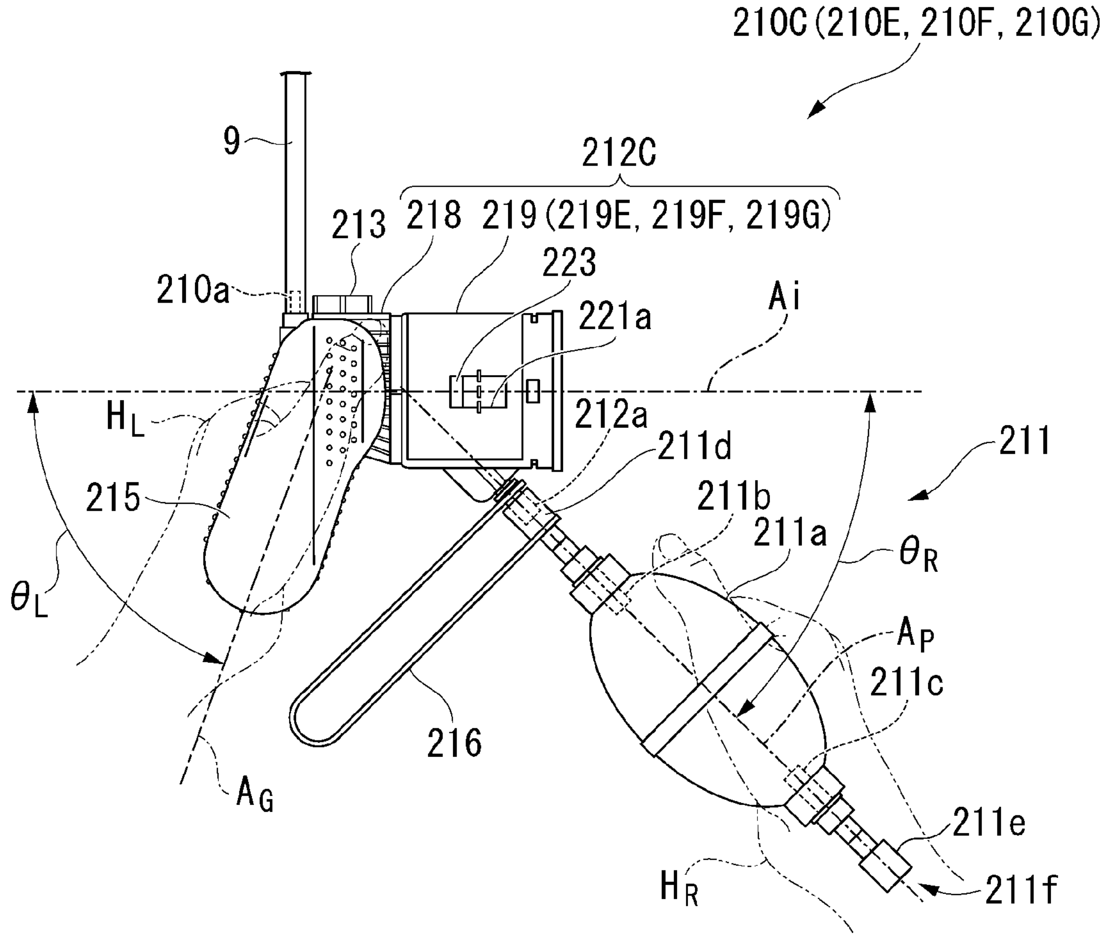
FIG. 45 is a schematic front view showing the modified example (the third modified example) of the air supply device used in the overtube for an endoscope according to the third embodiment of the present invention.
Figure 46:
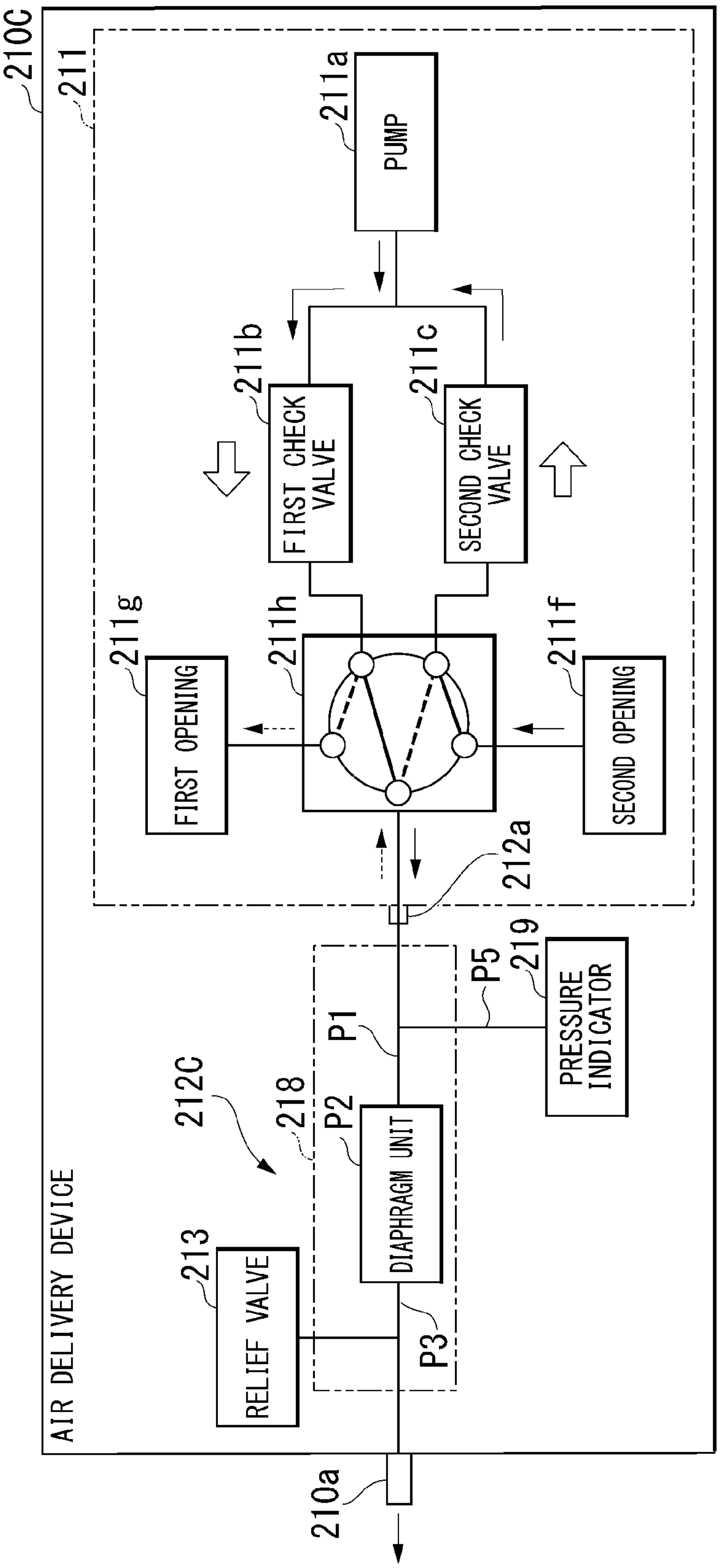
FIG. 46 is a block diagram showing the modified example (the third modified example) of the air supply device used in the overtube for an endoscope according to the third embodiment of the present invention.

FIG. 45 is a schematic front view showing the modified example (the third modified example) of the air supply device used in the overtube for an endoscope according to the third embodiment of the present invention. FIG. 46 is a block diagram showing the modified example (the third modified example) of the air supply device used in the overtube for an endoscope according to the third embodiment of the present invention.

As shown in FIG. 45, the air supply device 210C includes a main body portion 212C instead of the main body portion 212 of the air supply device 210.

The main body portion 212C includes a pressure indicator 219 and a casing 218 that is the same as that in the second modified example between the connection tube 212*a* and the air supply tube 210*a*.

As shown in FIG. 46, the pressure indicator 219 communicates with the first conduit P1 via the third conduit P5, as in the pressure adjustment part 217 in the second modified example.

The grip 215 in this modified example is formed on the casing 218, as in the second modified example.

In the following, differences from the third embodiment will be mainly described.

FIG. 45 shows a standard arrangement when the operator grips and operates the air supply device 210C with the right hand $H_R$ and left hand $H_L$. The operator grips the grip 215 with the left hand $H_L$ to support the air supply device 210C. The operator grips the pump 211*a* with the right hand $H_R$. The operator presses the pump 211*a* when the air supply or suction operation is performed. A state in which the air supply device 210C is gripped in both hands and disposed in front of the operator is referred to as a standard operation state.

An exterior of the pressure indicator 219 is a columnar shape extending along a central axis Ai. A cross-sectional shape in a direction orthogonal to the central axis Ai is not particularly limited. For example, the cross-sectional shape of pressure indicator 219 may be circular, elliptical, rectangular, polygonal, or the like. In the example shown in FIG. 45, the exterior of the pressure indicator 219 has a cylindrical shape extending along the central axis Ai.

In the air supply device 210C, in the standard operation state, the grip 215 and the manual air supply mechanism 211 are disposed so that the central axis Ai can easily take a posture that extends in the right-left direction of the operator.

The grip 215 in this modified example is inclined from the casing 218 disposed on the left side of the pressure indicator 219 in FIG. 45 toward the operator side (the lower side in the drawing) as it moves leftward in the drawing along the central axis Ai. A central axis $A_G$ of the grip 215 is inclined counterclockwise in the drawing by an angle $\theta_L$ with respect to the central axis Ai. For example, the angle $\theta_L$ may be 15° or more and 90° or less. For example, the angle $\theta_L$ is more preferably in a range of 60°±15°.

The manual air supply mechanism 211 in this modified example is inclined from the connection tube 212*a* of the casing 218 adjacent to the lower side of the air supply device 210 in FIG. 45 toward the operator side (the lower side in the drawing) as it moves toward the right side in the drawing along the central axis Ai. A central axis $A_P$ of the manual air supply mechanism 211 is inclined clockwise in the drawing by an angle $\theta_R$ with respect to the central axis Ai. For example, the angle $\theta_R$ may be 15° or more and 90° or less. For example, the angle $\theta_R$ is more preferably in a range of 60°±15°.

When the pump 211*a* is a rubber bulb pump, the central axis $A_P$ coincides with a central axis of the pump 211*a*, and is an axis that connects the center of the first connection portion 211*d* and the center of the second connection portion 211*e*.

In this case, the angle $\theta_R$ coincides with an inclination angle of the central axis of the connection tube 212*a* with respect to the central axis Ai.

Magnitudes of the angles $\theta_L$ and $\theta_R$ may be changed according to gripping positions of the left hand $H_L$ and the right hand $H_R$. For example, as shown in FIG. 45, in the standard operation state, when the gripping position of the manual air supply mechanism 211 leans toward the operator side (the lower side in the drawing) compared to the gripping position of the grip 215, the angle $\theta_L$ may be 60°±15° and the angle $\theta_R$ may be 45°±15° considering ease of operation by the operator.

Since the grip 215 and the manual air supply mechanism 211 are disposed in this way, the grip 215 and the manual air supply mechanism 211 extend in an inverted V shape with an apex near a left end portion of the pressure indicator 219 as seen from the operator in the standard operation state.

According to such an arrangement, in the standard operation state, the central axis Ai can be easily disposed in a posture along the right-left direction of the operator or inclined at an acute angle with the right-left direction.

In particular, when a pressure display window (a display window 221*a* to be described below) in the pressure indicator 219 is formed long along the central axis Ai, the operator is likely to be guided to a posture in which the central axis Ai extends in the right-left direction so that the display window can be easily seen.

Next, a detailed shape of the pressure indicator 219 will be described.

Figure 47:
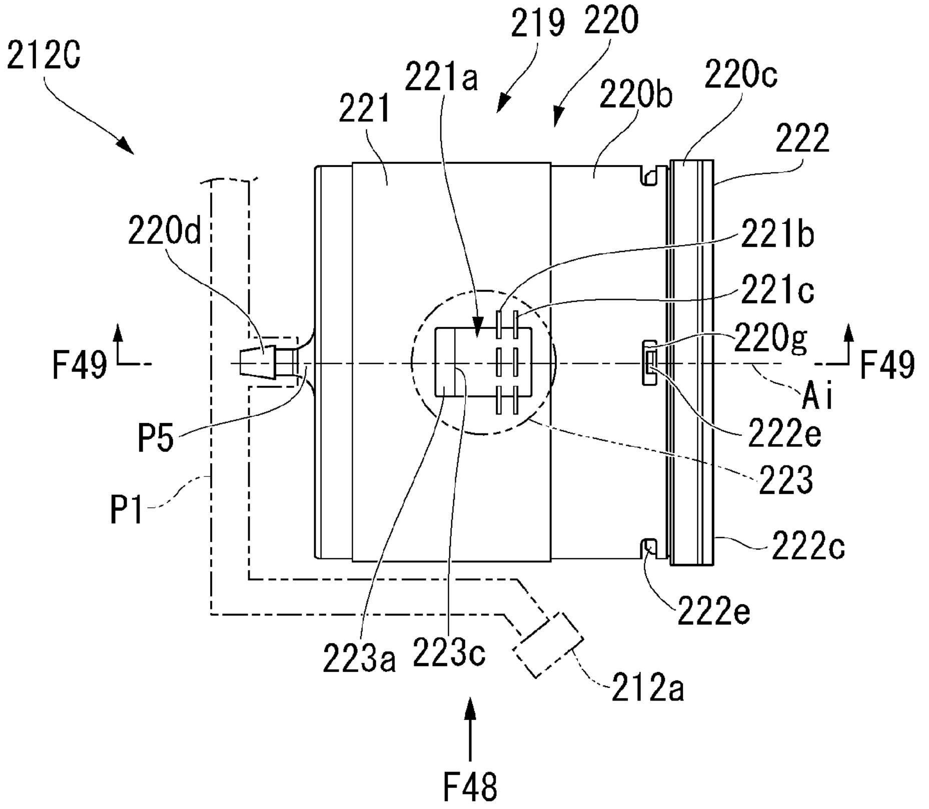
FIG. 47 is a schematic front view showing an example of a pressure indicator in the modified example (the third modified example) of the air supply device.
Figure 48:
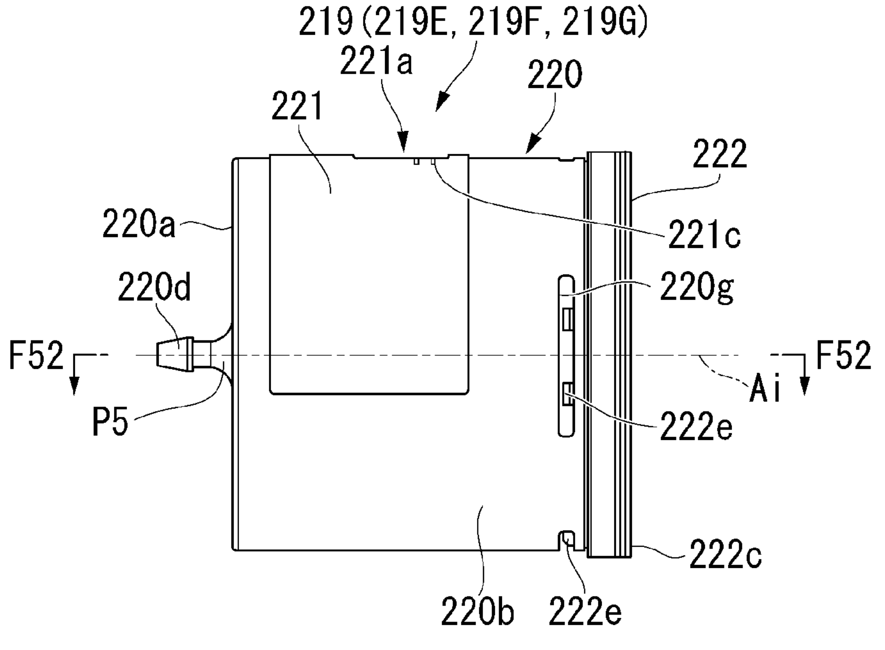
FIG. 48 is a bottom view seen from F48 in FIG. 47.
Figure 49:
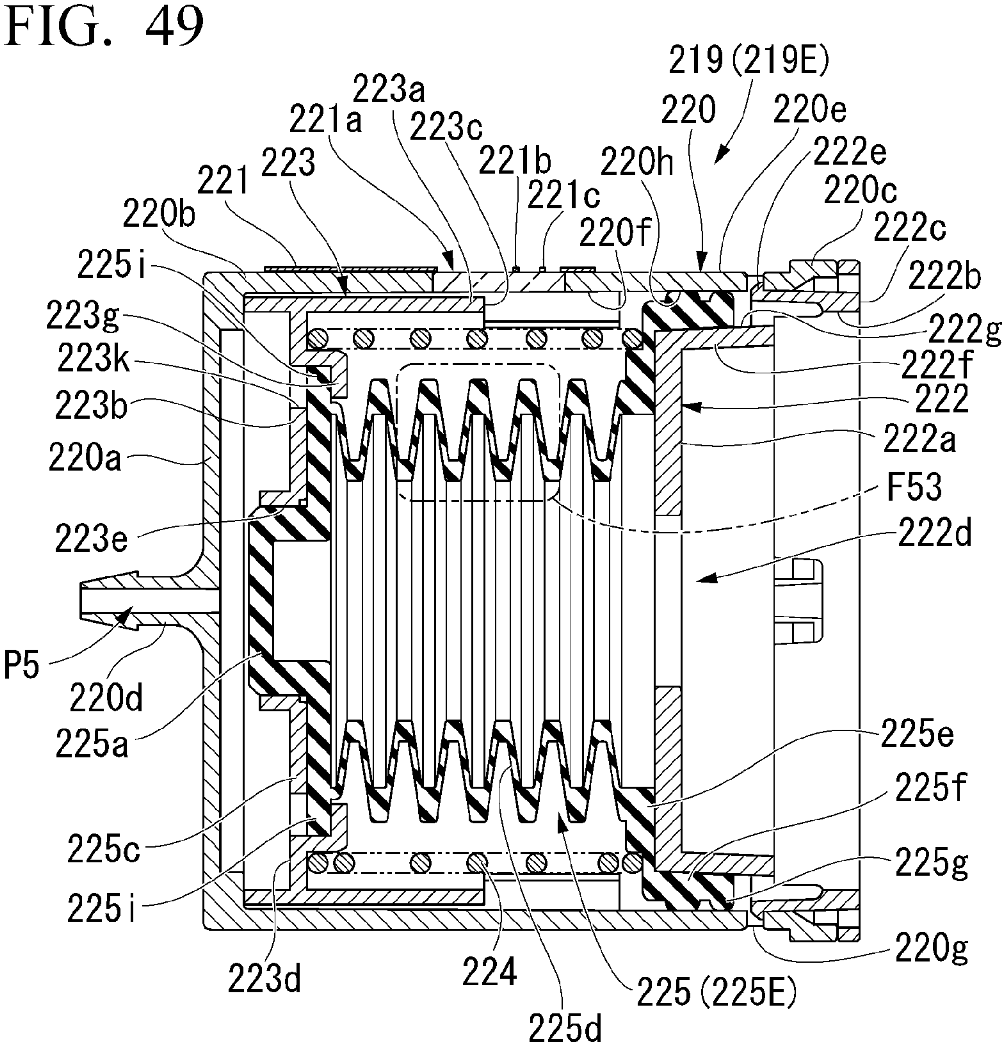
FIG. 49 is a cross-sectional view taken along line F49-F49 in FIG. 47.

FIG. 47 is a front view showing an example of the pressure indicator in the modified example (the third modified example) of the air supply device. FIG. 48 is a bottom view from F48 in FIG. 47. FIG. 49 is a cross-sectional view taken along line F49-F49 in FIG. 47.

An example in which the exterior of the pressure indicator 219 is a cylindrical shape will be described below.

Regarding the shape of the pressure indicator 219 and constituent members included in the pressure indicator 219, the axial, circumferential, and radial directions may be used based on the arrangement of the pressure indicator 219 in an assembled state.

The axial direction is a direction along the central axis Ai. The circumferential direction is a direction of rotation around the central axis Ai. The radial direction is a direction along a line intersecting the central axis Ai on a plane orthogonal to the central axis Ai.

On a semi-straight line extending in the radial direction from the central axis Ai, a position closer to the central axis Ai than a specific position may be referred to as it is located inward in the radial direction from the specific position. Similarly, a position farther from the central axis Ai than the specific position may be referred to as it is located outward in the radial direction from the specific position.

Regarding the axial positional relationship regarding the pressure indicator 219, the side closer to the third conduit P5 (the left side in FIG. 47) may be referred to as the base end side, and the side farther from the third conduit P5 (the right side in FIG. 47) may be referred to as the distal end side. A portion on the base end side may be referred to as a base end portion, and a portion on the distal end side may be referred to as a distal end portion. The most base end side portion is a base end, and the most distal end portion is a distal end.

As shown in FIGS. 47 and 48, the pressure indicator 219 includes a case 220 (a casing), a display window forming member 221, and a fixing frame 222.

FIG. 47 shows a state in which the pressure indicator 219 is disposed in the same posture as in FIG. 45. Therefore, FIG. 47 shows a shape of an outer surface seen by the operator in the standard operation state.

As shown in FIG. 49, the pressure indicator 219 further includes a collar 223 (a moving member), an airtight member 225 (a sealing member, a pressing member), and a coil spring 224 (an elastic member) therein.

The case 220 has a cylindrical shape with a bottom that forms a side surface and a base end portion of the pressure indicator 219 in the axial direction. A material of the case 220 is not particularly limited. For example, the material of the case 220 may be a resin, a metal, glass, or a composite material in which two or more of them are combined. It is more preferable that the case 220 is a resin molded product.

The components of the overtube 301 including the case 220 may have a draft angle necessary for manufacturing when they are molded products. In the following description, for the sake of simplification, a shape ignoring the draft angle will be described. For example, a "cylindrical surface" includes a strict cylindrical surface and an approximate cylindrical surface that has a draft angle and is inclined from the cylindrical surface.

Although a color of the case 220 is not particularly limited, a region overlapping the display window 221*a* which will be described below needs to have light transmittance. In the case 220, only a portion that overlaps the display window 221*a* may have light transmittance. However, it is more preferable that the entire case 220 has light transmittance.

In the following, unless otherwise specified, an example in which the entire case 220 is made of a transparent resin material will be described. However, in FIG. 49, for the purpose of emphasizing that when a part of the case 220 has light transmittance, at least a region of the display window forming member 221 that will be described below, which overlaps the display window 221*a*, should have light transmittance, corresponding regions are indicated by diagonal and dashed hatching with alternating diagonal lines and broken lines. That is, in the following description, portions with diagonal hatching in the illustration of the case 220 are also made of a transparent material, as in portions with diagonal and dashed hatching, but when an opaque material is used in the case 220, it may be used in a range of the portions with diagonal hatching.

The kind of transparent resin material is not particularly limited. For example, suitable resin materials for the case 220 include polycarbonate, acrylic, polysulfone, and the like.

As shown in FIG. 49, the case 220 includes a bottom surface portion 220*a*, a side surface portion 220*b* (a moving conduit), a distal end frame 220*c*, and a connection tube 220*d*.

The bottom surface portion 220*a* is a circular plate-shaped portion disposed at the base end of the case 220.

The side surface portion 220*b* has a cylindrical shape extending from an outer circumferential portion of the bottom surface portion 220*a* toward the distal end side in the axial direction. Both an outer circumferential surface 220*e* and an inner circumferential surface 220*f* of the side surface portion 220*b* are cylindrical surfaces.

A locking portion 220*g* for locking a locking claw 222*e* of the fixing frame 222, which will be described below, is provided at the distal end portion of the side surface portion 220*b*.

A shape of the locking portion 220*g* is not particularly limited as long as it can lock the locking claw 222*e*. In the example shown in FIG. 49, the locking portion 220*g* is formed by an inner circumferential portion of a rectangular hole that passes through the side surface portion 220*b* in a thickness direction.

The number and arrangement of the locking portions 220*g* are determined appropriately according to the number and arrangement of the locking claws 222*e* which will be described below. For example, in the examples shown in FIGS. 47 and 48, the locking portions 220*g* are provided one by one at four positions that divide the side surface portion 220*b* into approximately four equal portions in the circumferential direction. Each of the locking portions 220*g* can lock one or more locking claws 222*e*.

The distal end frame 220*c* is an annular frame formed coaxially with the side surface portion 220*b* at the distal end of the side surface portion 220*b*. An outer diameter of the distal end frame 220*c* is slightly larger than an outer diameter of the distal end frame 220*c*. Thus, a stepped portion extending outward in the radial direction is formed at a connection portion between the side surface portion 220*b* and the distal end frame 220*c*.

The same holds true for the relationship between an inner diameter of the distal end frame 220*c* and an inner diameter of the side surface portion 220*b*.

The connection tube 220*d* protrudes from the center of the bottom surface portion 220*a* to the outside of the case 220 along the central axis Ai. The connection tube 220*d* has an appropriate shape that can be connected to an end portion of the third conduit P5.

In the main body portion 212C, routes of the first conduit P1 and the third conduit P5 are not particularly limited, but in the example shown by a two-dot chain line in FIG. 47, the third conduit P5 extends along the central axis Ai, and is connected to the first conduit P1 extending from the bottom to the top in the drawing along the bottom surface portion 220*a*.

The first conduit P1 is bent in a direction parallel to the central axis Ai at a lower end portion in the drawing, and extends along the side surface portion 220*b* to substantially the center of the side surface portion 220*b* in the axial direction. Further, the first conduit P1 is bent along an angle of the connection tube 212*a* and is connected to the connection tube 212*a*.

As shown in FIGS. 47 and 48, the display window forming member 221 is a film that is wound in the circumferential direction along the outer circumferential surface 220*e* of the side surface portion 220*b* of the case 220 and fixed.

As a material of the display window forming member 221, a film that does not have light transmittance or has low light transmittance is used.

A means for reducing the light transmittance of the display window forming member 221 is not particularly limited. For example, a film made of a colored material with low light transmittance may be used as the display window forming member 221. For example, a multilayer film in which an opaque layered portion is formed on a surface of a transparent base material may be used as the display window forming member 221. For example, the opaque layered portion may be formed by printing, vapor deposition, lamination, laser processing, pasting of a sticker, or the like.

The exterior of the display window forming member 221 has a rectangular shape that is elongated in the axial direction. That is, the display window forming member 221 is wound around the side surface portion 220*b* such that a longitudinal direction of the elongated rectangular film follows the circumferential direction.

The display window forming member 221 may cover the entire side surface portion 220*b* of the case 220, but in the example shown in FIGS. 47 and 48, it covers a part of the side surface portion 220*b*.

The display window forming member 221 covers the side surface portion 220*b* from a position on the distal end side with respect to the center to the vicinity of the base end of the case 220 in the axial direction. The display window forming member 221 covers a range longer than half of the entire circumference of the case 220 in the circumferential direction.

The display window forming member 221 is fixed to the side surface portion 220*b* with, for example, an adhesive or a sticking agent.

The display window 221*a* which is a rectangular opening elongated in the axial direction penetrates in the thickness direction at the center of the display window forming member 221 in the circumferential direction (the longitudinal direction) and near the distal end in the axial direction (the transverse direction).

However, when the display window forming member 221 is formed of an opaque layered portion and a transparent base material, a hole passing through the opaque layered portion and the base material overlapping the hole also form the display window 221*a*. That is, the display window 221*a* only needs to be optically open.

A central axis of the display window 221*a* in the longitudinal direction overlaps the central axis Ai in the front view shown in FIG. 47.

A first scale line 221*b* (a reference scale) and a second scale line 221*c* (a reference scale) are formed inside the display window 221*a* and on an edge portion surrounding the display window 221*a*.

The first scale line 221*b* indicates, for example, a lower limit value of the appropriate internal pressure of the fixing balloon 3.

The second scale line 221*c* indicates, for example, an upper limit value of the appropriate internal pressure of the fixing balloon 3.

The first scale line 221*b* and the second scale line 221*c* may be formed integrally with the display window forming member 221, or may be formed after the display window forming member 221 is fixed to the side surface portion 220*b*.

In this modified example, the first scale line 221*b* and the second scale line 221*c* are formed by printing or the like after the display window forming member 221 is fixed to the side surface portion 220*b*. In this case, positions of the first scale line 221*b* and the second scale line 221*c* can be formed based on an actually measured pressure display value by inspecting the assembled pressure indicator 219, or the like.

As shown in FIG. 49, the fixing frame 222 pushes the distal end portion of the airtight member 225 to be described below and fixes a position of the distal end portion of the airtight member 225. The fixing frame 222 is fitted inside the distal end frame 220*c* that forms an opening at the distal end portion of the case 220. The fixing frame 222 is formed in a cylindrical shape with a bottom and disposed coaxially with the central axis Ai.

The fixing frame 222 includes a bottom surface portion 222*a*, a first cylindrical portion 222*f*, a second cylindrical portion 222*b*, a locking claw 222*e*, and a flange portion 222*c*.

The bottom surface portion 222*a* is a circular plate having a diameter smaller than that of the bottom surface portion 220*a*. A through hole 222*d* passes through a center portion of the bottom surface portion 222*a* in the thickness direction.

The first cylindrical portion 222*f* forms a side surface portion of the fixing frame 222 on the base end side. The first cylindrical portion 222*f* extends from the outer circumference of the bottom surface portion 222*a* toward the distal end side in the axial direction. An outer circumferential surface 222*g* of the first cylindrical portion 222*f* is tapered slightly outward from the base end toward the distal end.

An outer diameter of the outer circumferential surface 222*g* is smaller than an inner diameter of the inner circumferential surface 220*f* of the side surface portion 220*b* of the case 220. A gap is formed between the outer circumferential surface 222*g* and the inner circumferential surface 220*f* of the side surface portion 220*b* to sandwich the distal end portion of the airtight member 225 which will be described below.

The second cylindrical portion 222*b* forms a side surface portion of the fixing frame 222 on the distal end side. A shape of the second cylindrical portion 222*b* is an annular shape connected to the distal end of the first cylindrical portion 222*f*. The second cylindrical portion 222*b* is fitted into the distal end portion of the side surface portion 220*b*.

The locking claw 222*e* that is locked to the locking portion 220*g* of the case 220 is formed on the second cylindrical portion 222*b*. For example, the locking claw 222*e* is elastically deformable in the radial direction and extends in the axial direction. A locking protrusion that protrudes outward in the radial direction is formed at the distal end of the locking claw 222*e* in the extending direction.

For example, in the example shown in FIGS. 47 and 48, as in the locking portion 220*g*, one or two locking claws 222*e* are provided at four locations that divide the second cylindrical portion 222*b* into approximately four equal portions in the circumferential direction.

The locking protrusion of the locking claw 222*e* penetrates into a hole of the locking claw 222*e* from the inside of the side surface portion 220*b*, and is locked to the inner surface of the locking portion 220*g*. Thus, the fixing frame 222 fitted into the case 220 is prevented from coming off in the axial direction.

As shown in FIG. 49, the flange portion 222*c* extends outward in the radial direction from the distal end of the side surface portion 220*b*. A shape of the flange portion 222*c* seen in the axial direction is an annular shape as shown in FIG. 49. An outer diameter of the flange portion 222*c* is equal to an outer diameter of the distal end frame 220*c* of the case 220.

In a state in which the fixing frame 222 is fitted into the case 220 and each of the locking claws 222*e* is locked to the locking portion 220*g*, the flange portion 222*c* is in contact with the distal end of the distal end frame 220*c*.

In this way, axial and circumferential positions of the fixing frame 222 with respect to the case 220 are fixed while the fixing frame 222 is fitted into the case 220.

The collar 223 is provided so as to be axially movable inside the side surface portion 220*b* of the case 220. In FIG.

49, the base end of the collar 223 is in contact with the bottom surface portion 220*a* of the case 220, and the collar 223 is disposed at a position on the most base end side in a movement range.

An exterior of the collar 223 is a cylindrical shape with a slightly smaller diameter than the inner circumferential surface 220*f* of the side surface portion 220*b*. A base end portion of the airtight member 225 which will be described below is inserted inside the collar 223. The base end portion of the airtight member 225 is fixed to the collar 223.

The collar 223 includes an outer cylinder portion 223*a* (a tubular portion), a locking plate 223*b*, a circular hole 223*h*, a square groove 223*i*, a guide 223*e*, a fitting claw 223*f*, and a pressing claw 223*g*.

The outer cylinder portion 223*a* is a cylinder having a slightly smaller diameter than the inner circumferential surface 220*f* of the side surface portion 220*b*. In the example shown in FIG. 49, the distal end of the outer cylinder portion 223*a* is aligned on the same plane orthogonal to the central axis Ai.

The distal end of the outer cylinder portion 223*a* crosses the display window 221*a* in the circumferential direction when seen from the outside within a range in which the collar 223 moves in the axial direction. A portion of the distal end of the outer cylinder portion 223*a* that crosses the display window 221*a* is referred to as a distal end edge portion 223*c*. However, the distal end edge portion 223*c* may protrude toward the distal end side from the distal end of the outer cylinder portion 223*a*, or may be recessed toward the base end side.

In the collar 223, the vicinity of the distal end edge portion 223*c* is colored with an appropriate color so that the operator can easily recognize it visually from the outside. For example, the entire collar 223 including the distal end edge portion 223*c* may be colored.

The locking plate 223*b* is a circular plate orthogonal to the central axis Ai. The locking plate 223*b* locks the base end portion of the airtight member 225 which will be described below. Particularly in this modified example, the airtight member 225 is locked to the locking plate 223*b* and is detachably fixed to the locking plate 223*b*.

The locking plate 223*b* is provided inside the outer cylinder portion 223*a* near the base end of the outer cylinder portion 223*a*.

Figure 50:
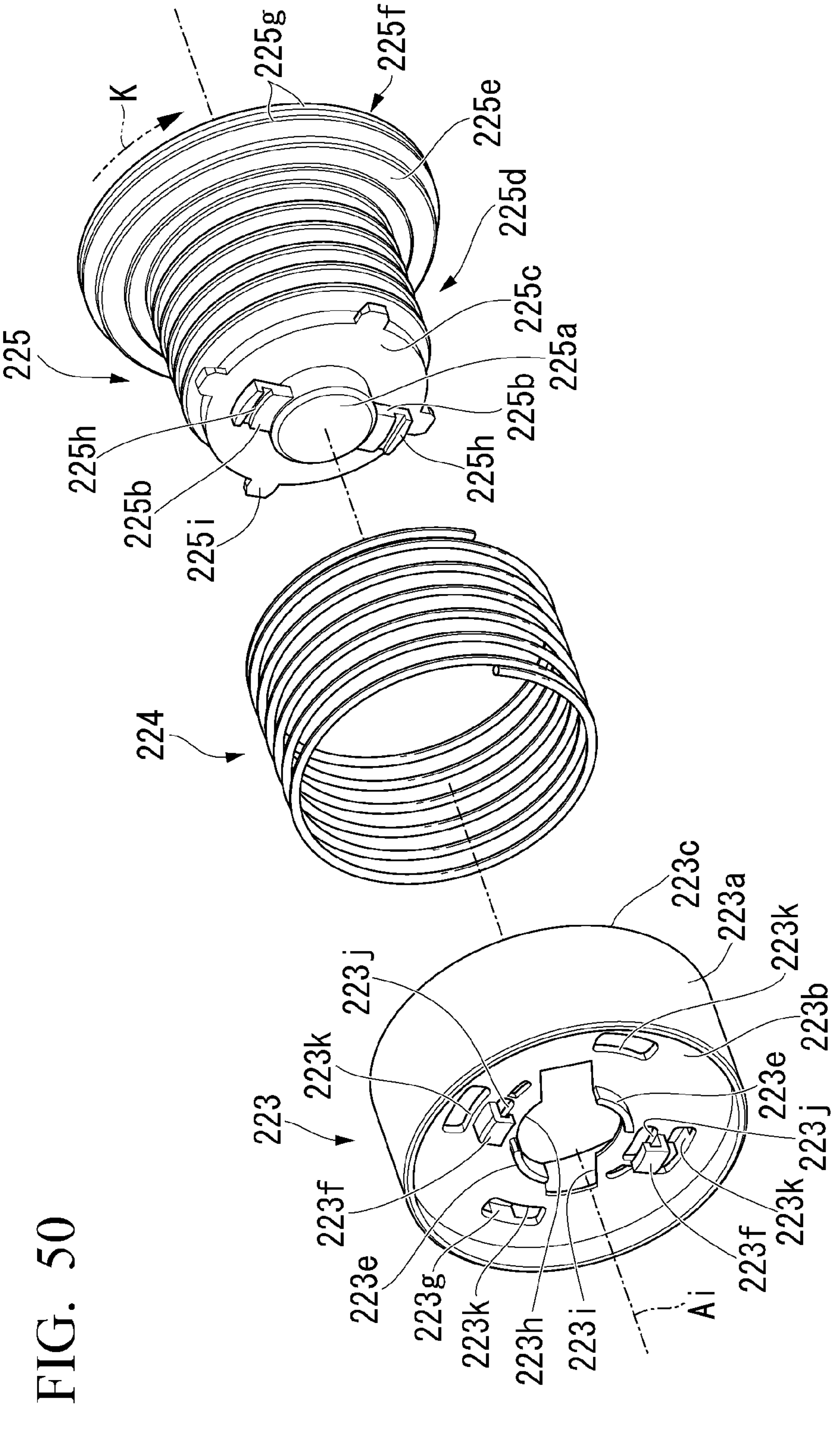
FIG. 50 is an exploded perspective view showing an example of a collar, a coil spring, and an airtight member in the modified example (the third modified example) of the air supply device.
Figure 51:
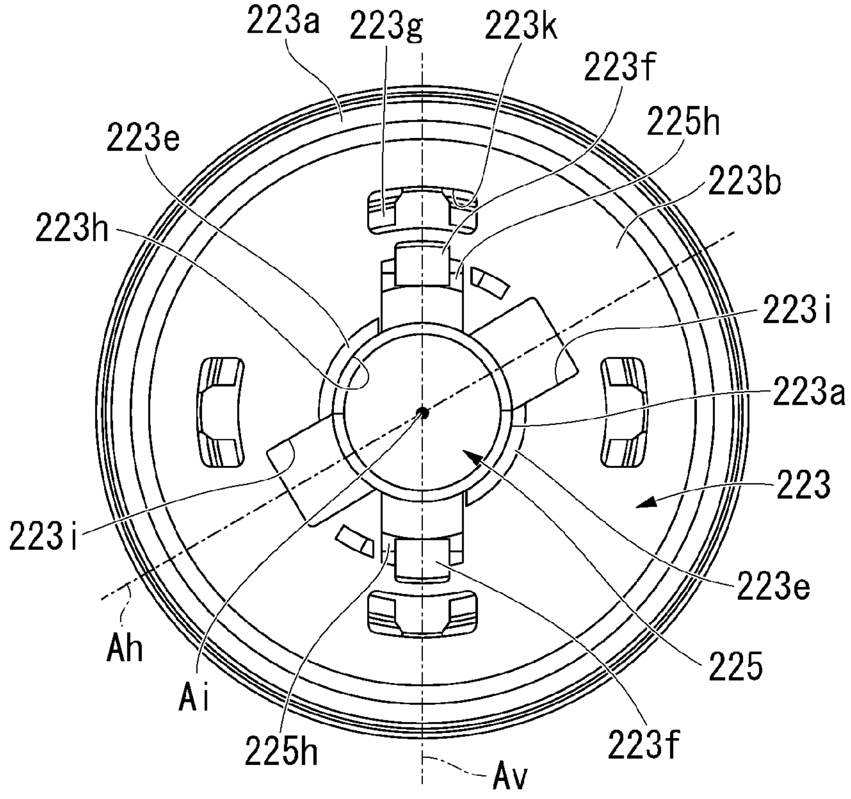
FIG. 51 is a schematic diagram showing a structure for fixing the airtight member to the collar in the modified example (the third modified example) of the air supply device.
Figure 52:
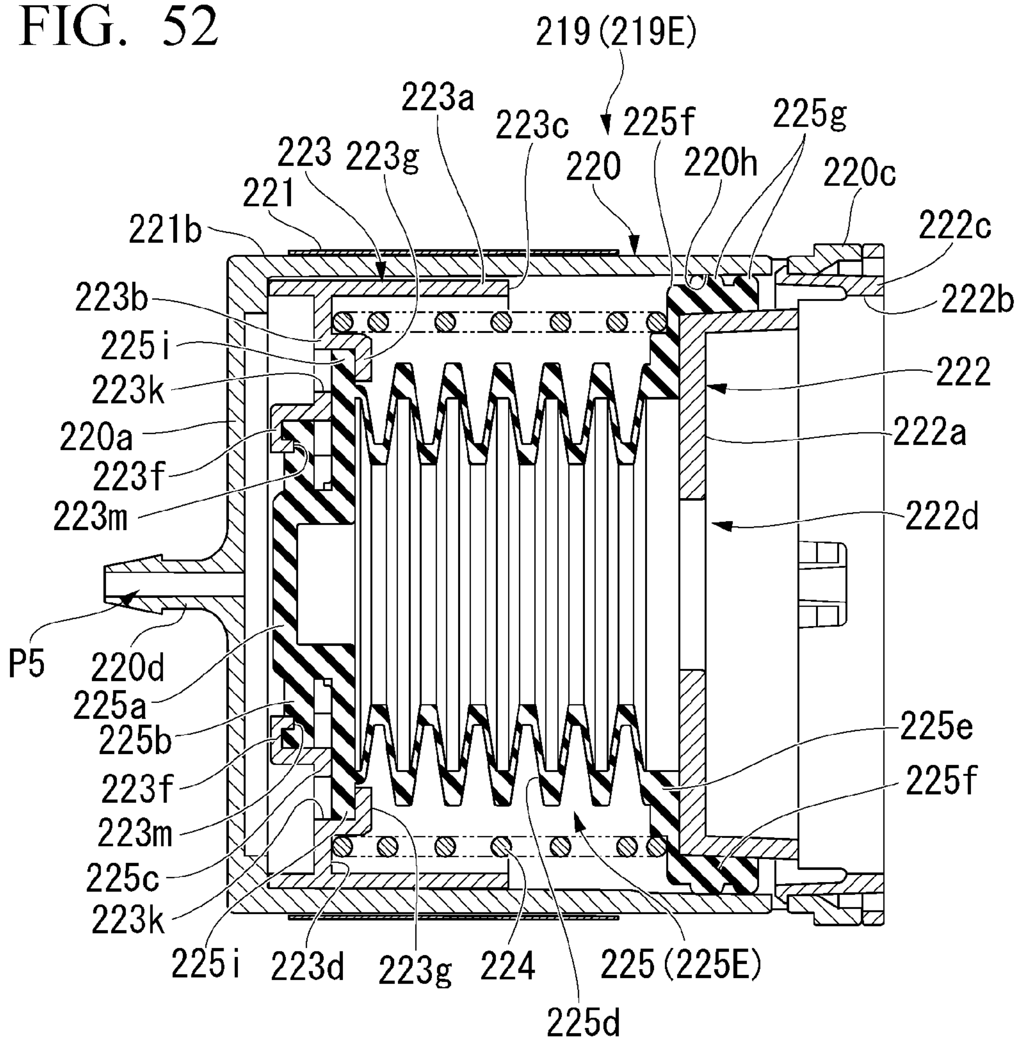
FIG. 52 is a cross-sectional view taken along line F52-F52 in FIG. 48.

FIG. 50 is an exploded perspective view showing an example of the collar, the coil spring, and the airtight member in the modified example (the third modified example) of the air supply device. FIG. 51 is a schematic diagram showing a structure for fixing the airtight member to the collar in the modified example (the third modified example) of the air supply device. FIG. 52 is a cross-sectional view taken along line F52-F52 in FIG. 48.

As shown in FIG. 50, a circular hole 223*h* passes through the center of the locking plate 223*b* in the thickness direction. The circular hole 223*h* is formed coaxially with the central axis Ai.

A pair of square grooves 223*i* are formed by partially cutting out the locking plate 223*b* along the circular hole 223*h*. The square grooves 223*i* face each other in the radial direction of the circular hole 223*h* with the center of the circular hole 223*h* interposed therebetween.

The arc-shaped guide 223*e* extends toward the base end side when seen in the axial direction at the inner circumferential portion of the circular hole 223*h* excluding each of the square grooves 223*i*.

As shown in FIG. 49, each of the guides 223*e* has a height that does not protrude to the base end side beyond the base end of the outer cylinder portion 223*a*.

The pressing claw 223*g* having a hook-shaped cross section that protrudes toward the distal end side and then bends toward the central axis Ai is provided on a locking surface 223*d* which is a surface of the locking plate 223*b* on the distal end side. A certain gap is formed between the distal end portion of the pressing claw 223*g* and the locking plate 223*b*.

In this modified example, since the collar 223 is formed by resin molding, a hole 223*k* for avoiding undercut passes through the locking plate 223*b* facing the distal end portion of the pressing claw 223*g*.

As shown in FIG. 51, one pressing claw 223*g* and one hole 223*k* are provided at each of four positions that divide the circumference around the central axis Ai into four equal portions.

As shown in FIG. 50, a pair of fitting claws 223*f* are provided on the base end side of the locking plate 223*b*.

As shown in FIG. 52, the fitting claw 223*f* has a hook-shaped cross section that protrudes toward the base end side and then bends toward the central axis Ai. In the fitting claw 223*f*, a fitting protrusion 223*m* that protrudes toward the distal end side in the axial direction is formed at the distal end portion of the hook. A gap into which a fitting protrusion 225*b* of the airtight member 225 which will be described below is fitted is formed between the fitting claw 223*f* and the locking plate 223*b*.

In this modified example, since the collar 223 is formed by resin molding, a hole 223*j* for avoiding undercut passes through the locking plate 223*b* facing the distal end portion of the fitting claw 223*f* in the protruding direction.

As shown in FIG. 51, one fitting claw 223*f* is provided at each of two positions facing each other in the radial direction with the central axis Ai interposed therebetween. Each of the fitting claws 223*f* is formed on an axis Av orthogonal to the central axis Ai. A pair of pressing claws 223*g* that face each other in the radial direction are disposed on the axis Av with each of the fitting claws 223*f* interposed therebetween.

A central axis Ah extending in a facing direction of each of the square grooves 223*i* is inclined clockwise in the drawing by 45° with respect to the axis Av.

As shown in FIG. 49, the airtight member 225 has a cup shape, as a whole, which opens to the distal end side in the axial direction and of which a length in the axial direction can be expanded and contracted. The airtight member 225 is sandwiched between the collar 223 and the fixing frame 222 inside the case 220.

The airtight member 225 is formed of a soft elastomer molded product.

For example, examples of a material of the airtight member 225 include silicone rubber, urethane rubber, nitrile rubber, and the like.

As shown in FIG. 50, the airtight member 225 includes a bottom plate portion 225*c* (a second fixing portion), a boss portion 225*a* (a second fixing portion), a fitting protrusion 225*b*, a bellows tube portion 225*d*, a flange portion 225*e*, and a sealing portion 225*f* (a first fixing portion).

The bottom plate portion 225*c* is a flat plate orthogonal to the central axis Ai, and is provided at the base end portion of the airtight member 225. On the outer circumferential portion of the bottom plate portion 225*c* when seen in the axial direction, engaging protrusions 225*i* protrude outward in the radial direction from four positions that divide the outer periphery into four equal portions in the circumferential direction.

As shown in FIGS. 49 and 52, each of the engaging protrusions 225*i* is inserted into a gap between the locking surface 223*d* of the collar 223 and the pressing claw 223*g*, and is engaged with the collar 223 in the axial direction.

As shown in FIG. 50, the boss portion 225*a* is formed such that a center portion of the bottom plate portion 225*c* bulges toward the base end side in the axial direction. An exterior of the boss portion 225*a* when seen in the axial direction is circular. The boss portion 225*a* is fitted into the circular hole 223*h* of the collar 223 and the inner circumferential surface of the guide 223*e* so as to be rotatable around the central axis Ai.

As shown in FIG. 52, the fitting protrusion 225*b* is a plate that protrudes from a side surface of the boss portion 225*a* in parallel to the bottom plate portion 225*c*. An amount of protrusion and a thickness of the fitting protrusion 225*b* are large enough to fit into a gap between the locking plate 223*b* and the fitting claw 223*f*.

A fitting groove 225*h* into which the fitting protrusion 223*m* of the pressing claw 223*g* is fitted is formed in a surface of the fitting protrusion 225*b* on the base end side.

The fitting groove 225*h* extends in the circumferential direction along an orbit in which the fitting protrusion 223*m* rotates around the central axis Ai.

The fitting protrusion 225*b* is provided at two locations facing each other in the radial direction with the central axis Ai interposed therebetween.

The bellows tube portion 225*d* extends from the outer circumferential portion of the bottom plate portion 225*c* excluding the engaging protrusion 225*i* toward the distal end side in the axial direction. An outer diameter of the bellows tube portion 225*d* on the outer side in the radial direction is smaller than a diameter of a circumference at which an end of the engaging protrusion 225*i* in the radial direction is located.

Here, with reference to FIG. 53, a detailed cross-sectional shape of the bellows tube portion 225*d* will be described.

Figure 53:
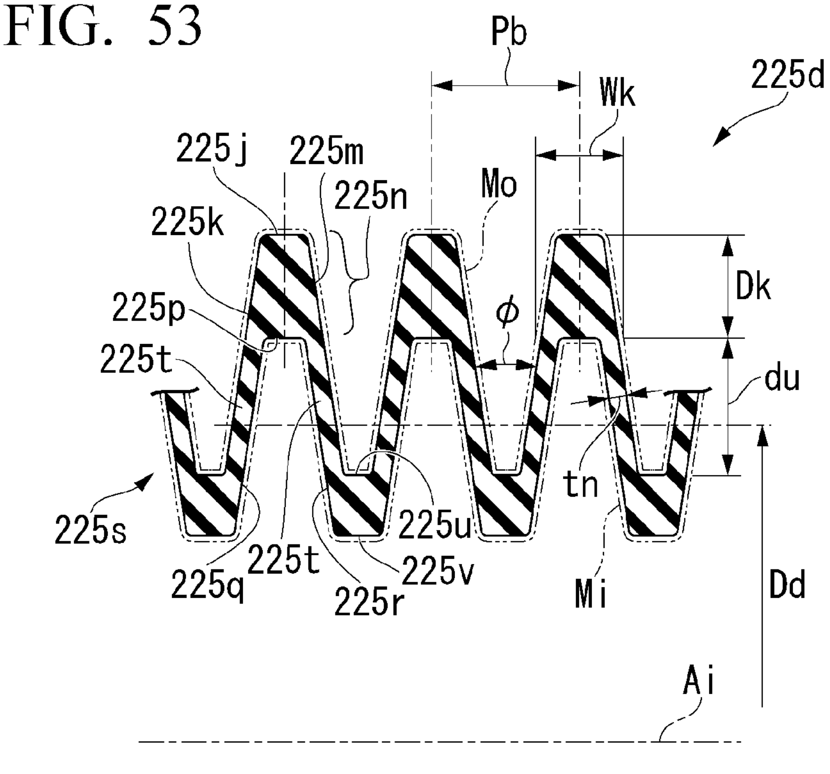
FIG. 53 is an enlarged view of an F53 portion in FIG. 49.

FIG. 53 is an enlarged view of an F53 portion in FIG. 52.

The bellows tube portion 225*d* shown in FIG. 53 has a shape in a natural state on which no external force is applied in the axial direction. Hereinafter, unless otherwise specified, the bellows tube portion 225*d* in the natural state will be described. Although the bellows tube portion 225*d* may be assembled into the pressure indicator 219 in a state in which it is more compressed than the natural state, in the following, an example in which the collar 223 is moved to the most base end side as shown in FIG. 49, and the bellows tube portion 225*d* is in the natural state will be described.

The bellows tube portion 225*d* has a tapered shape that is inclined with respect to a plane orthogonal to the central axis Ai, and has an annular thin portion 225*t* when seen in the axial direction. The thin portions 225*t* are disposed so that the inclination thereof alternates in the axial direction, and the adjacent thin portions 225*t* at the inner and outer circumferential portions are connected to each other.

They are connected by a bent portion 225*s* at the inner circumferential portion and by a thick portion 225*n* at the outer circumferential portion.

An outer circumferential surface of the bellows tube portion 225*d* is an uneven surface in which a first outer inclined surface 225*k*, a first outer surface 225*j*, a second outer inclined surface 225*m*, and a second outer surface 225*u* repeat in the axial direction.

The first outer inclined surface 225*k* is inclined outward in the radial direction as it goes from the base end side (the left side in the drawing) to the distal end side (the right side in the drawing) in the axial direction.

The first outer surface 225*j* is a cylindrical surface that extends from a radially outer end of the first outer inclined surface 225*k* toward the distal end side in the axial direction. The first outer surface 225*j* forms the outermost outer surface of the bellows tube portion 225*d*.

The second outer inclined surface 225*m* inclines inward in the radial direction from the distal end of the first outer surface 225*j* toward the distal end side.

The second outer surface 225*u* is a cylindrical surface that extends from the radially inner end of the second outer inclined surface 225*m* toward the distal end side in the axial direction.

The inner circumferential surface of the bellows tube portion 225*d* is an uneven surface in which a first inner inclined surface 225*q*, a first inner surface 225*p*, a second inner inclined surface 225*r*, and a second inner surface 225*v* repeat in the axial direction.

A distance between the first inner inclined surface 225*q* and the first outer surface 225*j* in the thin portion 225*t* is tn. The first inner inclined surface 225*q* also forms a surface of the bent portion 225*s* on the distal end side in the axial direction.

The first inner surface 225*p* forms the inner circumferential surface of the thick portion 225*n*. A distance between the first inner surface 225*p* and the first outer surface 225*j* in the radial direction is Dk.

The second inner inclined surface 225*r* is inclined inward in the radial direction from the distal end of the first inner surface 225*p* to the distal end side.

The second inner surface 225*v* is a cylindrical surface in the axial direction from the radially inner end of the second inner inclined surface 225*r*.

The thick portion 225*n* has an annular shape formed by rotating a trapezoidal cross section surrounded by the first outer inclined surface 225*k*, the first outer surface 225*j*, the second outer inclined surface 225*m*, and the first inner surface 225*p* around the central axis Ai.

A first width (a maximum thickness in the axial direction) of the thick portion 225*n* in the axial direction along the central axis Ai is Wk, and a second width (a distance between the first inner surface 225*p* and the first outer surface 225*j*) of the thick portion 225*n* in the radial direction orthogonal to the central axis Ai is Dk.

An angle formed by the adjacent thin portions 225*t* in a cross section including the central axis Ai is φ. A pitch of a bellows shape of the bellows tube portion 225*d* in the axial direction is defined as a pitch Pb of the center in the thickness direction of the thick portion 225*n* in a natural state in which the bellows tube portion 225*d* is not deformed by an external force.

The thick portion 225*n* in this modified example is formed for the purpose of curbing buckling of the thin portion 225*t* due to an external force directed inward in the radial direction from the outer circumferential portion. When the rigidity of the thick portion 225*n* is appropriate, collapsing deformation of the thick portion 225*n* in the radial direction due to an external force is curbed, and thus the thin portion 225*t* is less likely to buckle. For example, an average thickness of the thin portion 225*t* may be 0.3 mm or more and 0.7 mm or less.

For example, the first width Wk of the thick portion 225*n* in the axial direction is at least three times a thickness tn (an average thickness) of the thin portion 225*t*, and is more preferably ⅔ or less of the pitch Pb of the bellows tube portion 225*d*.

For example, it is more preferable that the second width Dk of the thick portion 225*n* in the radial direction is three times or more the thickness tn of the thin portion 225*t*. However, when Dk is made too large, resistance against an external force in the radial direction is not improved so much, and thus it is more preferable that Dk is set to about 3.1 mm or less, for example.

thin portion 225*t* and between the bent portion 225*s* and the thin portion 225*t*, the moldability is improved. Furthermore, molding is facilitated in that a molded product is less likely to be removed from the molds Mo and Mi during demolding.

[Table 1] below shows shape examples 1 to 3 of the bellows tube portion 225*d*.

In [Table 1], dimensions other than those described above are as follows.

Dd represents an average diameter of the bellows tube portion 225*d*. Dd is obtained from an average of the diameter of the first inner surface 225*p* and the diameter of the second inner surface 225*v*.

du is a depth of the valley portion formed by the thin portion 225*t*, that is, a distance in the radial direction from the first inner surface 225*p* to the second outer surface 225*u*.

TABLE 1

| | SHAPE EXAMPLE 1 | SHAPE EXAMPLE 2 | SHAPE EXAMPLE 3 |
|---|---|---|---|
| THICKNESS OF THIN PART tn[mm] | 0.5 | 0.7 | 0.7 |
| AVERAGE DIAMETER OF BELLOWS TUBE PART Dd[mm] | 26.5 | 26.5 | 26.5 |
| ANGLE OF VALLEY OF THIN PART ø[°] | 22.7 | 20.5 | 20.5 |
| DEPTH OF VALLEY AT OUTER PERIPHERY du[mm] | 3.2 | 4.1 | 4.1 |
| PITCH OF BELLOWS TUBE PART Pb[mm] | 4.3 | 4.3 | 4.3 |
| WIDTH OF THICK PART IN AXIAL DIRECTION J Wk[mm] | 2.5 | 2.3 | 2.3 |
| WIDTH OF THICK PART IN RADIAL DIRECTION J Dk[mm] | 3.0 | 3.0 | 3.0 |
| RUBBER HARDNESS (SHORE A) | A45 | A40 | A50 |

It is preferable that the angle φ between the thin portions 225*t* be as small as possible within a range in which moldability is not deteriorated. For example, the angle φ is measured by an angle between the second outer inclined surface 225*m* and the first outer inclined surface 225*k* that form a V-shaped concave portion. Therefore, the angle φ is an angle of a valley portion formed by the thin portion 225*t*.

Since the rigidity of the bent portion 225*s* does not significantly affect the buckling of the thin portion 225*t*, a width of the bent portion 225*s* in the axial direction may be thinner than the thick portion 225*n*. For example, a width of the second outer surface 225*u* in the axial direction may be zero. When the moldability does not deteriorate, a width of the second inner inclined surface 225*r* may be zero.

In this modified example, in the natural state of the airtight member 225, the first outer inclined surface 225*k* and the second outer inclined surface 225*m* are tapered surfaces having a common inclination in both the thick portion 225*n* and the thin portion 225*t*.

Similarly, the first inner inclined surface 225*q* and the second inner inclined surface 225*r* are tapered surfaces having a common inclination in both the bent portion 225*s* and the thin portion 225*t*.

Therefore, when the airtight member 225 is formed by resin molding, a shape of a mold Mo in which convex portions and concave portions each having a trapezoidal cross-sectional shape appear alternately in the axial direction is transferred to the outer circumferential surface of the airtight member 225. A shape of a mold Mi in which convex portions and concave portions each having a trapezoidal cross-sectional shape appear alternately in the axial direction is transferred to the inner circumferential surface of the airtight member 225.

In this way, since no steps or discontinuous inclined surfaces are formed between the thick portion 225*n* and the In shape examples 1 to 3, an appropriate shape of the thick portion 225*n* that curbs the buckling of the thin portion 225*t* is realized by changing the specifications according to the rubber hardness (Shore A).

In shape examples 1 to 3, Wk is 2.5 nm, 2.3 mm, and 2.3 mm, and tn is 0.5 mm, 0.7 mm, and 0.7 mm. That is, Wk/tn is 5.0, 3.3, and 3.3, respectively, and thus Wk is three times or more tn.

In shape examples 1 to 3, ⅔ of the pitch Pb is all 2.9, and thus Wk is all ⅔ or more of Pb.

In shape examples 1 to 3, Dk is all 3.0 nm, and three times of tn is 1.5 mm, 2.1 mm, and 2.1 mm, respectively. Therefore, Dk is three times or more of tn and is 3.1 mm or less.

As the average diameter Dd becomes larger, a drag force when the bellows tube portion 225*d* is contracted in the axial direction decreases, and the moldability is also improved. On the other hand, the rigidity in the radial direction that is required to curb buckling of the thin portion 225*t* in the radial direction increases.

The angle φ is preferably larger from the viewpoint of moldability. On the other hand, as φ increases, the drag force increases, and the required rigidity in the radial direction decreases.

As the valley depth du becomes deeper, the drag force decreases. On the other hand, the rigidity in the radial direction and the moldability are reduced.

When the pitch Pb of the bellows tube portion 225*d* is large, the drag force increases, and the rigidity in the radial direction decreases. On the other hand, the moldability is improved.

As the width Wk of the thick portion 225*n* in the axial direction becomes larger, the drag force increases. On the other hand, the rigidity in the radial direction and the moldability are improved.

As shown in FIG. 49, the flange portion 225*e* extends outward in the radial direction from the distal end of the bellows tube portion 225*d* in the axial direction. An outer diameter of the flange portion 225*c* is smaller than an inner diameter of the side surface portion 220*b* of the case 220, and is larger than an outer diameter of the coil spring 224 which will be described below.

The sealing portion 225*f* has a cylindrical shape that extends from the outer circumferential portion of the flange portion 225*e* toward the distal end side in the axial direction. The sealing portion 225*f* is sandwiched between the inner circumferential surface 220*f* of the side surface portion 220*b* and the outer circumferential surface 222*g* of the first cylindrical portion 222*f* of the fixing frame 222.

The inner circumferential surface of the sealing portion 225*f* is a cylindrical surface that can be brought into close contact with the outer circumferential surface 222*g*.

A projection claw 225*g* that protrudes outward in the radial direction and extends around the entire circumference of the outer circumferential surface is provided on the outer circumferential surface of the sealing portion 225*f*. In the example shown in FIG. 49, the protrusion claws 225*g* are formed one by one at two positions separated in the axial direction.

A distance in the radial direction between the inner circumferential surface of the sealing portion 225*f* and a top portion of the projection claw 225*g* is greater than a gap between the inner circumferential surface 220*f* and the outer circumferential surface 222*g*. Therefore, when the sealing portion 225*f* is sandwiched between the inner circumferential surface 220*f* and the outer circumferential surface 222*g*, the inner circumferential surface of the sealing portion 225*f* is in close contact with the first cylindrical portion 222*f* while the projection claw 225*g* is pressed in the radial direction. Thus, a gap between the distal end portion of the side surface portion 220*b* and the fixing frame 222 is airtightly and liquid tightly sealed.

The through hole 222*d* in the fixing frame 222 opens to the inside of the bellows tube portion 225*d*. Therefore, the inside of the bellows tube portion 225*d* communicates with the outside through the through hole 222*d*.

As shown in FIG. 50, the coil spring 224 is a compression coil spring. The coil spring 224 may be made of a metal or a resin material with excellent elasticity.

As shown in FIG. 49, an inner diameter of the coil spring 224 is larger than the outer diameter of the bellows tube portion 225*d*, and is large enough to surround the pressing claw 223*g* from the outside in the radial direction. Further, the outer diameter of the coil spring 224 is smaller than the inner diameter of the outer cylinder portion 223*a* of the collar 223, and approximately the same as the outer diameter of the bottom surface portion 222*a* of the fixing frame 222.

Therefore, each of end portions of the coil spring 224 in the axial direction is locked to the locking surface 223*d* of the collar 223 and the flange portion 225*e* of the airtight member 225, respectively. In this modified example, the flange portion 225*e* is held in the axial direction by the distal end of the coil spring 224 and the bottom surface portion 222*a*.

Since the coil spring 224 is compressed when the collar 223 moves to the distal end side in the axial direction, the collar 223 is biased to the base end side in the axial direction.

A spring constant of the coil spring 224 is set so that the pressure inside the case 220 can be displayed on the display window 221*a* according to an amount of movement of the collar 223.

The coil spring 224 is not limited to a coil spring as long as it can bias the collar 223 to the base end side. As the coil spring 224, an appropriate elastic member that generates a biasing force may be used.

Here, a fixing structure between the distal end portion of the airtight member 225 and the collar 223 will be described.

As shown in FIGS. 49 and 51, in the airtight member 225 fixed to the collar 223, the boss portion 225*a* is inserted into the circular hole 223*h* and the guide 223*e*, and is positioned in the radial direction.

As shown in FIG. 52, each of the engaging protrusions 225*i* is inserted in a space between the locking surface 223*d* and the pressing claw 223*g*. Further, each of the fitting protrusions 225*b* is fitted into a space between the surface of the locking plate 223*b* on the base end side and the fitting claw 223*f*. Thus, the locking plate 223*b* is fixed to the distal end portion of the airtight member 225 while being sandwiched between each of the engaging protrusions 225*i* and each of the fitting protrusions 225*b*.

In order to form such a fixing structure, in FIG. 50, the airtight member 225 is inserted into the inside of the coil spring 224 and the inside of the outer cylinder portion 223*a* of the collar 223 while being rotated by 45° around the central axis Ai in a direction of an arrow K shown by a two-dot chain line. At this time, when the bottom plate portion 225*c* comes into contact with the locking surface 223*d*, the fitting protrusion 225*b* passes through the inside of the square groove 223*i*. At this time, the surface of the fitting protrusion 225*b* on the distal end side reaches approximately the same position as a surface of the locking plate 223*b* on the base end side.

In this state, when the airtight member 225 is rotated by 45° in a direction opposite to the arrow K, the boss portion 225*a* is guided along the circular hole 223*h* and the guide 223*e*.

As the rotation progresses, each of the engaging protrusions 225*i* engages with the pressing claw 223*g*, and each of the fitting protrusions 225*b* engages with the fitting claw 223*f*. In particular, since the fitting groove 225*h* into which the fitting protrusion 223*m* is fitted is formed in the fitting protrusion 225*b*, a rotation center of the airtight member 225 during rotation of the airtight member 225 is easily aligned with the central axis Ai.

In this way, the airtight member 225 is fixed to the collar 223 by engagement between the members due to parallel movement in the axial direction and rotational movement in the circumferential direction relative to the collar 223. Since the airtight member 225 is made of a soft elastomer, an engagement position is stabilized by friction with the collar 223 after engagement.

According to this modified example, the airtight member 225 can be fixed without using screws, adhesives, or the like, which reduces component costs and facilitates manufacturing.

Next, the motion of this modified example will be described focusing on the motion and action of the pressure indicator 219.

Figure 54:
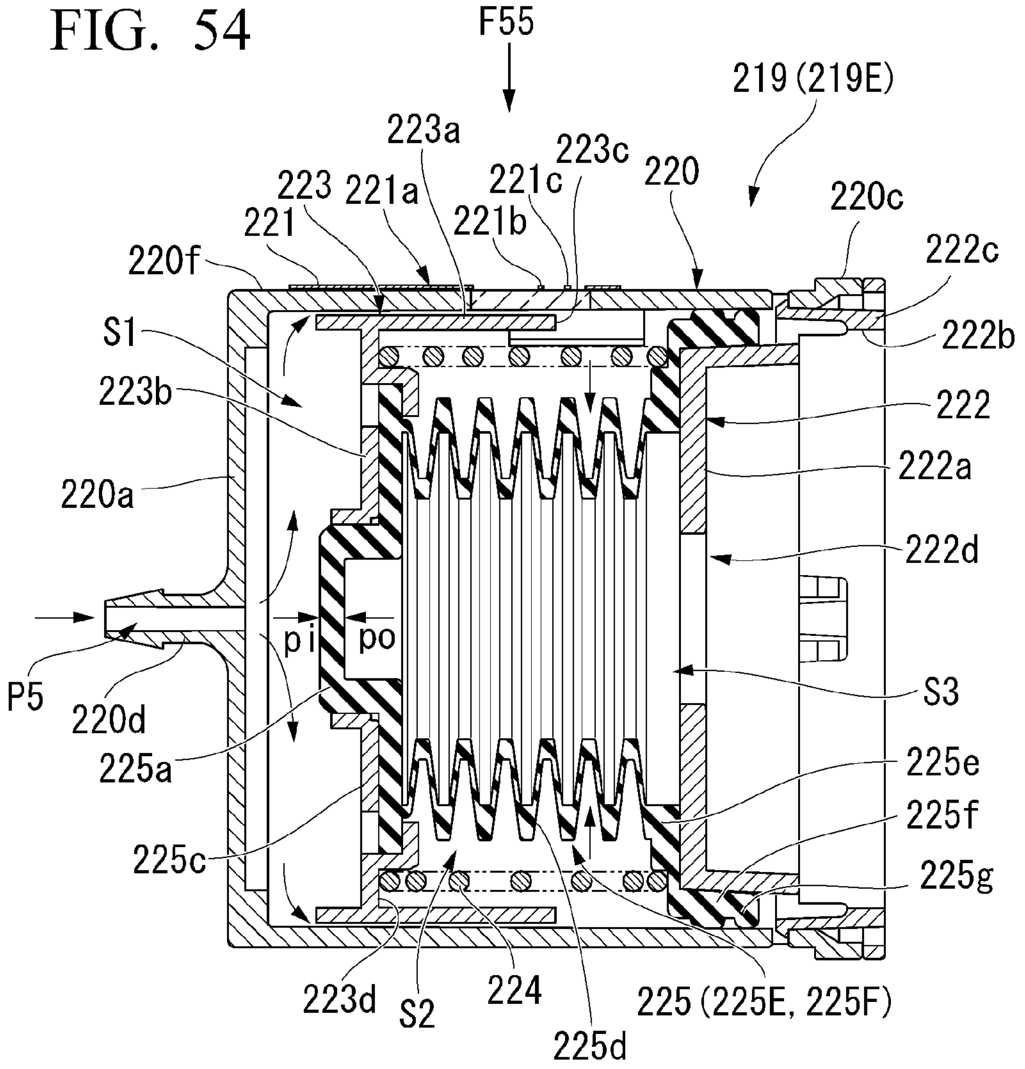
FIG. 54 is a schematic cross-sectional view showing an operation of the pressure indicator in the modified example (the third modified example) of the air supply device.
Figure 55:
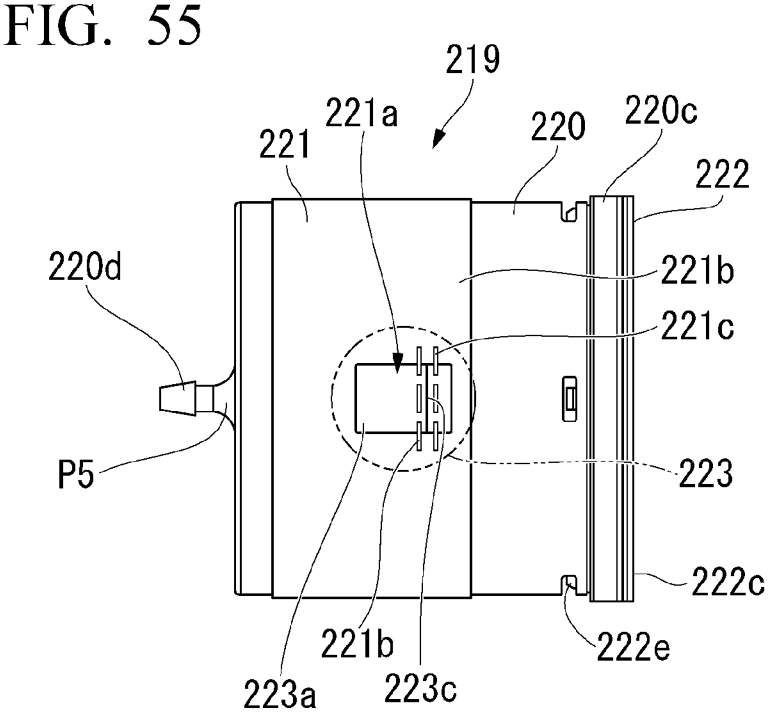
FIG. 55 is a view seen from F55 in FIG. 54.

FIG. 54 is a schematic cross-sectional view showing an operation of the pressure indicator in the modified example (the third modified example) of the air supply device. FIG. 55 is a view from F55 in FIG. 54.

When the air supply operation of the manual air supply mechanism 211 is performed by the operator, air flows into the case 220 through the third conduit P5 as indicated by an arrow shown in FIG. 54. The case 220 is airtightly sealed by the airtight member 225 fixed to the distal end portion of the side surface portion 220*b* by the fixing frame 222.

An internal space of the case 220 sealed by the airtight member 225 is roughly divided into a first space S1 on the base end side of the locking plate 223*b* of the collar 223 and a second space S2 on the distal end side. However, the first space S1 and the second space S2 communicate with each other through various gaps. Examples of various gaps include, for example, a gap between the outer cylinder portion 223*a* and the side surface portion 220*b*, and gaps in the holes 223*j* and 223*k* that are not closed by the airtight member 225.

On the other hand, a third space S3 inside the airtight member 225 does not communicate with the first space S1 and the second space S2, and communicates with the outside through the through hole 222*d*.

Therefore, an internal pressure pi of the air flowing into the first space S1 and the second space S2 acts on the inner circumferential surface of the case 220 and the outer circumferential surface of the airtight member 225.

The airtight member 225 has the bellows tube portion 225*d* that can easily expand and contract in the axial direction. In the bellows tube portion 225*d*, the rigidity in the axial direction is smaller than the rigidity in the radial direction. The bellows tube portion 225*d* contracts in the axial direction according to an axial resultant force of the internal pressure pi acting through the boss portion 225*a* and the locking plate 223*b*. Thus, the collar 223 moves to the distal end side in the axial direction.

The collar 223 moves in the axial direction so that the resultant force of the internal pressure pi in the axial direction is balanced with a resultant force of the biasing force of the coil spring 224 and the atmospheric pressure po acting in the axial direction. Thus, the first space S1 expands and the second space S2 contracts.

The position of the collar 223 and the internal pressure pi within the case 220 can be correlated one-to-one by investigating a relationship between the spring constant of the coil spring 224 and the internal pressure of the case 220 in advance.

In this modified example, since the distal end edge portion 223*c* of the collar 223 is visible through the display window 221*a*, the operator can visually recognize the position of the collar 223 representing the internal pressure pi by the position of the distal end edge portion 223*c*.

For example, as shown in FIG. 55, when the distal end edge portion 223*c* is between the first scale line 221*b* and the second scale line 221*c*, the operator can know that the internal pressure of the fixing balloon 3 is in an appropriate state.

The first space S1 and the second space S2 in this modified example have the same function as the first space Sa of the pressure adjustment part 217A in the second modified example. Therefore, the pressure indicator 219 is an example of a diameter-expanded portion of which a volume changes in the second modified example.

In this modified example, by providing the thick portion 225*n* in the bellows tube portion 225*d*, the rigidity in the radial direction of the airtight member 225 is greater than the rigidity in the axial direction.

The action of the thick portion 225*n* will be described with reference to a comparative example.

Figure 56:
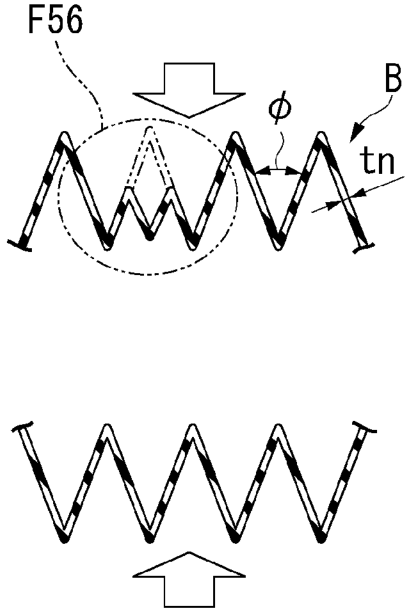
FIG. 56 is a schematic cross-sectional view showing a comparative example of the airtight member having a bellows structure deformed by pressure.

FIG. 56 is a schematic cross-sectional view showing a comparative example of the airtight member having a bellows structure deformed by pressure.

A bellows tube portion B of the comparative example shown in FIG. 56 is formed of an elastomer film having the same thickness tn as the thin portion 225*t* of the bellows tube portion 225*d* of this modified example. The bellows tube portion B is bent into an inverted V shape at a mountain fold portion on the outer circumference. However, since the bellows tube portion B is formed with a uniform thickness, the thick portion as in this modified example is not formed in the outer circumferential portion of the bellows tube portion B.

The mountain fold portion in FIG. 56 is schematically drawn in an inverted V shape with no roundness within the bend. However, in order to improve the moldability of the bellows tube portion B, a corner portion at the distal end of the mountain fold portion is rounded and an average thickness is maintained.

Since the bellows tube portion B has low rigidity in the radial direction at the outer circumferential portion, when the internal pressure of the second space S2 acts in the radial direction, the mountain fold portion of the outer circumferential portion buckles inward and becomes a valley fold, as shown at an F56 portion. Thus, the rigidity of the bellows tube portion B in the radial direction increases, and thus it is difficult for the collar 223 to move to the distal end side. Furthermore, since the bellows tube portion B is bent inward, the volume of the second space S2 is expanded, which also reduces the internal pressure pi.

As a result, an amount of movement of the collar 223 no longer indicates the accurate internal pressure pi.

On the other hand, in this modified example, since the thick portion 225*n* is formed, the bellows tube portion 225*d* is not buckled and deformed inward, and thus the pressure indicator 219 can display an accurate pressure.

Even when the pressure indicator 219 can accurately display the pressure, the pressure display may not be able to be read accurately according to a viewing direction of the operator.

Figure 57:
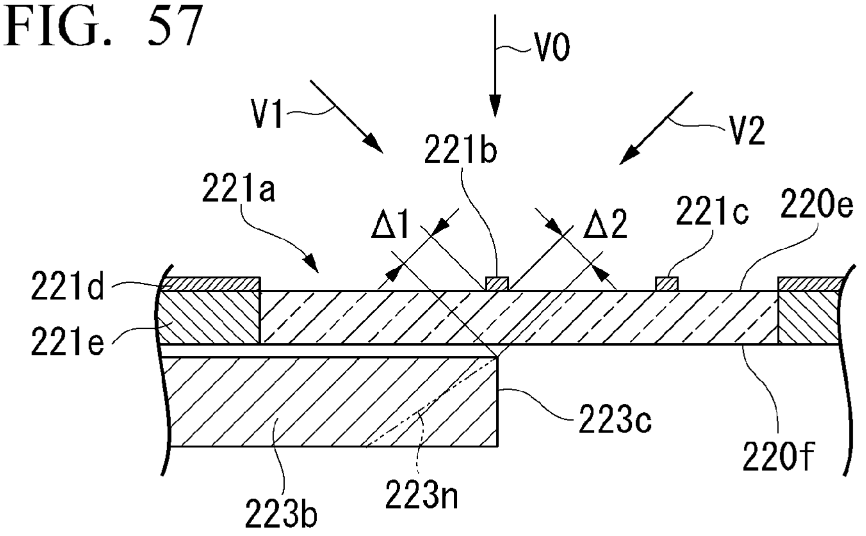
FIG. 57 is a schematic cross-sectional view showing a reading error in the pressure indicator in the modified example (the third modified example) of the air supply device.

FIG. 57 is a schematic cross-sectional view for describing a reading error in the pressure indicator in the modified example (the third modified example) of the air supply device.

FIG. 57 shows a cross section along the axial direction in a state in which the distal end edge portion 223*c* has moved to the position of the first scale line 221*b*.

When the viewing direction of the operator is indicated by an arrow V0 that coincides with the radial direction, the operator can accurately read that the distal end edge portion 223*c* has reached the first scale line 221*b*.

For example, when the viewing direction of the operator is indicated by an arrow V1 that is inclined to the base end side with respect to the radial direction, the distal end edge portion 223*c* appears to be located on the base end side by Δ1 up to the first scale line 221*b*. Similarly, when the viewing direction of the operator is indicated by an arrow V2 that is inclined to the distal end side with respect to the radial direction, the distal end edge portion 223*c* appears to be located on the distal end side by Δ2 up to the first scale line 221*b*.

In this modified example, as shown in FIG. 45, the grip 215 and the manual air supply mechanism 211 are disposed in an inverted V shape. Thus, in the standard operation state, the central axis Ai substantially coincides with the right-left direction of the operator. The display window 221*a* is elongated in the axial direction along the central axis Ai, and the distal end edge portion 223*c* within the display window 221*a* extends in a direction orthogonal to the central axis Ai. Therefore, the distal end edge portion 223*c* extends in the up-down direction of the operator's visual field in front of the operator in the standard operation state.

Therefore, when the operator reads the pressure, the operator arranges the display window 221*a* in the center in front of his/her body so that it can be easily seen. Thus, the viewing direction of the operator becomes the direction of the arrow V0.

At this time, even when the arrow V0 is inclined in the circumferential direction with respect to a normal direction of the side surface portion 220*b*, since the viewing direction is only inclined in a direction in which the distal end edge portion 223*c* extends, the reading error for the distal end edge portion 223*c* does not occur.

On the other hand, a configuration in which the axial direction of the pressure indicator 219 is placed in the up-down direction of the visual field of the operator, or in which the distal end edge portion 223*c* moves in the up-down direction can be conceivable.

In this case, in the standard operation state, even when the display window is disposed in front of the operator, the operator will not be able to see the arrow V0 in the viewing direction unless he or she looks at the display window from directly above. Generally, in the standard operation state, since the left hand $H_L$. and the right hand $H_R$ are located considerably below the operator's face, the viewing direction of the operator is guided in the directions of arrows V1 and V2, for example.

As a result, the reading error by the operator becomes large, and the action as in this modified example cannot be obtained.

The overtube 201 having the air supply device 210C of this modified example is the same as the overtube 201 except that it includes the air supply device 210C instead of the air supply device 210 of the overtube 201 according to the third embodiment. Therefore, according to this modified example, as in the third embodiment, it is possible to provide an overtube for an endoscope that reduces the load on the patient and allows a smooth operation of the endoscope.

Particularly, according to this modified example, a pressure indicator 219 which is an example of a diameter-expanded portion of which a volume changes, like the pressure adjustment part 217, is provided instead of the pressure adjustment part 217 in the second modified example. Therefore, this modified example has the same action as the second modified example.

Further, according to this modified example, the pressure indicator 219 displays the pressure inside the case 220 according to the position of the distal end edge portion 223*c* with respect to the first scale line 221*b* and the second scale line 221*c*. Thus, the operator can determine when the air supply operation should be stopped, in consideration of the resistance feeling of the manual air supply mechanism 211 and the pressure display in the display window 221*a*. As a result, the loss of the amount of air supply is further reduced.

According to this modified example, since the bellows tube portion 225*d* of the airtight member 225 has the thick portion 225*n*, the airtight member 225 smoothly expands and contracts in the axial direction without collapsing in the radial direction. Thus, the correspondence between the internal pressure pi and the position of the distal end edge portion 223*c* seen from the display window 221*a* becomes accurate.

According to this modified example, in the standard operation state, since the distal end edge portion 223*c* extends in the up-down direction of the view field of the operator, even when the operator's line of sight is inclined from directly above the display window 221*a* to the circumferential direction, the reading error for the pressure display is reduced.

The pressure indicator 219 in the air supply device 210C is an example of a pressure indicator that is connected to the first conduit, has a flow path that has a flow path cross-sectional area that is larger than that of the first conduit, and displays the pressure of the first conduit.

The first space S1 in the pressure indicator 219 forms a flow path through which air flows, and has a flow path cross-sectional area larger than that of the first conduit P1.

In the pressure indicator 219, the case 220 is an example of a casing in which a display window 221*a* through which the inside thereof can be seen is provided at at least a portion thereof. In the pressure indicator 219, the collar 223 is an example of a moving member that moves within the casing according to the pressure inside the casing, and of which a moving position can be observed from the display window.

In the pressure indicator 219, the first scale line 221*b* and the second scale line 221*c* are examples of reference scales that are formed on or around the display window, and indicate pressure according to the position of the moving member.

The airtight member 225 in the pressure indicator 219 is an example of a sealing member that airtightly seals an opening formed at the end portion of the casing in the moving direction of the moving member.

The sealing portion 225*f* of the airtight member 225 is an example of a first fixing portion that is airtightly fixed to the end portion of the casing. The bellows tube portion 225*d* of the airtight member 225 is an example of a bellows tube portion that extends from the first fixing portion toward the moving member and has a bellows shape that is expandable and contractible in the moving direction on the side surface.

The boss portion 225*a* and the bottom plate portion 225*c* of the airtight member 225 are examples of a second fixing portion that closes the distal end of the bellows tube portion in the extending direction and is fixed to the moving member.

The thin portion 225*t* of the airtight member 225 is an example of an inclined surface portion that forms a part of a side surface of the bellows tube portion and is disposed in an inverted V shape that is tapered toward the outside in the radial direction in a cross section including a central axis of the bellows tube portion.

The thick portion 225*n* of the airtight member 225 is an example of a thick portion that is formed to be thicker than the average thickness of the inclined surface portion and airtightly closes the outer circumferential portions of the inclined surface portions forming an inverted V shape.

The main body portion 212 included in the air supply device 210C is an example of a main body portion that includes a pressure indicator and connected to a manual pump.

The grip 215 is an example of a gripping portion that extends in a direction intersecting a central axis of the manual pump connected to the main body portion and is disposed to form an inverted V shape with the central axis.

In the main body portion 212, the central axis of the manual pump and the extending direction of the gripping portion are each at an acute angle with respect to the moving direction of the moving member, and the display window is located between the manual pump and a grip position of the gripping portion in the moving direction.

Fourth Modified Example

A modified example (a fourth modified example) of the air supply device used in place of the air supply device 210 in the overtube 201 of the third embodiment will be described.

As shown in FIG. 17, an air supply device 210D of this modified example can be used in place of the air supply device 210 of the overtube 201.

Figure 58:
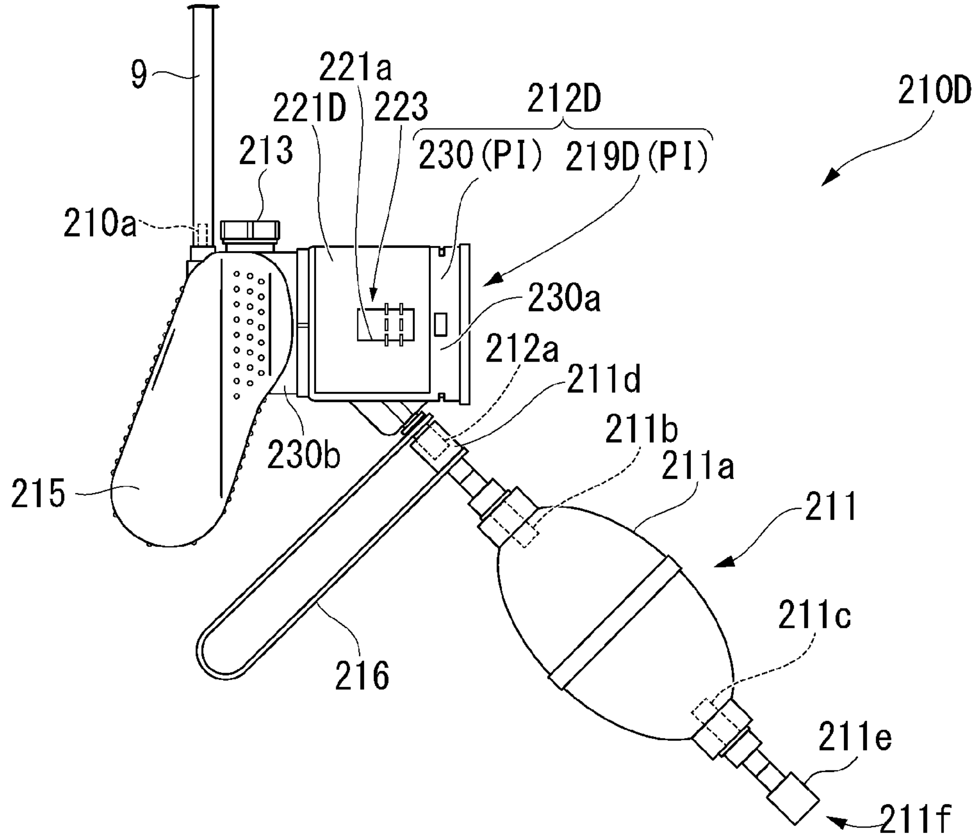
FIG. 58 is a schematic front view showing a modified example (a fourth modified example) of the air supply device used in the overtube for an endoscope according to the third embodiment of the present invention.
Figure 60:
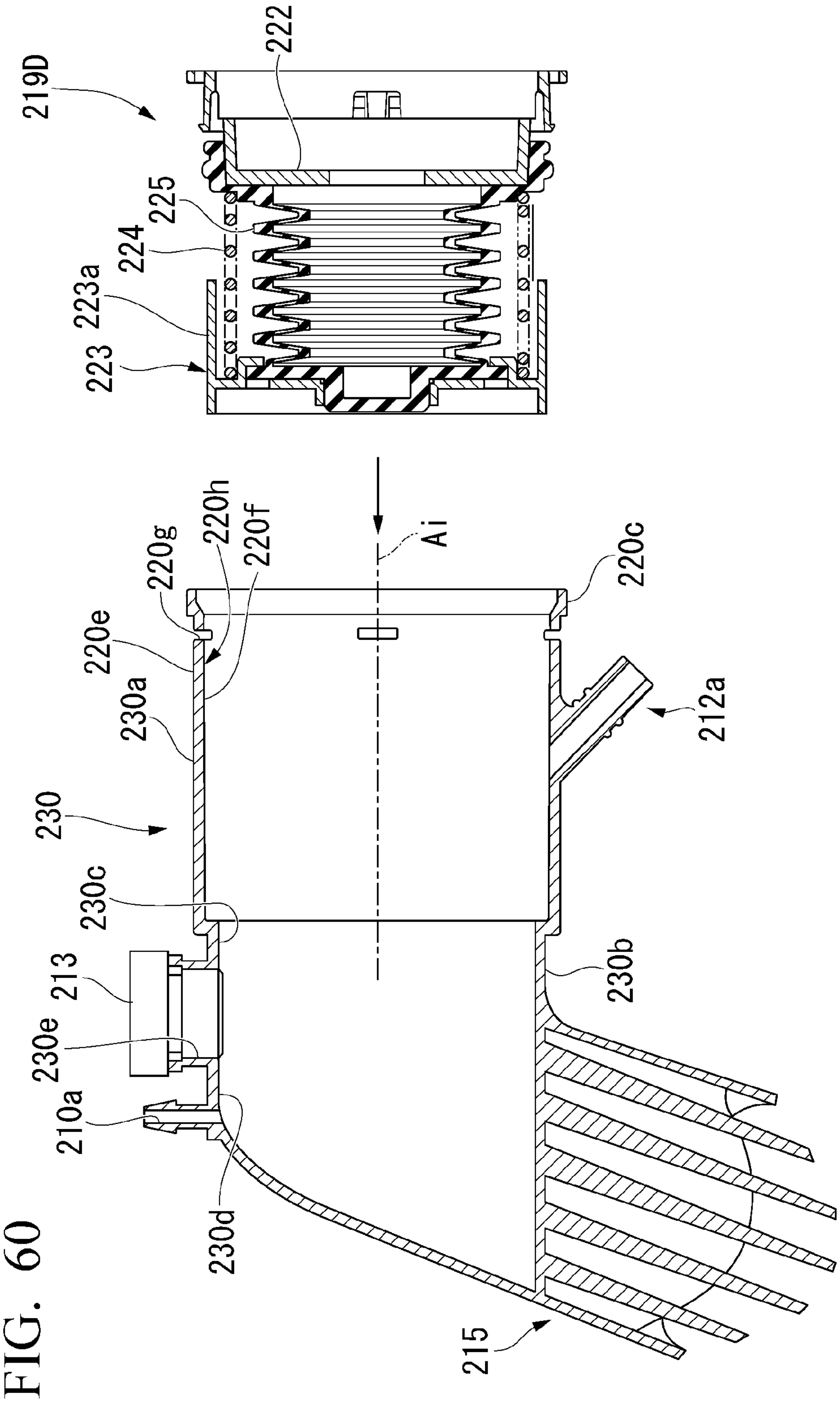
FIG. 60 is a schematic cross-sectional view showing an exploded state of the modified example (the fourth modified example) of the air supply device.
Figure 61:
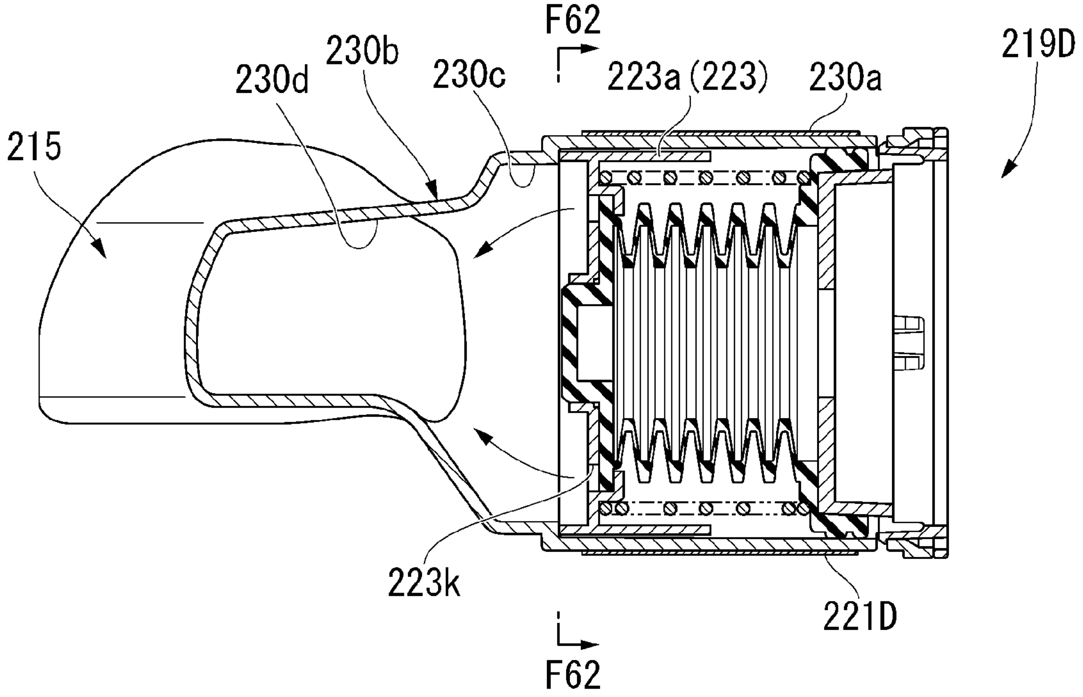
FIG. 61 is a cross-sectional view taken along line F61-F61 in FIG. 59.
Figure 62:
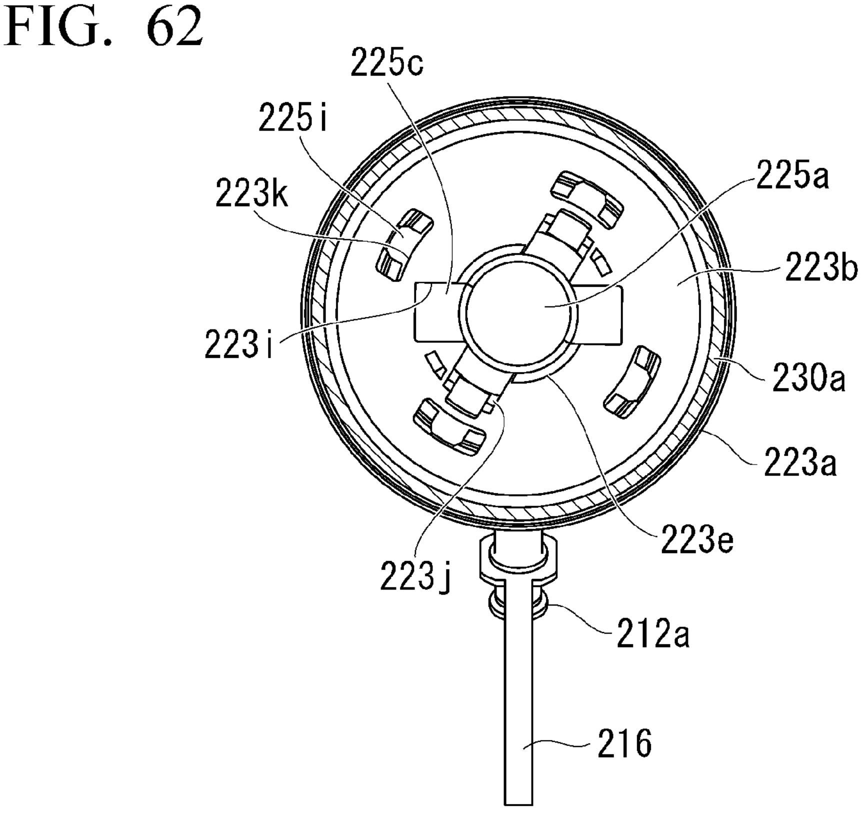
FIG. 62 is a cross-sectional view taken along line F62-F62 in FIG. 61.

FIG. 58 is a schematic front view showing the modified example (the fourth modified example) of the air supply device used in the overtube for an endoscope according to the third embodiment of the present invention. FIG. 60 is a schematic cross-sectional view showing an exploded state of the modified example (the fourth modified example) of the air supply device. FIG. 61 is a cross-sectional view taken along line F61-F61 in FIG. 59. FIG. 62 is a cross-sectional view taken along line F62-F62 in FIG. 61.

As shown in FIG. 58, the air supply device 210D includes a main body portion 212D instead of the main body portion 212 of the air supply device 210.

The main body portion 212D includes a pressure display part 219D, a main body case 230, and a display window forming member 221D.

In the following, differences from the third embodiment and the third modified example will be mainly described.

Figure 59:
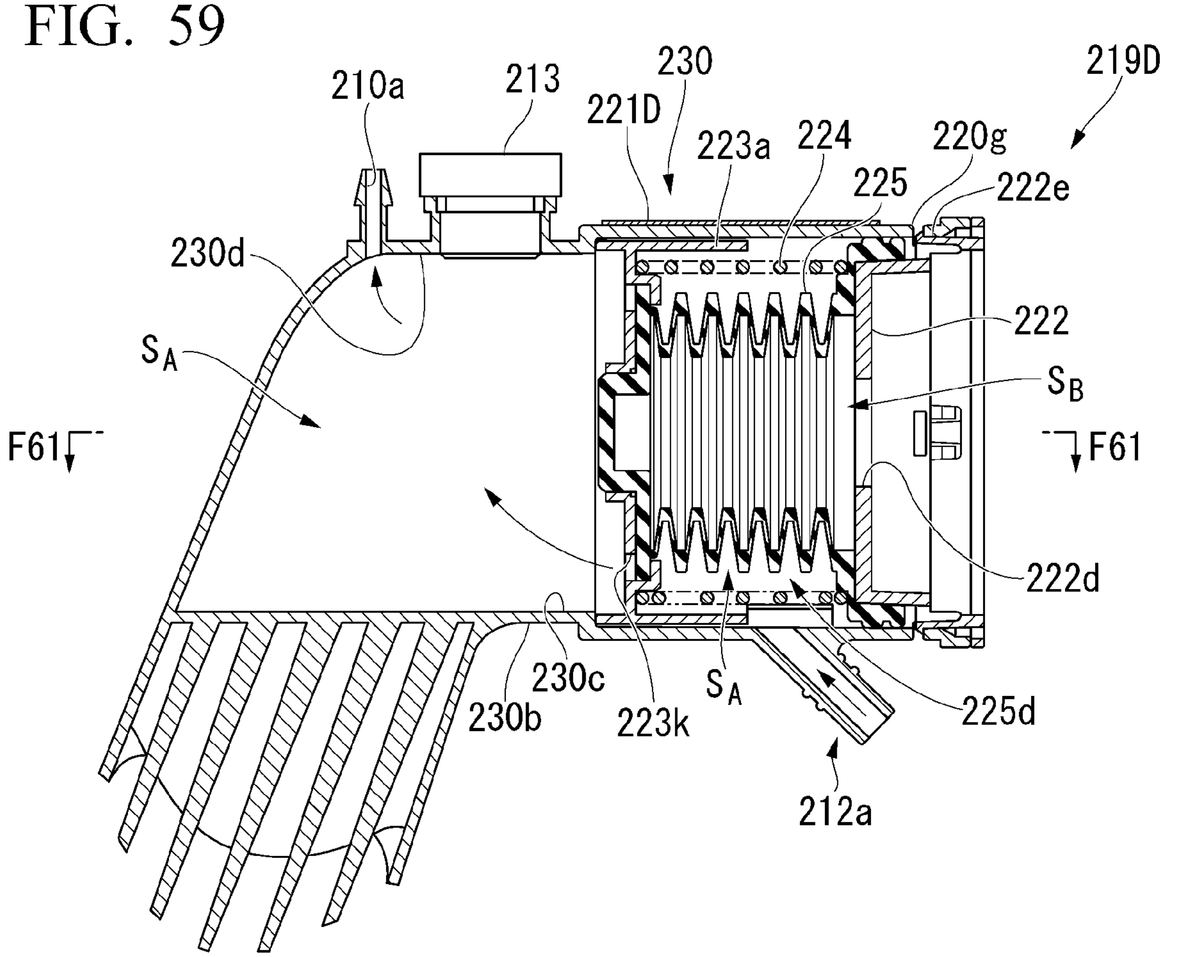
FIG. 59 is a schematic cross-sectional view showing an internal structure of the modified example (the fourth modified example) of the air supply device.

As shown in FIG. 59, the pressure display part 219D is the same as the pressure indicator 219 in the third modified example, except for the case 220.

The main body case 230 has the same exterior as that in which the casing 218 and the side surface portion 220*b* of the case 220 in the third modified example are integrated.

Like the case 220 in the third modified example, the main body case 230 has light transmittance at least in a region overlapping a portion in which the display window 221*a* is formed by the display window forming member 221D which will be described below. Thus, the main body case 230 may partially have a portion that does not have light transmittance. In the following, an example in which the main body case 230 is entirely made of a transparent resin material will be described.

The main body case 230 includes a grip 215, a relief valve 213, a connection tube 212*a*, and an air supply tube 210*a*, as in the third modified example.

Furthermore, the main body case 230 includes an accommodation portion 230*a* and a buffer portion 230*b* therein.

The accommodation portion 230*a* accommodates the pressure display part 219D. The accommodation portion 230*a* has the same shape as the side surface portion 220*b* of the case 220 in the third modified example, except that it protrudes to the outside of the connection tube 212*a* which is the same as the casing 218 in the third modified example.

Hereinafter, a central axis of a cylindrical portion of the accommodation portion 230*a* will be referred to as the central axis Ai, as in the third modified example. The same applies to the axial direction, the radial direction, and the circumferential direction with respect to the central axis Ai.

The connection tube 212*a* in this modified example opens inside the accommodation portion 230*a* at a position in which it is not closed by the movement of the collar 223 in the pressure display part 219D.

An opening at the distal end portion of the accommodation portion 230*a* is formed by the distal end frame 220*c* as in the side surface portion 220*b*. A locking portion 220*g* is formed at the distal end portion of the accommodation portion 230*a*, as in the side surface portion 220*b*.

The outer circumferential surface of the accommodation portion 230*a* is an outer circumferential surface 220*e* that is the same as the side surface portion 220*b*. The display window forming member 221D that is substantially the same as the display window forming member 221 is attached on the outer circumferential surface 220*e* of the accommodation portion 230*a*.

The display window forming member 221D is the same as the display window forming member 221 in the third modified example, except that it is provided in a shape that avoids the connection tube 212*a* protruding from the accommodation portion 230*a*. Although the shape that avoids the connection tube 212*a* is not particularly limited, for example, in the example shown in FIG. 58, a length of a portion thereof from the display window 221*a* toward the connection tube 212*a* is shorter than the display window forming member 221.

The buffer portion 230*b* in which a flow path cross-sectional area wider than the flow path cross-sectional area of the connection tube 212*a* is formed is provided at the base end portion of the accommodation portion 230*a*.

The buffer portion 230*b* retains a certain volume or more of air flowing in from the connection tube 212*a* due to the air supply operation of the operator in a state in which the pressure is reduced.

The buffer portion 230*b* has an opening 230*c* formed at a connection portion with the accommodation portion 230*a*. The opening 230*c* is open in the axial direction. The opening 230*c* has a cylindrical shape of which a diameter is smaller than that of the inner circumferential surface 220*f* of the accommodation portion 230*a* and is also smaller than that of the outer cylinder portion 223*a* of the collar 223.

The pressure display part 219D is inserted into the accommodation portion 230*a*. As shown in FIGS. 59 and 61, the fixing frame 222 in the pressure display part 219D is locked to the locking portion 220*g* of the accommodation portion 230*a* by the locking claw 222*e* that is the same as in third modified example. Thus, the axial and circumferential positions of the pressure display part 219D with respect to the accommodation portion 230*a* are fixed.

In such an assembled state, the collar 223 can move inside the accommodation portion 230*a* in the axial direction, as in the third modified example.

As shown in FIG. 61, the buffer portion 230*b* has an inner circumferential surface 230*d* of which a flow path cross-sectional area decreases as it goes away from the accommodation portion 230*a* in the axial direction.

As shown in FIG. 60, the inner circumferential surface 230*d* extends inside the grip 215. A mounting portion 230*e* of the relief valve 213 and an air supply tube 210*a* are open at an upper portion of the inner circumferential surface 230*d* in the drawing.

Figure 63:
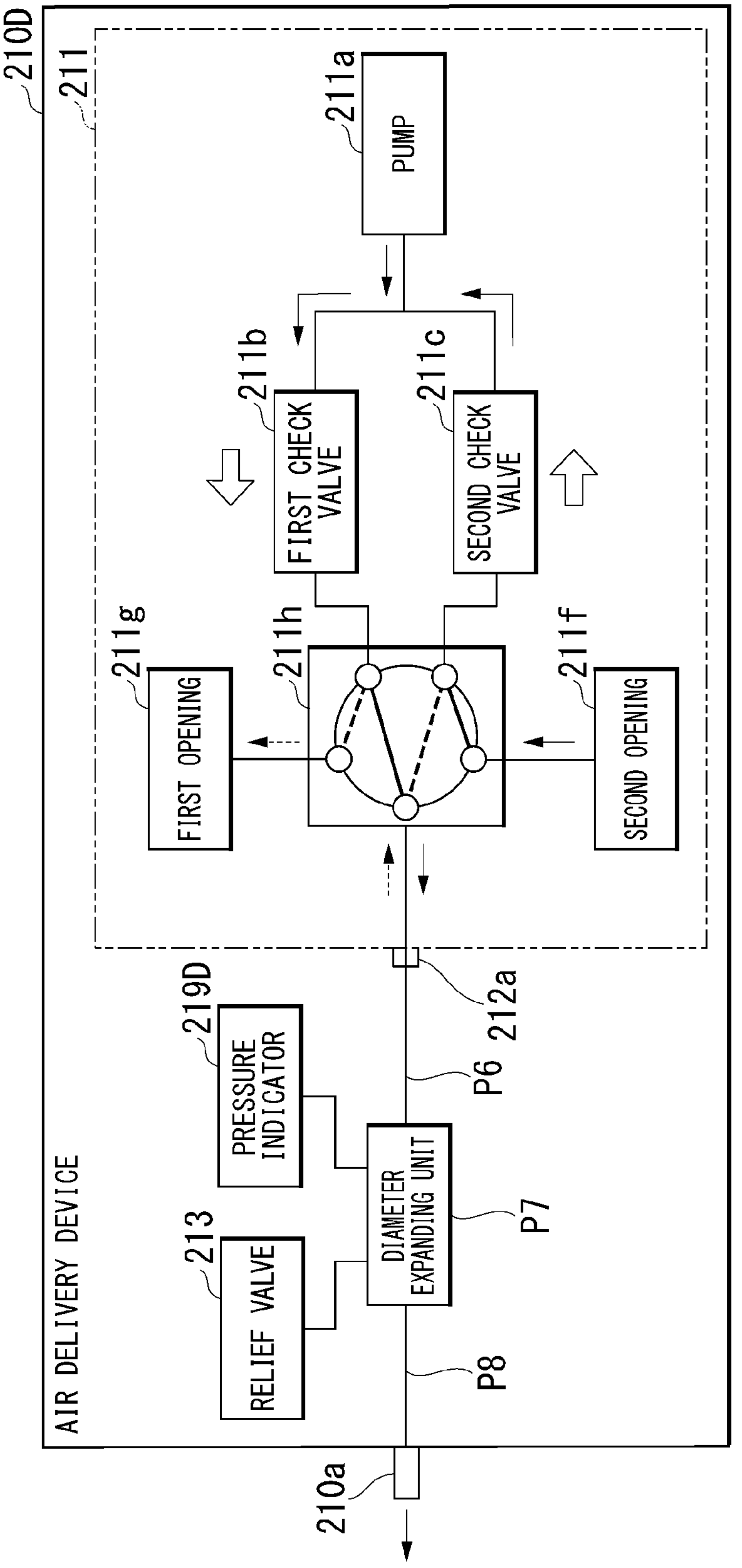
FIG. 63 is a block diagram showing the modified example (the fourth modified example) of the air supply device.
Figure 64:
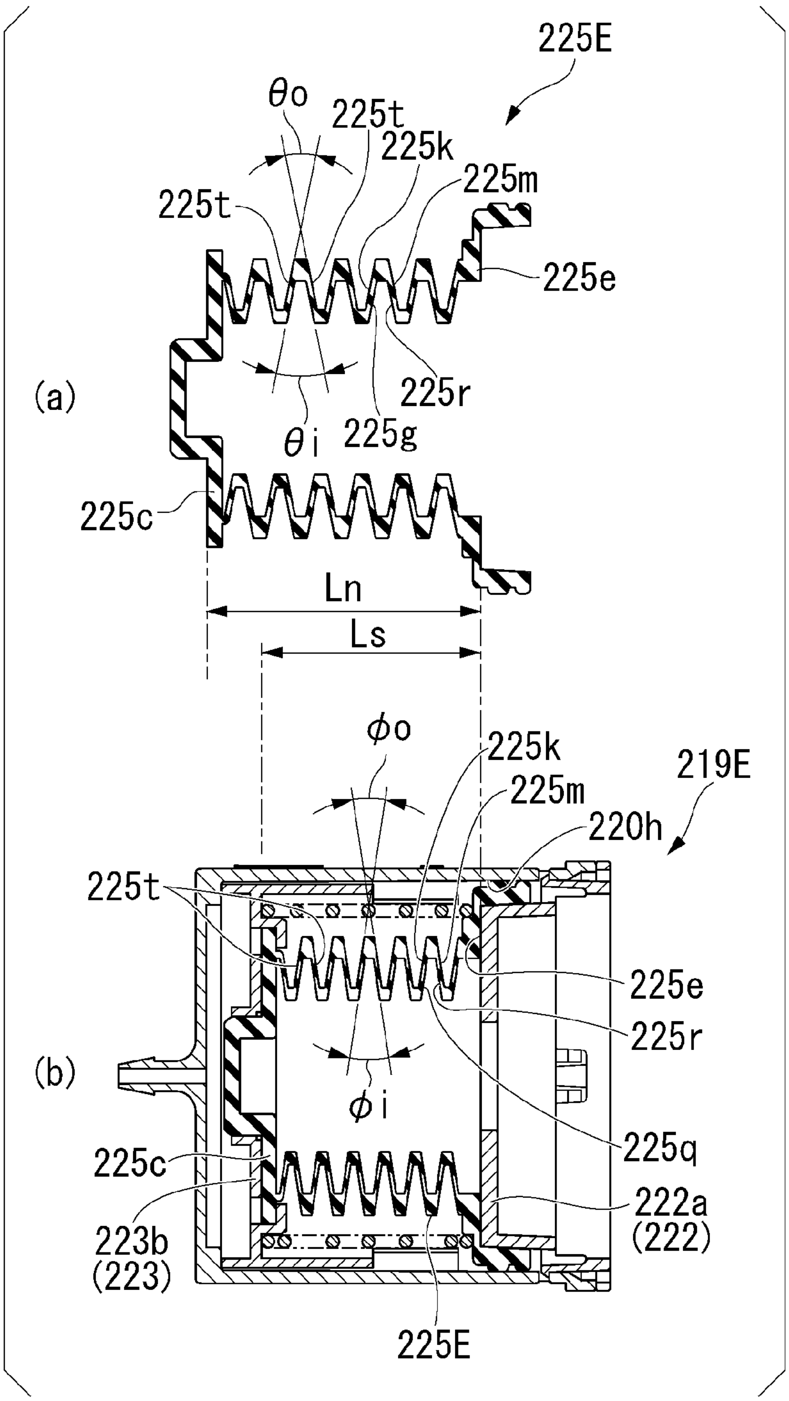
FIG. 64 is a schematic cross-sectional view showing an example of the airtight member used in a modified example (a fifth modified example) of the air supply device used in the overtube for an endoscope according to the third embodiment of the present invention.

As shown in FIG. 62 to 64, when the collar 223 of the pressure display part 219D is seen from inside the buffer portion 230*b*, as in the third modified example, the locking plate 223*b* has a gap between the outer cylinder portion 223*a* and the accommodation portion 230*a*, and a gap that is not covered by the engaging protrusion 225*i* in each of the holes 223*k*. These gaps allow a space surrounded by the accommodation portion 230*a* and the outer circumferential portion of the airtight member 225 and a space inside the buffer portion 230*b* to communicate with each other.

The airtight member 225 in the pressure display part 219D seals an internal space of the main body case 230 on the distal end side of the accommodation portion 230*a*. Thus, the inside of the main body case 230 is divided into a first space $S_A$ surrounded by the main body case 230 and the bellows tube portion 225*d*, and a second space $S_B$ inside the airtight member 225.

Air flows into the first space $S_A$ from the connection tube 212*a* by the air supply operation of the operator.

The second space SF communicates with the external air through the through hole 222*d* and is maintained at atmospheric pressure.

A volume of each of the first space $S_A$ and the second space $S_B$ changes as the collar 223 moves and the airtight member 225 expands and contracts due to the internal pressure of the first space $S_A$.

With such a configuration, as indicated by an arrow in FIG. 59, the air flowing into the connection tube 212*a* enters the first space $S_A$ outside the bellows tube portion 225*d* inside the accommodation portion 230*a*, the air passes through the gap between the holes 223*k* or the gap outside the outer cylinder portion 223*a*, and is directed toward the first space $S_A$ within the buffer portion 230*b*. The air flowing into the buffer portion 230*b* moves the collar 223 in the axial direction according to the internal pressure of the first space $S_A$, and some of the air is exhausted to the outside of the main body case 230 through one or both of the air supply tube 210*a* and the relief valve 213.

The distal end edge portion 223*c* of the collar 223 displays the internal pressure of the first space $S_A$ in the display window 221*a* of the display window forming member 221D, as in the third modified example.

Therefore, the accommodation portion 230*a*, the buffer portion 230*b*, and the pressure display part 219D form a pressure indicator P1 (refer to FIG. 58) that is the same as that in the third modified example.

The internal flow path in the main body case 230 can be schematically shown as in the block diagram of FIG. 63.

FIG. 63 is a block diagram showing the modified example (the fourth modified example) of the air supply device.

As shown in FIG. 63, the first space $S_A$ forms a diameter-expanded portion P7 having a larger flow path cross-sectional area than that of the first conduit P6 formed by the connection tube 212*a*. A volume of the diameter-expanded portion P7 changes according to the internal pressure.

The relief valve 213 and the air supply tube 210*a* are connected to the diameter-expanded portion P7. The air supply tube 210*a* in this modified example forms a second conduit P8 having a flow path cross-sectional area smaller than that of the diameter-expanded portion P7.

The configuration of this modified example corresponds to replacing the diameter-expanded portion P4 in the first modified example with the diameter-expanded portion P7 of which the volume changes.

The overtube 201 having the air supply device 210D of this modified example is the same as the overtube 201 except that it includes the air supply device 210D instead of the air supply device 210 of the overtube 201 according to the third embodiment. Therefore, according to this modified example, as in the third embodiment, it is possible to provide an overtube for an endoscope that reduces the load on the patient and allows a smooth operation of the endoscope.

In particular, according to this modified example, since the pressure indicator P1 that is the same as the pressure indicator 219 in the third modified example is provided, pressure can be displayed as in the third modified example. Therefore, this modified example has the same action as in the third modified example.

According to this modified example, as in the first modified example, since the relief valve 213 is provided in the diameter-expanded portion P7 of which the volume changes, it has the same action as in the first modified example.

Further, according to this modified example, in the main body case 230, the side surface portion 220*b* and the casing 218 in the third modified example are integrated. Therefore, compared to the third modified example, the number of components is reduced, and thus the component costs and assembly costs are reduced.

Since no conduit is particularly provided inside the main body case 230 to form a flow path, a structure thereof is simpler than that of the third modified example.

Fifth Modified Example

A modified example (a fifth modified example) of the air supply device used in place of the air supply device 210 in the overtube 201 of the third embodiment will be described.

As shown in FIG. 17, an air supply device 210E of this modified example can be used in place of the air supply device 210 of the overtube 201.

As shown in FIG. 45, the air supply device 210E includes a pressure indicator 219E instead of the pressure indicator 219 of the third modified example.

As shown in FIG. 49, the pressure indicator 219E is the same as the pressure indicator 219, except that it includes an airtight member 225E (a sealing member, a pressing member) instead of the airtight member 225 of the third modified example.

In the following, differences from the third embodiment and the third modified example will be mainly described.

FIG. 64 is a schematic cross-sectional view showing an example of an airtight member used in the modified example (the fifth modified example) of the air supply device used in the overtube for an endoscope according to the third embodiment of the present invention. (a) in FIG. 64 is a cross-sectional view showing a shape of the airtight member 225E in a natural state in which no external force acts in the axial direction. Similarly, (b) is a cross-sectional view showing a state in which the airtight member 225E is mounted in the pressure indicator 219E.

As shown in FIG. 64, the airtight member 225E in this modified example has the same configuration as the airtight member 225. However, in the natural state, a length (an outer dimension) Ln from the bottom plate portion 225*c* to the flange portion 225*e* in the axial direction is longer than the maximum distance (an inner dimension) Ls from the locking plate 223*b* to the bottom surface portion 222*a* in the pressure indicator 219E.

Thus, in the state in which the airtight member 225E is mounted in the pressure indicator 219E, the airtight member 225E is compressed in the axial direction.

When the airtight member 225E is compressed in the axial direction, an angle formed by the adjacent thin portions 225*t* is shallower than that in the natural state. For example, as shown in FIG. 64(*a*), in the thin portion 225*t* forming a mountain shape protruding toward the outer circumference, it is assumed that an angle between the first outer inclined surface 225*k* and the second outer inclined surface 225*m* is θo, and an angle between the first inner inclined surface 225*q* and the second inner inclined surface 225*r* is θi.

The angles θo and θi are set to appropriate angles that do not cause a mold to be caught during molding. For example, it is more preferable that the angles θo and θi are equal to each other, but they may be different from each other.

As the angles θo and θi become larger, the molding becomes easier. For example, it is preferable that the angles θo and θi are 200 or more.

As shown (b) in FIG. 64, in the same angle when the airtight member 225E is mounted, an angle between the first outer inclined surface 225*k* and the second outer inclined surface 225*m* is φo (however, φ0<θ0), and an angle between the first inner inclined surface 225*q* and the second inner inclined surface 225*r* is pi (however, φi<θi).

As described in the third modified example, as an angle φ corresponding to φo and φi becomes smaller, the rigidity of the bellows tube portion 225*d* in the radial direction is improved.

In this modified example, since the airtight member 225E is molded in a shape in which an angle between the thin portions 225*t* is large, the moldability of the airtight member 225E is improved.

In this modified example, in the state in which the airtight member 225E is mounted in the pressure indicator 219E, the airtight member 225E is compressed in the axial direction. The angle between the thin portions 225*t* becomes smaller than in the natural state, and the rigidity in the radial direction increases. Thus, like the third modified example, the pressure indicator 219E can display accurate pressure.

The airtight member 225E is compressed in the axial direction, and a drag force against movement of the collar 223 increases slightly due to an elastic restoring force caused by the deformation. However, since the internal pressure of the case 220 and the movement position of the collar 223 are correlated with each other in a state in which the airtight member 225E is deformed, the pressure indicator 319E can also accurately display the pressure.

The overtube 201 having the air supply device 210E of this modified example is the same as the overtube 201, except that it includes the air supply device 210E instead of the air supply device 210 of the overtube 201 according to the third embodiment. Therefore, according to this modified example, as in the third embodiment, it is possible to provide an overtube for an endoscope that reduces the load on the patient and allows a smooth operation of the endoscope.

In particular, according to this modified example, as in the third modified example, the pressure can be displayed accurately, and the moldability of the airtight member 225E is significantly improved. Thus, the airtight member 225E can be manufactured at low cost.

Sixth Modified Example

A modified example (a sixth modified example) of the air supply device used in place of the air supply device 210 in the overtube 201 of the third embodiment will be described.

As shown in FIG. 17, an air supply device 210F of this modified example can be used in place of the air supply device 210 of the overtube 201.

As shown in FIG. 45, the air supply device 210F includes a pressure indicator 219F instead of the pressure indicator 219 of the third modified example.

Figure 65:
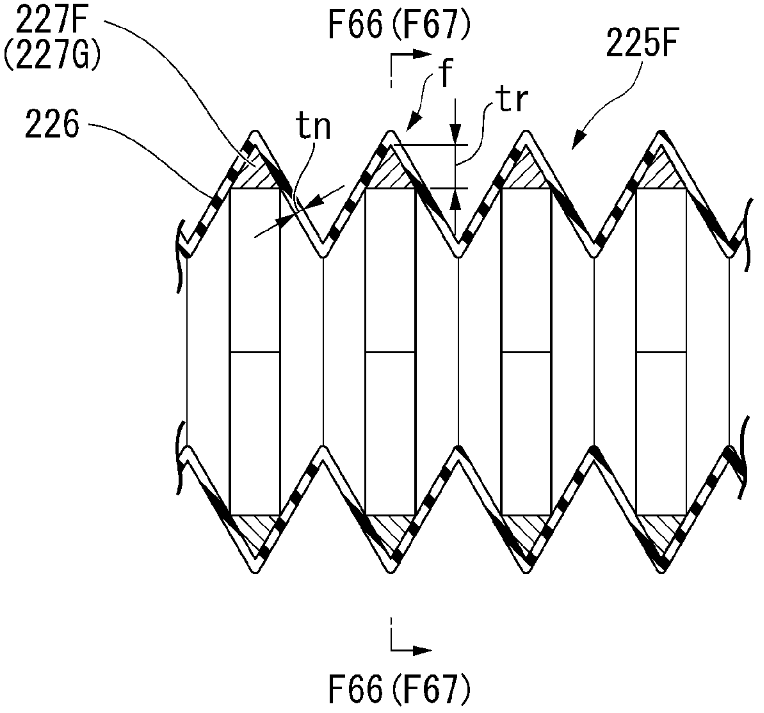
FIG. 65 is a schematic cross-sectional view showing an example of the airtight member used in a modified example (a sixth modified example) of the air supply device used in the overtube for an endoscope according to the third embodiment of the present invention.

The pressure indicator 219F is the same as the pressure indicator 219, except that it includes an airtight member 225F (a sealing member, a pressing member) and a reinforcing member 227F shown in FIG. 65 instead of the airtight member 225 of the third modified example.

Figure 66:
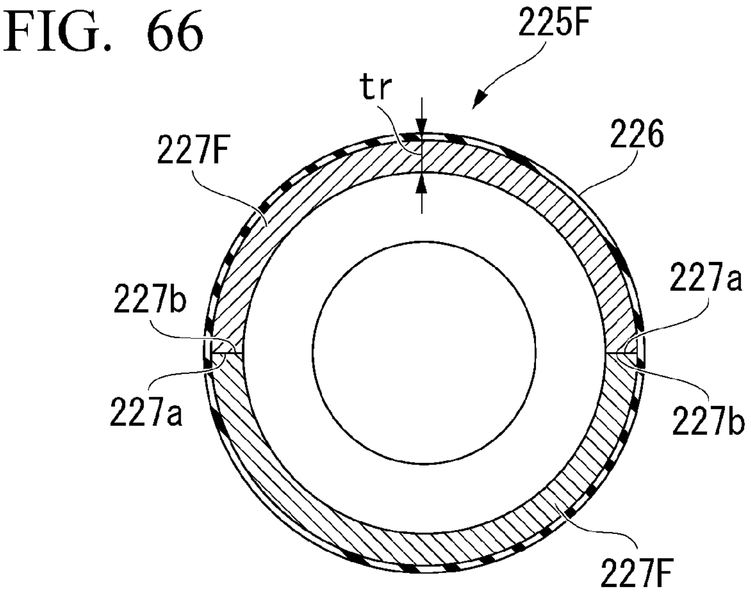
FIG. 66 is a cross-sectional view taken along line F66-F66 in FIG. 65.

FIG. 65 is a schematic cross-sectional view showing an example of an airtight member used in the modified example (the sixth modified example) of the air supply device used in the overtube for an endoscope according to the third embodiment of the present invention. FIG. 66 is a cross-sectional view taken along line F66-F66 in FIG. 65.

Hereafter, differences from the third embodiment and the third modified example will be mainly described.

As shown in FIG. 65, the airtight member 225F is the same as the airtight member 225, except that it includes a bellows tube portion 226 instead of the bellows tube portion 225*d*.

The bellows tube portion 226 is formed of an elastomer film having the same thickness tn as the thin portion 225*t* of the bellows tube portion 225*d*. The bellows tube portion 226 is bent in an inverted V shape at the mountain fold portion on the outer circumference. Therefore, the thick portion 225*n* is not formed on the outer circumferential portion of the bellows tube portion 226.

The reinforcing member 227F reinforces a mountain fold portion f on the outer circumference of the bellows tube portion 226, which has low rigidity in the radial direction, from the inner surface side. The reinforcing member 227F is a linear body having a triangular cross section and is mounted on the inside of the mountain fold portion f of the bellows tube portion 226.

As shown in FIG. 66, a shape of the reinforcing member 227F when seen in the axial direction is curved in a semicircular shape along a half of the inner circumference of the bellows tube portion 226.

A thickness tr of the reinforcing member 227F in the radial direction is not particularly limited as long as the same degree of rigidity as that of the thick portion 225*n* can be obtained. The thickness tr can be appropriately set according to the rigidity of the material of the reinforcing member 227F.

Two reinforcing members 227F are disposed inside each of the mountain fold portions f. In a pair of reinforcing members 227F in one mountain fold portion f, for example, one end portion 227*a* in the circumferential direction is in contact with the other end portion 227*b* in the circumferential direction, and an annular shape is formed as a whole.

As the material of the reinforcing member 227F, for example, a metal, a resin, or the like may be used.

Since the airtight member 225F has the pair of reinforcing members 227F disposed inside each of the mountain fold portions f of the bellows tube portion 226, the rigidity in the radial direction is improved according to the rigidity of the reinforcing members 227F.

The rigidity of the airtight member 225F in the radial direction is determined by the rigidity of the bellows tube portion 226 excluding the portion in which the reinforcing member 227F is disposed. Therefore, the rigidity of the airtight member 225F in the axial direction is equivalent to the rigidity of the airtight member 225 in the axial direction.

The overtube 201 having the air supply device 210F of this modified example is the same as the overtube 201, except that it includes the air supply device 210F instead of the air supply device 210 of the overtube 201 according to the third embodiment. Therefore, according to this modified example, as in the third embodiment, it is possible to provide an overtube for an endoscope that reduces the load on the patient and allows a smooth operation of the endoscope.

In particular, according to this modified example, the rigidity of the bellows tube portion 226 in the radial direction can be improved without providing a thick portion in the bellows tube portion 226. Therefore, even when the required rigidity in the radial direction is formed, and thus a width of the thick portion becomes too large, the rigidity can be improved using a highly rigid material as the reinforcing member 227F. Thus, a size of the airtight member 225F can be reduced.

Since the reinforcing member 227F has a semicircular shape, it can be easily inserted into the airtight member 225F. Thus, assembly is facilitated.

Seventh Modified Example

A modified example (a seventh modified example) of the air supply device used in place of the air supply device 210 in the overtube 201 of the third embodiment will be described.

As shown in FIG. 17, an air supply device 210G of this modified example can be used in place of the air supply device 210 of the overtube 201.

As shown in FIG. 45, the air supply device 210G includes a pressure indicator 219G instead of the pressure indicator 219 of the third modified example.

The pressure indicator 219G is the same as the pressure indicator 219, except that it includes an airtight member 225F and a reinforcing member 227G shown in FIG. 65 instead of the airtight member 225 of the third modified example. The airtight member 225F is the same member as in the sixth modified example.

In the following, differences from the third embodiment, the third modified example, and the sixth modified example will be mainly described.

Like the reinforcing member 227F in the sixth modified example, the reinforcing member 227G reinforces the mountain fold portion f on the outer circumference of the bellows tube portion 226, which has low rigidity in the radial direction, from the inner surface side.

The reinforcing member 227G has the same shape as the reinforcing member 227F, except that the shape seen in the axial direction is different.

Figure 67:
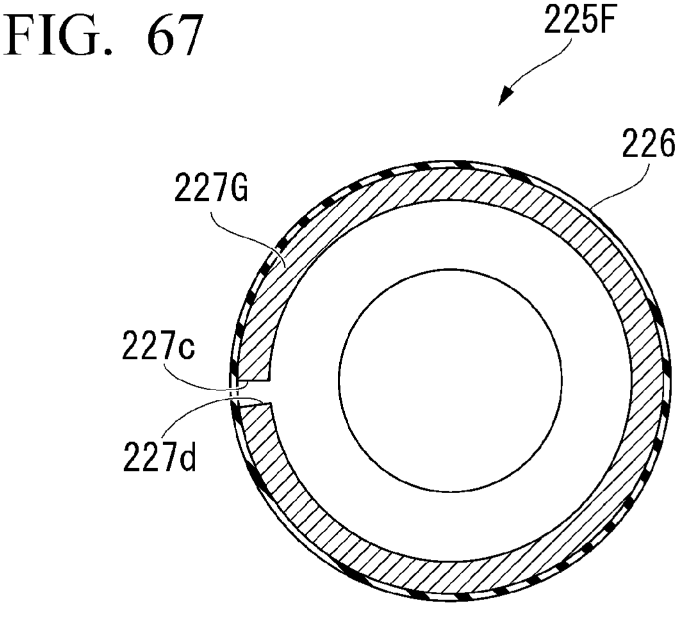
FIG. 67 is a cross-sectional view taken along line F67-F67 in FIG. 65.

FIG. 67 is a cross-sectional view along line F67-F67 in FIG. 65.

As shown in FIG. 67, the reinforcing member 227G has a C shape that extends substantially all around the inside of the mountain fold portion f. Therefore, one reinforcing member 227G is disposed at each of the mountain fold portions f.

As shown in FIG. 67, in the example, end portions 227*c* and 227*d* of the reinforcing member 227G in the circumferential direction face each other with a gap in the circumferential direction. Therefore, when the end portions 227*c* and 227*d* are deformed so as to be in contact with each other, the diameter is reduced, and thus they can be easily disposed inside the bellows tube portion 226. A diameter of the reinforcing member 227G inserted inside the mountain fold portion f expands due to an elastic restoring force, and the reinforcing member 227G comes into close contact with the inside of the mountain fold portion f.

The reinforcing member 227G in this modified example can improve the rigidity of the bellows tube portion 226 in the radial direction, like the pair of reinforcing members 227F in the sixth modified example.

While the pair of reinforcing members 227F reinforce each of the mountain fold portions f, one reinforcing member 227G can perform the same reinforcement for each of the mountain fold portions f. Thus, compared to the sixth modified example, the number of assembly steps is reduced.

The overtube 201 having the air supply device 210F of this modified example is the same as the overtube 201, except that it includes the air supply device 2100 instead of the air supply device 210 of the overtube 201 according to the third embodiment. Therefore, according to this modified example, as in the third embodiment, it is possible to provide an overtube for an endoscope that reduces the load on the patient and allows a smooth operation of the endoscope.

In particular, according to this modified example, the rigidity of the bellows tube portion 226 in the radial direction can be improved without providing a thick portion in the bellows tube portion 226, as in the sixth modified example.

The third embodiment and each of the modified examples described above may be implemented with various modifications.

In the third modified example, the example in which the display window forming member 221 is a film has been described. However, the display window forming member 221 is not limited to the film.

For example, the display window forming member 221 may be formed of a printed layer printed on the side surface portion 220*b*.

For example, when the display window 221*a* can be formed by forming the case 220 by two-color molding, the display window forming member 221 may be omitted.

In the third modified example, it has been described that the outer cylinder portion 223*a* has a constant thickness, and the distal end edge portion 223*c* is formed by the distal end surface of the outer cylinder portion 223*a*. However, the shape of the distal end edge portion 223*c* is not limited thereto. For example, as shown by a two-dot chain line in FIG. 57, an inclined surface 223*n* that is inclined from the inner circumferential side toward the outer circumferential side as it goes from the base end side toward the distal end may be formed at the distal end portion of the outer cylinder portion 223*a*. That is, the distal end edge portion 223*c* may be formed by the distal end of the tapered portion at the distal end portion of the outer cylinder portion 223*a*. In this case, since the width of the distal end edge portion 223*c* in the radial direction is narrowed, the distal end edge portion 223*c* is formed in a linear shape close to the inner circumferential surface 220*f* of the side surface portion 220*b*. The inner circumferential surface 220*f* is located near the inner circumferential surface 220*f* in the radial direction.

Thus, the operator can visually recognize the position of the distal end edge portion 223*c* near the inner circumferential surface 220*f* which is closer to the first scale line 221*b* and the second scale line 221*c*. Thus, the reading error by the operator is further reduced.

Fourth Embodiment

An overtube for an endoscope according to a fourth embodiment of the present invention will be described.

Figure 68:
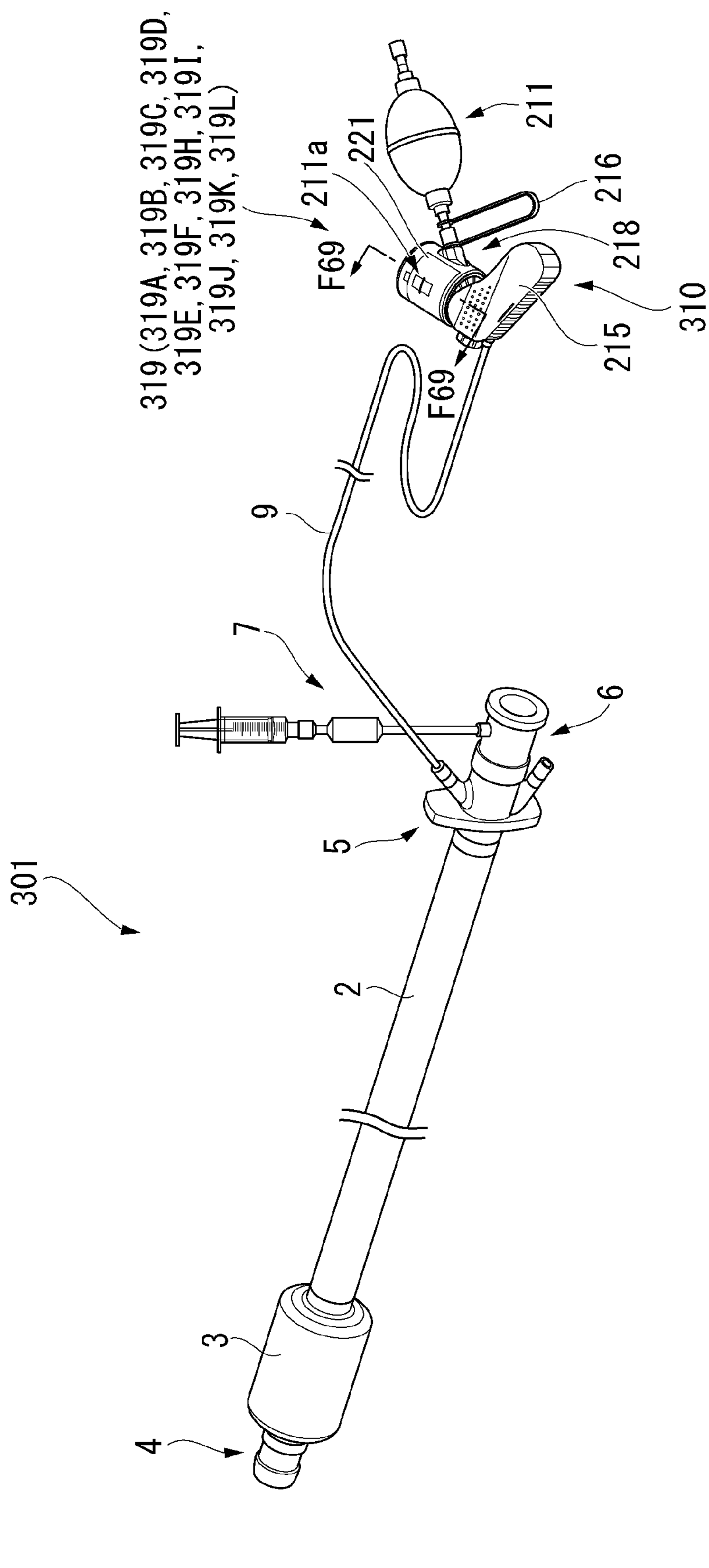
FIG. 68 is a schematic perspective view showing an example of an overtube for an endoscope according to a fourth embodiment of the present invention.
Figure 69:
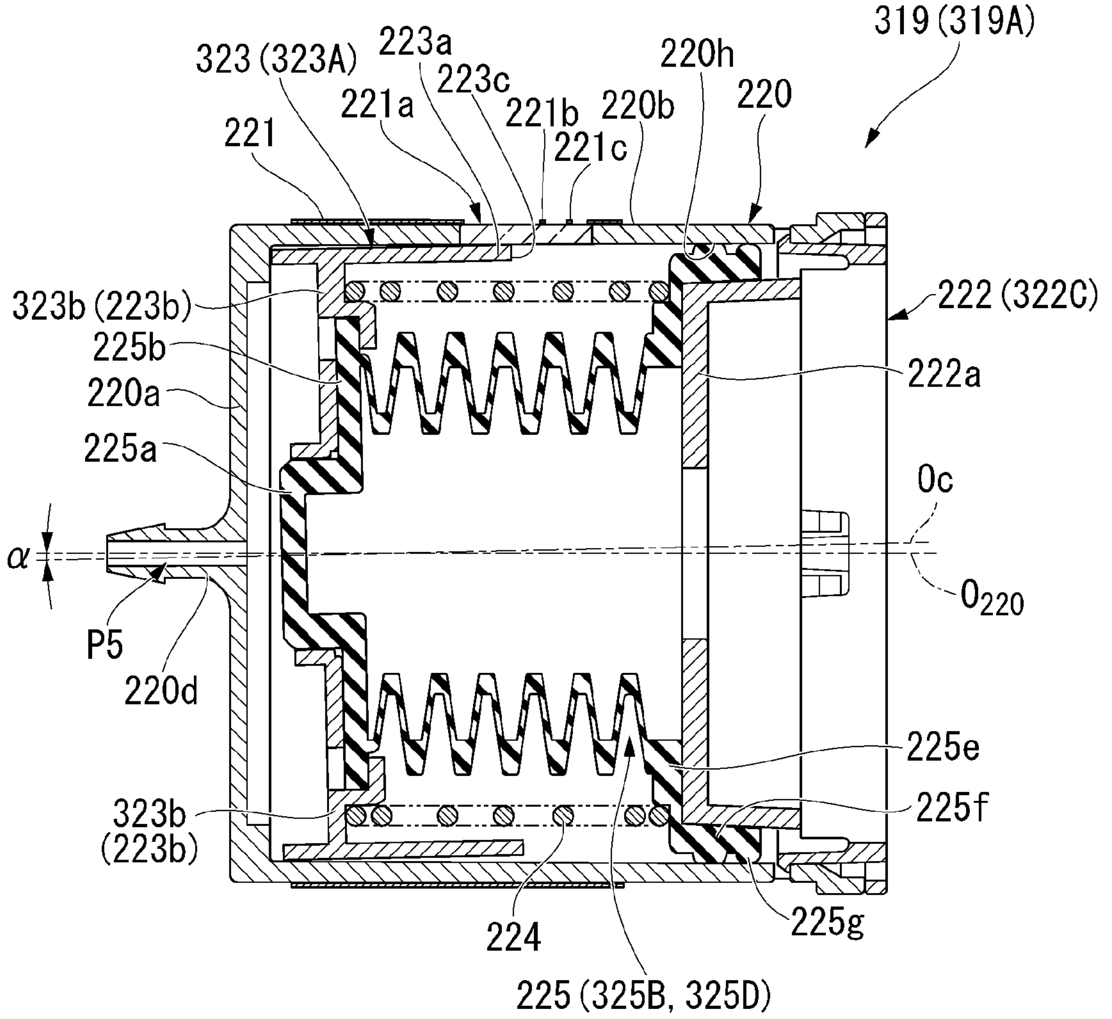
FIG. 69 is a cross-sectional view taken along line F69-F69 in FIG. 68.

FIG. 68 is a schematic perspective view showing an example of the overtube for an endoscope according to the fourth embodiment of the present invention. FIG. 69 is a cross-sectional view taken along line F69-F69 in FIG. 68.

The overtube 301 shown in FIG. 68 is an example of the overtube for an endoscope according to this embodiment.

The overtube 301 includes an air supply device 310 instead of the air supply device 10 of the overtube 1 according to the first embodiment.

The air supply device 310 includes a pressure indicator 319 instead of the pressure indicator 219 of the air supply device 210C in the third modified example.

In the following, differences from the first embodiment and the third modified example will be mainly described.

As shown in FIG. 69, the pressure indicator 319 includes a collar 323 (a moving member) instead of the collar 223 of the pressure indicator 219. The collar 323 includes a locking plate 323*b* (an elastic member support portion) instead of the locking plate 223*b* of the collar 223.

FIG. 69 shows a cross section passing through a center of the display window 221*a* in the circumferential direction and a central axis $O_{220}$ of the case 220, as in FIG. 49.

Figure 70:
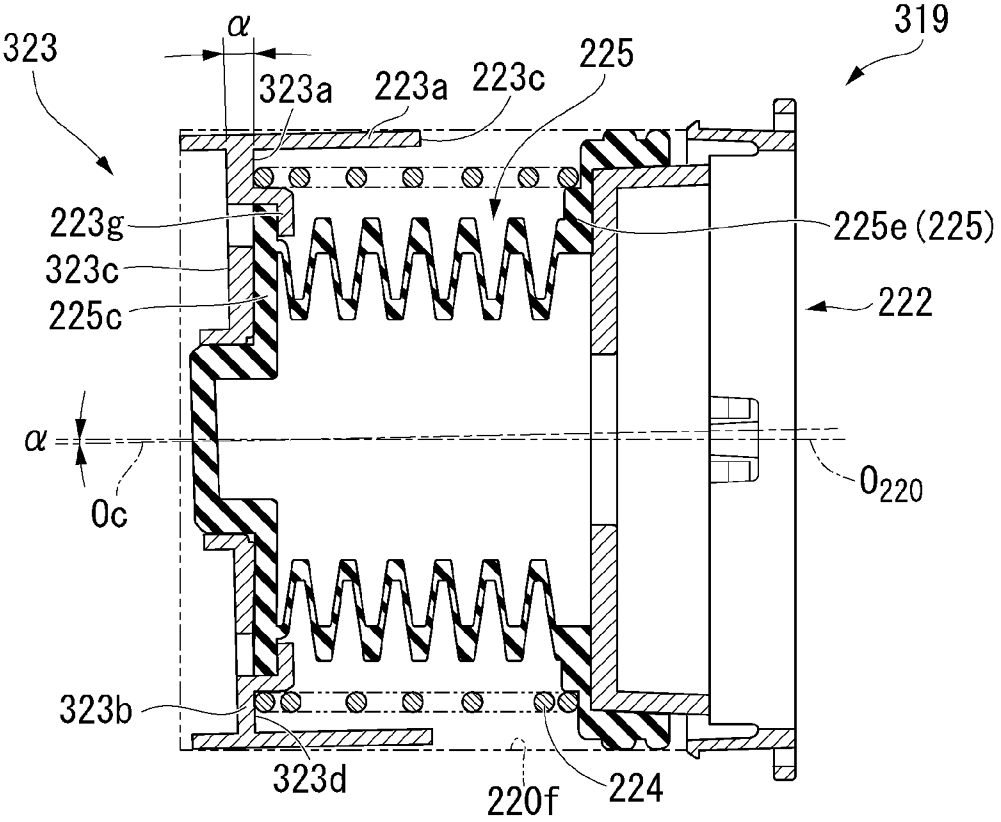
FIG. 70 is a schematic cross-sectional view showing a main portion of a pressure indicator used in the overtube for an endoscope according to the fourth embodiment of the present invention.

FIG. 70 shows main components extracted and disposed in a cross section that is the same as in FIG. 69.

As shown in FIG. 70, the locking plate 323*b* is a wedge-shaped plate member of which a thickness along one diameter gradually decreases from a maximum value to a minimum value.

A plane 323*c* forming the surface of the locking plate 323*b* on the base end side (the left side in the drawing) in the axial direction is orthogonal to a central axis Oc of the locking plate 323*b*.

An inclined surface 323*d* forming the surface of the locking plate 323*b* on the distal end side (the right side in the drawing) in the axial direction is rotated clockwise in the drawing by an angle α with respect to a plane orthogonal to the central axis Oc, like the plane 323*c*.

As in the locking surface 223*d* of the collar 223, the base end of the coil spring 224 is locked on the inclined surface 323*d*.

A magnitude of the angle α is not particularly limited as long as it is a magnitude that the coil spring 224 acts on the collar 323 with a biasing force that inclines the collar 323 in a certain direction in a range of a gap between the inner circumferential surface 220*f* and the outer circumferential surface of the outer cylinder portion 223*a* of the collar 323.

As shown in FIG. 69, the collar 323 is disposed such that a position of a portion of the locking plate 323*b* having the maximum thickness is located closer to the display window 221*a* in the radial direction.

Hereinafter, in accordance with the direction shown in FIGS. 69 and 70, the side closer to the display window 221*a* in the radial direction will be referred to as the upper side, and the side farther away from the display window 221*a* will be referred to as the lower side.

According to this modified example, when the central axis Oc of the collar 323 is disposed coaxially with the central axis $O_{220}$, a distance between the surface of the flange portion 225*e* on the base end side and the inclined surface 323*d*, on the upper side in the radial direction is shorter than a distance between the surface of the flange portion 225*e* on the base end side and the inclined surface 323*d*, on the lower side. Thus, the pressing force of the coil spring 224 is greater on the upper side than on the lower side.

As a result, as shown in FIG. 70, the collar 323 rotates counterclockwise in the drawing. In particular, when a gap between the outer cylinder portion 223*a* and the inner circumferential surface 220*f* of the case 220 is large enough to allow rotation by the angle α, the collar 323 rotates counterclockwise in the drawing by the angle α. When the collar 323 cannot be rotated by the angle α because the gap is narrow, the collar 323 is rotated by an angle less than a at which the outer circumferential portion of the outer cylinder portion 223*a* comes into contact with the inner circumferential surface 220*f*.

In the following, an example in which the collar 323 can be rotated by the angle α will be described.

The distance between the surface of the flange portion 225*e* on the base end side on which the coil spring 224 is locked and the inclined surface 323*d* is maintained constant corresponding to the entire length of the coil spring 224 when it is expanded or contracted.

Thus, the distal end of the outer cylinder portion 223*a* is close to the outer circumferential surface 220*e* on the upper side and is away from the outer circumferential surface 220*e* on the lower side. Similarly, the base end of the outer cylinder portion 223*a* is away from the outer circumferential surface 220*e* on the upper side and is close to the outer circumferential surface 220*e* on the lower side.

The collar 323 engages with the airtight member 225, like the collar 223 in the third modified example. Thus, the rotation of the collar 323 around the central axis O220 is restricted. As a result, the inclination of the collar 323 remains the same even when moving in the axial direction.

In this embodiment, when the collar 323 moves along the central axis $O_{220}$ inside the case 220 of the pressure indicator 319, pressure can be displayed in the same manner as the pressure indicator 219 of the third modified example, except that it moves toward the display window 221*a* while maintaining an inclined state.

The distal end edge portion 223*c* approaches the display window 221*a* by the collar 323 being inclined. The reading error when the viewing direction of the operator is inclined in the right-left direction of the operator is reduced in the radial direction compared to when the distal end edge portion 223*c* is located farther from the display window 221*a*. Thus, the operator is allowed to read more accurate pressure.

Since the inclined state of the collar 323 is formed by the coil spring 224 in contact with the collar 323 pressing the collar 323 to the base end side with an elastic force thereof, an angle of inclination and a direction of inclination are maintained constant in a movement range of the collar 323 in which the pressing force of the coil spring 224 acts.

Rotation of the collar 323 around the central axis Oc is curbed by torsional rigidity of the airtight member 225 and a frictional force at the base end of the coil spring 224.

The overtube 301 according to this embodiment is the same as the overtube 101, except that it includes an air supply device 310 instead of the air supply device 10 of the overtube 101 according to the first embodiment. Therefore, according to this modified example, as in the first embodiment, it is possible to provide an overtube for an endoscope that reduces the load on the patient and allows a smooth operation of the endoscope.

In particular, according to this embodiment, since the air supply device 310 includes the pressure indicator 319 instead of the pressure indicator 219 of the third modified example, the reading error in the pressure display due to a change in the viewing direction can be reduced.

In the pressure indicator 319 of the air supply device 310, the case 220 is an example of a casing in which the display window 221*a* through which the inside can be seen is provided at at least a portion thereof.

In the pressure indicator 319, the collar 323 is an example of a moving member that moves within the casing according to the pressure inside the casing and of which a movement position can be observed through the display window.

In the pressure indicator 319, the first scale line 221*b* and the second scale line 221*c* are examples of a reference scale that is formed on or around the display window, and indicates pressure according to the position of the moving member.

The side surface portion 220*b* of the case 220 is an example of a moving conduit through which the moving member moves.

The outer cylinder portion 223*a* of the collar 323 is an example of a tubular portion that moves along a central axis of the moving conduit. The distal end edge portion 223*c* is an example of an end portion of the tubular portion closer to the display window.

In the pressure indicator 319, the tubular portion moves in an inclined posture in a certain direction with respect to the central axis of the moving conduit, and the display window is formed at a position in which the end portion of the tubular portion close to the display window can be seen due to the inclination of the tubular portion.

The coil spring 224 in the pressure indicator 319 is an example of an elastic member that biases the moving member against the pressure acting on the moving member and restricts the movement position of the moving member according to the pressure.

The airtight member 225 and the fixing frame 222 in the pressure indicator 319 are examples of a pressing member that is disposed to face the moving member in the moving direction of the moving member and presses an end portion of the elastic member on the side opposite to the moving member.

The locking plate 323*b* having the inclined surface 323*d* in the collar 323 is an example of an elastic member support portion that is included in the moving member and supports the elastic member on the inclined surface inclined in a certain direction with respect to the central axis when the tubular portion is disposed coaxially with the central axis.

The fourth embodiment described above may be implemented with the following modifications.

It has been described that the inclined surface 323*d* in this modified example is formed on the entire locking plate 323*b*. However, the inclined surface 323*d* may be formed in a range in which it comes into contact with the base end of the coil spring 224. The inclined surface 323*d* may be provided in an annular shape when seen in the axial direction in a range in which it comes into contact with the coil spring 224, for example, between the pressing claw 223*g* and the outer cylinder portion 223*a*. In this case, a portion of the locking plate 323*b* that the bottom plate portion 225*c* of the airtight member 225 comes into contact with is formed in a plane parallel to the plane 323*c*.

Eighth Modified Example

A modified example (an eighth modified example) of the pressure indicator used in place of the pressure indicator 319 in the overtube 301 of the fourth embodiment will be described.

As shown in FIG. 68, a pressure indicator 319A of this modified example can be used in place of the pressure indicator 319 in the overtube 301.

As shown in FIG. 69, the pressure indicator 319A includes a collar 323A (a moving member) instead of the collar 323.

In the following, differences from the fourth embodiment will be mainly described.

Figure 71:
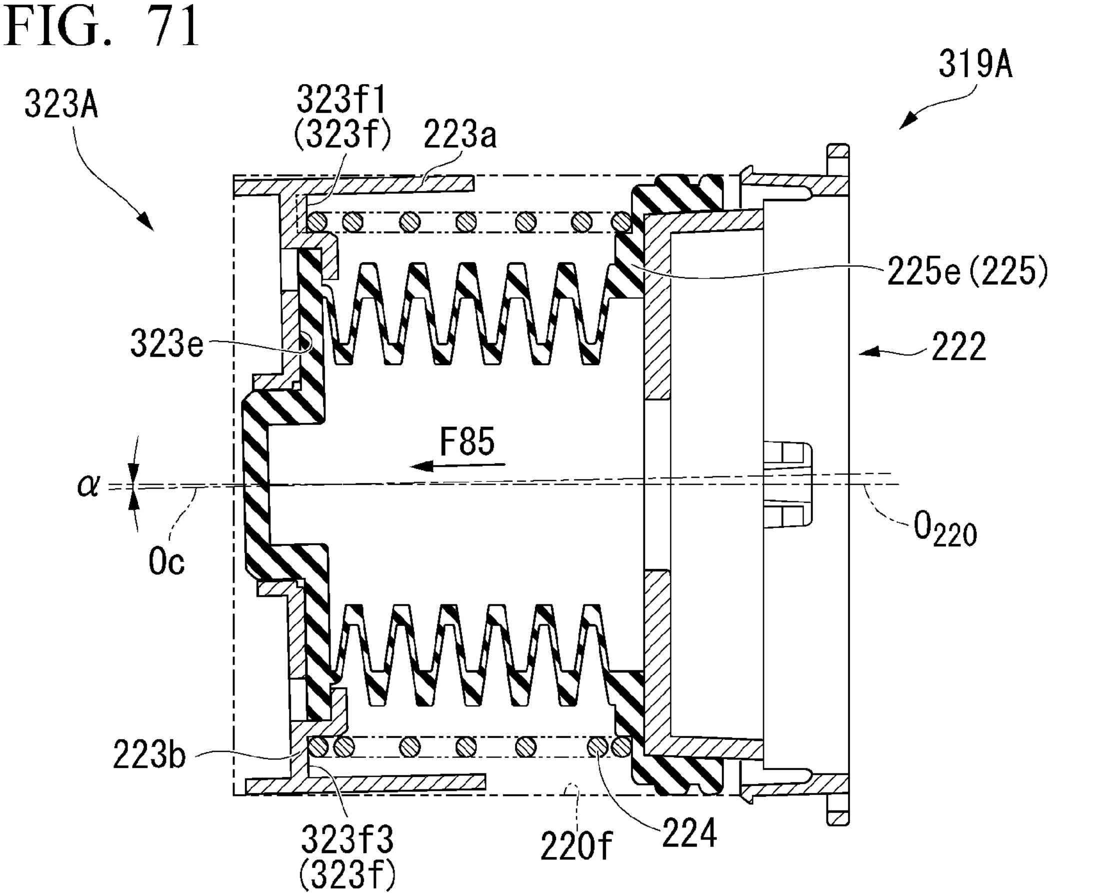
FIG. 71 is a schematic cross-sectional view showing a main portion of a modified example (an eighth modified example) of the pressure indicator used in the overtube for an endoscope according to the fourth embodiment of the present invention.
Figure 72:
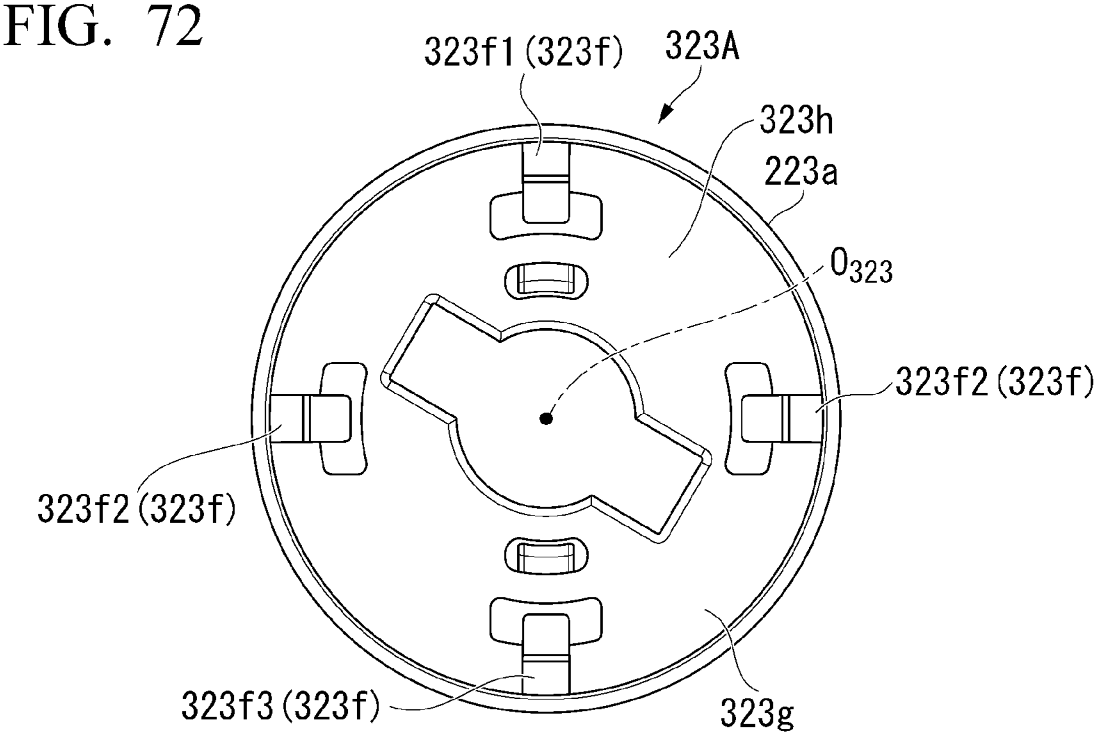
FIG. 72 is a right side view of a collar in the eighth modified example.

FIG. 71 is a schematic cross-sectional view showing a main portion of the modified example (the eighth modified example) of the pressure indicator used in the overtube for an endoscope according to the fourth embodiment of the present invention. FIG. 72 is a right side view of the collar in the eighth modified example.

As shown in FIG. 71, the collar 323A includes the locking plate 223*b* in the third modified example instead of the locking plate 323*b* and a plurality of protruding portions 323*f* (elastic member support portions).

The locking plate 223*b* is orthogonal to the central axis Oc. A distal end surface 323*e* of the locking plate 223*b* on the distal end side in the axial direction along the central axis Oc is also orthogonal to the central axis Oc.

Distal end surfaces of the plurality of protruding portions 323*f* in the axial direction along the central axis Oc are located on the same plane rotated clockwise in the drawing by an angle $\alpha$ with respect to the distal end surface 323*e*, on the distal end side of the distal end surface 323*e* of the locking plate 223*b*.

The base end of the coil spring 224 is locked to the plurality of protruding portions 323*f*, as in the inclined surface 323*d* in the fourth embodiment.

The arrangement position and the number of the plurality of protruding portions 323*f* in the circumferential direction are not particularly limited as long as the base end of the coil spring 224 can be disposed on the same plane.

For example, as shown in FIG. 72, the plurality of protruding portions 323*f* may include a first protruding portion 323*f*1, a second protruding portion 323*f*2, and a third protruding portion 323*f*3.

The first protruding portion 323*f*1 and the third protruding portion 323*f*3 face each other with the central axis Oc interposed therebetween in the radial direction extending in the up-down direction in the drawing. Among the plurality of protruding portions 323*f*, the first protruding portion 323*f*1 has the largest amount of protrusion from the distal end surface 323*e*. Similarly, the amount of protrusion from the distal end surface 323*e* of the third protruding portion 323*f*3 is the smallest.

One second protruding portion 323*f*2 is provided in the middle between the first protruding portion 323*f*1 and the third protruding portion 323*f*3 in the circumferential direction. The amount of protrusion of each of the second protruding portions 323*f*2 from the distal end surface 323*e* is equal to an average of the amounts of protrusion of the first protruding portion 323*f*1 and the third protruding portion 323*f*3.

An exterior of each of the protruding portions 323*f* when seen in the axial direction is not particularly limited. For example, the exterior of each of the protruding portions 323*f* may be rectangular, polygonal, circular, or the like. In the example shown in FIG. 72, the exterior of each of the protruding portions 323*f* is rectangular.

A shape of the distal end of each of the protruding portions 323*f* is not particularly limited as long as it can stably come into contact with the coil spring 224. For example, it may be a plane that forms a part of the inclined surface 323*d*, or a convex curved surface that is in contact with the same plane as the inclined surface 323*d* at at least one location.

This modified example has the plurality of protruding portions 323*f* instead of the inclined surface 323*d*. Since the distal end surfaces of the plurality of protruding portions 323*f* are located on the same plane with the same inclination as a whole, when the base ends of the coil springs 224 come into contact therewith, like the collar 323, the collar 323A is inclined in a certain direction inside the side surface portion 220*b*.

Thus, as in the collar 323, since the distal end edge portion 223*c* is close to the display window 221*a*, the operator can read the accurate pressure.

The overtube 301 having the pressure indicator 319A of this modified example has the same action as in the overtube 301 according to the fourth embodiment.

In particular, in this modified example, the inclination of the collar 323A is defined by the plurality of protruding portions 323*f* provided in a narrower range than in the fourth embodiment. Thus, accuracy of the inclination angle can be obtained more easily than a case in which a wider inclined surface 323*d* is formed.

In this modified example, it has been described that the base end of the coil spring 224 comes into contact only with the plurality of protruding portion 323*f*. However, when the base end of the coil spring 224 can be aligned on the same plane, a part of the coil spring 224 may come into contact with the distal end surface 323*e*. For example, the third protruding portion 323*f*3 may be deleted, and the lower side of the base end of the coil spring 224 may be brought into contact with the distal end surface 323*e*.

The plurality of protruding portions 323*f* in the collar 323A are examples of an elastic member support portion that is included in the moving member and supports an elastic member on an inclined surface inclined in a certain direction with respect to the central axis when the tubular portion is disposed coaxially with the central axis.

Ninth Modified Example

A modified example (a ninth modified example) of the pressure indicator used instead of the pressure indicator 319 in the overtube 301 of the fourth embodiment will be described.

As shown in FIG. 68, a pressure indicator 319B of this modified example can be used in place of the pressure indicator 319 in the overtube 301.

In the following, differences from the fourth embodiment will be mainly described.

Figure 73:
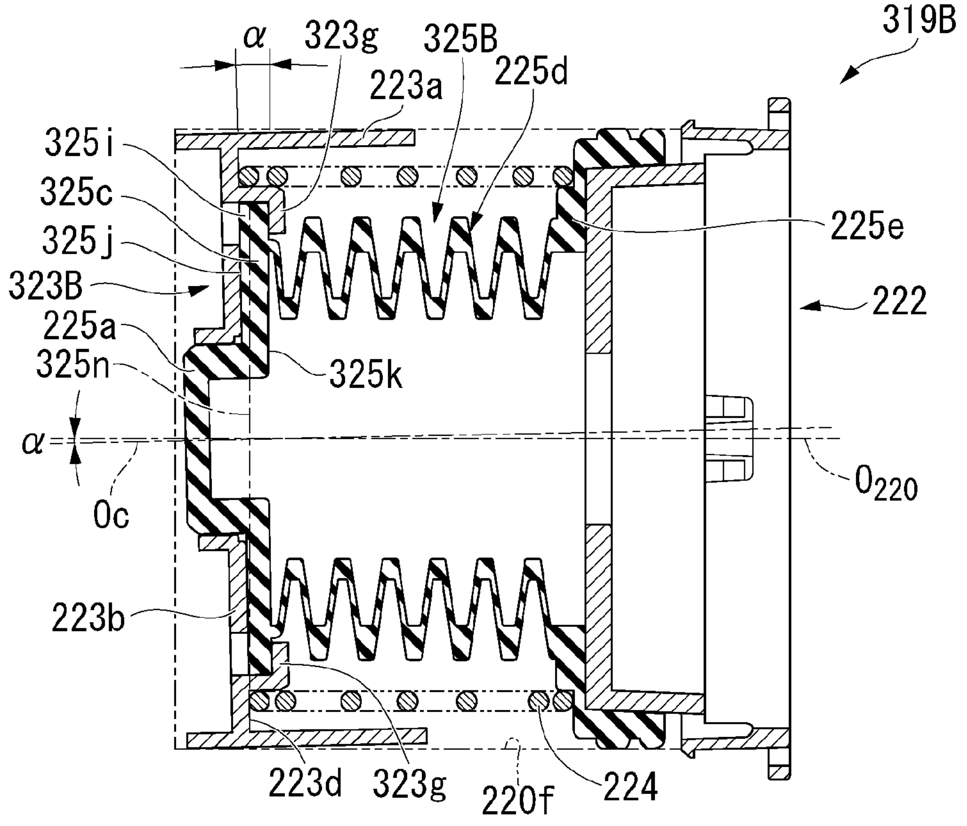
FIG. 73 is a schematic cross-sectional view showing a main portion of a modified example (a ninth modified example) of the pressure indicator used in the overtube for an endoscope according to the fourth embodiment of the present invention.

FIG. 73 is a schematic cross-sectional view showing a main portion of the modified example (the ninth modified example) of the pressure indicator used in the overtube for an endoscope according to the fourth embodiment of the present invention.

As shown in FIG. 73, the pressure indicator 319B includes an airtight member 325B (a sealing member, a pressing member) and a collar 323B (a moving member) instead of the airtight member 225 and the collar 323.

As shown in FIG. 73, the airtight member 325B has a bottom plate portion 325*c* instead of the bottom plate portion 225*c* of the airtight member 225 in the third modified example.

The bottom plate portion 325*c* is a wedge-shaped plate member of which a thickness along one diameter gradually decreases from a maximum value to a minimum value.

A plane 325*k* forming a surface of the bottom plate portion 325*c* on the distal end side (the right side in the drawing) in the axial direction is orthogonal to the central axis $O_{220}$, like the surface on the distal end side of the bottom plate portion 225*c* of the airtight member 225.

An inclined surface 325*j* forming the surface of the bottom plate portion 325*c* on the base end side (the left side in the drawing) in the axial direction is rotated counterclockwise in the drawing by an angle α with respect to the plane 325*k*.

The boss portion 225*a* in this modified example protrudes from the inclined surface 325*j* in a normal direction of the inclined surface 325*j*.

In this modified example, each of engaging protrusions 325*i* protrudes in place of each of the engaging protrusions 225*i* of the third modified example. However, a thickness of each of the engaging protrusions 325*i* differs according to a change in the thickness of the bottom plate portion 325*c*. That is, a base end surface of each of the engaging protrusion 325*i* extends in the radial direction along the inclined surface 325*j*, and a distal end surface thereof extends in the radial direction along the plane 325*k*.

The airtight member 325B is disposed such that a portion of the bottom plate portion 325*c* having the maximum thickness is located closer to the display window 221*a* in the radial direction.

The collar 323B is the same as the collar 223 in the third modified example except that it includes a pressing claw 323*g* instead of the pressing claw 223*g*.

The pressing claw 323*g* is the same as the pressing claw 223*g*, except that the amount of protrusion to the distal end side differs according to the thickness of the engaging protrusion 325*i* to be engaged.

According to this modified example, the inclined surface 325*j* of the bottom plate portion 325*c* of the airtight member 325B is locked to the locking surface 223*d* of the collar 223. Thus, the collar 223 rotates, like the collar 323 of the fourth embodiment. The central axis Oc rotates counterclockwise in the drawing by an angle α with respect to the central axis $O_{220}$.

Thus, as in the collar 323, since the distal end edge portion 223*c* of the collar 223 in this modified example is close to the display window 221*a*, the operator can read accurate pressure.

The overtube 301 having the pressure indicator 319B of this modified example has the same action as the overtube 301 according to the fourth embodiment.

This modified example is an example in which the collar 223 in this modified example is rotated by providing the inclined surface 325*j* on the base end side of the airtight member 325B.

The ninth modified example described above may be implemented with the following modifications.

The inclined surfaces 325*j* in this modified example may be formed entirely in the circumferential direction, or may be formed apart in the circumferential direction. When it is formed entirely in the circumferential direction, in the radial direction, it may be formed in an annular shape when seen in the axial direction within a range in contact with the coil spring 224.

Figure 74:
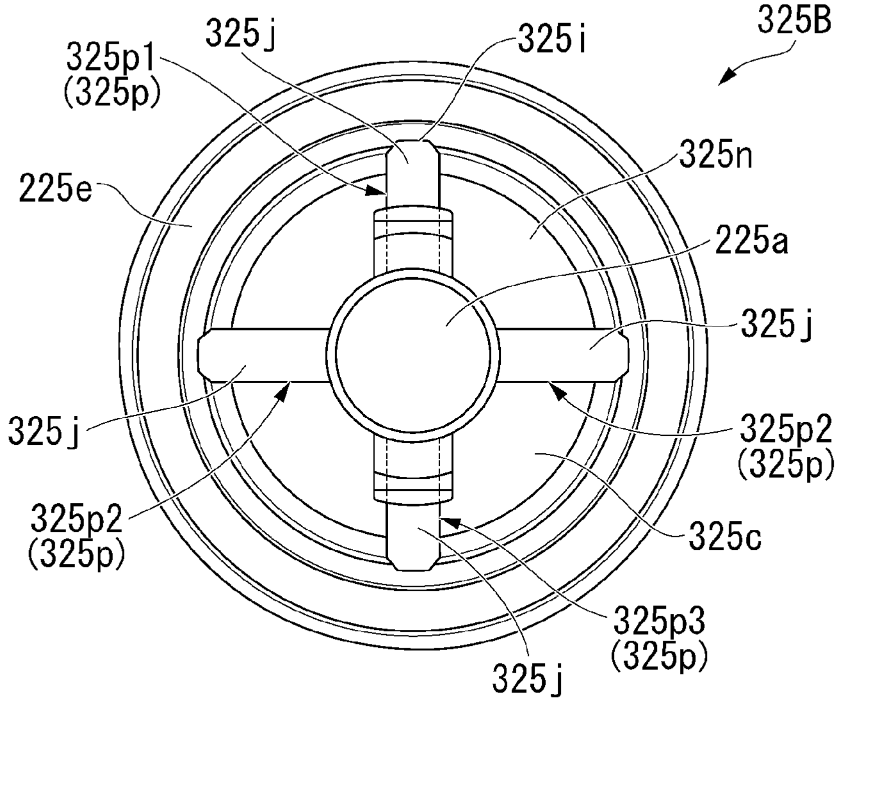
FIG. 74 is a left side view of the airtight member in the ninth modified example.

FIG. 74 is a left side view of the airtight member in the ninth modified example.

The example shown in FIG. 74 is an example in which the inclined surface 325*j* is formed at a base end of each of a plurality of protruding portions 325*p* in the axial direction. The plurality of protruding portions 325*p* protrude to the base end side from a plane 325*n* parallel to the plane 325*k*.

For example, the plurality of protruding portions 325*p* may include a first protruding portion 325*p*1, a second protruding portion 325*p*2, and a third protruding portion 325*p*3, like the plurality of protruding portions 323*f* in the eighth modified example.

The first protruding portion 325*p*1, the second protruding portion 325*p*2, and the third protruding portion 325*p*3 may be formed in the same position and shape as the first protruding portion 323*f*1, the second protruding portion 323*f*2 and the third protruding portion 323*f*3 in the eighth modified example, except that they protrude from the plane 325*n* to the base end side and the inclined surface 325*j* is formed on a surface of the base end.

Furthermore, a shape of a distal end of each of the protruding portions 325*p* is not particularly limited as long as it can stably come into contact with the coil spring 224, as in the protruding portion 323*f* in the eighth modified example.

Tenth Modified Example

A modified example (a tenth modified example) of the pressure indicator used in place of the pressure indicator 319 in the overtube 301 of the fourth embodiment will be described.

As shown in FIG. 68, a pressure indicator 319C of this modified example can be used in place of the pressure indicator 319 in the overtube 301.

In the following, differences from the fourth embodiment will be mainly described.

Figure 75:
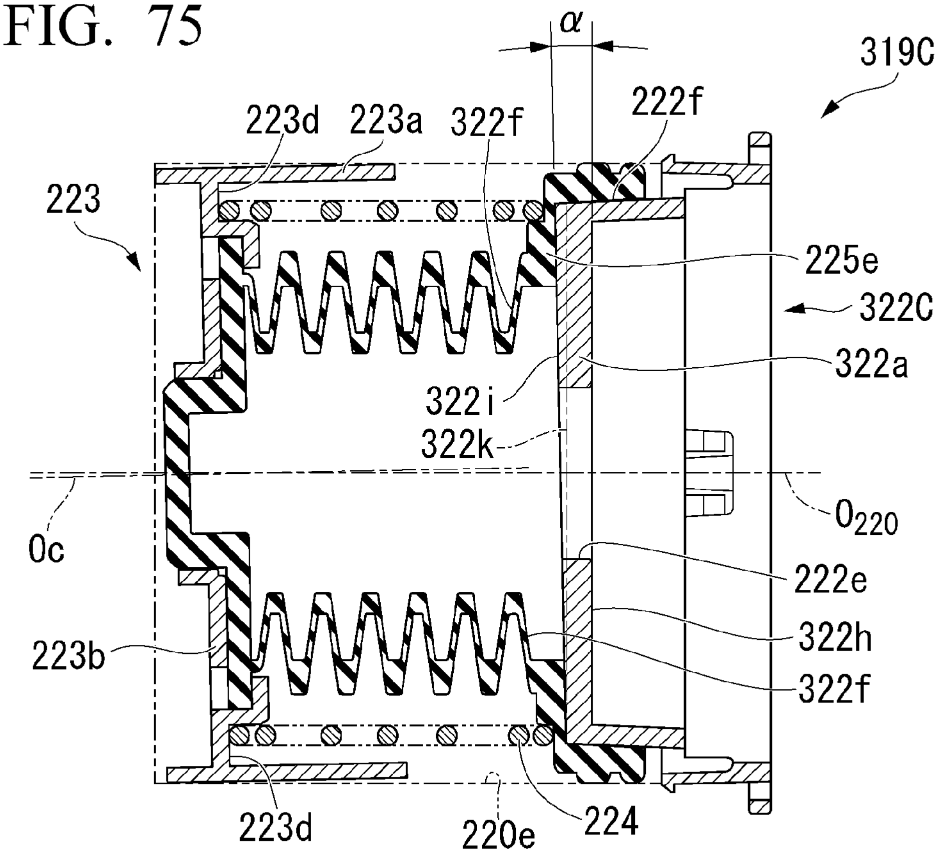
FIG. 75 is a schematic cross-sectional view showing a main portion of a modified example (a tenth modified example) of the pressure indicator used in the overtube for an endoscope according to the fourth embodiment of the present invention.

FIG. 75 is a schematic cross-sectional view showing a main portion of the modified example (the tenth modified example) of the pressure indicator used in the overtube for an endoscope according to the fourth embodiment of the present invention.

As shown in FIG. 75, the pressure indicator 319C includes a fixing frame 322C (a pressing member) and a collar 223 instead of the fixing frame 222 and the collar 323. The collar 223 is a member that is the same as the collar 223 in the third modified example.

As shown in FIG. 75, the fixing frame 322C has a bottom surface portion 322*a* instead of the bottom surface portion 222*a* of the fixing frame 222 in the third modified example.

The bottom surface portion 322*a* is a wedge-shaped plate member of which a thickness along one diameter gradually decreases from a maximum value to a minimum value.

A plane 322*h* forming a surface of the bottom surface portion 322*a* on the distal end side (the right side in the drawing) in the axial direction is orthogonal to the central axis $O_{220}$.

An inclined surface 322*i* that forms the surface of the bottom surface portion 322*a* on the base end side (the left side in the drawing) in the axial direction rotates counterclockwise in the drawing by an angle α with respect to the plane 322*h*.

The surface of the flange portion 225*e* on the distal end side is in contact with the inclined surface 322*i*.

The fixing frame 322C is fixed to the case 220 so that a position of a portion of the bottom surface portion 322*a* having the maximum thickness is located closer to the display window 221*a* in the radial direction.

According to this modified example, the flange portion 225*e* of the airtight member 225 is locked on the inclined surface 322*i* of the bottom surface portion 322*a* of the fixing frame 322C. Thus, an upper distal end of the coil spring 224 locked on the surface of the flange portion 225*e* on the base end side is pushed out more to the base end side than a lower distal end thereof. Since the locking surface 223*d* of the collar 223 in this modified example is pressed more strongly on the upper side than on the lower side by the base end of the coil spring 224, the collar 223 rotates, like the collar 323 of the fourth embodiment. The central axis Oc rotates counterclockwise in the drawing by an angle α with respect to the central axis $O_{220}$.

Thus, as in the collar 323, since the distal end edge portion 223*c* of the collar 223 in this modified example is close to the display window 221*a*, the operator can read accurate pressure.

The overtube 301 having the pressure indicator 319C of this modified example has the same action as the overtube 301 according to the fourth embodiment.

This modified example is an example in which the collar 223 in this modified example is rotated by providing the inclined surface 322*i* on the base end side of the fixing frame 322C.

The tenth modified example described above may be implemented with the following modifications.

The inclined surface 322*i* in this modified example may be formed entirely in the circumferential direction, or may be formed separately in the circumferential direction. When it is formed entirely in the circumferential direction, in the radial direction, it may be provided in an annular shape when seen in the axial direction within a range facing the coil spring 224 with the flange portion 225*e* interposed therebetween.

Figure 76:
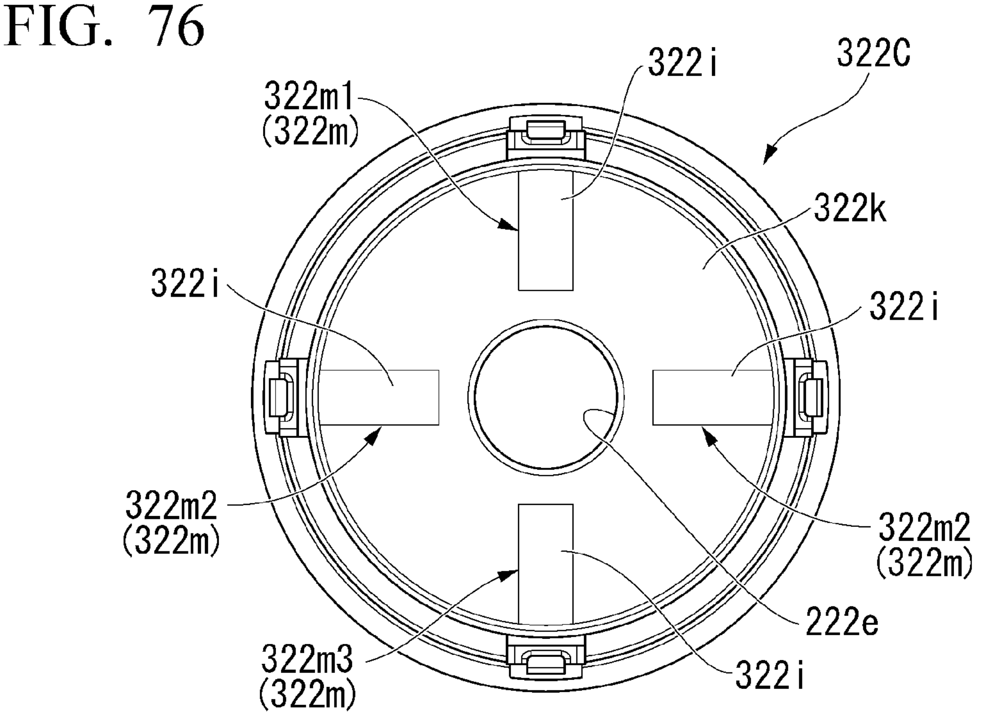
FIG. 76 is a left side view of a fixing frame in the tenth modified example.

FIG. 76 is a left side view of the fixing frame in the tenth modified example.

The example shown in FIG. 76 is an example in which the inclined surface 322*i* is formed at the base ends of a plurality of protruding portions 322*m* (elastic member support portions) in the axial direction. The plurality of protruding portions 322*m* protrude to the base end side from a plane 322*k* parallel to the plane 322*h*.

For example, the plurality of protruding portions 322*m* may include a first protruding portion 322*m*1, a second protruding portion 322*m*2, and a third protruding portion 322*m*3, like the plurality of protruding portions 323*f* in the eighth modified example.

The first protruding portion 322*m*1, the second protruding portion 322*m*2, and the third protruding portion 322*m*3 may be formed in the same position and shape as the first protruding portion 323*f*1, the second protruding portion 323*f*2 and the third protruding portion 323*f*3 in the eighth modified example, except that they protrude from the plane 322*k* to the base end side and the base end surfaces are formed by the inclined surface 322*i*.

Furthermore, a shape of the distal end of each of the protruding portions 322*m* is not particularly limited as long as it can stably come into contact with the coil spring 224, like the protruding portion 323*f* in the eighth modified example.

The airtight member 225 and the fixing frame 322C of the pressure indicator 319C are examples of a pressing member that is disposed to face the moving member in the moving direction of the moving member and presses the end portion of the elastic member on the side opposite to the moving member.

The bottom surface portion 322*a* having the inclined surface 322*i* or the plurality of protruding portions 323*f* in the fixing frame 322C are examples of an elastic member support portion that is included in the pressing member and supports the elastic member on an inclined surface inclined in a certain direction with respect to the central axis when the tubular portion is disposed coaxially with the central axis.

Eleventh Modified Example

A modified example (an eleventh modified example) of the pressure indicator used in place of the pressure indicator 319 in the overtube 301 of the fourth embodiment will be described.

As shown in FIG. 68, a pressure indicator 319D of this modified example can be used in place of the pressure indicator 319 in the overtube 301.

In the following, differences from the fourth embodiment will be mainly described.

Figure 77:
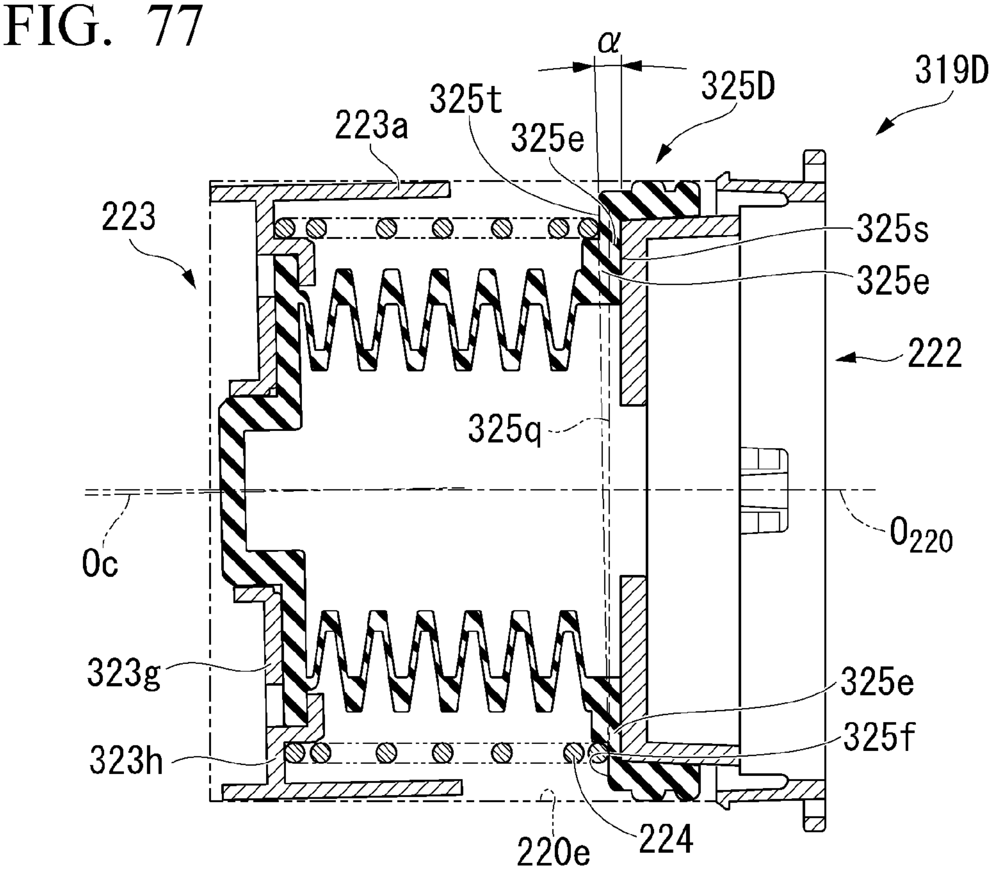
FIG. 77 is a schematic cross-sectional view showing a main portion of a modified example (an eleventh modified example) of the pressure indicator used in the overtube for an endoscope according to the fourth embodiment of the present invention.

FIG. 77 is a schematic cross-sectional view showing a main portion of the modified example (the eleventh modified example) of the pressure indicator used in the overtube for an endoscope according to the fourth embodiment of the present invention.

As shown in FIG. 77, the pressure indicator 319D includes an airtight member 325D (a sealing member, a pressing member) and a collar 223 instead of the airtight member 225 and the collar 323. The collar 223 is a member that is the same as the collar 223 in the third modified example.

As shown in FIG. 77, the airtight member 325D has a flange portion 325*e* (an elastic member support portion) instead of the flange portion 225*e* of the airtight member 225 in the third modified example.

The flange portion 325*e* is an annular plate member when seen in the axial direction and of which a thickness along one diameter gradually decreases from a maximum value to a minimum value at least at a portion with which the distal end of the coil spring 224 comes into contact.

A plane 325*s* forming a surface of the flange portion 325*e* on the distal end side (the right side in the drawing) in the axial direction is orthogonal to the central axis $O_{220}$.

An inclined surface 325*t* forming a surface of the flange portion 325*e* on the base end side (the left side in the drawing) in the axial direction is rotated counterclockwise in the drawing by an angle α with respect to the plane 325*s*.

The plane 325*s* comes into contact with the surface of the bottom surface portion 222*a* of the fixing frame 222 on the base end side.

The distal end of the coil spring 224 comes into contact with the inclined surface 325*t*.

The airtight member 325D is fixed by the case 220 and the fixing frame 222 such that a position of a portion of the flange portion 325*e* having the maximum thickness is located closer to the display window 221*a* in the radial direction.

According to this modified example, when the plane 325*s* of the flange portion 325*e* of the airtight member 325D is locked to the bottom surface portion 222*a* of the fixing frame 222, the inclined surface 325*t* is inclined in a direction of rotation counterclockwise in the drawing by an angle α with respect to a plane orthogonal to the central axis $O_{220}$.

Thus, the upper distal end of the coil spring 224 that is locked to the inclined surface 325*t* of the flange portion 325*e* is pushed out further toward the base end than the lower distal end thereof. Since the locking surface 223*d* of the collar 223 in this modified example is pressed more strongly on the upper side than on the lower side by the base end of the coil spring 224, the collar 223 rotates, like the collar 323 of the fourth embodiment. The central axis Oc rotates counterclockwise in the drawing by an angle α with respect to the central axis $O_{220}$.

Thus, as in the collar 323, since the distal end edge portion 223*c* of the collar 223 in this modified example is close to the display window 221*a*, the operator can read accurate pressure.

The overtube 301 having the pressure indicator 319D of this modified example has the same action as the overtube 301 according to the fourth embodiment.

This modified example is an example in which the collar 223 in this modified example is rotated by providing the inclined surface 325*t* on the base end side of the flange portion 325*e* of the airtight member 325D.

The eleventh modified example described above may be implemented with the following modifications.

The inclined surface 325*t* in this modified example may be formed entirely in the circumferential direction, or may be formed separately in the circumferential direction. When it is formed entirely in the circumferential direction, in the radial direction, it may be provided in an annular shape when seen in the axial direction in a range facing the coil spring 224.

Figure 78:
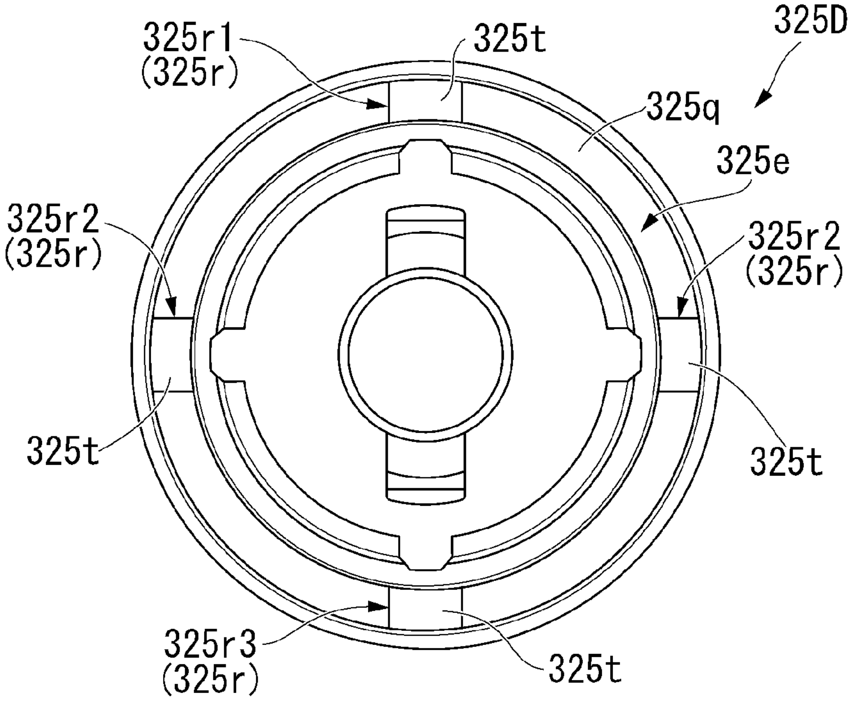
FIG. 78 is a left side view of an airtight member in the eleventh modified example.

FIG. 78 is a left side view of the airtight member in the eleventh modified example.

The example shown in FIG. 78 is an example in which the inclined surface 325*t* is formed at base ends of a plurality of protruding portions 325*r* (elastic member support portions) in the axial direction. The plurality of protruding portions 325*r* protrude to the base end side from a plane 325*q* parallel to the plane 325*s*.

For example, the plurality of protruding portions 325*r* may include a first protruding portion 325*r*1, a second protruding portion 325*r*2, and a third protruding portion 325*r*3, like the plurality of protruding portions 323*f* in the eighth modified example.

The first protruding portion 325*r*1, the second protruding portion 325*r*2, and the third protruding portion 325*r*3 may be formed similarly to the first protruding portion 323*f*1, the second protruding portion 323*f*2, and the third protruding portion 323*f*3 in the eighth modified example, except that they protrude from the plane 325*q* to the base end side and the inclined surface 325*t* is formed on a surface of the base end.

Further, a shape of a distal end of each of the protruding portions 325*r* is not particularly limited as long as it can stably come into contact with the coil spring 224, as in the protruding portion 323*f* in the eighth modified example.

The airtight member 325D and the fixing frame 222 in the pressure indicator 319D are examples of a pressing member that is disposed to face the moving member in the moving direction of the moving member and presses an end portion of the elastic member on the side opposite to the moving member.

The flange portion 325*e* having the inclined surface 325*t* or the plurality of protruding portions 325*r* in the airtight member 325D are examples of an elastic member support portion that is included in the pressing member and supports the elastic member on an inclined surface inclined in a certain direction with respect to the central axis when the tubular portion is disposed coaxially with the central axis.

Twelfth Modified Example

A modified example (a twelfth modified example) of the pressure indicator used in place of the pressure indicator 319 in the overtube 301 of the fourth embodiment will be described.

As shown in FIG. 68, a pressure indicator 319E of this modified example can be used in place of the pressure indicator 319 in the overtube 301.

In the following, differences from the fourth embodiment will be mainly described.

Figure 79:
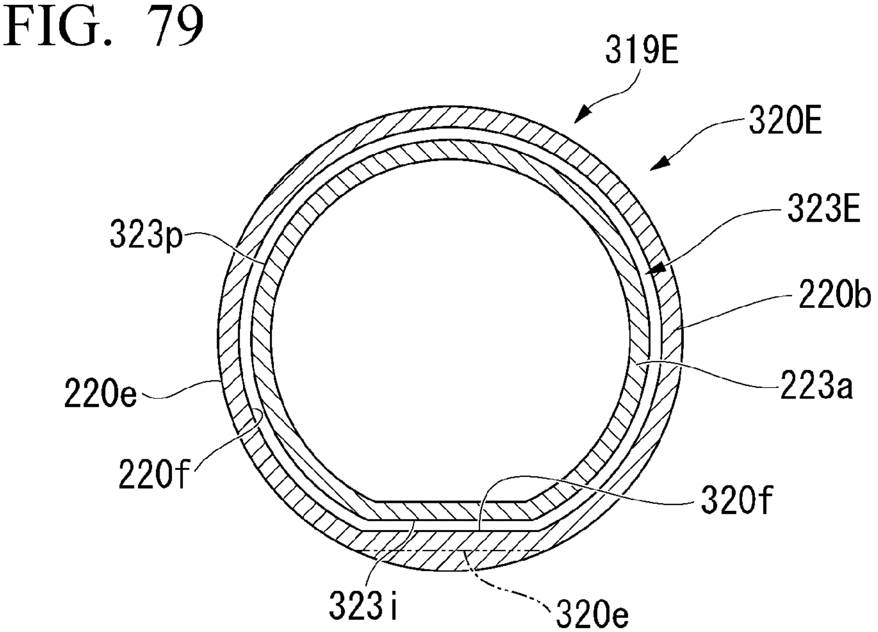
FIG. 79 is a schematic cross-sectional view showing a main portion of a modified example (a twelfth modified example) of the pressure indicator used in the overtube for an endoscope according to the fourth embodiment of the present invention.

FIG. 79 is a schematic cross-sectional view showing a main portion of the modified example (the twelfth modified example) of the pressure indicator used in the overtube for an endoscope according to the fourth embodiment of the present invention.

As shown in FIG. 79, the pressure indicator 319E includes a case 320E (a casing) and a collar 323E (a moving member) instead of the case 220 and collar 323 in the fourth embodiment.

The case 320E has a convex portion 320*f* that bulges inward in the radial direction from the inner circumferential surface 220*f* of the side surface portion 220*b*. A cross-sectional shape of the convex portion 320*f* is the same in the axial direction.

The cross-sectional shape of the convex portion 320*f* is not particularly limited as long as it can restrict rotation of the collar 323E in the circumferential direction by protruding from the inner circumferential surface 220*f*. In the example shown in FIG. 79, the convex portion 320*f* is a plane appearing as a chord of a circle along the inner circumferential surface 220*f* in a cross section orthogonal to the axial direction. Thus, an inner surface of the case 320E when seen in the axial direction has a D shape.

A position of the convex portion 320*f* in the circumferential direction is not particularly limited. However, when the convex portion 320*f* is provided at a position crossing the display window 221*a*, as shown by a two-dot chain line, a concave portion 320*e* that forms a surface parallel to a surface of the convex portion 320*f* may be formed at a portion corresponding to the inside of the display window 221*a*. In this case, since a thickness of the convex portion 320*f* inside the display window 221*a* is constant, the distal end edge portion 223*c* can be visually recognized without distortion.

The collar 323E is the same as the collar 323, except that it has a concave portion 323*i* that is recessed inward in the radial direction with respect to the outer circumferential surface 323*p* of the outer cylinder portion 223*a*. A cross-sectional shape of the concave portion 323*i* is the same in the axial direction.

The cross-sectional shape of the concave portion 323*i* is not particularly limited as long as it is recessed further than the outer circumferential surface 323*p* and can restrict rotation of the collar 323E in the circumferential direction when sliding in close proximity to the convex portion 320*f*. In the example shown in FIG. 79, the concave portion 323*i* is a plane that appears as a chord of a circle along the outer circumferential surface 323*p* in a cross section orthogonal to the axial direction. Thus, an outer surface of the collar 323E when seen in the axial direction has a D shape that fits slidably into an inner surface of the case 320E in the axial direction.

However, a gap is formed between the inner surface of the case 320E and the outer surface of the collar 323E so that the collar 323E can be inclined, like the collar 323.

According to this modified example, in a state in which the collar 323E is inserted into the side surface portion 220*b* of the case 320E, the convex portion 320*f* and the concave portion 323*i* face each other closely. Thus, the rotation of the collar 323E in the circumferential direction is restricted.

For example, in the case of the fourth embodiment that does not have the convex portion 320*f*, the rotation of the collar 323 in the circumferential direction is restricted by the collar 323 being fixed to the airtight member 225 and coming into contact with the coil spring 224. However, when the torsional rigidity of the airtight member 225 is low or when the frictional force between the coil spring 224 and the locking plate 323*b* decreases, the collar 323 may rotate in the circumferential direction. In this case, since the position of the distal end edge portion 223*c* appearing in the display window 221*a* is not constant, there is a possibility that the display accuracy of the pressure is lowered.

In contrast, in this modified example, the rotation of the collar 323E is more reliably restricted by the convex portion 320*f*. According to this modified example, since the position of the distal end edge portion 223*c* appearing in the display window 221*a* is constant, the internal pressure of the case 220 can be displayed with high accuracy.

The overtube 301 having the pressure indicator 319E of this modified example has the same action as the overtube 301 according to the fourth embodiment.

This modified example is an example in which the rotation of the collar 323 with respect to the case 320E is restricted by fitting the D-shaped outer surface and the D-shaped inner surface respectively formed by the concave portion 323*i* of the collar 323E and the convex portion 320*f* of the case 320E.

Thirteenth Modified Example

A modified example (a thirteenth modified example) of the pressure indicator used in place of the pressure indicator 319 in the overtube 301 of the fourth embodiment will be described.

As shown in FIG. 68, a pressure indicator 319F of this modified example can be used in place of the pressure indicator 319 in the overtube 301.

In the following, differences from the fourth embodiment will be mainly described.

Figure 80:
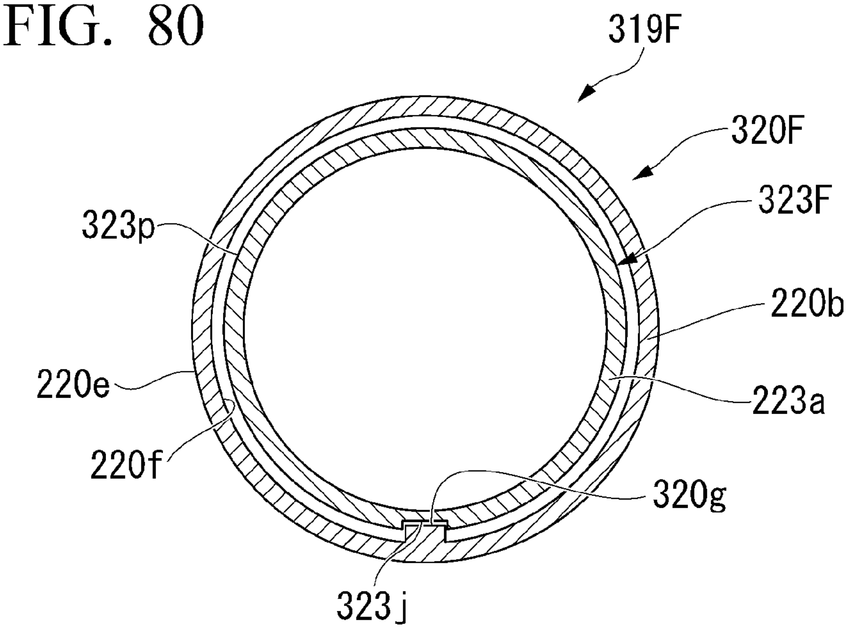
FIG. 80 is a schematic cross-sectional view showing a main portion of a modified example (a thirteenth modified example) of the pressure indicator used in the overtube for an endoscope according to the fourth embodiment of the present invention.

FIG. 80 is a schematic cross-sectional view showing a main portion of the modified example (the thirteenth modified example) of the pressure indicator used in the overtube for an endoscope according to the fourth embodiment of the present invention.

As shown in FIG. 80, the pressure indicator 319F includes a case 320F (a casing) and a collar 323F (a moving member) instead of the case 220 and the collar 323 in the fourth embodiment.

The case 320F is the same as case 220 except that it has a projection claw 320*g*. The projection claw 320*g* protrudes inward in the radial direction from the inner circumferential surface 220*f* of the side surface portion 220*b* and extends in the axial direction. A cross-sectional shape of the projection claw 320*g* is the same in the axial direction.

The cross-sectional shape of the projection claw 320*g* is not particularly limited as long as it can restrict rotation of the outer cylinder portion 223*a* in the circumferential direction. For example, the cross-sectional shape of the projection claw 320*g* may be rectangular, triangular, trapezoidal, semicircular, or the like. In the example shown in FIG. 80, the projection claw 320*g* is a rectangle that protrudes inward in the radial direction from the inner circumferential surface 220*f*.

The position of the convex portion 320*f* in the circumferential direction is not particularly limited as long as it does not cross the display window 221*a*.

The collar 323F is the same as the collar 323 except that it has a groove 323*j*. The groove 323*j* is recessed inward in the radial direction front the outer circumferential surface 323*p* of the outer cylinder portion 223*a*, and extends in the axial direction.

The groove 323*j* is not particularly limited as long as it has a shape that fits the projection claw 320*g* therein so as to be slidable in the axial direction. In the example shown in FIG. 80, a cross section of the groove 323*j* is also rectangular in correspondence with the rectangular shape of the projection claw 320*g*.

However, as in the twelfth modified example, a gap is formed between the inner surface of the case 320F and the outer surface of the collar 323F so that the collar 323F can be inclined, like the collar 323.

According to this modified example, in a state in which the collar 323F is inserted into the side surface portion 220*b* of the case 320F, the projection claw 320*g* is fitted into the groove 323*j* so as to be movable in the axial direction. Thus, the rotation of the collar 323F in the circumferential direction is restricted. The collar 323F can move in the axial direction using the projection claw 320*g* as a track.

The overtube 301 having the pressure indicator 319F of this modified example has the same action as the overtube 301 according to the fourth embodiment.

This modified example is an example in which the rotation of the collar 323F and the case 320F are restricted by fitting between the groove 323*j* and the projection claw 320*g* respectively formed on them.

A similar fitting may be formed by a protrusion claw similar to the projection claw 320*g* except that it protrudes outward in the radial direction from the outer circumferential surface 323*p* of the collar 323F and a groove similar to the groove 323*j* except that it is recessed outward in the radial direction from the inner circumferential surface 220*f* of the case 320F. Also in this case, the rotation of the collar 323F and the case 320F can be restricted.

Fourteenth Modified Example

A modified example (a fourteenth modified example) of the pressure indicator used in place of the pressure indicator 319 in the overtube 301 of the fourth embodiment will be described.

As shown in FIG. 68, a pressure indicator 319H of this modified example can be used in place of the pressure indicator 319 in the overtube 301.

In the following, differences from the fourth embodiment will be mainly described.

Figure 81:
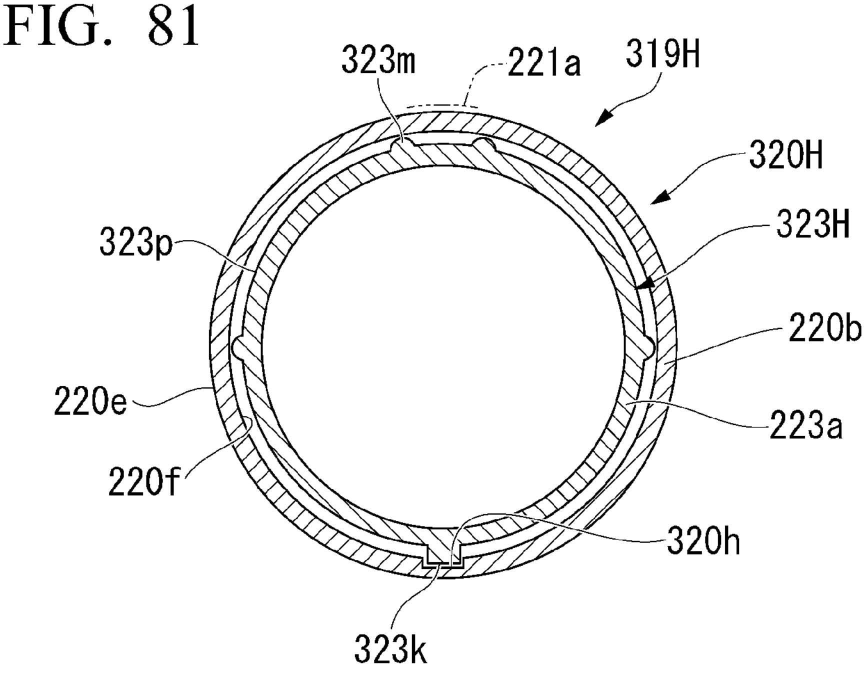
FIG. 81 is a schematic cross-sectional view showing a main portion of a modified example (a fourteenth modified example) of the pressure indicator used in the overtube for an endoscope according to the fourth embodiment of the present invention.

FIG. 81 is a schematic cross-sectional view showing a main portion of the modified example (the fourteenth modified example) of the pressure indicator used in the overtube for an endoscope according to the fourth embodiment of the present invention.

As shown in FIG. 81, the pressure indicator 319H includes a case 320H (a casing) and a collar 323H (a moving member) instead of the case 220 and the collar 323 in the fourth embodiment.

The case 320H is the same as the case 220 except that it has a groove 320*h*. The groove 320*h* is recessed outward in the radial direction from the inner circumferential surface 220*f* of the side surface portion 220*b* and extends in the axial direction. A cross-sectional shape of the groove 320*h* can have various cross-sectional shapes, like the groove 323*j* in the thirteenth modified example.

A position of the groove 320*h* in the circumferential direction is not particularly limited as long as it does not cross the display window 221*a*.

The collar 323H is the same as the collar 323 except that it has a protrusion claw 323*k* and a convex portion 323*m*.

The protrusion claw 323*k* protrudes outward in the radial direction from the outer circumferential surface 323*p* of the outer cylinder portion 223*a* and extends in the axial direction. A cross-sectional shape of the protrusion claw 323*k* is a shape that fits in the groove 320*h* and is relatively movable in the axial direction. As in the projection claw 320*g* in the thirteenth modified example, the protrusion claw 323*k* can have various cross-sectional shapes as long as it can fit into the groove 320*h*.

The convex portion 323*m* protrudes outward in the radial direction from the outer circumferential surface 323*p*. The convex portion 323*m* is spaced apart from the protrusion claw 323*k* in the circumferential direction, and is provided at a position at which it is not visible from the display window 221*a* indicated by a two-dot chain line. The convex portion 323*m* may be provided at one location, or may be provided in plurality in the circumferential direction or the axial direction. In the example shown in FIG. 81, the convex portions 323*m* are provided at four locations in the circumferential direction.

An arrangement position of the convex portion 323*m* may be selected in consideration of the inclination of the collar 323H so that it can easily come into contact with the inner circumferential surface 220*f*.

The convex portion 323*m* is provided for the purpose of reducing sliding resistance with the inner circumferential surface 220*f*. Therefore, the shape, number, and formation position of the convex portions 323*m* are not particularly limited as long as the sliding resistance with the inner circumferential surface 220*f* can be reduced. It is more preferable that the convex portion 323*m* is formed of a convex curved surface that smoothly comes into point contact with the inner circumferential surface 220*f*.

For example, the convex portion 323*m* may be a protrusion claw extending in the axial direction or the circumferential direction, or may be a spot-shaped protruding portion when seen in the radial direction. A particularly preferable shape for the convex portion 323*m* is an axially extending protrusion claw with a semicircular cross section or a hemispherical protrusion.

According to this modified example, in a state in which the collar 323H is inserted into the side surface portion 220*b* of the case 320H, the protrusion claw 323*k* fits into the groove 320*h*. Thus, the rotation of the collar 323H in the circumferential direction is restricted. The collar 323H can move in the axial direction using the protrusion claw 323*k* as a track.

In this modified example, since the convex portion 323*m* protrudes from the outer circumferential surface 323*p*, the sliding resistance of the collar 323H with respect to the inner circumferential surface 220*f* is reduced compared to the case in which the convex portion 323*m* is not provided. In the pressure indicator 319H, even when a change in the internal pressure of the case 320H is small, the collar 323H can smoothly follow the change in the pressure. Thus, the internal pressure of the case 320H can be displayed more accurately.

The overtube 301 having the pressure indicator 319H of this modified example has the same action as the overtube 301 according to the fourth embodiment.

This modified example is an example in which the rotation of the collar 323H and the case 320H is restricted by fitting between the protrusion claw 323*k* and the grooves 320*h* respectively formed on them.

The fourteenth modified example described above may be implemented with the following modifications.

A protrusion height of the convex portion 323*m* may be changed according to the arrangement position. For example, the convex portion 323*m* may be formed at a height that allows the convex portion 323*m* to be located at an equal distance from the inner circumferential surface 220*f* when the collar 323H is inclined by an angle α. In this case, in the state in which the collar 323H is inclined, the convex portion 323*m* is in contact with the inner circumferential surface 220*f* approximately evenly in the axial direction. Thus, variations in an inclined posture of the collar 323H are reduced. In addition to the function of reducing the sliding resistance, the convex portion 323*m* has a function of keeping the inclination of the collar 323H substantially constant.

Fifteenth Modified Example

A modified example (a fifteenth modified example) of the pressure indicator used in place of the pressure indicator 319 in the overtube 301 of the fourth embodiment will be described.

As shown in FIG. 68, a pressure indicator 319J of this modified example can be used in place of the pressure indicator 319 in the overtube 301.

Figure 82:
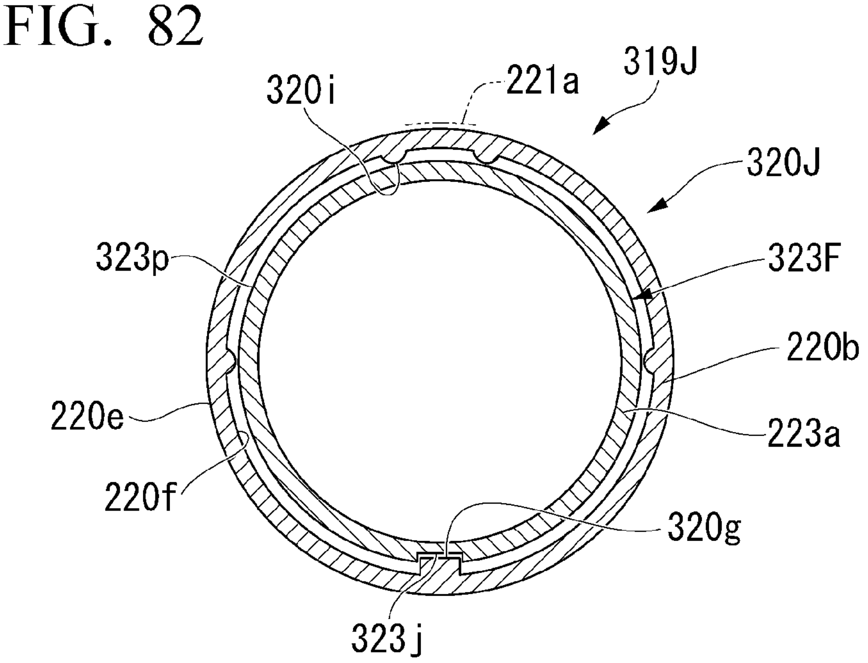
FIG. 82 is a schematic cross-sectional view showing a main portion of a modified example (a fifteenth modified example) of the pressure indicator used in the overtube for an endoscope according to the fourth embodiment of the present invention.

FIG. 82 is a schematic cross-sectional view showing a main portion of the modified example (the fifteenth modified example) of the pressure indicator used in the overtube for an endoscope according to the fourth embodiment of the present invention.

As shown in FIG. 82, the pressure indicator 319J includes a case 320J (a casing) and a collar 323F instead of the case

220 and the collar 323 in the fourth embodiment. The collar 323F is a member that is the same as the collar 323F in the thirteenth modified example.

In the following, differences from the fourth embodiment and the thirteenth modified example will be mainly described.

The case 320J is the same as the case 220, except that it has a convex portion 320*i*.

The convex portion 320*i* is the same as the convex portion 323*m* in the fourteenth modified example, except that it protrudes inward in the radial direction from the inner circumferential surface 220*f* at a constant protrusion height. However, in order to prevent the convex portion 320*i* from being easily caught on the distal ends and base ends when the collar 323F moves, it is more preferable that the convex portion 320*i* is a continuous protrusion claw in the axial direction.

A top portion of the convex portion 320*i* in a protruding direction has a smaller diameter than the inner circumferential surface 220*f* and is located on the same coaxial cylindrical surface.

According to this modified example, in a state in which the collar 323F is inserted into the side surface portion 220*b* of the case 320J, the projection claw 320*g* fits into the groove 323*j* so as to be movable in the axial direction, as in the thirteenth modified example. Thus, as in the thirteenth modified example, the rotation of the collar 323F is restricted. The collar 323F can move in the axial direction using the projection claw 320*g* as a track.

Furthermore, in this modified example, since the convex portion 320*i* protrudes from the inner circumferential surface 220*f*, the sliding resistance of the collar 323F with respect to the case 320J is reduced compared to the thirteenth modified example. Therefore, in the pressure indicator 319J, even when the change in the internal pressure of the case 320H is small, the collar 323F can smoothly follow the change in the pressure, and the internal pressure of the case 320J can be displayed more accurately.

The overtube 301 having the pressure indicator 319J of this modified example has the same action as the overtube 301 according to the fourth embodiment.

This modified example is an example in which the sliding resistance applied to the collar 323F is reduced by providing the convex portion 320*i* on the inner circumferential surface 220*f*.

Sixteenth Modified Example

A modified example (a sixteenth modified example) of the pressure indicator used instead of the pressure indicator 319 in the overtube 301 of the fourth embodiment will be described.

As shown in FIG. 68, a pressure indicator 319K of this modified example can be used in place of the pressure indicator 319 in the overtube 301.

Figure 83:
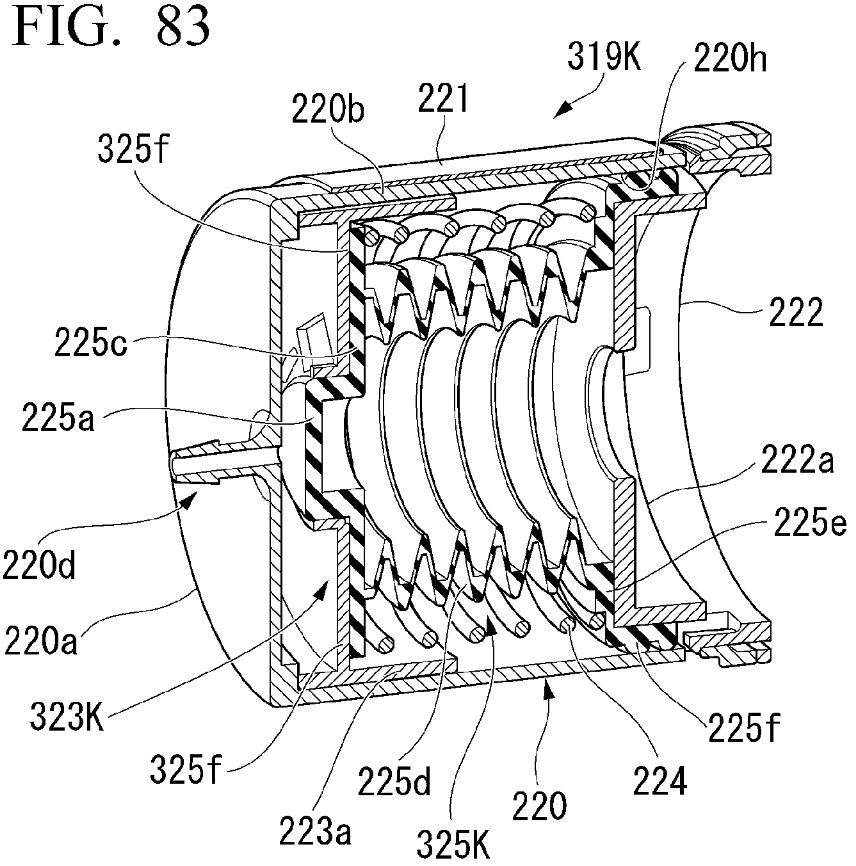
FIG. 83 is a schematic perspective partial sectional view showing a main portion of a modified example (a sixteenth modified example) of the pressure indicator used in the overtube for an endoscope according to the fourth embodiment of the present invention.
Figure 84:
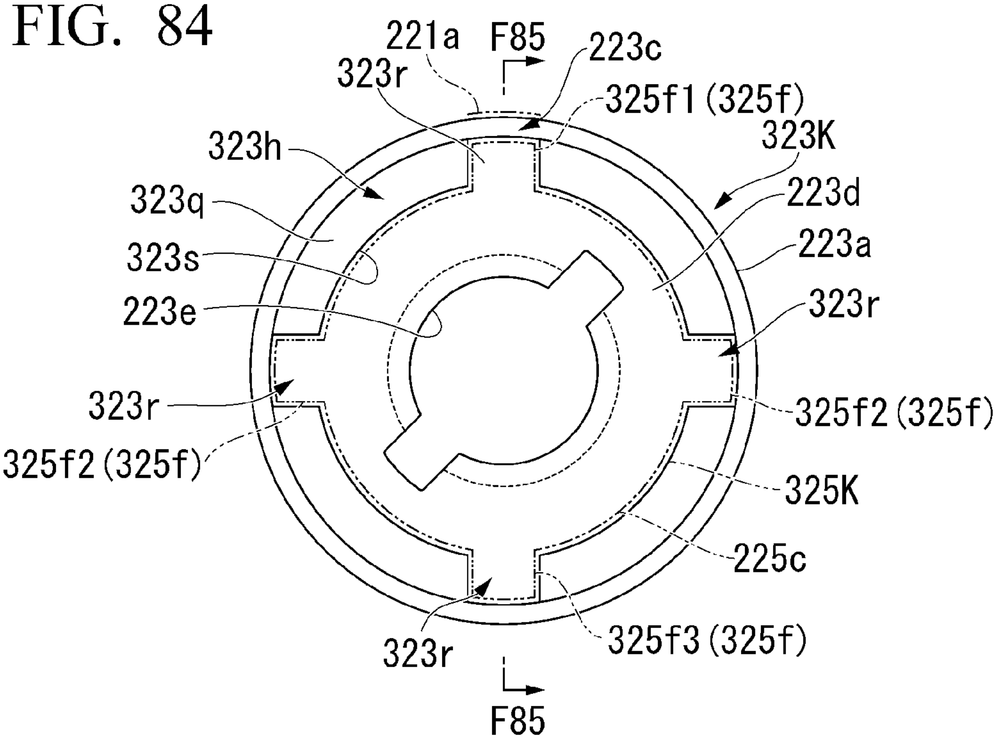
FIG. 84 is a right side view of a collar used in the modified example (the sixteenth modified example) of the pressure indicator.
Figure 85:
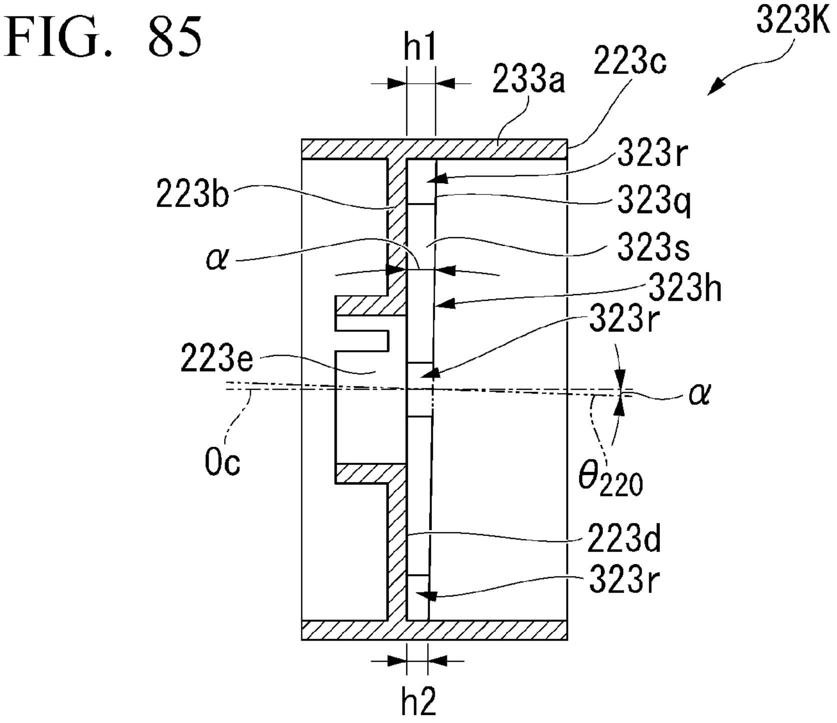
FIG. 85 is a cross-sectional view along line F85-F85 in FIG. 84.

FIG. 83 is a schematic perspective partial cross-sectional view showing a main portion of the modified example (the sixteenth modified example) of the pressure indicator used in the overtube for an endoscope according to the fourth embodiment of the present invention. FIG. 84 is a right side view of a collar used in the modified example (the sixteenth modified example) of the pressure indicator. FIG. 85 is a cross-sectional view taken along line F85-F85 in FIG. 84.

As shown in FIG. 83, the pressure indicator 319K includes a collar 323K (a moving member) and an airtight member 325K (a sealing member, a pressing member) instead of the collar 323 and the airtight member 225.

In the following, differences from the fourth embodiment will be mainly described.

As shown in FIG. 84, the collar 323K is the same as the collar 223 in the third modified example, except that the fitting claw 223*f*, the pressing claw 223*g*, the hole 223*j*, and the hole 223*k* are removed from the locking plate 223*b*, and a stepped portion 323*q* (an elastic member support portion) is added.

The stepped portion 323*q* protrudes from the locking surface 223*d* of the locking plate 323*b* to the distal end side in the axial direction and extends along the inner circumferential surface of the outer cylinder portion 223*a*.

In the stepped portion 323*q*, concave portions 323*r* that are recessed to the same height as the locking surface 223*d* are formed at four positions that divide the inner circumference of the outer cylinder portion 223*a* into four equal portions in the circumferential direction.

A width of each of the concave portions 323*r* in the circumferential direction is such that it can be engaged with an engaging protrusion 325*f* of the airtight member 325K which will be described below.

An inner circumferential surface 323*s* of each of the stepped portions 323*q* in the radial direction is a curved surface along a cylindrical surface having a size that allows a bottom plate portion 225*c* of the airtight member 325K, which will be described below, to be inserted along an outer circumferential surface of the bottom plate portion 225*c*.

As shown in FIG. 85, an inclined surface 323*h* is formed at the distal end of each of the stepped portions 323*q* in the axial direction.

Each of the inclined surfaces 323*h* is located on the same plane having an inclination rotated by an angle α clockwise in the drawing with respect to the locking surface 223*d* orthogonal to the central axis Oc.

On the upper side in which the distal end edge portion 223*c* is close to the display window 221*a*, a distance between the locking surface 223*d* and the inclined surface 323*h* is h1. On the lower side opposite thereto in the radial direction, the distance between the locking surface 223*d* and the inclined surface 323*h* is h2 which is shorter than h1.

Figure 86:
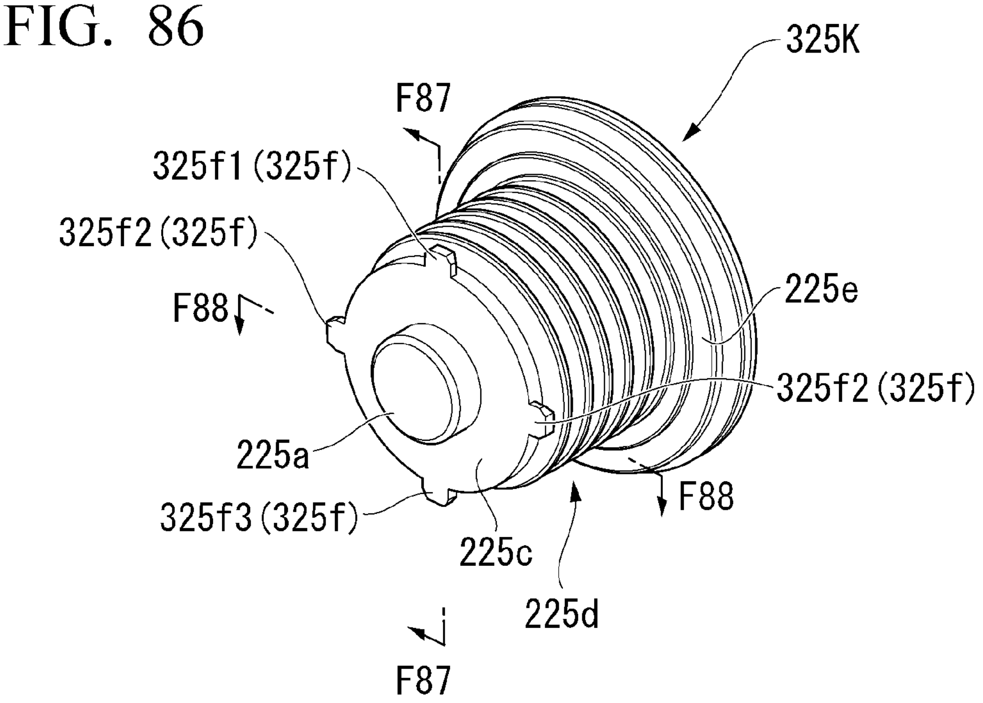
FIG. 86 is a perspective view of an airtight member used in the modified example (the sixteenth modified example) of the pressure indicator.
Figure 87:
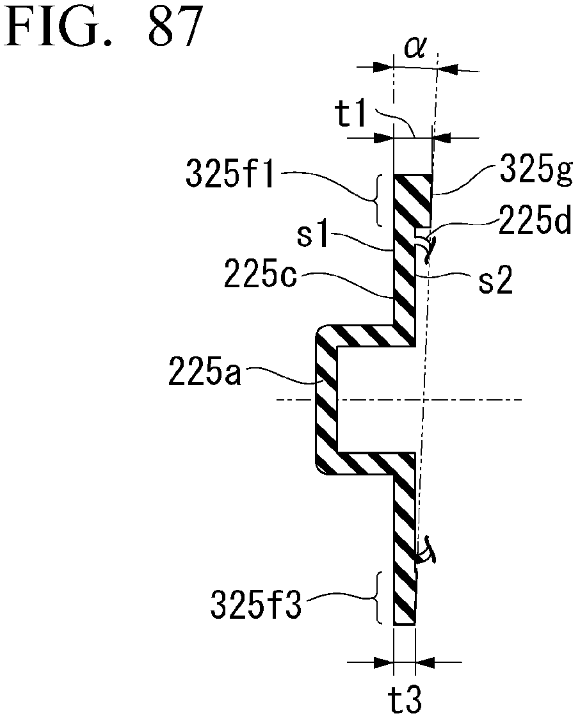
FIG. 87 is a cross-sectional view taken along line F87-F87 in FIG. 86.
Figure 88:
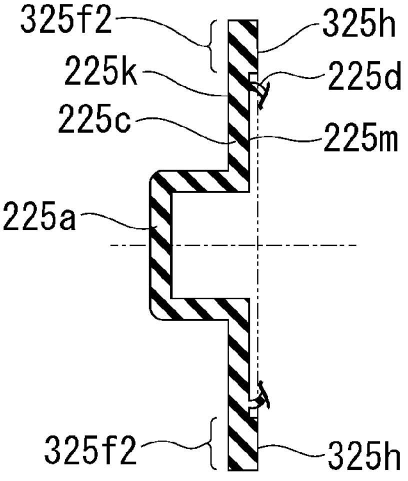
FIG. 88 is a cross-sectional view taken along line F88-F88 in FIG. 86.

FIG. 86 is a perspective view of the airtight member used in the modified example (the sixteenth modified example) of the pressure indicator. FIG. 87 is a cross-sectional view taken along line F87-F87 in FIG. 86. FIG. 88 is a cross-sectional view taken along line F88-F88 in FIG. 86.

As shown in FIG. 86, the airtight member 325K is the same as the airtight member 225, except that the fitting protrusion 225*b* is removed and an engaging protrusion 325*f* is provided in place of the engaging protrusion 225*i*.

Like the engaging protrusions 225*i*, the engaging protrusions 325*f* extend outward in the radial direction from four positions that divide the outer circumference of the bottom plate portion 225*c* into four equal portions in the circumferential direction. Each of the engaging protrusions 325*f* extends close to the inner circumferential surface of the outer cylinder portion 223*a*, as indicated by a two-dot chain line in FIG. 84. Each of the engaging protrusions 325*f* is inserted into each of the concave portions 323*r* of the collar 323K. Thus, since movement of the engaging protrusion 325*f* in the circumferential direction is restricted, rotation of the airtight member 325K in the circumferential direction is restricted.

The engaging protrusions 325*f* include, for example, a first engaging protrusion 325*f*1, a second engaging protrusion 325*f*2, and a third engaging protrusion 325*f*3.

The first engaging protrusion 325*f*1 is inserted into the concave portion 323*r* on the upper side in the drawing near the display window 221*a* (refer to a two-dot chain line) and the distal end edge portion 223*c* in the radial direction.

The third engaging protrusion 325*f*3 is disposed on the lower side in the drawing opposite to the first engaging protrusion 325*f*1 in the radial direction.

A pair of the second engaging protrusions 325*f*2 are provided at positions facing each other in the radial direction orthogonal to a facing direction of the first engaging protrusions 325*f*1 and the third engaging protrusions 325*f*3.

As shown in FIG. 87, surfaces of the first engaging protrusion 325*f*1 and the third engaging protrusion 325*f*3 on the base end side (the left side in the drawing) extend along a first surface s1 of the bottom plate portion 225*c* on the base end side.

The first engaging protrusion 325*f*1 and the third engaging protrusion 325*f*3 protrude toward the distal end side (to the right in the drawing) with respect to a second surface s2 of the bottom plate portion 225*c* on the distal end side.

An inclined surface 325*g* located on the same plane that is inclined clockwise in the drawing by an angle α with respect to the first surface s1 is formed on surfaces of the first engaging protrusion 325*f*1 and the third engaging protrusion 325*f*3 on the distal end side.

A maximum thickness t1 of the first engaging protrusion 325*f*1 is slightly thicker than a depth h1 of the upper concave portion 323*r*.

A minimum thickness t3 of the third engaging protrusion 325*f*3 is slightly thicker than a depth h2 of the lower concave portion 323*r*.

As shown in FIG. 88, the surface of each of the second engaging protrusions 325*f*2 on the base end side (the left side in the drawing) extends along the first surface s1.

A distal end side surface 325*h* which is a surface of each of the second engaging protrusions 325*f*2 on the distal end side (the right side in the drawing) may be an inclined surface that is the same as the inclined surface 325*g*, and may be a plane parallel to the second surface s2 when it is equivalent to a depth of the concave portion 323*r* into which each of the second engaging protrusions 325*f*2 is inserted. When the distal end side surface 325*h* has the same inclination as the inclined surface 325*g*, the distal end side surface 325*h* is located on the same plane as each of the inclined surfaces 325*g* of the first engaging protrusion 325*f*1 and the third engaging protrusion 325*f*3.

In this modified example, the coil spring 224 is disposed between each of the stepped portions 323*q* and the flange portion 225*e* of the airtight member 325K. Therefore, as shown in FIG. 83, the base end of the coil spring 224 is located on the distal end side of each of the engaging protrusions 325*f*. A portion of each of the engaging protrusions 325*f* that protrudes from the concave portion 323*r* is pressed from the distal end side by the base end of the coil spring 224. Thus, the engaging protrusion 325*f* is prevented from coming off from the concave portion 323*r* in the axial direction.

Since each of the pressed engaging protrusions 325*f* deforms in the thickness direction, the base end of the coil spring 224 comes into contact with the inclined surface 325*g* of each of the stepped portions 323*q*.

According to this modified example, the inclined surface 325*g* with which the base end of the coil spring 224 comes into contact is inclined by an angle α. When the base end of the coil spring 224 comes into contact with each of the inclined surfaces 325*g*, the collar 323K is inclined by an angle α inside the side surface portion 220*b*, like the collar 323 in the fourth embodiment.

Thus, as in the collar 323, since the distal end edge portion 223*c* of the collar 323K is close to the display window 221*a*, the operator can read accurate pressure.

The overtube 301 having the pressure indicator 319K of this modified example has the same action as the overtube 301 according to the fourth embodiment.

In particular, in this modified example, the rotation of the airtight member 325K is restricted by inserting each of the engaging protrusions 325*f* at the distal end portion of the airtight member 325K into each of the concave portions 323*r* of the collar 323K, and the airtight member 325*k* is prevented from coming off in the axial direction by the coil spring 224.

Thus, assemblability of the pressure indicator 319K is improved.

This modified example is an example in which the convex portion formed on the distal end side of the locking plate 223*b* is formed of the stepped portion 323*q* protruding from the locking surface 223*d* to the distal end side for the purpose of inclining the collar 323K.

In the pressure indicator 319K, the stepped portion 323*q* having the inclined surface 323*h* in the collar 323K is an example of an elastic member support portion that is included in the moving member and supports an elastic member on an inclined surface inclined in a certain direction with respect to the central axis when the tubular portion is disposed coaxially with the central axis.

Seventeenth Modified Example

A modified example (a seventeenth modified example) of the pressure indicator used in place of the pressure indicator 319 in the overtube 301 of the fourth embodiment will be described.

As shown in FIG. 68, a pressure indicator 319L of this modified example can be used in place of the pressure indicator 319 in the overtube 301.

Figure 89:
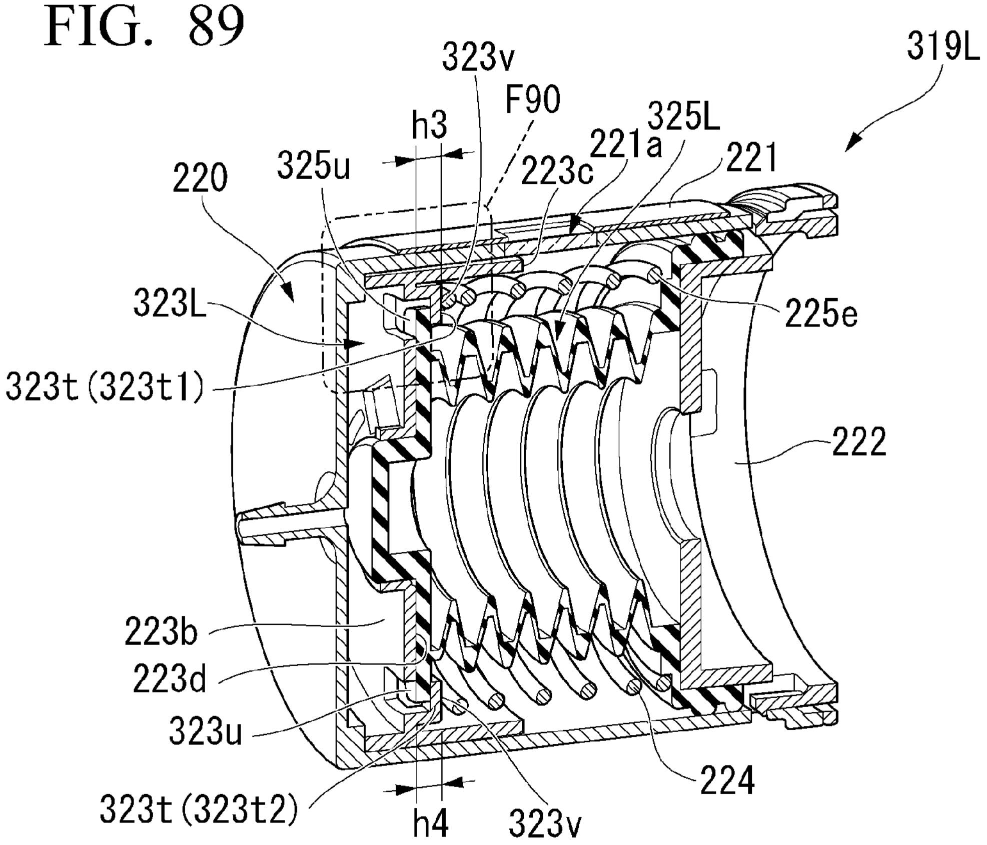
FIG. 89 is a schematic perspective partial sectional view showing a main portion of a modified example (a seventeenth modified example) of the pressure indicator used in the overtube for an endoscope according to the fourth embodiment of the present invention.
Figure 90:
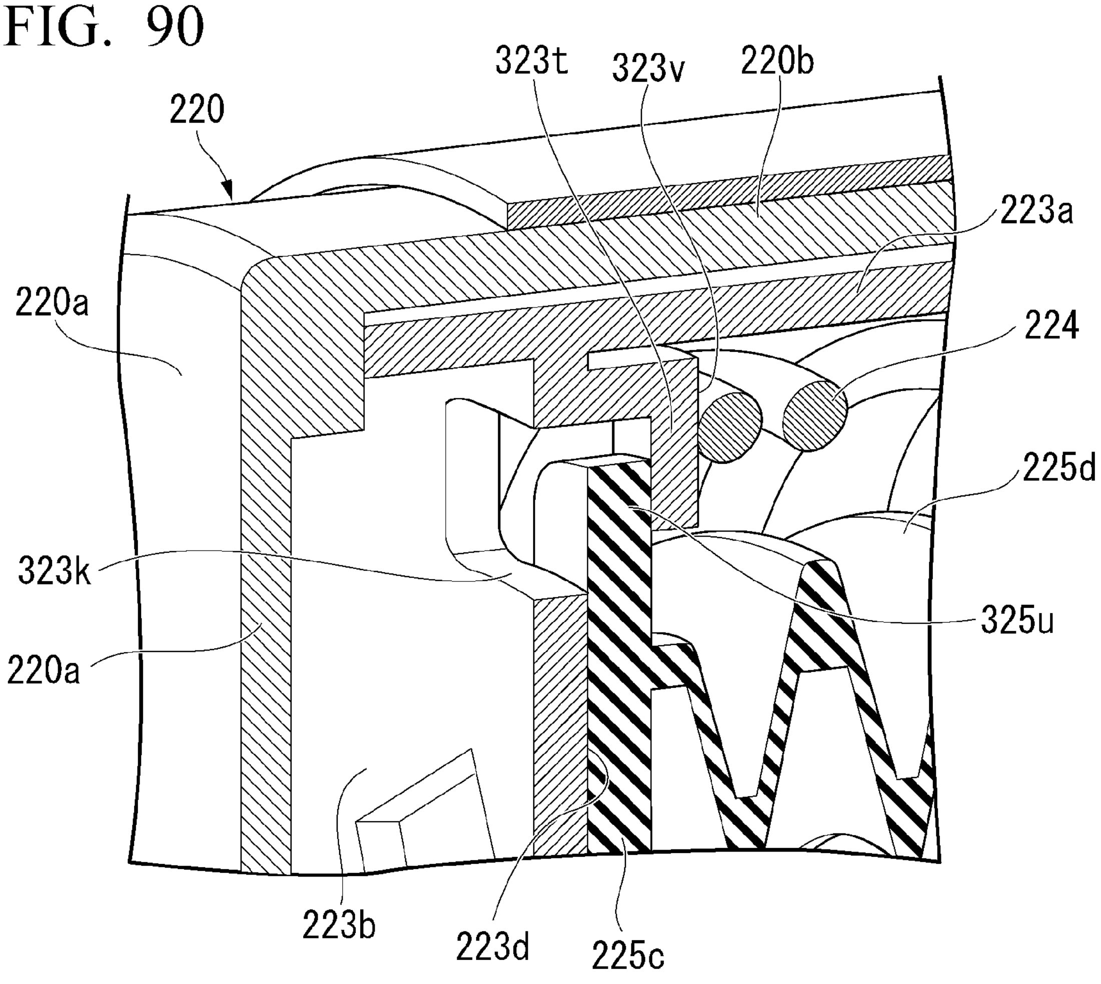
FIG. 90 is an enlarged view of an F90 portion in FIG. 89.

FIG. 89 is a schematic perspective partial sectional view showing a main portion of the modified example (the seventeenth modified example) of the pressure indicator used in the overtube for an endoscope according to the fourth embodiment of the present invention. FIG. 90 is an enlarged view of an F90 portion in FIG. 89.

As shown in FIG. 89, the pressure indicator 319L includes a collar 323L (a moving member) and an airtight member 325L (a sealing member, a pressing member) instead of the collar 323 and the airtight member 225.

In the following, differences from the fourth embodiment and the sixteenth modified example will be mainly described.

The collar 323L is the same as the collar 223 in the third modified example, except that it has a pressing claw 323*t* (an elastic member support portion) instead of the pressing claw 223*g*.

All of the pressing claws 323*t* are provided outward in the radial direction from the pressing claws 223*g*. A position of each of the pressing claws 323*t* in the radial direction is such that the distal end portion of the pressing claw 323*t* comes into contact with the base end of the coil spring 224.

Each of the pressing claws 323*t* is the same as the pressing claw 223*g*, except that an inclined surface 323*v* having the same inclination as the inclined surface 323*h* in the sixteenth modified example is formed at the distal end portion in the axial direction. However, each of the pressing claws 323*t* differs from the pressing claw 223*g* in that it axially engages an engaging protrusion 325*u* of the airtight member 325L, which will be described below, instead of the engaging protrusion 325*i*.

The inclined surface 323*v* is formed on each of the pressing claws 323*t*, and is located on the same plane that is inclined by an angle α with respect to the locking surface 223*d*.

Thus, a maximum height h3 from the locking surface 223*d* of the upper pressing claw 323*t*1 near the display window 221*a* in the radial direction is higher than a minimum height h4 of the pressing claw 323*t*2 on the opposite side in the radial direction.

As shown in FIG. 89, the airtight member 325L has an engaging protrusion 325*u* instead of the engaging protrusion 225*i* of the airtight member 225 in the fourth embodiment.

The engaging protrusion 325*u* is the same as the engaging protrusion 225*i*, except that it has a length that allows it to be inserted between the pressing claw 323*t* and the locking plate 223*b*.

The length of the engaging protrusion 325*u* is such that it can enter a gap between the pressing claw 323*t* and the locking surface 223*d* in the axial direction.

As shown in FIG. 90, in the assembled state of the pressure indicator 319L, a surface of the engaging protrusion 325*u* on the distal end side in the axial direction engages with a base end surface of the pressing claw 323*t*. Thus, the engaging protrusion 325*u* is sandwiched between the locking surface 223*d* and the pressing claw 323*t*, and engages in the axial direction. Although not shown in FIG. 90, a fitting protrusion 225*b* of the airtight member 325L engages with a fitting claw 223*f* (not shown) of the collar 323L in the axial direction, as in the collar 223 in the third modified example.

The base end of the coil spring 224 is in contact with the inclined surface 323*v*. Since the inclined surface 323*v* is the same inclined surface as the inclined surface 323*h* in the sixteenth modified example, the collar 323L is inclined by an angle α within the case 220, like the collar 323K in the sixteenth modified example.

According to this modified example, the distal end of the pressing claw 323*t* with which the base end of the coil spring 224 comes into contact is inclined by an angle α. When the base end of the coil spring 224 comes into contact with each of the pressing claws 323*t*, the collar 323L is inclined by an angle α inside the side surface portion 220*b*, like the collar 323 in the fourth embodiment.

Thus, as in the collar 323, since the distal end edge portion 223*c* of the collar 323L is close to the display window 221*a*, the operator can read accurate pressure.

The overtube 301 having the pressure indicator 319L of this modified example has the same action as the overtube 301 according to the fourth embodiment.

This modified example is an example in which a convex portion formed on the distal end side of the locking plate 223*b* is formed by the pressing claw 323*t* for the purpose of inclining the collar 323L.

In the pressure indicator 319L, the pressing claw 323*t* of the collar 323L having the inclined surface 323*v* is an example of an elastic member support portion that is included in the moving member and supports an elastic member on an inclined surface inclined in a certain direction with respect to the central axis when the tubular portion is disposed coaxially with the central axis.

The fourth embodiment and modified examples described above may be implemented with various modifications.

For example, each of the configurations of the twelfth modified example to the fifteenth modified example may be used in combination as appropriate. Each of the configurations of the twelfth modified example to the fifteenth modified example is not limited to the case or the collar in the fourth embodiment, and may be combined with the eighth to eleventh, sixteenth, and seventeenth modified examples.

Fifth Embodiment

An overtube for an endoscope according to a fifth embodiment of the present invention will be described.

An overtube 401 shown in FIG. 17 is an example of an overtube for an endoscope according to this embodiment.

The overtube 401 includes an air supply device 410 instead of the air supply device 310 of the overtube 301 according to the third embodiment.

In the following, differences from the third embodiment will be mainly described.

Figure 91:
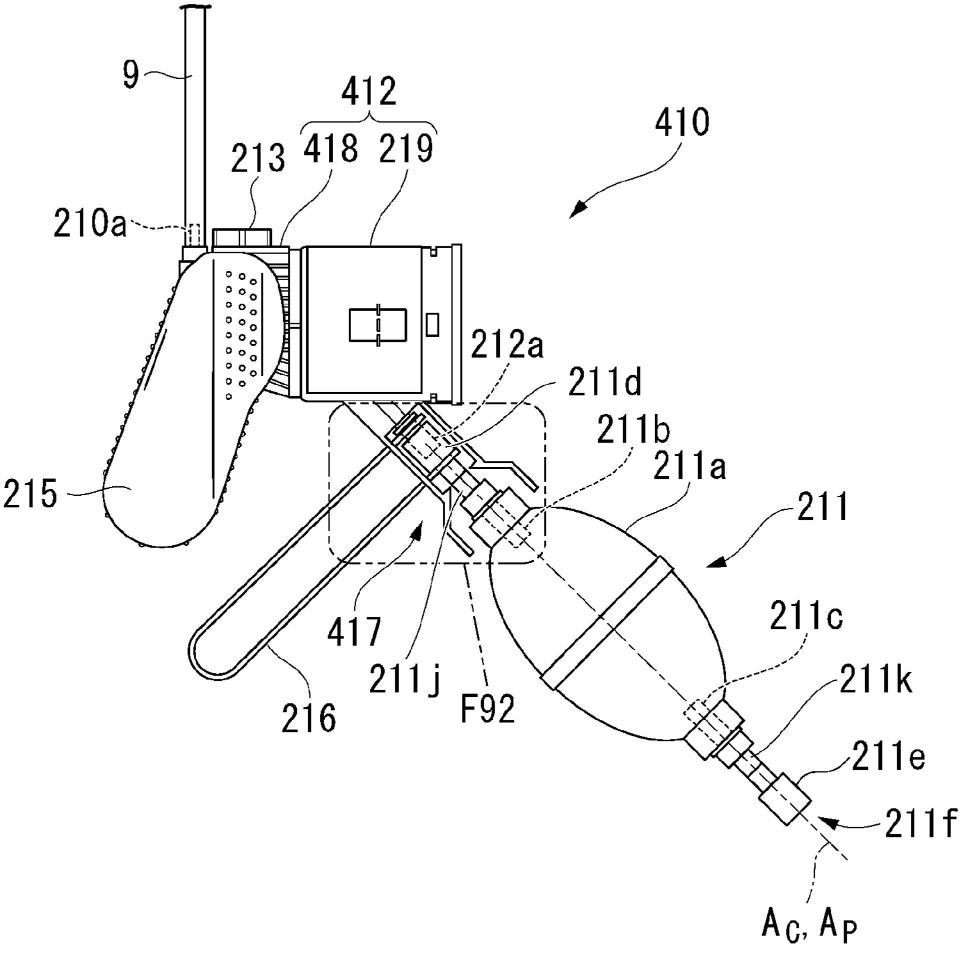
FIG. 91 is a schematic front view showing an example of an air supply device used in an overtube for an endoscope according to a fifth embodiment of the present invention.
Figure 92:
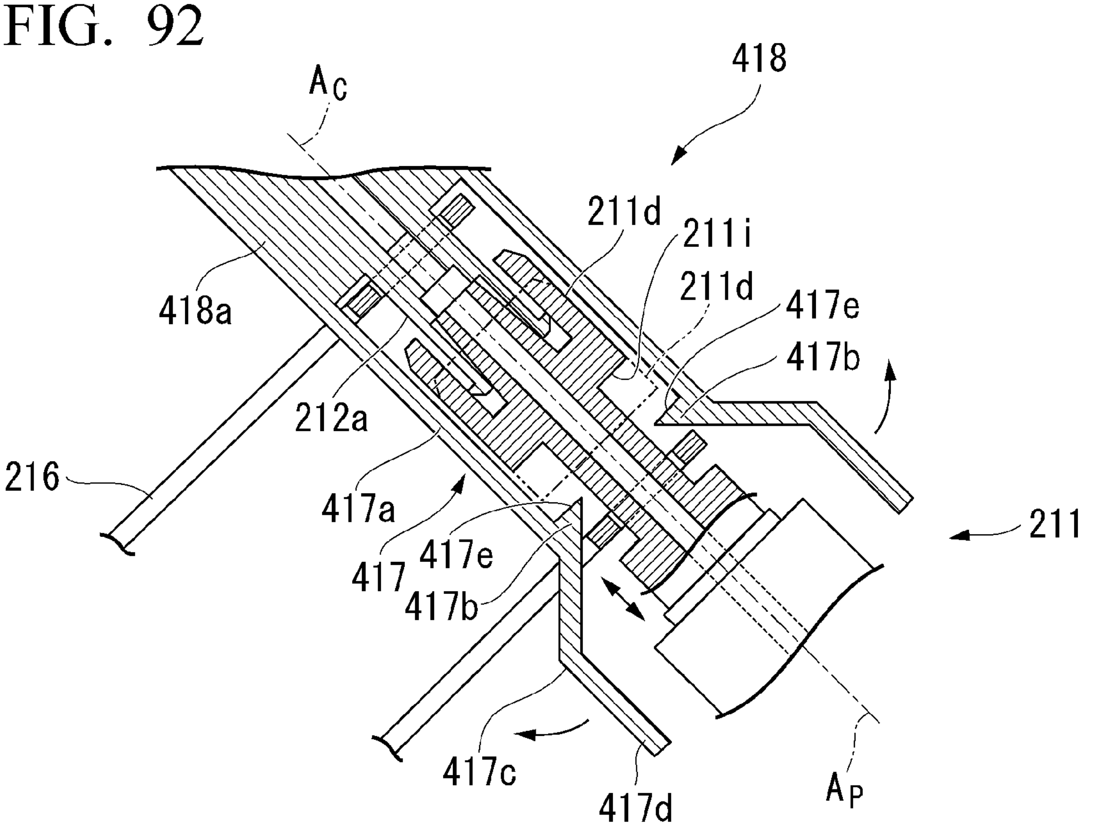
FIG. 92 is an enlarged view of an F92 portion in FIG. 91.

FIG. 91 is a schematic front view showing the air supply device in the overtube for an endoscope according to the fifth embodiment of the present invention. FIG. 92 is an enlarged view of an F92 portion in FIG. 91.

As shown in FIG. 91, the air supply device 410 in this embodiment has a main body portion 412 instead of the main body portion 212 in the third embodiment. The main body portion 412 has a casing 418 instead of the casing 218 of the main body portion 212.

The casing 418 is the same as the casing 218 in the third embodiment, except that a limiter 417 is provided near the connection tube 212*a*.

A pump 211*a* in this embodiment has the same configuration as in the third embodiment.

The first connection portion 211*d* is provided at a distal end of an air supply tube 211*j*. The first check valve 211*b* is provided inside the air supply tube 211*j*. When the operator operates the pump 211*a*, gas is sent out of the air supply tube 211*j*.

The first connection portion 211*d* is an example of a first connector that detachably connects the air supply tube 211*j* to the connection tube 212*a*.

The second connection portion 211*e* is provided at a distal end of an air suction tube 211*k*. The second check valve 211*c* is provided inside the air suction tube 211*k*. When the operator operates the pump 211*a*, gas is suctioned into the air suction tube 211*k* from the outside.

The second connection portion 211*e* is an example of a second connector that detachably connects the air suction tube 211*k* to the connection tube 212*a*.

In the following, differences from the third embodiment will be mainly described.

When the first connection portion 211*d* or the second connection portion 211*e* of the manual air supply mechanism 211 is removed from the connection tube 212*a*, the limiter 417 restricts the position of the manual air supply mechanism 211 in a state in which the first connection portion 211*d* or the second connection portion 211*e* is unlocked.

Hereinafter, a direction along a central axis $A_C$ of the connection tube 212*a* is referred to as an attachment-detachment direction. When the manual air supply mechanism 211 is a rubber bulb pump, the central axis $A_C$ is coaxial with a central axis $A_P$ of the manual air supply mechanism 211.

As shown in FIG. 92, the limiter 417 is provided on a side portion 418*a* of a casing 418 to which the connection tube 212*a* is fixed.

A shape of the limiter 417 is not particularly limited as long as it can restrict the movement of the first connection portion 211*d* or the second connection portion 211*e* in the attachment-detachment direction when the first connection portion 211*d* or the second connection portion 211*e* is unlocked. In the following, an example in which the exterior of the first connection portion 211*d* or the second connection portion 211*e* is approximately cylindrical, and an end surface 211*i* that intersects the attachment-detachment direction is formed at an end portion thereof on the side opposite to the side portion 418*a* in the attachment-detachment direction will be described.

The limiter 417 includes a side plate portion 417*a* (a locking member), an operating part 417*c*, and a locking protrusion 417*b* (a locking member).

The side plate portion 417*a* is an elastic plate that extends in the attachment-detachment direction from the outside of the side portion 418*a*. The side plate portions 417*a* face each other with the connection tube 212*a* interposed therebetween. A facing direction of each of the side plate portions 417*a* is a direction orthogonal to the attachment-detachment direction.

A facing distance between the side plate portions 417*a* is equal to or greater than the outer diameter of the first connection portion 211*d*.

A width of the side plate portion 417*a* in the transverse direction is narrower than the outer diameter of the first connection portion 211*d*. Thus, a side surface of a part of the first connection portion 211*d* sandwiched between the side plate portions 417*a* protrudes outward in the transverse direction of the side plate portion 417*a*. Thus, the operator can perform operations such as attaching, locking, unlocking, and moving in the attachment-detachment direction of the first connection portion 211*d* sandwiched between the side plate portions 417*a* with respect to the connection tube 212*a*.

The side plate portion 417*a* can be made of an elastic resin or metal. The side plate portion 417*a* can be elastically deformed outward in the facing direction from a state in which it extends in the attachment-detachment direction due to an external force acting on the distal end in the extending direction.

The operating part 417*c* is provided for the operator to perform an operation to open the distal end of each of the side plate portion 417*a* in the extending direction outward.

A shape of the operating part 417*c* is not particularly limited as long as the operator can apply an operating force in a direction in which the facing distance between the side plate portions 417*a* is widened. In the example shown in FIG. 92, the operating part 417*c* is formed of a bent plate that bends outward in the facing direction from the distal end of each of the side plate portions 417*a* in the extending direction and extends in a direction away from the side portion 418*a* in the attachment-detachment direction.

An operating lever 417*d* extending parallel to the central axis $A_P$ is formed at the distal end portion of each of the operating parts 417*c* in the extending direction.

The locking protrusion 417*b* protrudes inward in the facing direction from the distal end portion of each of the side plate portions 417*a*. A distance between the distal ends of the locking protrusions 417*b* in the protruding direction is smaller than the outer diameter of the first connection portion 211*d*.

A locking surface 417*e* is formed on each of the locking protrusions 417*b* toward the connection tube 212*a* in the attachment-detachment direction.

The locking surface 417*e* is a plane extending in a direction substantially orthogonal to the central axis $A_C$.

Since the operation of the overtube 401 is the same as that of the overtube 301 except for the operation of the limiter 417, the operation of the overtube 401 will be described with a focus on the operation of the limiter 417.

According to the limiter 417, for example, when the first connection portion 211*d* of the connection tube 212*a* is unlocked, as shown by a two-dot chain line, the first connection portion 211*d* can move in the attachment-detachment direction between a locked position with the connection tube 212*a* and a locking position in which the end surface 211*i* is locked on the locking surface 417*e*.

However, even when an attempt is made to pull out the manual air supply mechanism 211 in the attachment-detachment direction, the first connection portion 211*d* stops at the locking surface 417*e*. Therefore, the manual air supply mechanism 211 cannot be separated from the limiter 417. Even when the operator takes his/her hand off the manual air supply mechanism 211 in the unlocked state, the manual air supply mechanism 211 will not fall.

However, when the operator opens the operating lever 417*d* outward, each of the side plate portions 417*a* is deformed to open outward. The operator can separate the first connection portion 211*d* from the limiter 417 by opening the operating lever 417*d* until the facing distance between the locking protrusions 417*b* becomes larger than the outer diameter of the first connection portion 211*d*.

On the other hand, when the first connection portion 211*d* is connected to the connection tube 212*a*, the first connection portion 211*d* may be inserted into a space between the operating levers 417*d*, and the first connection portion 211*d* may be pushed between the locking protrusions 417*b*. In this case, each of the side plate portions 417*a* receives an external force from each of the locking protrusions 417*b* that are in contact with the side surface of the first connection portion 211*d*, and bends outward. When the end surface 211*i* of the first connection portion 211*d* passes between the respective locking protrusions 417*b*, each of the side plate portions 417*a* closes inward.

The same applies to a case in which the second connection portion 211*e* is connected to the connection tube 212*a*, instead of the first connection portion 211*d*.

According to this embodiment, since the air supply device 410 includes the limiter 417, the first connection portion 211*d* can be moved within a certain distance range from the connection tube 212*a* while the first connection portion 211*d* is unlocked. Furthermore, the manual air supply mechanism 211 will not come off the limiter 417 unless the operator operates the operating part 417*c*.

With such a limiter 417, the operator can exhaust the air inside the fixing balloon 3 without switching the manual air supply mechanism 211 from the first connection state to the second connection state.

That is, when the first connection portion 211*d* is unlocked and the first connection portion 211*d* is retracted in a direction away from the connection tube 212*a*, a gap may be created in the radial direction at a connection portion between a conduit in the first connection portion 211*d* and a conduit in the connection tube 212*a*. Thus, air in the conduit on the downstream side of the connection tube 212*a* leaks to the outside of the connection tube 212*a*.

A leakage flow rate of air increases according to a distance separating the unlocked first connection portion 211*d* from the connection tube 212*a*. Therefore, the operator can finely adjust an amount of exhaust of air by finely adjusting the position of the first connection portion 211*d* in the attachment-detachment direction.

For example, when the pressure of the fixing balloon 3 becomes too high due to excessive air supply, the pressure of the fixing balloon 3 can be quickly reduced by the operator performing such an exhaust operation.

At that time, since the locking protrusion 417*b* restricts an amount of movement of the first connection portion 211*d*, it is possible to prevent a large amount of air in the fixing balloon 3 from being exhausted.

Air can also be suctioned from the fixing balloon 3 by switching the manual air supply mechanism 211 to the second connection state, but in this case, since a lot of air will leak while the connection state is switched, the air is supplied again after the diameter of the fixing balloon 3 is reduced, which is less efficient than this embodiment.

The overtube 401 according to this embodiment is the same as the overtube 301 according to the third embodiment, except that it includes the limiter 417, and thus has the same action as the third embodiment. Therefore, as in the third embodiment, it is possible to provide an overtube for an endoscope that reduces the load on the patient and allows a smooth operation of the endoscope.

In particular, in this embodiment, since a small amount of air can be quickly exhausted from the fixing balloon 3 during the air supply operation, the fixing balloon 3 can be expanded and contracted quickly and efficiently.

The pump 211*a* in the air supply device 410 is an example of a manual pump that delivers gas. The main body portion 412 of the air supply device 410 is an example of a main body portion to which a manual pump is connected.

The connection tube 212*a* in the main body portion 412 is an example of a main body side connector that protrudes from the main body portion and detachably connects the manual pump in a first direction. Here, the first direction is a direction along the central axis $A_C$.

The first connection portion 211*d* and the second connection portion 211*e* are examples of a pump side connector in the manual pump that advances and retracts in the first direction, are airtightly connected to the main body side connector when advancing, and causes gas to leak when retracting.

The limiter 417 is an example of a limiter that restricts a retracted position of the pump side connector by locking to the pump side connector when the pump side connector retracts, and prevents the pump side connector from coining off.

The side plate portion 417*a* and the locking protrusion 417*b* of the limiter 417 are examples of a locking member that is movable between a locking position in which it can be locked to the pump side connector and a separating position in which the pump side connector can be separated from the main body side connector.

Eighteenth Modified Example

A modified example (an eighteenth modified example) of the air supply device used in place of the air supply device 410 in the overtube 401 according to the fifth embodiment will be described.

As shown in FIG. 17, an air supply device 410A of this modified example can be used in place of the air supply device 210 of the overtube 301.

Figure 93:
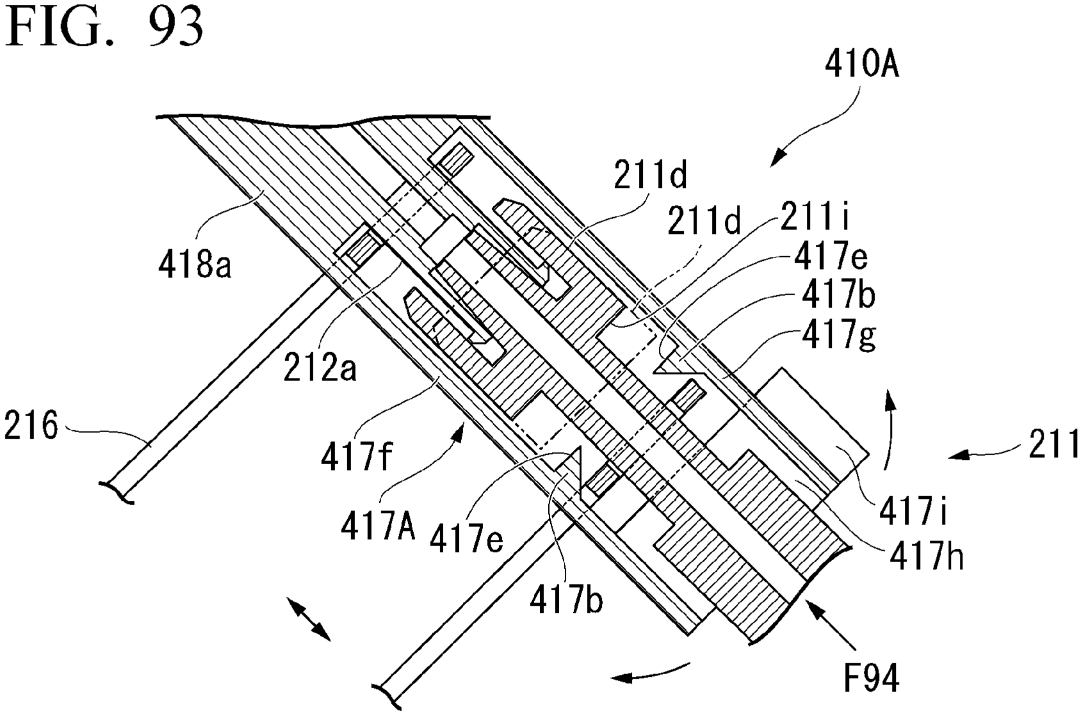
FIG. 93 is a schematic cross-sectional view showing a modified example (an eighteenth modified example) of a limiter used in the overtube for an endoscope according to the fifth embodiment of the present invention.
Figure 94:
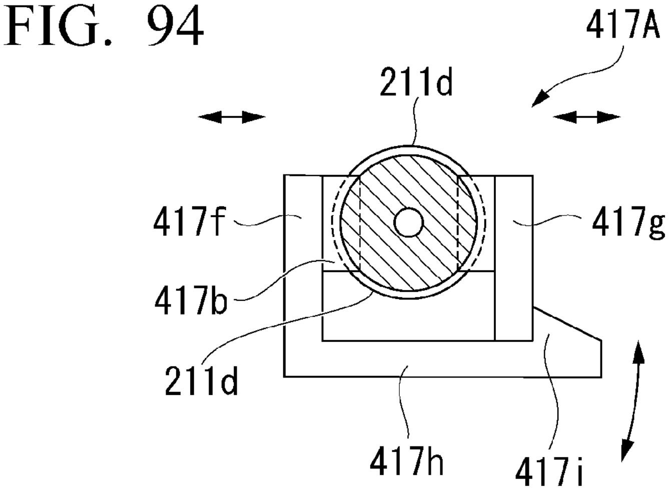
FIG. 94 is a schematic view seen from F94 in FIG. 93.

FIG. 93 is a schematic cross-sectional view showing an example of the modified example (the eighteenth modified example) of the limiter used in the overtube for an endoscope according to the fifth embodiment of the present invention. FIG. 94 is a schematic view from F94 in FIG. 93.

As shown in FIG. 93, the air supply device 410A of this modified example has a limiter 417A instead of the limiter 417 of the fifth embodiment.

In the following, differences from the fifth embodiment will be mainly described.

The limiter 417A includes a first side plate portion 417*f* (a locking member), a second side plate portion 417*g* (a locking member), and a fastener 417*h* (a fixing member).

The first side plate portion 417*f* and the second side plate portion 417*g* are the same as the side plate portion 417*a* in the fifth embodiment, except that they extend longer than the side plate portion 417*a*. Therefore, a locking protrusion 417*b* is provided at each of the first side plate portion 417*f* and the second side plate portion 417*g*, as in the fifth embodiment.

The fastener 417*h* fixes a facing distance between the first side plate portion 417*f* and the second side plate portion 417*g* that face each other so as to be expandable.

The configuration of the fastener 417*h* is not particularly limited as long as it can fix the facing distance between the first side plate portion 417*f* and the second side plate portion 417*g* to be expandable. In the example shown in FIG. 94, it is an elastic claw that extends from the side end of the distal end portion of the first side plate portion 417*f* toward the side end of the second side plate portion 417*g* and is detachably engaged with the second side plate portion 417*g* at the distal end portion in the extending direction.

An engaging protrusion 417*i* that detachably engages with the side end of the second side plate portion 417*g* protrudes from the distal end portion of the fastener 417*h*.

In FIG. 94, the engaging protrusion 417*i* is a protrusion that engages from the outside of the second side plate portion 417*g*. However, the engaging protrusion 417*i* may be a protrusion in which a groove that engages the second side plate portion 417*g* is engaged.

The fastener 417*h* is disengaged from the second side plate portion 417*g* by rotating clockwise in the drawing around the base end portion connected to the first side plate portion 417*f*.

The first side plate portion 417*f* and the second side plate portion 417*g* may be parallel to each other as in the fifth embodiment, or may be open in a shape such that the facing distance between them increases as they move away from the side portion 418*a*.

When they are parallel to each other, the operator can separate the manual air supply mechanism 211 by opening the first side plate portion 417*f* and the second side plate portion 417*g* outward in the facing direction in a state in which the fastener 417*h* is rotated clockwise in the drawing to release the engagement with the second side plate portion 417*g*.

In the case in which the first side plate portion 417*f* and the second side plate portion 417*g* before engagement have a shape that opens in the opposite direction, when engaging, an interval between the first side plate portion 417*f* and the second side plate portion 417*g* is narrowed, and then the engagement is performed by the fasteners 417*h*. Thus, the interval between the first side plate portion 417*f* and the second side plate portion 417*g* is fixed.

When the operator operates the fastener 417*h* to release the engagement between the fastener 417*h* and the second side plate portion 417*g*, the first side plate portion 417*f* and the second side plate portion 417*g* return to the open state due to an elastic force, and thus the manual air supply mechanism 211 can be separated.

According to the limiter 417A, in the engaged state of the fastener 417*h*, the movement range of the first connection portion 211*d* is restricted by the locking protrusion 417*b*, as in the fifth embodiment.

When the engagement of the fastener 417*h* is released, the operator can separate the manual air supply mechanism 211 from the limiter 417A, as described above.

According to this modified example, since the air supply device 410A includes the limiter 417A, it has the same action as the fifth embodiment.

The limiter 417A in the air supply device 410A is an example of a limiter that restricts the retracted position of the pump side connector and prevents the pump side connector from coming off by being locked to the pump side connector when the pump side connector is retracted.

The first side plate portion 417*f*, the second side plate portion 417*g*, and the locking protrusion 417*b* provided on each of them in the limiter 417A are examples of a locking member that is movable between a locking position in which it can be locked to the pump side connector and a separating position in which the pump side connector can be removed from the main body side connector.

The fastener 417*h* in the limiter 417A is an example of a fixing member that can fix the locking member in one or both of the locking position and the separating position.

Sixth Embodiment

An overtube for an endoscope according to a sixth embodiment of the present invention will be described.

An overtube 501 shown in FIG. 1 is an example of the overtube for an endoscope according to this embodiment.

The overtube 501 includes an airtight valve unit 506 instead of the airtight valve unit 6 of the overtube 1 according to the first embodiment.

In the following, differences from the first embodiment will be mainly described.

Figure 95:
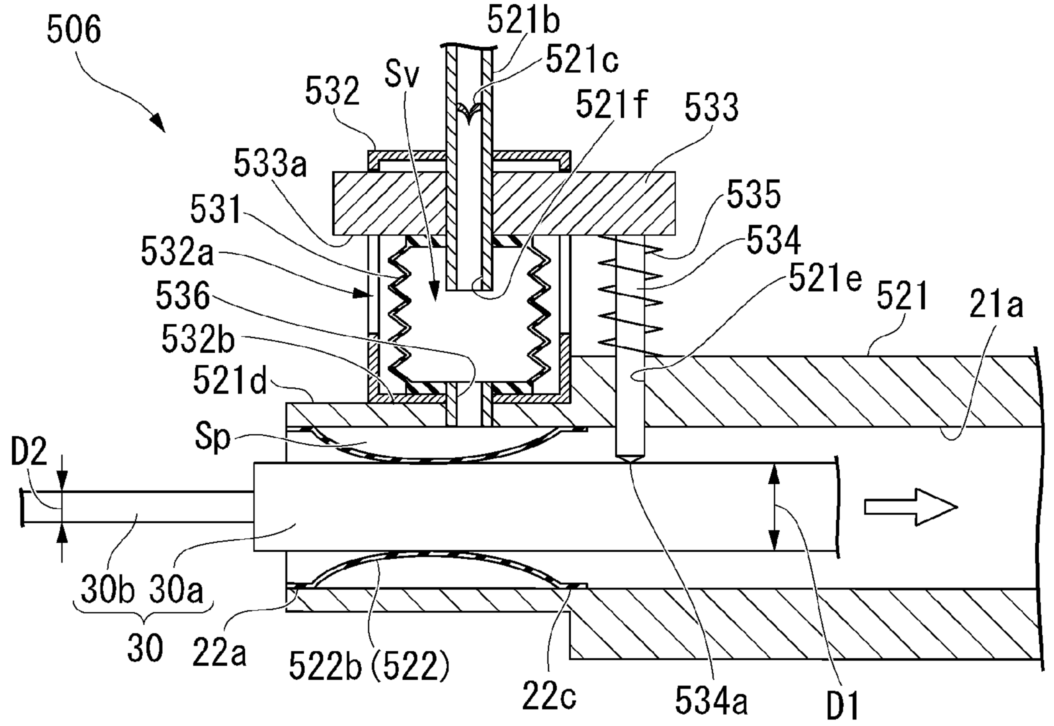
FIG. 95 is a schematic cross-sectional view showing an example of an airtight valve unit used in an overtube for an endoscope according to a sixth embodiment of the present invention.

FIG. 95 is a schematic cross-sectional view showing an example of the airtight valve unit used in the overtube for an endoscope according to the sixth embodiment of the present invention.

As shown in FIG. 95, the airtight valve unit 506 in this embodiment is particularly suitable for inserting an endoscope 30 of which a thickness changes in the longitudinal direction.

As in the airtight valve unit 6 in the first embodiment, the airtight valve unit 506 can provide good airtightness even with a non-circular cross section like the endoscope 11. However, hereinafter, an example in which the exterior of the endoscope 30 is a cylindrical surface will be described so that the features of this embodiment can be more easily understood.

The thickness of the endoscope 30 may change at any number of locations according to the location, or the thickness may change continuously. However, for the sake of simplicity, an example in which the endoscope 30 has a large diameter portion 30*a* and a small diameter portion 30*b* will be described below.

The large diameter portion 30*a* has a cylindrical shape with an outer diameter D1.

The small diameter portion 30*b* has a cylindrical shape with an outer diameter D2. However, D2 is smaller than D1.

The cause of the change in the outer diameter of the endoscope 30 is not particularly limited. For example, the fixing balloon 3 of which the diameter is reduced outside the main tube 2 often has an outer diameter larger than the outer diameter of the main tube 2 even when the diameter is reduced. In this case, the fixing balloon 3 in the diameter-contracted state forms the large diameter portion 30*a*. For example, even when the endoscope 30 is pulled out of the body with the diameter of the fixing balloon 3 incompletely reduced for some reason, the fixing balloon 3 forms the large diameter portion 30*a*.

For example, an accessory such as the endoscope cap 13 in the first embodiment may be mounted on the distal end portion of the endoscope 30 to form the large diameter portion 30*a*.

For example, when the endoscope 30 is inserted into the overtube 1 in the first embodiment, the airtightness of the airtight valve unit 6 can be maintained by increasing the internal pressure of the space Sp and reducing the inner diameter of the middle portion 22*b* even when the outer diameter of the endoscope 30 changes slightly.

However, when the change in the outer diameter of the endoscope 30 becomes too large, insertion resistance of the large diameter portion 30*a* will increase, and thus there is a possibility that the endoscope 30 cannot be smoothly inserted and removed.

It is also conceivable that the operator or the like manually adjusts the amount of air in the space Sp to reduce the insertion resistance at the large diameter portion 30*a*. However, from the viewpoint of reducing the load on the patient and improving the efficiency of the surgery, the endoscope 30 needs to be inserted and removed quickly. Since the operator or the like cannot accurately know a diameter changing portion of the endoscope 30 inserted through the overtube 1, the operator cannot accurately grasp the timing at which the diameter changing portion passes through the airtight valve unit 6. Thus, it is quite difficult for the operator or the like to appropriately adjust the degree of opening of the airtight valve unit 6.

There is a strong demand for an airtight valve with a simple configuration that opens and closes following the change in the outer diameter of the endoscope 30 even when the outer diameter thereof changes.

The airtight valve unit 506 includes a cylinder frame portion 521, an airtight balloon 522, and a connection port 521*b* (a gas supply tube) instead of the cylinder frame portion 21 (the tubular portion), the airtight balloon 22, and the connection port 21*b* in the first embodiment.

Furthermore, the airtight valve unit 506 includes a guide member 532, a probe 534, a spring 535 (a biasing member), and a variable volume portion 531.

In the following, differences from the first embodiment will be mainly described.

The cylinder frame portion 521 has the same inner circumferential surface 21*a* as that of the cylinder frame portion 21.

The airtight balloon 522 is fixed to the inner circumferential surface 21*a* of the cylinder frame portion 521.

The airtight balloon 522 has a middle portion 522*b* instead of the middle portion 22*b* of the airtight balloon 22 in the first embodiment.

In the natural state in which no gas is supplied to the space Sp, the middle portion 522*b* is a cylindrical surface that comes into close contact with the inner circumferential surface 21*a* from the inside. When gas is supplied to the space Sp, it expands inward in the radial direction according to the internal pressure of the space Sp. As in the middle portion 22*b* in the first embodiment, the expanded middle portion 522*b* forms a curved shape in which the inner diameter gradually decreases from the first joint portion 22*a* toward the second joint portion 22*c*, becomes the minimum, and then expands. The minimum diameter of the middle portion 522*b* changes according to the pressure of the space Sp.

When the amount of expansion of the middle portion 522*b* is adjusted according to the outer diameters of the large diameter portion 30*a* and the small diameter portion 30*b*, the outer circumferential portions of the large diameter portion 30*a* and the small diameter portion 30*b* can be airtightly covered without changing the sliding load with the large diameter portion 30*a* and the small diameter portion 30*b*.

Hereinafter, unless otherwise specified, a direction along the central axis of the inner circumferential surface 21*a* will be referred to as an axial direction, and a direction orthogonal to the axial direction will be referred to as a radial direction. Like the first embodiment, according to the insertion direction of the overtube 501, a distal end portion and a proximal end portion in the axial direction may be used.

A fixing portion 521*d* for fixing the guide member 532, which will be described below, is formed on the outer circumferential portion of the proximal end portion of the cylinder frame portion 521 in a range overlapping the middle portion 522*b* when seen in the radial direction. A guide hole 521*e* through which the probe 534 (described below) is inserted passes through in the radial direction on the distal end side from the fixing portion 521*d*.

As shown in FIG. 1, the operation tube main body 25 is connected to the connection port 521*b*, as in the connection port 21*b* in the first embodiment.

As shown in FIG. 95, a check valve 521*c* that prevents gas supplied to the space Sp from flowing back is disposed inside the connection port 521*b*.

The end portion of the connection port 521*b* close to the space Sp is fixed to the guide member 532 (described below), passes through a movable member 533 (described below), and opens into the inside of the variable volume portion 531 (described below). The portion passing through the movable member 533 is airtightly sealed so that a load of movement of the movable member 533 does not increase.

However, the connection port 521*b* may be fixed to the movable member 533 when the load of movement of the movable member 533 does not become large.

The movable member 533 is disposed at a position at which it faces the fixing portion 521*d* in the radial direction so as to be movable in the radial direction. In the example shown in FIG. 95, the movable member 533 is supported by the guide member 532 so as to be movable in the radial direction and is biased by the spring 535 in the radial direction toward the cylinder frame portion 521.

The guide member 532 is fixed to the fixing portion 521*d*. A guide portion 532*a* that moves the movable member 533 in parallel in the radial direction is formed in the guide member 532.

A shape of the guide member 532 is not particularly limited. For example, the guide member 532 may be a casing, a frame, a columnar body, a cylinder, or the like.

An appropriate shape is used for a shape of the guide portion 532*a* according to the shape of the guide member 532. For example, the guide portion 532*a* formed in the guide member 532 may be a hole, a groove, a projection claw, or the like that extends in the radial direction.

In the example schematically shown in FIG. 95, the guide member 532 is a frame or a casing having a rectangular parallelepiped exterior. The guide portion 532*a* is a through hole formed in the side surface of the guide member 532 and extending in the radial direction. In this case, the movable member 533 is inserted inside the guide portion 532*a*, thereby moving in parallel in the radial direction.

In the movable member 533, the probe 534 extending in the radial direction is fixed to a surface 533*a* facing the outer circumferential portion of the cylinder frame portion 521 in the radial direction.

The probe 534 is slidably inserted into the guide hole 521*e*. A sliding contact portion 534*a* (a distal end portion) formed on the distal end side of the probe 534 has a length that allows it to come into contact with the outer circumferential surface of the endoscope 30 that moves in the axial direction inside the inner circumferential surface 21*a* within a movable range of the movable member 533.

The sliding contact portion 534*a* has a curved surface that smoothly slides on the outer circumferential surface of the endoscope 30. The sliding contact portion 534*a* has a curvature that allows it to smoothly overcome a step in the outer diameter of the endoscope 30.

The movable member 533 moves in the same direction as the probe 534 that moves in the radial direction along the guide hole 521*e*.

The type and shape of the spring 535 are not particularly limited as long as it can bias the movable member 533 in the radial direction toward the cylinder frame portion 521.

For example, the type of the spring 535 is not particularly limited as long as it is an elastic member that generates an elastic restoring force according to a displacement of movable member 533 in the radial direction. Examples of the spring 535 include a coil spring, a plate rubber, an elastic sheet, and the like. In the example shown in FIG. 95, the spring 535 is a coil spring into which the probe 534 is inserted. In this case, the spring 535 biases the movable member 533 with a tensile force.

When the endoscope 30 is inserted into the inner circumferential surface 21*a*, the movable member 533 can move to a position in which the sliding contact portion 534*a* of the probe 534 comes into contact with the side surface of the endoscope 30.

The variable volume portion 531 accommodates gas supplied from the outside through the connection port 521*b* in an internal space Sv. A volume of the variable volume portion 531 changes according to the pressure of the gas.

The variable volume portion 531 in this embodiment is a member in which a volume of the space Sv changes without elastically expanding or contracting. For example, in the example shown in FIG. 95, the variable volume portion 531 is a bellows tube in which a plurality of folds are disposed in a zigzag shape in the radial direction.

Both end portions of the variable volume portion 531 in the radial direction are airtightly fixed to a bottom surface portion 532*b* of the guide member 532 fixed to the fixing portion 521*d* and the surface 533*a* of the movable member 533, respectively.

An opening 521*f* of the connection port 521*b* fixed to the movable member 533 opens into the variable volume portion 531. The opening 521*f* allows the space Sv and the inside of the connection port 521*b* to communicate with each other.

The bottom surface portion 532*b* and the fixing portion 521*d* are provided with a conduit 536 passing through them in the radial direction.

The conduit 536 opens to the inside of the variable volume portion 531 and to the space Sp between the middle portion 522*b* and the inner circumferential surface 21*a*. Thus, the conduit 536 allows the space Sp and the space Sv to communicate with each other.

In the airtight valve unit 506, when a certain volume of gas is supplied through the connection port 521*b*, the gas is sealed in the spaces Sp and Sv by the check valve 521*c*.

Since the movable member 533 is supported to be movable in the radial direction, the volume of the space Sv changes according to the position of the movable member 533. For example, when the movable member 533 moves toward the cylinder frame portion 521 in the radial direction, the variable volume portion 531 contracts in the radial direction, and thus the volume of the space Sv is reduced. The gas that cannot enter the space Sv moves to the space Sp through the conduit 536 and expands the middle portion 522*b*.

At this time, since the internal pressure in the spaces Sv and Sp increases, the movable member 533 is biased in a direction opposite to the moving direction according to the internal pressure.

Figure 96:
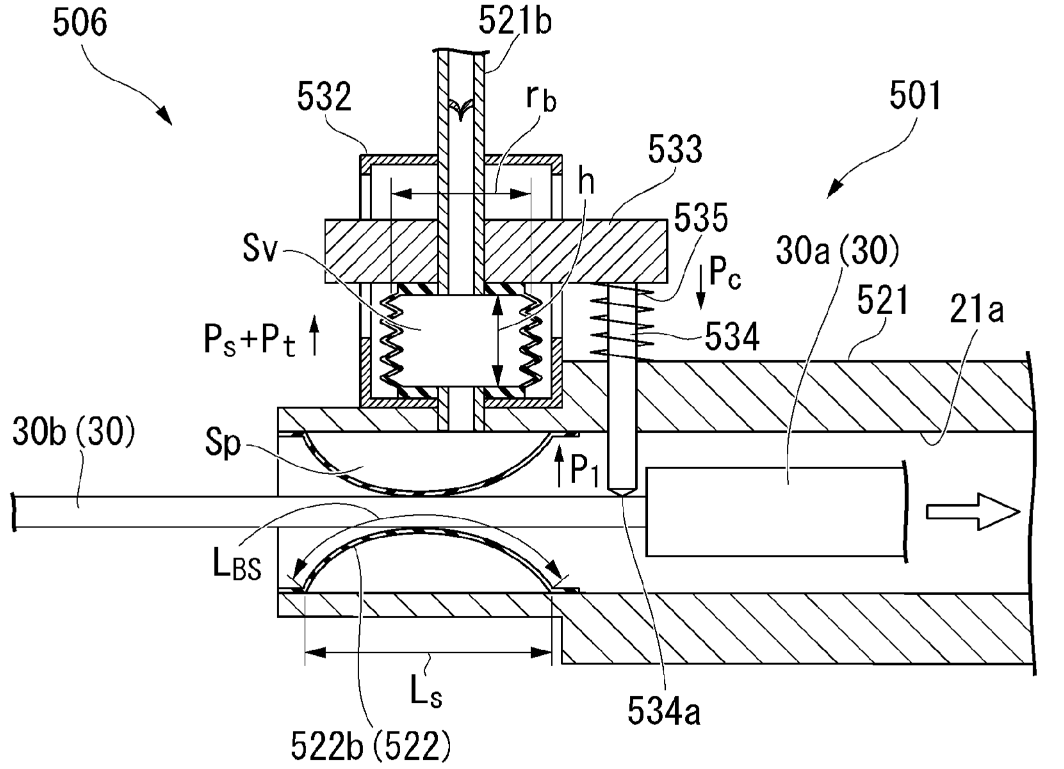
FIG. 96 is an explanatory diagram of an operation of the airtight valve unit used in the overtube for an endoscope according to the sixth embodiment of the present invention.

FIG. 96 is an operation explanatory view of the airtight valve unit used in the overtube for an endoscope according to the sixth embodiment of the present invention.

In this embodiment, as shown in FIGS. 95 and 96, gas is injected into the variable volume portion 531 so that the sliding contact portion 534*a* of the probe 534 is kept in contact with the side surface of the endoscope 30.

In this state, the middle portion 522*b* of the airtight balloon 522 is brought into close contact with the outer circumferential portion of the endoscope 30 by optimizing the volume of the gas introduced from the connection port 521*b*, and thus airtightness can be maintained.

For example, the airtight valve unit 506 satisfies the condition indicated by the following Equation (6a) using pressures $P_1$, $P_t$, $P_S$ and $P_C$ shown in FIG. 96.

[Math 12]

$$P_1 + P_t < P_S \leq P_C \tag{6a}$$

Here, $P_1$ is the internal pressure on the distal end side from the airtight balloon 522 in the overtube 501. $P_t$ is the pressure due to a tension generated in the airtight balloon 522. $P_S$ is the internal pressure of the spaces Sp and Sv. $P_C$ is the pressure corresponding to the biasing force of the spring 535.

Since the middle portion 522*b* needs to be expanded to maintain airtightness by the airtight balloon 522, $P_S$ has to be greater than the sum of $P_1$ and $P_t$.

$P_1$ is determined in advance according to the type of surgery in which the overtube 501 is used and the type of lumen into which it is inserted.

$P_t$ is indicated by the following Equation (6b) based on the distortion of the airtight balloon 522 when expanded.

[Math 13]

$$P_t = \frac{E_S(L_{BS} - L_S)}{L_S} \tag{6b}$$

Here, $E_S$ is a Young's modulus of a material of the airtight balloon 522, $L_{BS}$ is an outer circumferential length of the airtight balloon 522 when expanded, and $L_S$ is an outer circumferential length of the airtight balloon 522 before expanded. However, the "outer circumferential length" of the airtight balloon 522 is a length of the middle portion 522*b* in a cross-section in the axial direction including the central axis of the airtight balloon 522.

$P_S$ is determined based on Boyle-Charles' law according to the volume of the gas injected into the variable volume portion 531, and is indicated by the following Equation (6c).

[Math 14]

$$P_S = \frac{V}{(V_S + \pi r_b h)} \cdot p \tag{6c}$$

Here, V is the volume of the gas injected into the variable volume portion 531. $V_S$ is the volume of the space Sp, $r_b$ is the inner diameter of the variable volume portion 531, h is the height of the variable volume portion 531, and p is the atmospheric pressure. However, the inner diameter of the variable volume portion 531 is an equivalent diameter converted into a cylinder. For example, in the case of a bellows tube, an average value of the maximum inner diameter and the minimum inner diameter is used.

h changes according to the position of the movable member 533. However, the position of the movable member 533, that is, h in this embodiment is uniquely determined corresponding to the outer diameter of the endoscope 30 with which the probe 534 comes into contact.

In this embodiment, since the variable volume portion 531 is not elastically deformed, the volume of the space Sv is a function of h. Therefore, $V_S$ is a function of V and h.

Once $V_S$ is determined, the inner diameter of the middle portion 522*b* is determined by numerical calculation or actual measurement of the expanded shape of the material of the middle portion 522*b*. The inner diameter of the middle portion 522*b* is D1 or less when the probe 534 comes into contact with the large diameter portion 30*a*, and is D2 or less when the probe 534 comes into contact with the small diameter portion 30*b*.

When $P_S$ exceeds $P_C$, the sliding contact portion 534*a* is away from the side surface of the endoscope 30, and thus $P_S$ has to be less than or equal to $P_C$. $P_C$ is indicated by the following Equation (6c).

[Math 15]

$$P_C = kx \cdot \pi r_C^2 \tag{6d}$$

Here, k is a spring constant of the spring 535, x is a change length of the spring 535, and $r_C$ is a radius of the spring 535. However, the change length of the spring 535 is a displacement of the spring 535 from a natural length thereof.

When the elasticity and amount of deformation of the spring 535, the material and shape of the airtight balloon 522, and the volume V of the gas injected into the variable volume portion 531 are determined so as to satisfy Equation (6a), as shown in FIG. 95, the middle portion 522*b* of the airtight balloon 522 presses the large diameter portion 30*a* in a state in which the sliding contact portion 534*a* is in contact with the large diameter portion 30*a*, and the periphery of the large diameter portion 30*a* is airtightly sealed.

As shown in FIG. 96, when the small diameter portion 30*b* faces the middle portion 522*b* and the sliding contact portion 534*a* as the endoscope 30 moves in the axial direction, the middle portion 522*b* further expands according to the amount of movement of the movable member 533. That is, the inner diameter of the airtight balloon 522 increases as the outer diameter of the outer circumferential portion of the endoscope 30 inserted into the cylinder frame portion 521 increases, and decreases as the outer diameter decreases.

Thus, the middle portion 522*b* presses the small diameter portion 30*b*, and the periphery of the small diameter portion 30*b* is airtightly sealed.

According to this embodiment, since Equation (6a) is satisfied in the airtight valve unit 506, the movable member 533 is maintained at a position in which the probe 534 comes into contact with the side surface of the endoscope 30 when the endoscope 30 is inserted. Furthermore, in this state, gas is injected into the variable volume portion 531 so as to satisfy Equation (6a). Thus, the gas moves between the space Sv and the space Sp following a change in the outer diameter of the endoscope 30 detected by the probe 534. As a result, even when the outer diameter of the endoscope 30 changes, the amount of expansion of the middle portion 522*b* automatically follows the change in the outer diameter of the endoscope 30, and thus the periphery of the endoscope 30 is airtightly sealed with almost no change in the sliding resistance.

Thus, the endoscope 30 can be easily inserted and removed, and gas and liquid inside the body can be prevented from flowing back out of the airtight valve unit 506 during insertion and removal.

As described above, the example in which the outer diameter of the endoscope 30 is a cylindrical shape has been described, but for example, when the channel tube 15 is disposed in a part of the radial direction like the endoscope 11, airtightness similar to that described above can be obtained by replacing the inner diameter of the middle portion 522*b* when expanded with an equivalent diameter in consideration of an amount of protrusion of the channel tube 15. In this case, the probe 534 is brought into contact with the outer circumferential portion of the endoscope 11 excluding the channel tube 15.

The overtube 501 according to this embodiment is the same as the overtube 1 according to the first embodiment, except that it includes the airtight valve unit 506, and thus has the same action as the first embodiment. Therefore, as in the first embodiment, it is possible to provide an overtube for an endoscope that reduces the load on the patient and allows a smooth operation of the endoscope.

In particular, in this embodiment, when an endoscope of which an outer diameter is not constant is inserted and removed, insertion and removal becomes easy, and backflow of gas and liquid in the body can be more reliably prevented during insertion and removal.

The cylinder frame portion 521 in the airtight valve unit 506 is an example of a tubular portion that communicates with the main lumen at the proximal end portion of the tube main body.

The airtight balloon 522 is an example of an airtight balloon that is fixed to the inner circumferential surface of the tubular portion and is expandable toward the inside of the tubular portion.

The variable volume portion 531 is an example of a variable volume portion which is disposed outside the tubular portion so as to communicate with the internal space of the airtight balloon formed between the airtight balloon and the inner circumferential surface and of which a height of an exterior at least in the radial direction of the tubular portion changes due to the volume changing according to the pressure of gas flowing in from the external or internal space.

The connection port 521*b* is an example of a gas supply tube that communicates with the inside of the variable volume portion and has a check valve that allows external gas to flow into the variable volume portion and prevents gas from flowing out to the outside.

The movable member 533 is an example of a movable member that is supported outside the tubular portion so as to be movable in the radial direction of the tubular portion, and of which a position in the radial direction changes according to a change in the height of the variable volume portion.

The probe 534 has the sliding contact portion 534*a* that is the distal end portion in the extending direction. The probe 534 is an example of a rod-shaped probe which is fixed to the movable member, and extends in the radial direction toward the inside of a tubular portion, and of which a distal end portion in the extending direction comes into contact with the outer circumferential portion of an endoscope inserted into the tubular portion.

The spring 535 is an example of a biasing member that biases the movable member toward the tubular portion in the radial direction so that the probe and the outer circumferential portion of the endoscope is not away from each other when the endoscope is inserted into the tubular portion.

Nineteenth Modified Example

A modified example (a nineteenth modified example) of the airtight valve unit used in place of the airtight valve unit 506 in the overtube 501 according to the sixth embodiment will be described.

As shown in FIG. 1, an airtight valve unit 506A of this modified example can be used in place of the airtight valve unit 506 of the overtube 501.

In the following, differences from the sixth embodiment will be mainly described.

Figure 97:
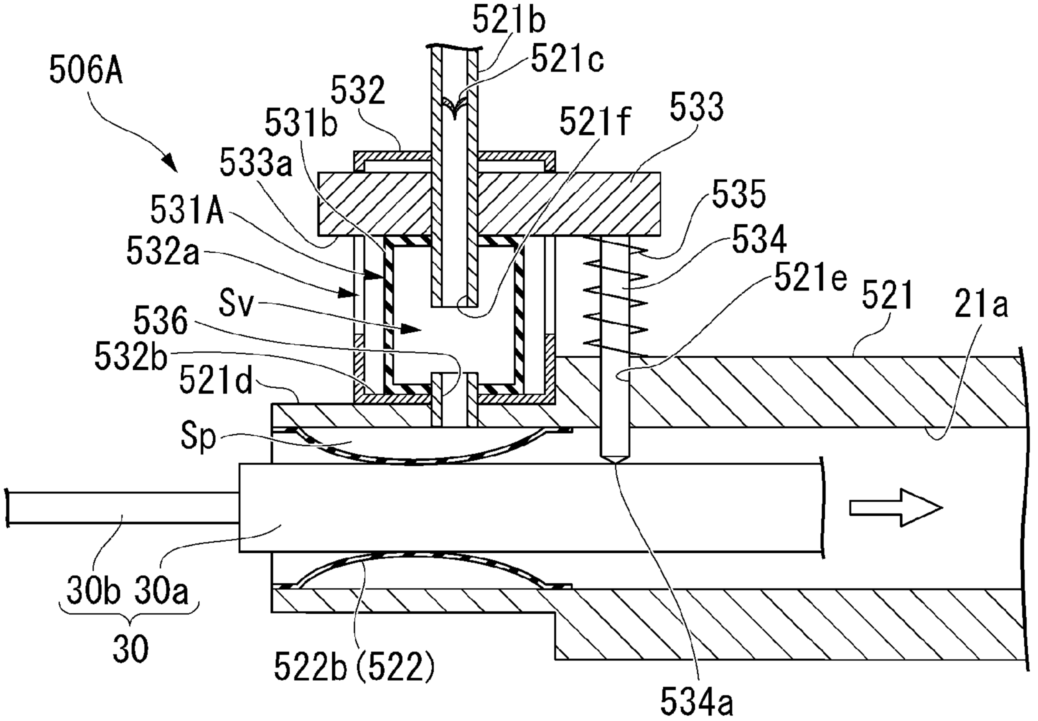
FIG. 97 is a schematic cross-sectional view showing a modified example (a nineteenth modified example) of the airtight valve unit used in the overtube for an endoscope according to the sixth embodiment of the present invention.
Figure 98:
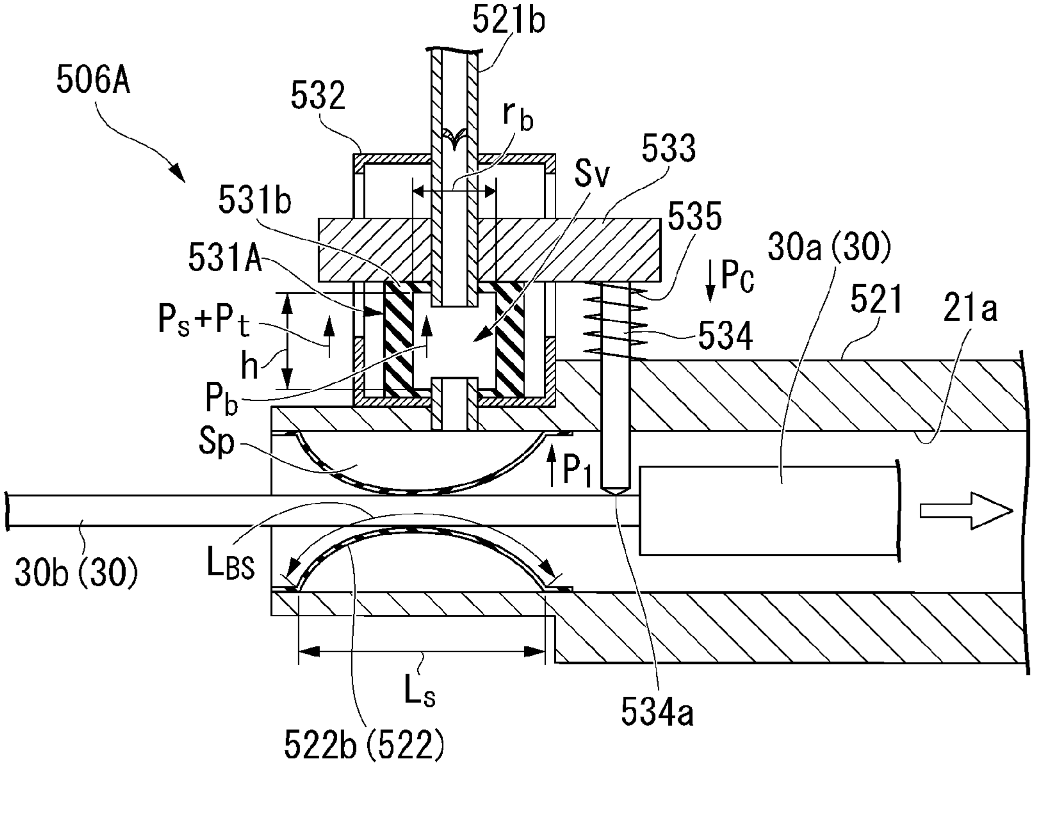
FIG. 98 is an explanatory diagram of an operation of the modified example (the nineteenth modified example) of the airtight valve unit.

FIG. 97 is a schematic cross-sectional view showing the modified example (the nineteenth modified example) of the airtight valve unit used in the overtube for an endoscope according to the sixth embodiment of the present invention. FIG. 98 is an explanatory diagram of the operation of the modified example (the nineteenth modified example) of the airtight valve unit.

As shown in FIG. 97, the airtight valve unit 506A of this modified example includes a variable volume portion 531A instead of the variable volume portion 531 in the sixth embodiment.

The variable volume portion 531A is a member that is the same as the variable volume portion 531, except that the volume of the internal space changes due to elastic deformation by an external force. However, the variable volume portion 531A has rigidity that makes it difficult to change the volume compared to the airtight balloon 522.

For example, the variable volume portion 531A is a container of which a side wall 531*b* is made of a soft elastomer that is more rigid than the middle portion 522*b*, and of which an exterior is cylindrical.

The variable volume portion 531A is fixed to the surface 533*a* of the movable member 533 and the bottom surface portion 532*b* of the guide member 532 in a posture in which the side wall 531*b* extends in the radial direction of the cylinder frame portion 521. An in the variable volume portion 531, the opening 521*f* of the connection port 521*b* and the conduit 536 are open at both end portions of the variable volume portion 531A in the radial direction.

For example, when the movable member 533 moves in the radial direction and a compressive force acts on the variable volume portion 531A, as shown in FIG. 98, the side wall 531*b* is compressed and the height h in the space Sv is reduced, and thus the volume of the space Sv is reduced.

Conversely, when the movable member 533 moves in the radial direction and a tensile force acts on the variable volume portion 531A, as shown in FIG. 98, the side wall 531*b* expands and the height h in the space Sv decreases, and thus the volume of the space Sv increases.

In according with the material of the side wall 531*b*, a thickness thereof also changes as the side wall 531*b* expands and contracts. In this case, when the side wall 531*b* is compressed, the inner diameter decreases, and when the side wall 531*b* is expanded, the inner diameter increases. That is, an increase or decrease in the inner diameter of the side wall 531*b* corresponds to an increase or decrease in the length.

As in the sixth embodiment, the airtight valve unit 506A satisfies the following Equation (6e) in order to change the space Sp of the middle portion 522*b* following the change in the outer diameter of the endoscope 30. Hereinafter, descriptions of variables common to above Equations (6a) to (6d) will be omitted.

[Math 16]

$$P_1 + P_t + P_b < P_S \leq P_C \tag{6e}$$

Here, $P_b$ is the pressure in the radial direction (the moving direction of the movable member 533) caused by the elastic deformation of the variable volume portion 531A.

$P_b$ is indicated by the following Equation (6f) based on the distortion during compression of the variable volume portion 531A.

[Math 17]

$$P_b = \frac{E_b \Delta L_b}{L_b} \tag{6f}$$

Here, $E_b$ is a Young's modulus of the material of the side wall 531*b* in the variable volume portion 531A, $L_b$ is the natural length of the side wall 531*b*, and $\Delta L_b$ is the change length of the side wall 531*b*.

$P_t$, $P_S$, and $P_C$ are indicated by Equations (6b), (6c), and (6d), respectively.

However, when the inner diameter of the side wall 531*b* changes, $r_b$ in Equation (6c) changes according to the deformation of the variable volume portion 531A.

In this modified example, the volume of the variable volume portion 531A changes due to elastic deformation thereof. Therefore, in Equation (6e), the pressure Pb required for elastic deformation of the variable volume portion 531A is taken into consideration as a condition for bringing the probe 534 into contact with the side surface of the endoscope 30.

Thus, the overtube 501 having the airtight valve unit 506A of this modified example has the same action as the overtube 501 according to the sixth embodiment even when the variable volume portion 531A is elastically deformed.

The variable volume portion 531A is an example of a variable volume portion which is disposed outside the tubular portion so as to communicate with the internal space of the airtight balloon formed between the airtight balloon and the inner circumferential surface and of which a height of an exterior at least in the radial direction of the tubular portion changes due to the volume changing in accordance with the pressure of gas flowing in from the external or internal space.

Twentieth Modified Example

A modified example (a twentieth modified example) of the airtight valve unit used in place of the airtight valve unit 506 in the overtube 501 according to the sixth embodiment will be described.

As shown in FIG. 1, an airtight valve unit 506B of this modified example can be used in place of the airtight valve unit 506 of the overtube 501.

Figure 99:
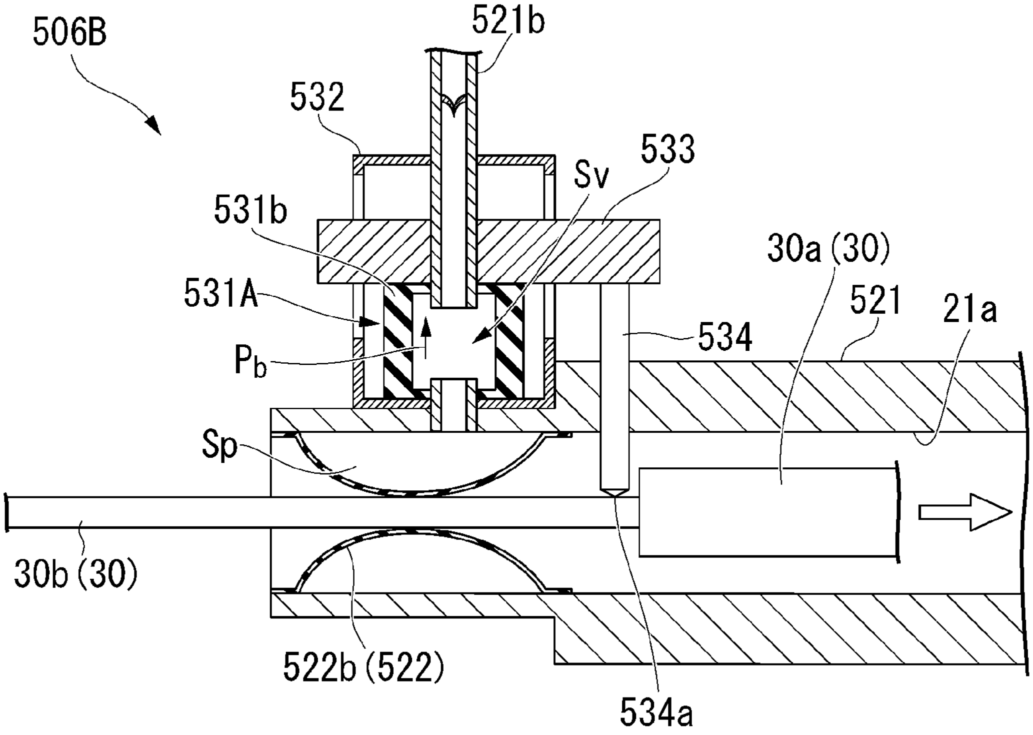
FIG. 99 is a schematic cross-sectional view showing a modified example (a twentieth modified example) of the airtight valve unit used in the overtube for an endoscope according to the sixth embodiment of the present invention.

FIG. 99 is a schematic cross-sectional view showing the modified example (the twentieth modified example) of the airtight valve unit used in the overtube for an endoscope according to the sixth embodiment of the present invention.

As shown in FIG. 99, the airtight valve unit 506B of this modified example is the same as the airtight valve unit 506A of the nineteenth modified example, except that the spring 535 in the airtight valve unit 506A of the nineteenth modified example is omitted.

In the following, differences from the nineteenth modified example will be mainly described.

In this modified example, since the spring 535 is not provided, the variable volume portion 531A has the function of an elastic member that biases the movable member 533 in the radial direction toward the cylinder frame portion 521.

When gas is injected into the variable volume portion 531A and the sliding contact portion 534*a* of the probe 534 comes into contact with the small diameter portion 30*b*, the middle portion 522*b* airtightly seals the periphery of the small diameter portion 30*b*, and tensile stress is generated in the side wall 531*b* of the variable volume portion 531A. Thus, the movable member 533 is biased in the radial direction toward the cylinder frame portion 521.

From this state, for example, when the large diameter portion 30*a* moves to the proximal end side, the probe 534 is pressed outward in the radial direction by the large diameter portion 30*a*, and the movable member 533 moves outward in the radial direction. Thus, the variable volume portion 531A is stretched, and the volume of the space Sv is expanded. Thus, since the gas in the space Sp moves to the space Sv, the middle portion 522*b* contracts, and the inner diameter of the middle portion 522*b* increases.

As a result, the inner diameter of the middle portion 522*b* is expanded to a size that allows the large diameter portion 30*a* to be airtightly sealed with less sliding load.

Such an airtight valve unit 506B satisfies the following Equation (6f). Hereinafter, description of variables common to Equations (6a) to (6d) will be omitted.

[Math 18]

$$P_1 + P_t < P_S \leq P_b \tag{6g}$$

Here, $P_b$ is obtained by Equation (6f) in the nineteenth modified example.

This modified example is an example in which the variable volume portion 531A also functions as the spring 535 and changes following the changes in the inner diameter of the middle portion 522*b*, the inner pressure of the space Sp, and the outer diameter of the endoscope 30 as in the nineteenth modified example.

Thus, the overtube 501 having the airtight valve unit 506B of this modified example has the same action as the overtube 501 according to the sixth embodiment even when the variable volume portion 531A is elastically deformed.

Seventh Embodiment

An overtube for an endoscope according to a seventh embodiment of the present invention will be described.

Figure 100:
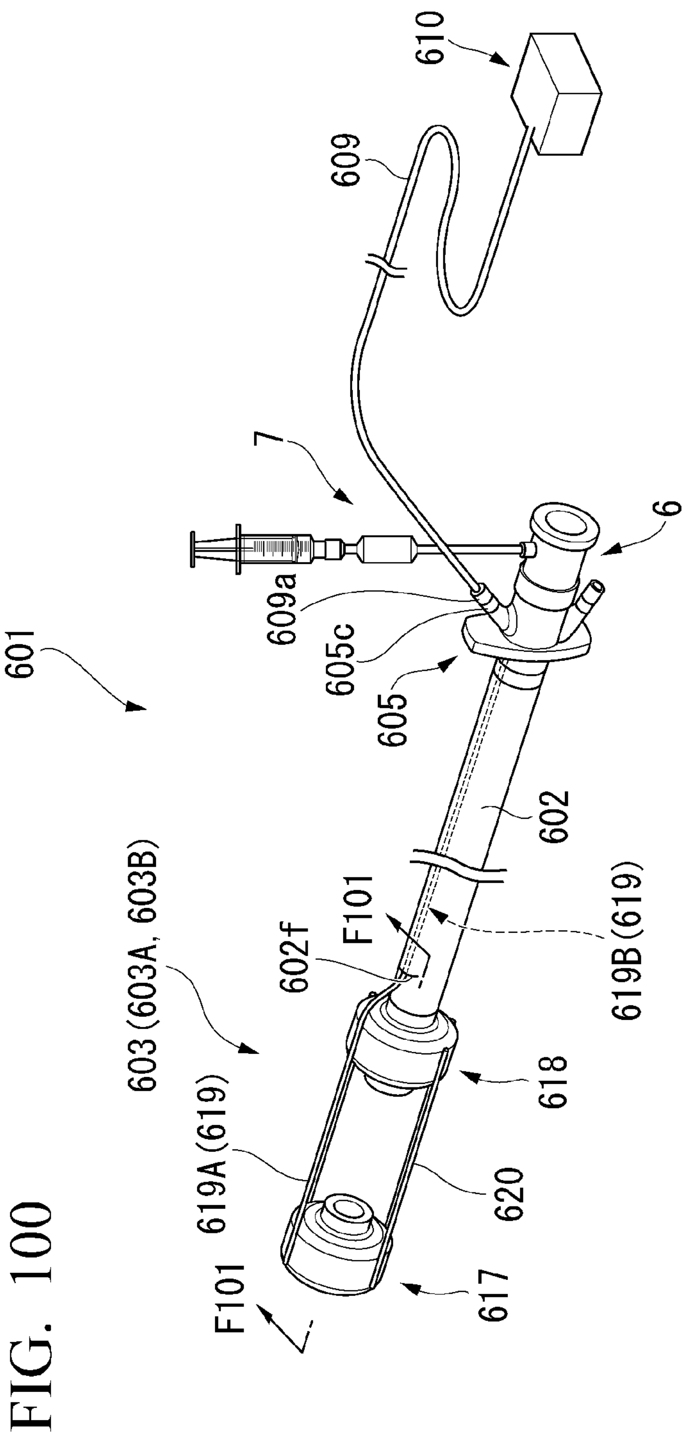
FIG. 100 is a schematic perspective view showing an example of an overtube for an endoscope according to a seventh embodiment of the present invention.
Figure 101:
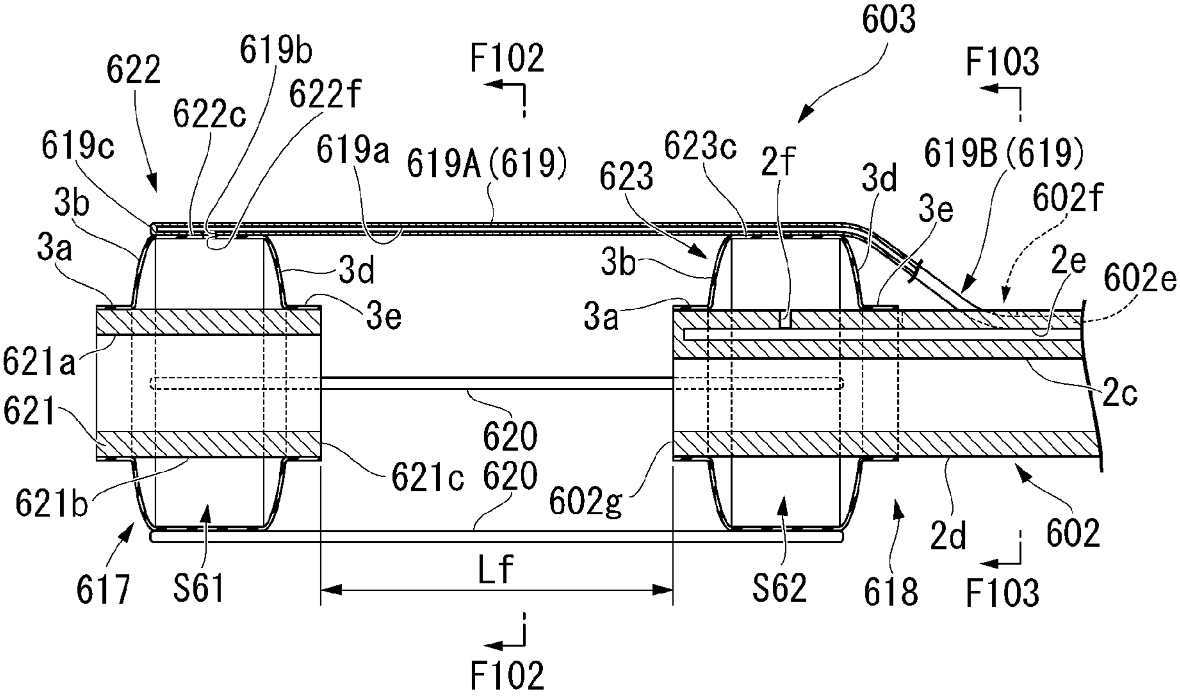
FIG. 101 is a cross-sectional view taken along line F101-F101 in FIG. 100.
Figure 102:
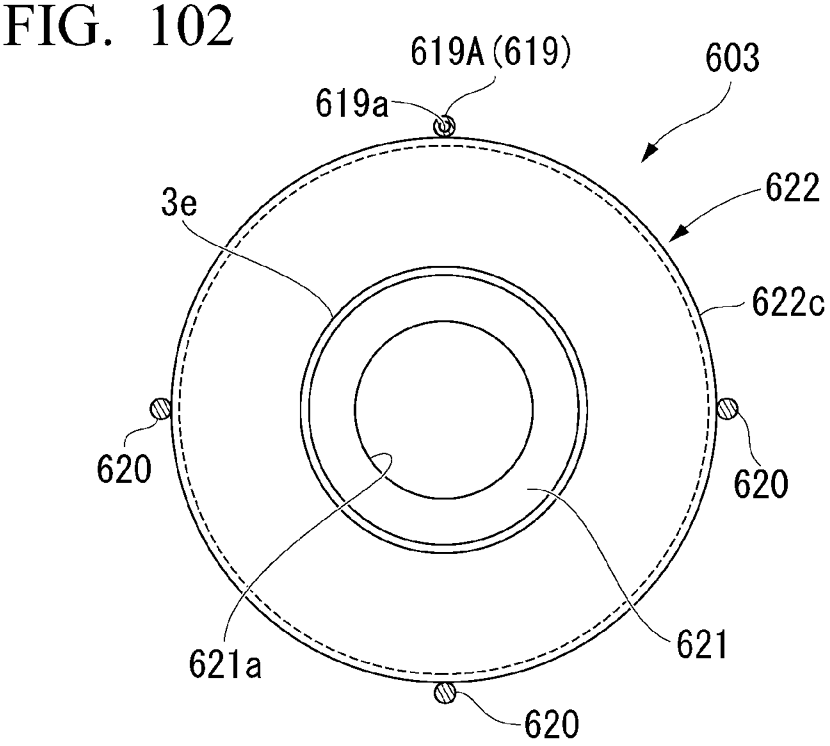
FIG. 102 is a cross-sectional view taken along line F102-F102 in FIG. 101.
Figure 103:
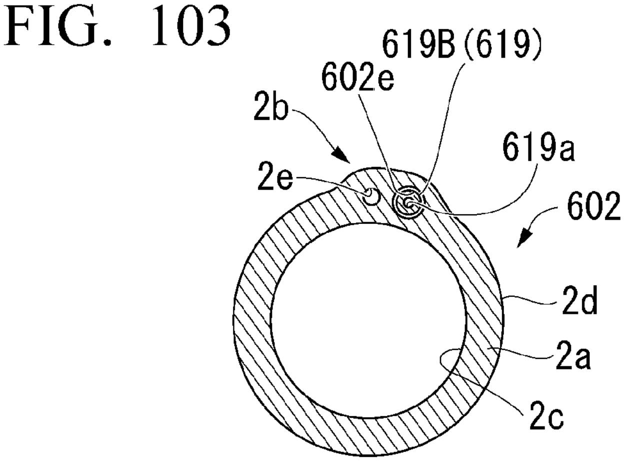
FIG. 103 is a cross-sectional view taken along line F103-F103 in FIG. 101.

FIG. 100 is a schematic perspective view showing an example of an overtube for an endoscope according to the seventh embodiment of the present invention. FIG. 101 is a cross-sectional view taken along line F101-F101 in FIG. 100. FIG. 102 is a cross-sectional view taken along line F102-F102 in FIG. 101. FIG. 103 is a cross-sectional view taken along line F103-F103 in FIG. 101.

An overtube 601 shown in FIG. 100 is an example of an overtube for an endoscope according to this embodiment.

In the overtube 601, the distal end tip 4 of the overtube 1 according to the first embodiment is deleted, and the overtube 601 includes a distal end fixing portion 603, a main tube 602 (a tube main body), a grip portion 605, an air flow tube 609, and an air supply device 610 instead of the fixing balloon 3, the main tube 2, the grip portion 5, the air flow tube 9, and the air supply device 10.

However, FIGS. 100 to 103 show a shape of the distal end fixing portion 603 in the diameter-expanded state, as in the first embodiment.

In the following, differences from the first embodiment will be mainly described.

As shown in FIG. 101, the distal end fixing portion 603 in this embodiment includes a first fixing portion 617, a second fixing portion 618, a first support member 619, and a second support member 620.

The first fixing portion 617 has a tube member 621 and a first balloon 622 (a balloon on the distal end side).

The tube member 621 is a circular tube having an internal space through which the distal end portion of the endoscope inserted into the overtube 601 can be inserted. An inner diameter of an inner circumferential surface 621*a* of the tube member 621 is equal to or larger than the inner diameter of the first lumen 2*c* in the main tube 602 which will be described below, and is smaller than the inner diameter of the lumen into which the overtube 601 is inserted.

An outer diameter of an outer circumferential surface 621*b* of the tube member 621 is smaller than the inner diameter of the lumen into which the overtube 601 is inserted, and has a size that facilitates insertion into the lumen to be treated, like the main tube 602 described below. In the following, an example in which the outer diameter of the outer circumferential surface 621*b* is approximately equal to the outer diameter of the main tube 602 which will be described below will be described. The first balloon 622 which will be described below is fixed to the outer circumferential surface 621*b*.

A length of the tube member 621 is not particularly limited as long as it can fix both end portions of the first balloon 622 in the axial direction which will be described below. For example, the length of the tube member 621 may be 20 mm or mom and 70 nm or less.

A material of the tube member 621 may be, for example, the same material as the main tube 2 in the first embodiment.

An opening 622*f* that communicates with an internal space of the first support member 619 at a joint portion with the first support member 619 which will be described below is formed in a second cylindrical portion 622*c*. The opening 622*f* is formed as a through hole passing through the second cylindrical portion 622*c* in the thickness direction.

The first balloon 622 airtightly covers the outer circumferential surface 621*b* of the tube member 621. The first balloon 622 is formed to be the same as the fixing balloon 3 in the first embodiment, except that it has an axial length to airtightly cover the outer circumferential surface 621*b*.

The first balloon 622 has the second cylindrical portion 622*c* instead of the second cylindrical portion 3*c* of the fixing balloon 3. A length of the second cylindrical portion 622*c* in the axial direction may be, for example, 10 mm or more and 60 mm or less.

The first cylindrical portion 3*a* and the third cylindrical portion 3*e* of the first balloon 622 are fixed to the outer circumferential surface 621*b*, like the first cylindrical portion 3*a* and the third cylindrical portion 3*e* of the fixing balloon 3 in the first embodiment. Thus, a space S61 through which gas can flow through the opening 622*f* is formed inside the first balloon 622 of which an inner circumferential portion is closed by the outer circumferential surface 621*b*.

As in the first embodiment, the gas is not particularly limited, but in the following, unless otherwise specified, an example in which the gas is air will be described.

Like the fixing balloon 3, the first balloon 622 has a diameter-expanded state as shown in FIG. 101 and a diameter-reduced state (not shown) according to an internal pressure of the space S61 determined by an amount of air supplied to the space S61.

The second fixing portion 618 is formed by a second balloon 623 (a fixing balloon) fixed to the distal end portion of the main tube 602 which will be described below.

The second balloon 623 airtightly covers the outer circumferential surface 2*d* of the main tube 602. The second balloon 623 is formed to be the same as the fixing balloon 3 in the first embodiment, except that an axial length thereof may be different from that of the fixing balloon 3.

The second balloon 623 has the second cylindrical portion 623*c* instead of the second cylindrical portion 3*c* of the fixing balloon 3. A length of the second cylindrical portion 623*c* in the axial direction may be, for example, 10 mm or more and 60 mm or less.

The first cylindrical portion 3*a* and the third cylindrical portion 3*e* of the second balloon 623 are fixed to the outer circumferential surface 2*d* of the main tube 602, like the first cylindrical portion 3*a* and the third cylindrical portion 3*e* of the fixing balloon 3 in the first embodiment. Thus, a space S62 is formed inside the second balloon 623 closed by the outer circumferential surface 2*d* of the main tube 602. The space S62 communicates with the second lumen 2*e* through an opening 2*f* formed in the main tube 602 as in the first embodiment so as to communicate with the second lumen 2*e*.

The second balloon 623 has the diameter-expanded state as shown in FIG. 101 and the diameter-contracted state (not shown) according to the internal pressure of the space S62. The internal pressure of the space S62 is determined by the amount of air supplied from the second lumen 2*e* through the opening 2*f*.

The first support member 619 is made of a tube of which a distal end 619*c* is closed. An air supply lumen 619*a* extending in the longitudinal direction of the first support member 619 is formed inside the first support member 619.

The air supply lumen 619*a* allows air for expanding and contracting the first balloon 622 to flow through the space S61. An opening 619*b* is formed in the air supply lumen 619*a* at a position facing the opening 622*f* of the first balloon 622 at the distal end portion of the first support member 619. The opening 622*f* and the opening 619*b* allow the air supply lumen 619*a* and the space S61 to communicate with each other.

The first support member 619 has a distal end portion 619A and a proximal end portion 619B (an air supply tube).

The distal end portion 619A of the first support member 619 connects the second cylindrical portion 622*c* of the first balloon 622 to the second cylindrical portion 623*c* of the second balloon 623 in the axial direction. In the example shown in FIGS. 101 and 102, the distal end portion 619A is joined to the outside of the second cylindrical portion 622*c* and the second cylindrical portion 623*c*. A method for joining the distal end portion 619A is not particularly limited. For example, the distal end portion 619A may be joined to the second cylindrical portion 622*c* and the second cylindrical portion 623*c* by gluing, welding, or the like.

In the example shown in FIG. 101, the distal end portion 619A is joined to the second cylindrical portion 622*c* and the second cylindrical portion 623*c* across the entirety of the second cylindrical portion 622*c* and the second cylindrical portion 623*c* in the axial direction. When required joining strength is obtained, the distal end portion 619A may be joined to a portion of each of the second cylindrical portion 622*c* and the second cylindrical portion 623*c* at one or more locations in the axial direction.

The distal end portion 619A of the first support member 619 connects the first balloon 622 and the second balloon 623 to each other such that the first balloon 622 and the second balloon 623 are spaced apart by a certain distance in the axial direction. The distance between the first balloon 622 and the second balloon 623 in the axial direction is a distance between the first balloon 622 and the second balloon 623 that ensures a width of a surgical field necessary for surgery performed with the endoscope inserted through the overtube 601.

For example, in order to enable the distal end portion 12 of the endoscope 11 to move over a wide range by operating a curved portion 17, it is more preferable that a distance Lf in the axial direction from the proximal end 621*c* of the tube member 621 to the distal end 602*g* of the main tube 602 is longer than a length of the curved portion 17.

For example, when the overtube 601 is used for endoscopic full-thickness resection of the intestinal wall in the large intestine, a necessary surgical field can be secured when the distance Lf is 70 mm or more and 120 mm or less.

For example, the same applies when the overtube 601 is used for ESD in the large intestine.

The proximal end portion 619B has a length extending from the proximal end of the distal end portion 619A fixed to the second balloon 623 to the proximal end side of the overtube 601 with respect to the second balloon 623.

In the example shown in FIG. 100, the proximal end portion 619B extends along the main tube 602 to the grip portion 605. The arrangement of the proximal end portion 619B will be described below in the description of the main tube 602.

However, the proximal end portion 619B may not extend to the grip portion 605 as long as an air supply flow path for supplying air to the first balloon 622 can be formed. In this case, an air supply tube extending along the main tube 602 to the grip portion 605 is connected to the proximal end of the proximal end portion 619B. The air supply tube has an air supply lumen that extends in the longitudinal direction. The air supply tube is connected to the proximal end of the proximal end portion 619B so that the air supply lumen communicates with the air supply lumen 619*a* of the first support member 619.

In this case, a length of the proximal end portion 619B is not particularly limited. For example, the proximal end portion 619B may be long enough to form a connection with the air supply tube.

Hereinafter, an example in which the proximal end portion 619B of the first support member 619 extends to the grip portion 605 as shown in FIG. 100 will be described below.

The outer diameters and inner diameters of the distal end portion 619A and the proximal end portion 619B may be equal to each other or may be different from each other. The outer diameter of the proximal end portion 619B is smaller than an inner diameter of an insertion lumen provided in the main tube 602 which will be described below.

For example, the outer diameter of the proximal end portion 619B may be 1 mm or more and 4 mm or less.

The inner diameters of the distal end portion 619A and the proximal end portion 619B are not particularly limited as long as air can be supplied without any problem. For example, the inner diameters of the distal end portion 619A and the proximal end portion 619B may be 0.5 mm or more and 2 mm or less.

In the following description, unless otherwise specified, the outer diameters and inner diameters of the distal end portion 619A and the proximal end portion 619B are equal to each other.

A material of the first support member 619 is not particularly limited as long as it has flexibility to the extent that it does not impair flexibility of the main tube 602 which will be described below.

For example, when the outer diameter and the inner diameter of the first support member 619 are within the range described above, suitable materials for the first support member 619 include polytetrafluoroethylene (PTFE), polycarbonate, and the like.

The second support member 620 connects the second cylindrical portion 622*c* of the first balloon 622 and the second cylindrical portion 623*c* of the second balloon 623 in the axial direction at positions different in the circumferential direction from the first support member 619. In the example shown in FIG. 102, three second support members 620 are provided at positions that divide the second cylindrical portion 622*c* and the second cylindrical portion 623*c* in the diameter-expanded state into four equal portions in the circumferential direction together with the first support member 619.

Each of the second support members 620 is joined to the second cylindrical portion 622*c* and the second cylindrical portion 623*c* from the outside, like the distal end portion 619A of the first support member 619.

Each of the second support members 620 connects the first balloon 622 and the second balloon 623 to each other with a certain distance in the axial direction, as in the distal end portion 619A of the first support member 619. However, each of the second support members 620 does not have the air supply function. Each of the second support members 620 may be, for example, a solid rod.

A length of each of the second support members 620 is not particularly limited as long as the first balloon 622 and the second balloon 623 can be connected, as in the first support member 619. In the example shown in FIG. 101, each of the second support members 620 is joined to the second cylindrical portion 622*c* and the second cylindrical portion 623*c* across the entirety of the second cylindrical portion 622*c* and the second cylindrical portion 623*c* in the axial direction. However, when necessary joining strength is obtained, each of the second support members 620 may be joined to a portion of each of the second cylindrical portion 622*c* and the second cylindrical portion 623*c* at one or more locations in the axial direction.

As shown in FIG. 103, the main tube 602 is the same as the main tube 2, except that the insertion lumen 602*e* is formed in the thick portion 2*b* of the main tube 2 in the first embodiment.

The first support member 619 extending to the proximal end side with respect to the second balloon 623 is inserted through the insertion lumen 602*e*. The insertion lumen 602*e* passes through the main tube 602 in the axial direction. The insertion lumen 602*e* is parallel to the second lumen 2*e* in the thick portion 2*b* of the main tube 602.

As shown by a broken line in FIG. 101, an opening 602*f* for inserting the first support member 619 into the insertion lumen 602*e* is formed at the distal end portion of the insertion lumen 602*e* at a position farther to the proximal end side than the second balloon 623.

The proximal end portion 619B of the first support member 619 is inserted through the inside of the insertion lumen 602*e* via the opening 602*f*, and communicates with an internal conduit of the grip portion 605, which will be described below, at the proximal end of the insertion lumen 602*e*.

Although a method for manufacturing the distal end fixing portion 603 is not particularly limited, it can be manufactured as follows, for example.

The first balloon 622 is joined to the tube member 621, and the second balloon 623 is joined to the distal end portion of the main tube 602. Then, the proximal end portion 619B of the first support member 619 is inserted from the opening 602*f* of the main tube 602 toward the proximal end. After the proximal end of the proximal end portion 619B reaches a position in which it is joined to the grip portion 605, the distal end portion 619A of the first support member 619 is aligned with joint portions of the first balloon 622 and the second balloon 623, and is joined to each of them. At this time, the first support member 619 is disposed so that the opening 619*b* and the opening 622*f* of the first balloon 622 face each other, and the opening 619*b* and the opening 622*f* airtightly communicate with each other. The distal end portion 619A is joined to the first balloon 622 around the opening 619*b* and the opening 622*f*.

After the first support member 619 is joined to the first balloon 622 and the second balloon 623, or at the same time as joining the first support member 619, each of the second support members 620 is joined to the first balloon 622 and the second balloon 623. However, after each of the second support members 620 is joined to the first balloon 622 and the second balloon 623, the first support member 619 may be joined as described above.

As shown in FIG. 100, the grip portion 605 includes a connector 605*c* instead of the first luer connector 5*c* of the grip portion 5 in the first embodiment.

The connector 605*c* detachably connects a first connection tube and a second connection tube which communicate with a first flow path and a second flow path formed inside the grip portion 605, respectively, to an air flow tube 609 which will be described below.

The first flow path allows the second lumen 2*e* of the main tube 602 (refer to FIG. 101) and the first connection tube to communicate with each other.

The second flow path allows the air supply lumen 619*a* of the first support member 619 and the second connection tube to communicate with each other.

The grip portion 605 and the proximal end portion of the main tube 602 are connected to each other, like the grip portion 5 and the proximal end portion of the main tube 2 in the first embodiment.

The air flow tube 609 extends from the air supply device 610. The connector 609*a* that is detachably connected to each of the first connection tube and the second connection tube of the grip portion 605 is provided at the distal end portion of the air flow tube 609. The air flow tube 609 has two systems of independent flow paths that communicate with the first connection tube and the second connection tube, respectively.

Thus, the air flow tube 609 connected to the connector 605*c* forms independent air flow paths between the second lumen 2*e* and the air supply lumen 619*a*, and the air supply device 610.

The air supply device 610 is the same as the air supply device 10 in the first embodiment, except that it supplies air to expand the diameters of the first balloon 622 and the second balloon 623, and suctions the air inside the first balloon 622 and the second balloon 623 as necessary.

In this embodiment, the air supply device 610 can independently change the amount of air flowing through two systems of flow paths of the air flow tube 609 based on an operator's operation. The means for changing the amount of air is not particularly limited.

For example, the air supply device 610 may include two systems of air supply and suction parts and a flow rate operating part that changes a flow rate of air in each of the air supply and suction parts according to the operator's operation.

For example, the air supply device 610 may include one system of air supply and suction part, a flow rate operating part that changes the flow rate of air in the air supply and suction part according to the operator's operation, and a flow path switching valve for two systems of flow paths. In this case, air can be supplied to and suctioned from the flow path of the air flow tube 609 that is made to be communicating by switching the flow path switching valve.

The air supply and suction part of the air supply device 610 may be an electric pump or a manual pump, as in the first embodiment. In the case of a manual pump, the air supply device 610 may be any air supply device including the manual air supply mechanism 211 in each of the embodiments and modified examples described above, for example.

When the flow path switching valve is used to switch the flow path for air supply and suction, the flow path switching valve is not limited to a configuration in which the flow path of the air flow tube 609 is switched. For example, the flow path switching valve may be provided on an appropriate flow path between the connector 605*c* and the air supply device 610. In this case, in the air flow tube 609, the flow path closer to the air supply device 610 than the flow path switching valve only needs to have one system of flow path.

Here, problems when a conventional overtube is used for endoscopic full-thickness resection will be described.

Figure 104:
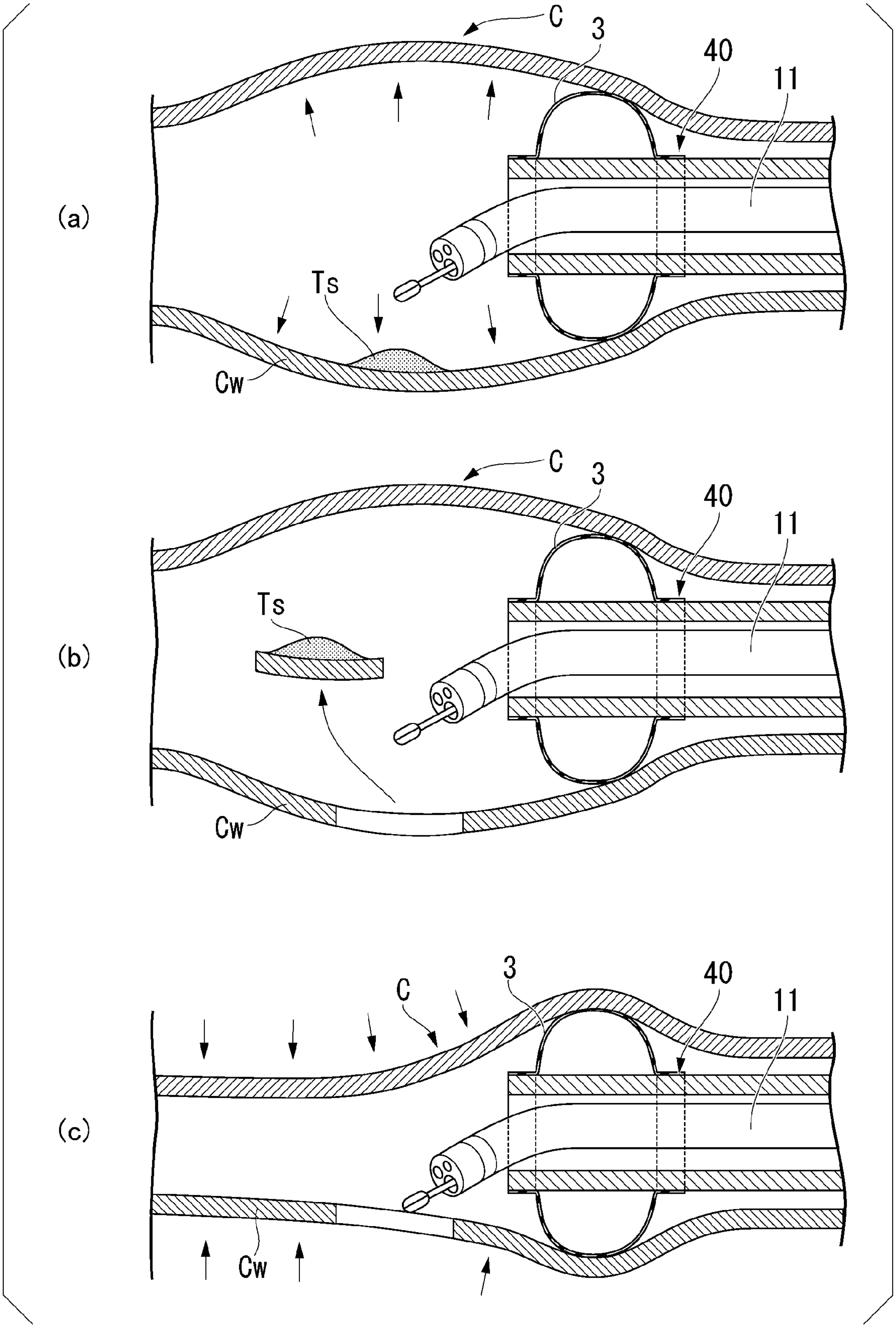
FIG. 104 is a schematic diagram showing an example of endoscopic full-thickness resection using a conventional overtube.

FIG. 104 is a schematic diagram showing an example of endoscopic full-thickness resection using a conventional overtube.

ESD which the submucosal layer in the patient's lumen is removed using an endoscope is becoming popular.

However, ESD is insufficient for the treatment of advanced cancer, for example, and full-thickness resection of the lumen is required. In this case, less invasive surgery becomes possible by performing full-thickness resection under an endoscope.

(a), (b), and (c) of FIG. 104 schematically shows a process of full-thickness resection of a treatment site Ts of the large intestine C using an endoscope 11 passed through a conventional overtube 40 having a fixing balloon 3 at the distal end which is the same as that of the first embodiment.

As shown in (a) of FIG. 104, an overtube 40 is inserted into the large intestine C near the treatment site Ts. The overtube 40 is fixed to the large intestine C by bringing the fixing balloon 3 into an expanded state. An operator inserts the endoscope 11 into the overtube 40 and arranges the distal end portion of the endoscope 11 near the treatment site Ts.

In this state, the operator supplies air from the endoscope 11 to expand the large intestine C. Thus, a surgical field is secured in front of the fixing balloon 3.

Then, as shown in (b) of FIG. 104, the operator uses a treatment tool passed through a treatment tool channel of the endoscope 11 to perform full-thickness resection of the treatment site Ts along with the surrounding intestinal wall Cw. Thus, an opening Ch is formed in the intestinal wall Cw.

During a process of forming the opening Ch, air in the large intestine C leaks out of a cut portion to the outside. Thus, the large intestine C is pressed and collapsed by body pressure from the outside as shown in (c). Since (b) is a schematic diagram, it is depicted as if the surgical field is secured when the opening Ch is formed, but in fact, when a through hole is formed in the thickness direction of the intestinal wall Cw, the surgical field begins to shrink rapidly, and thus it may be difficult for the operator to continue the resection procedure. Even when full-thickness resection can be completed, a treatment such as suturing the opening Ch after resection becomes difficult.

Thus, in the endoscopic full-thickness resection procedure, securing a sufficient surgical field around the treatment site Ts during and after resection is a problem.

A method for using the overtube 601 will be described with an example in which the overtube 601 is used for an endoscopic full-thickness resection.

Figure 105:
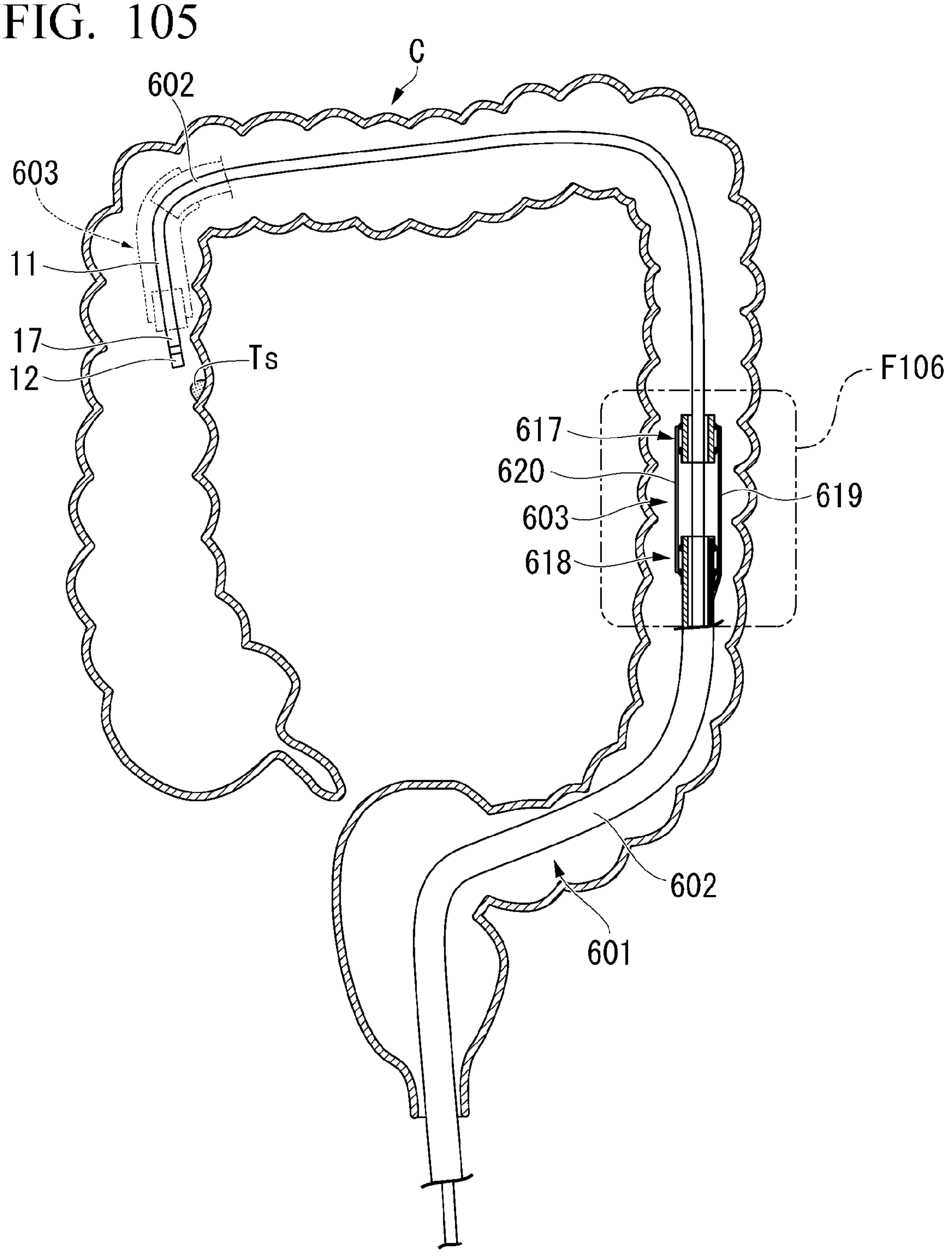
FIG. 105 is a schematic diagram showing an example of a method for using the overtube for an endoscope according to the seventh embodiment of the present invention.
Figure 106:
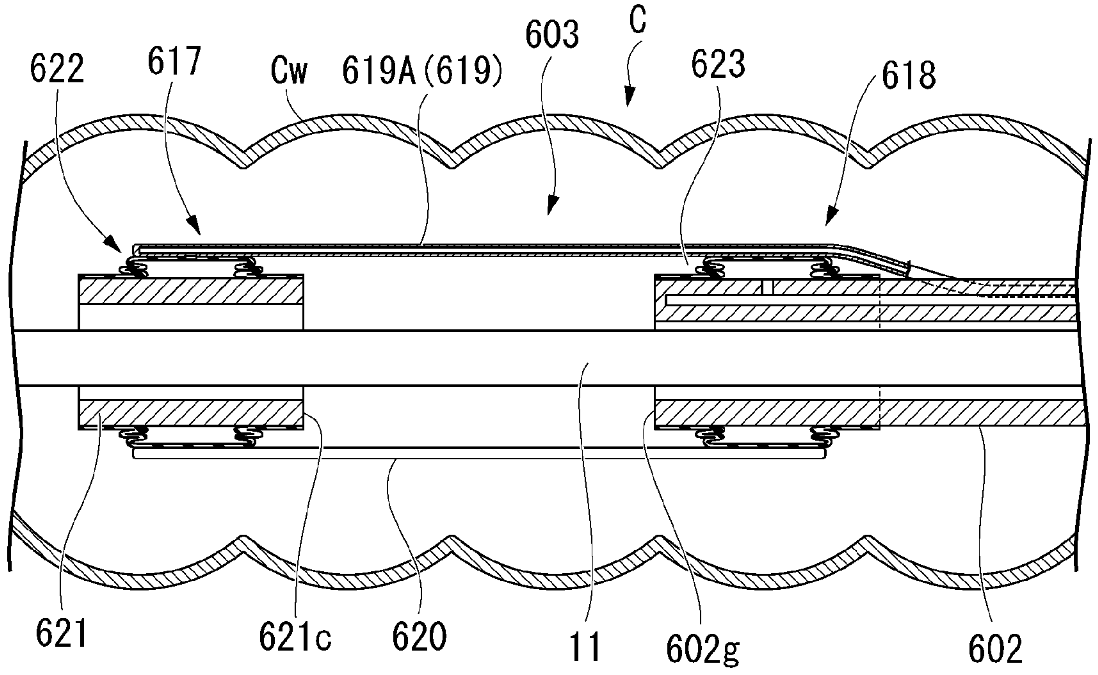
FIG. 106 is an enlarged view of an F106 portion in FIG. 105.
Figure 107:
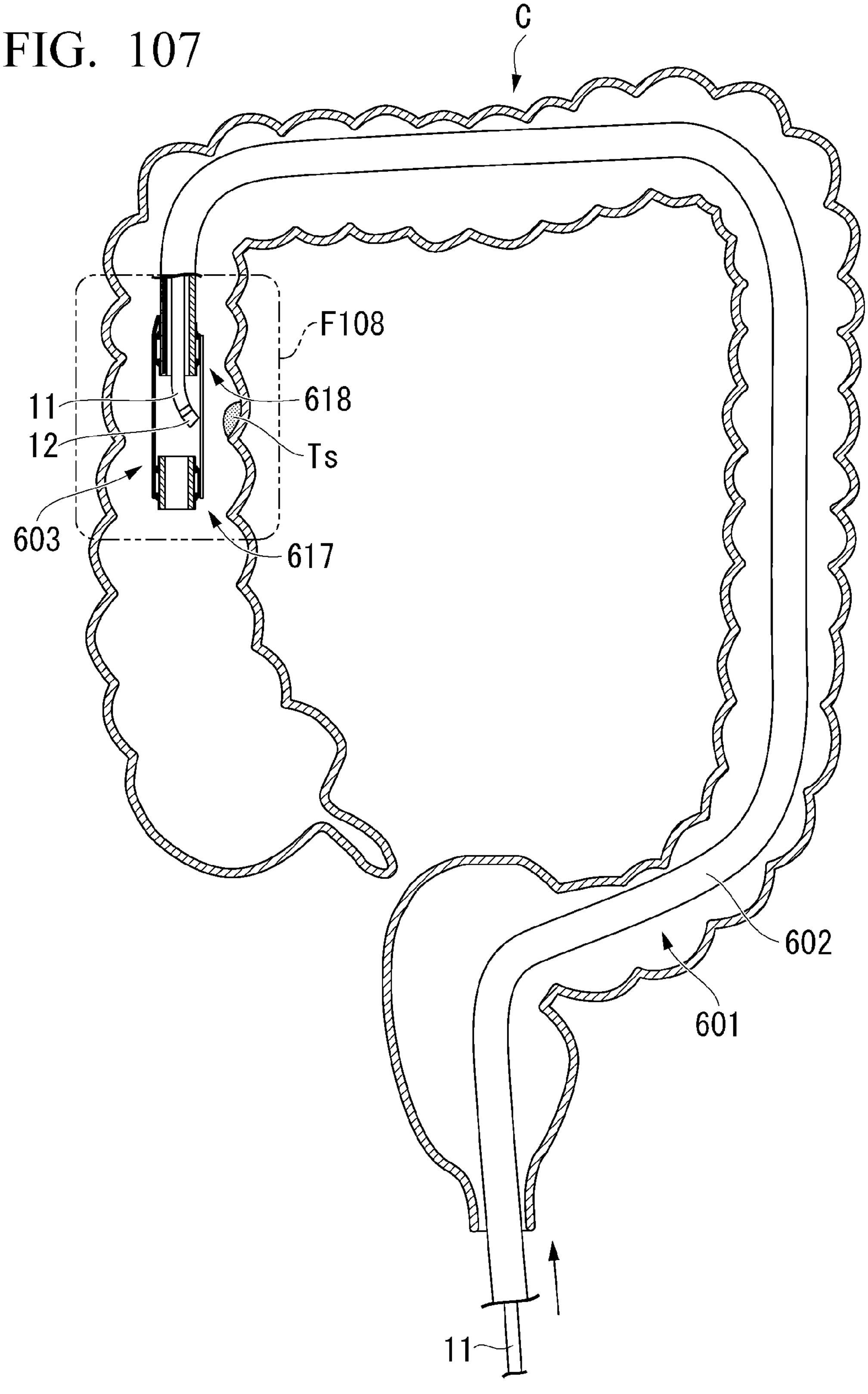
FIG. 107 is a schematic diagram showing an example of the method for using the overtube for an endoscope according to the seventh embodiment of the present invention.

FIG. 105 is a schematic diagram showing an example of the method for using the overtube for an endoscope according to the seventh embodiment of the present invention. FIG. 106 is an enlarged view of an F106 portion in FIG. 105. FIG. 107 is a schematic diagram showing an example of the method for using the overtube for an endoscope according to the seventh embodiment of the present invention.

However, in FIGS. 105 to 107, detailed shapes of the endoscope cap 13, the gripping device 14, the channel tube 15, and the like of the endoscope 11 are omitted for the sake of clarity. The same applies to the endoscopes 11 in other drawings in this embodiment.

First, the overtube 601 is prepared.

The prepared overtube 601 is the same as the overtube 1 used for ESD in the first embodiment, except that the distal end fixing portion 603 is in the diameter-contracted state, as in the fixing balloon 3.

In the following, differences from the method for using the overtube 1 described in the first embodiment will be mainly described.

In the prepared overtube 601, air in the space S61 inside the first balloon 622 is suctioned out by the air supply device 610. Therefore, the first balloon 622 is folded, like the fixing balloon 3 in the diameter-contracted state in the first embodiment, and is close to the outer circumferential surface 2*d* of the main tube 602. Thus, the outer diameter of the first fixing portion 617 is reduced to approximately the same diameter as the outer diameter of the main tube 602 in which the fixing balloon 3 is not provided. This state is hereinafter referred to as a diameter-contracted state of the first balloon 622.

Furthermore, in the overtube 601, the air in the space S62 inside the second balloon 623 is suctioned out by the air supply device 610. Therefore, the second balloon 623 is folded like the first balloon 622 and is close to the outer circumferential surface 2*d* of the main tube 602. Thus, the outer diameter of the second fixing portion 618 is contracted to approximately the same diameter as the outer diameter of the main tube 602. This state is hereinafter referred to as a diameter-contracted state of the second balloon 623.

In the prepared overtube 601, the airtight valve unit 6 allows an insertion portion of the endoscope 11 to be inserted with low resistance, as in the first embodiment.

Then, the operator inserts the distal end of the endoscope 11 into the inside of the airtight valve unit 6 of the overtube 601. Then, the insertion portion of the endoscope 11 is caused to pass through the grip portion 605, the first lumen 2*c* of the main tube 602, and the inner circumferential surface 621*a* of the tube member 621 and to extend from the tube member 621.

Then, the operator arranges the overtube 601 outside the patient's body, and inserts the insertion portion of the endoscope 11 protruding from the overtube 601 into the large intestine C through the anus, as in the first embodiment. After the treatment site Ts appears in an image acquired by the endoscope 11, the operator stops inserting the endoscope 11 (refer to FIG. 105).

Then, the operator inserts the overtube 601 into the large intestine C from the anus along the insertion portion of the endoscope 11. At this time, as in the first embodiment, air can be supplied from the airtight valve operation tube 7 to the airtight valve unit 6 (not shown) to bring the middle portion 22*b* into close contact with the outer circumferential portion of the endoscope 11. Thus, the airtight valve unit 6 seals airtightly and liquid tightly between the outer circumferential portion of the endoscope 11 and the airtight valve unit 6.

As the overtube 601 continues to be inserted, the middle portion 22*b* of the airtight valve unit 6 also moves to the distal side together with the overtube 601. At this time, even when the outer circumferential portion of the endoscope 11 has irregularities, the middle portion 22*b* deforms to follow the irregularities, and thus an airtight and liquid-tight state is maintained.

In this embodiment, unlike the first embodiment, the airtight valve unit 6 (not shown) may not be provided.

The first fixing portion 617 of the distal end fixing portion 603 is connected to the second fixing portion 618 by the first support member 619 and the second support member 620 having flexibility. Therefore, the distal end fixing portion 603 can smoothly move along the bent portion and curved portion of the endoscope 11 inserted in the bent state by curving the first support member 619 and the second support member 620.

As shown in FIG. 106, when the first balloon 622 and the second balloon 623 are in the diameter-contracted state, the outer diameter of the distal end fixing portion 603 is approximately the same as the outer diameter of the main tube 602 and is sufficiently smaller than the inner diameter of the intestinal wall Cw.

In the diameter-contracted state, the first support member 619 and each of the second support members 620 extend in the axial direction of the overtube 601 at the outermost circumferential portion of the distal end fixing portion 603. Therefore, when the overtube 601 moves along the endoscope 11, and the distal end fixing portion 603 comes into contact with the intestinal wall Cw, since the first support member 619 and each of the second support members 620 in the distal end fixing portion 603 come into line contact with the intestinal wall Cw as linear bodies extending in the moving direction, sliding resistance with the intestinal wall Cw is reduced. Further, the distal end portion 619A of the first support member 619 and each of the second support members 620 protrude further to the outer circumferential side with respect to the proximal end 621*c* of the tube member 621 and the distal end 602*g* of the main tube 602. Thus, since the distal end portion 619A of the first support member 619 or the second support member 620 come into contact with the intestinal wall Cw first, the proximal end 621*c* and the distal end 602*g* are prevented from being caught on the intestinal wall Cw during movement of the overtube 601. In this respect as well, the sliding resistance is reduced, and the load on the patient is reduced.

As shown by a two-dot chain line in FIG. 105, the operator inserts the overtube 601 until the distal end fixing portion 603 is located near the proximal end of the distal end portion 12 of the endoscope 11.

Then, as shown in FIG. 107, the operator further pushes the overtube 601 to the distal side so that the distal end portion 12 is located between the first fixing portion 617 and the second fixing portion 618.

Figure 108:
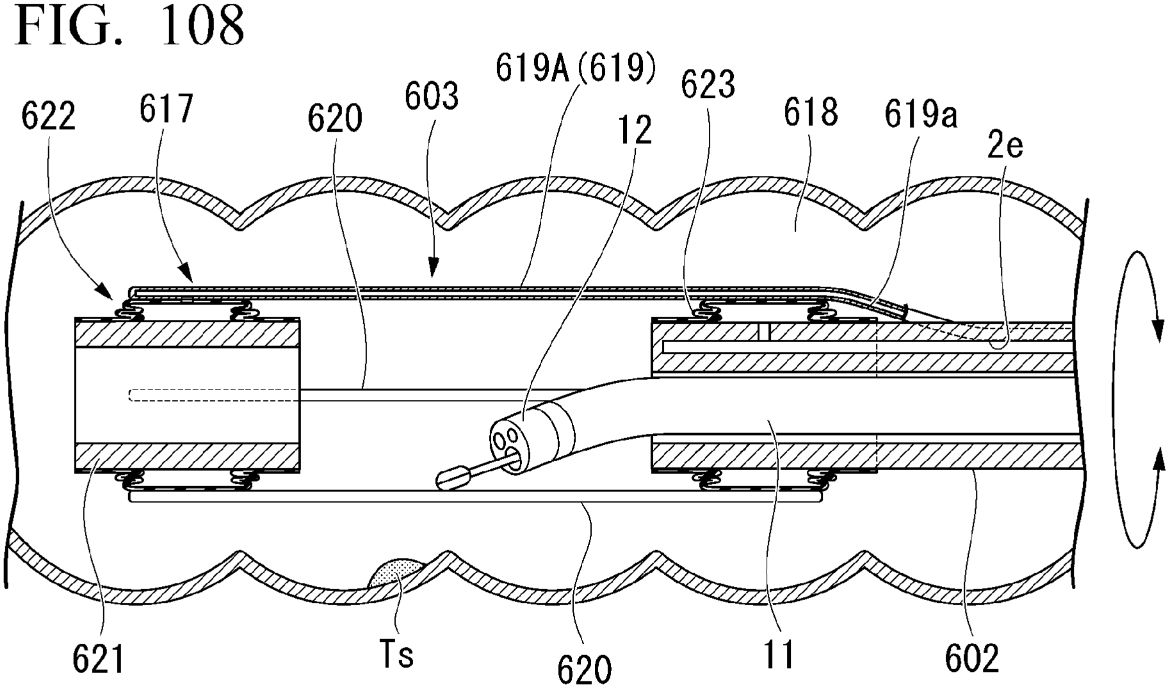
FIG. 108 is an enlarged view of an F108 portion in FIG. 107.
Figure 109:
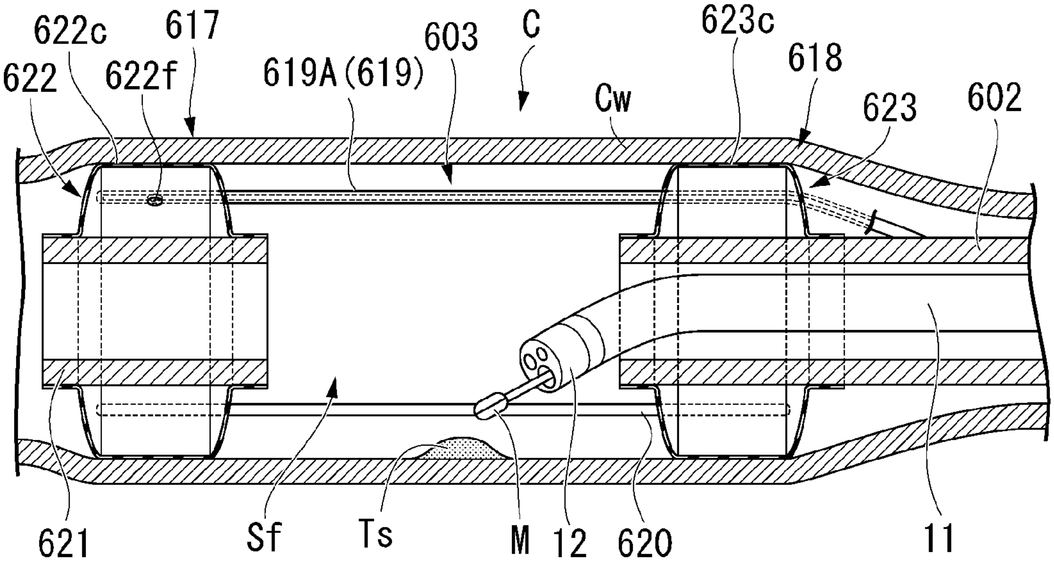
FIG. 109 is a cross-sectional view showing an example of the method for using the overtube for an endoscope according to the seventh embodiment of the present invention.
Figure 110:
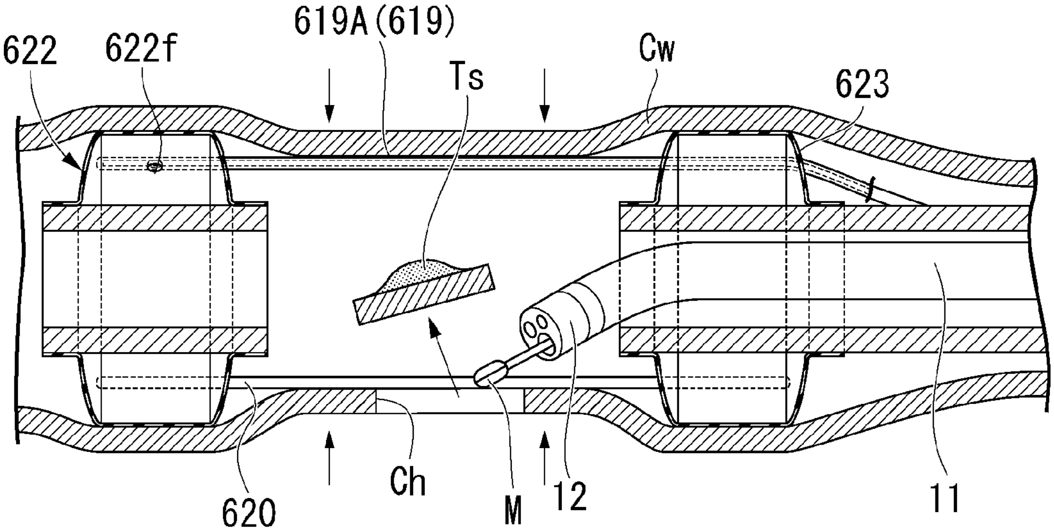
FIG. 110 is a cross-sectional view showing an example of the method for using the overtube for an endoscope according to the seventh embodiment of the present invention.

FIG. 108 is an enlarged view of an F108 portion in FIG. 107. FIG. 109 to 110 are cross-sectional views showing an example of the method for using the overtube for an endoscope according to the seventh embodiment of the present invention.

In the state shown in FIG. 108, when the operator looks at the image from the endoscope 11 and expands the diameters of the first balloon 622 and the second balloon 623, it is confirmed whether either the distal end portion 619A of the first support member 619 or the second support member 620 is in a position straddling the treatment site Ts.

When the diameter is expanded and there is a possibility that either the distal end portion 619A of the first support member 619 or the second support member 620 may straddle the treatment site Ts, the operator rotates the overtube 601 outside the body in the circumferential direction to shift the positions of the distal end portion 619A of the first support member 619 and the second support member 620 in the circumferential direction. At this time, the operator fixes the endoscope 11 and rotates the grip portion 605 of the overtube 601 around the endoscope 11. At this time, the middle portion 22*b* of the airtight valve unit 6 (not shown) can rotate smoothly along the outer circumference of the endoscope 11 while airtightness and liquid tightness are maintained.

The rotation of the grip portion 605 is transmitted to the distal end fixing portion 603 according to torsional rigidity of the main tube 602. Thus, the distal end portion 619A of the first support member 619 and the second support member 620 rotate in the same direction as a rotation direction of the grip portion 605.

However, when there is no possibility that either the distal end portion 619A of the first support member 619 or the second support member 620 will straddle the treatment site Ts, it is not necessary to rotate the overtube 601 in the circumferential direction.

In this way, the position adjustment of the distal end fixing portion 603 in the circumferential direction is completed.

The position adjustment of the distal end fixing portion 603 in the circumferential direction may be performed after the diameters of the first balloon 622 and the second balloon 623 are expanded to near the inner diameter of the intestinal wall Cw. In this case, even when the distal end fixing portion 603 causes contact rotation during rotation, the outer circumferential portions of the first balloon 622 and the second balloon 623 slide smoothly on the inner surface of the intestinal wall Cw. and thus the position adjustment in the circumferential direction can be performed in a state in which the center of the distal end fixing portion 603 substantially coincides with the center of the intestinal wall Cw.

Furthermore, since the positions of the distal end portion 619A of the first support member 619 and the second support member 620 in the radial direction is close to a position when the distal end fixing portion 603 is fixed to the intestinal wall Cw, displacement in the circumferential direction of the distal end portion 619A of the first support member 619 and the second support member 620 in the diameter-expanded state is unlikely to occur.

After the position adjustment of the distal end fixing portion 603 in the circumferential direction is completed, the operator operates the air supply device 610 to supply air to the first balloon 622 and the second balloon 623 to expand them.

At this time, the air from the air supply device 610 is independently supplied to the first balloon 622 and the second balloon 623 according to the configuration of the air supply device 610.

When the first balloon 622 and the second balloon 623 are sufficiently expanded, each of them comes into contact with the inner surface of the intestinal wall Cw. The second cylindrical portion 622*c* of the first balloon 622, the second cylindrical portion 623*c* of the second balloon 623, the distal end portion 619A of the first support member 619 fixed to the outer circumferential side of each of them, and each of the second support members 620 press the inner wall of the intestinal wall Cw.

Thus, the distal end fixing portion 603 is fixed to the intestinal wall Cw to the extent that it does not easily move relative to the large intestine C.

The first balloon 622 and the second balloon 623 may be expanded simultaneously or with a time difference.

When they are expanded with a time difference, it is more preferable that the first balloon 622 on the distal side is expanded and then the second balloon 623 on the proximal side is expanded.

In this case, the operator may expand the first balloon 622 to fix the first fixing portion 617 to the intestinal wall Cw, may pull the main tube 602 to the proximal side, and then may expand the second balloon 623. According to this order, even when the distal end portion 619A of the first support member 619 and the second support member 620 are bent or curved, the distal end portion 619A of the first support member 619 and the second support member 620 are extended in the axial direction. Thus, the bend or curvature of the distal end portion 619A of the first support member 619 and the second support member 620 is corrected.

When the position of the second balloon 623 in the axial direction is fixed while the distal end portion 619A of the first support member 619 and the second support member 620 are bent or curved, a distance between the proximal end 621*c* of the tube member 621 and the distal end 602*g* of the main tube 602 becomes shorter than Lf, and the surgical field in the axial direction becomes narrower.

On the other hand, when the bend or curvature is corrected, the distance between the proximal end 621*c* and the distal end 602*g* can be returned to the maximum Lf.

After the distance between the proximal end 621*c* and the distal end 602*g* is widened, the operator expands the second balloon 623 and fixes the second fixing portion 618 to the intestinal wall Cw.

When the distal end fixing portion 603 is fixed to the intestinal wall Cw, a space Sf surrounded by the first support member 619 and the second support members 620 is formed inside the intestinal wall Cw between the first fixing portion 617 and the second fixing portion 618.

The distal end portion 12 of the endoscope 11 and the treatment tool M extending from the treatment tool channel of the distal end portion 12 are movable within the space Sf. As the treatment tool M, for example, a high frequency knife may be used.

The space Sf forms a surgical field for performing full-thickness resection.

The intestinal wall Cw on the distal and proximal sides of the space Sf is supported in the radial direction by the first balloon 622 and the second balloon 623. Thus, the intestinal wall Cw has expanded to a size equal to the respective outer diameters of the first balloon 622 and the second balloon 623. The distal end portion 619A of the first support member 619 and the second support member 620 are stretched between the first balloon 622 and the second balloon 623.

Therefore, the intestinal wall Cw between the first balloon 622 and the second balloon 623 is supported in the radial direction by the distal end portion 619A of the first support member 619*b* and each of the second support members 620.

Therefore, a certain volume is ensured in the space Sf even if the space Sf is not particularly expanded by introducing air. Thus, since the treatment can be performed without expanding the large intestine C by sending air into the large intestine C, the load on the patient can be reduced.

For example, the operator uses the treatment tool M protruding from the endoscope 11 to resect the full thickness of the intestinal wall Cw around the treatment site Ts.

At this time, when a through hole is formed in the intestinal wall Cw, as shown in FIG. 110, gas and liquid in the large intestine C leak to the outside of the large intestine C, and thus the large intestine C is compressed from the outside. However, since the intestinal wall Cw is supported from the inside by the distal end fixing portion 603, it will not collapse. For example, even when the space Sf is reduced, a polygonal cross-sectional shape with the first support member 619 and each of the second support members 620 as vertices is ensured.

Thus, even when a through hole is formed in the intestinal wall Cw, a surgical field close to a size before the through hole is formed is ensured.

The operator can continue the treatment after full-thickness resection, such as suturing the opening Ch, using an appropriate treatment tool within the space Sf secured by the distal end fixing portion 603.

After all treatments necessary for endoscopic full-thickness resection is completed, the operator operates the air supply device 610 to suction out the air in the first balloon 622 and the second balloon 623. Thus, the first balloon 622 and the second balloon 623 are brought into the diameter-contracted state.

Then, the operator pulls out the endoscope 11 and overtube 601 from the anus.

In this way, the endoscopic full-thickness resection using the overtube 601 is completed.

The method for using the overtube 601 has been described with the example of endoscopic full-thickness resection. However, the overtube 601 may be used for a treatment other than endoscopic full-thickness resection, as long as the treatment is an endoscopic treatment that can be performed using the space Sf as the surgical site. For example, it may be used for ESD, endoscopic mucosal resection (EMR), polypectomy, and the like.

The overtube 601 according to this embodiment differs from the overtube 1 according to the first embodiment mainly in that it includes the distal end fixing portion 603 instead of the fixing balloon 3. The differences between the main tube 2, the grip portion, the air flow tube 9, and the air supply device 10 and the main tube 602, the grip portion 605, the air flow tube 609, and the air supply device 610 in this embodiment are caused by the distal end fixing portion 603 having the first balloon 622 and the second balloon 623.

Therefore, since the overtube 601 is configured in the same manner as the overtube 1, except that it includes the first balloon 622, the second balloon 623, the first support member 619, and the second support member 620 instead of the fixing balloon 3, it has the same action as in the first embodiment. Therefore, according to this embodiment, like the first embodiment, it is possible to provide an overtube for an endoscope that reduces the load on the patient and allows a smooth operation of the endoscope.

In particular, in this embodiment, since the distal end fixing portion 603 is provided, even when a through hole is formed in the inner wall of the lumen to be treated in front of the main tube 602, the space Sf serving as the surgical site can be formed, and thus various treatments including, for example, endoscopic full-thickness resection can be easily performed.

Twenty-First Modified Example

A modified example (a twenty-first modified example) in the method for using the overtube 601 will be described.

Figure 111:
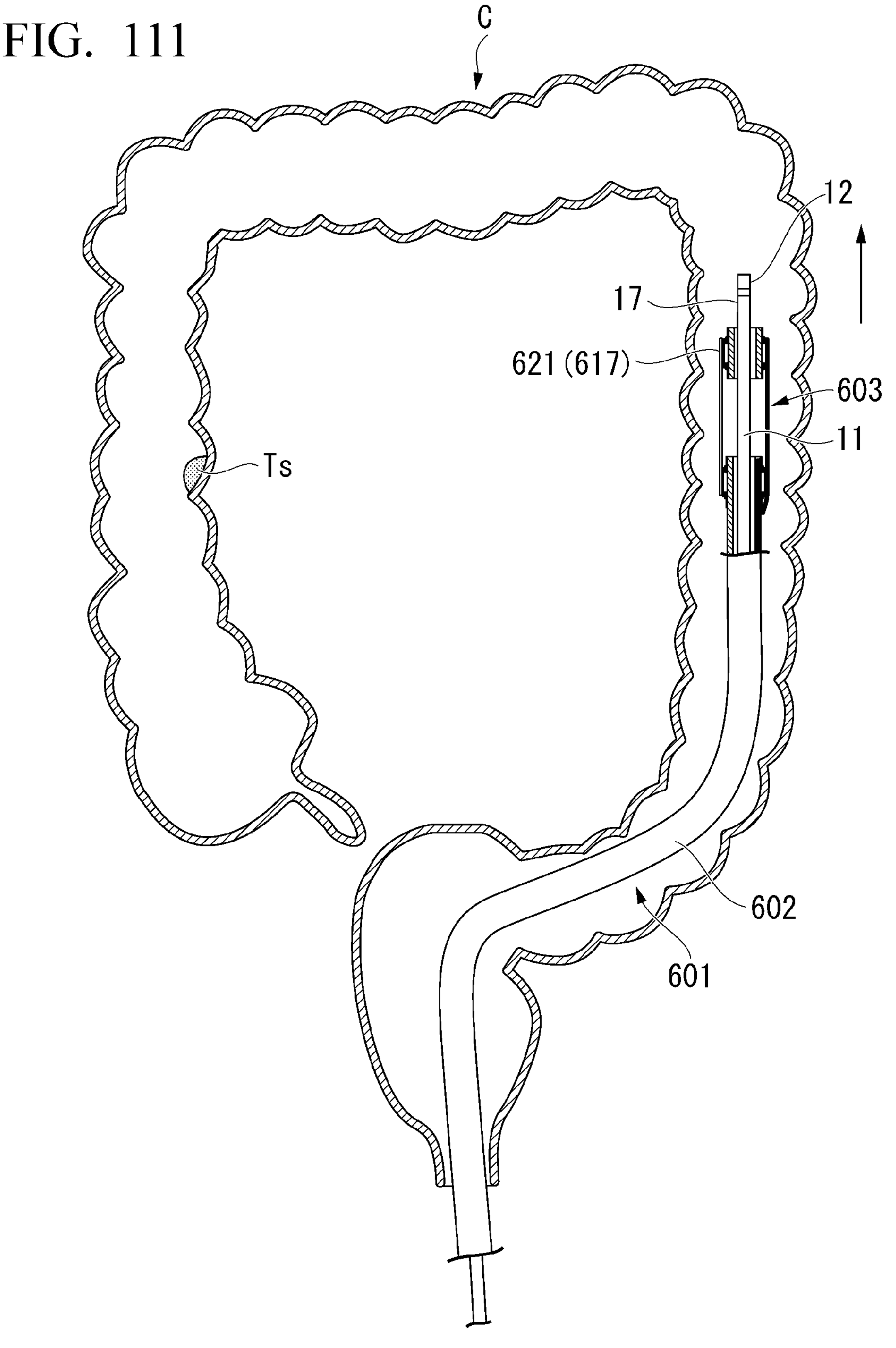
FIG. 111 is a cross-sectional view showing a modified example (a twenty-first modified example) of the method for using the overtube for an endoscope according to the seventh embodiment of the present invention.
Figure 112:
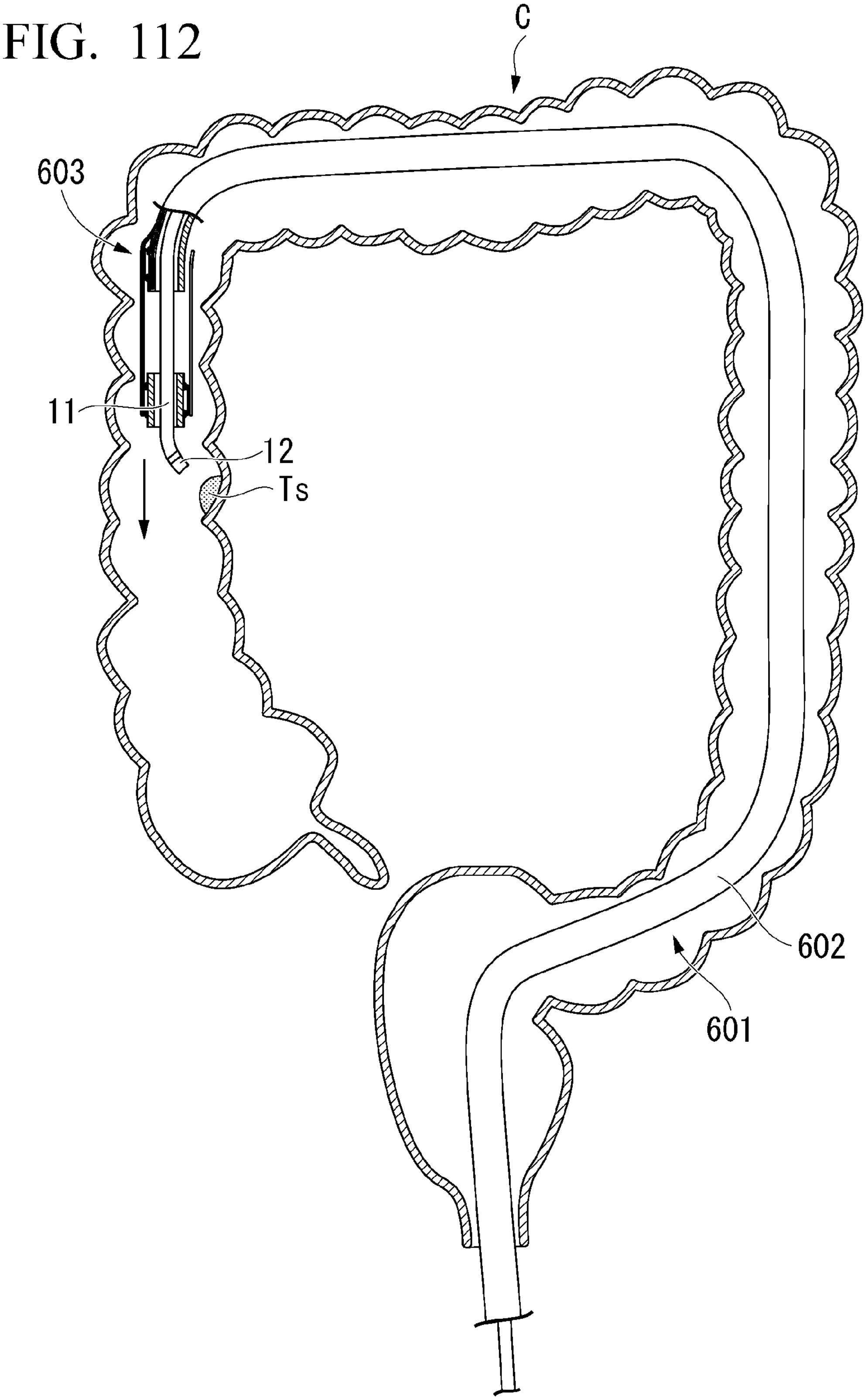
FIG. 112 is a cross-sectional view showing the modified example (the twenty-first modified example of the method for using the overtube for an endoscope according to the seventh embodiment of the present invention.
Figure 113:
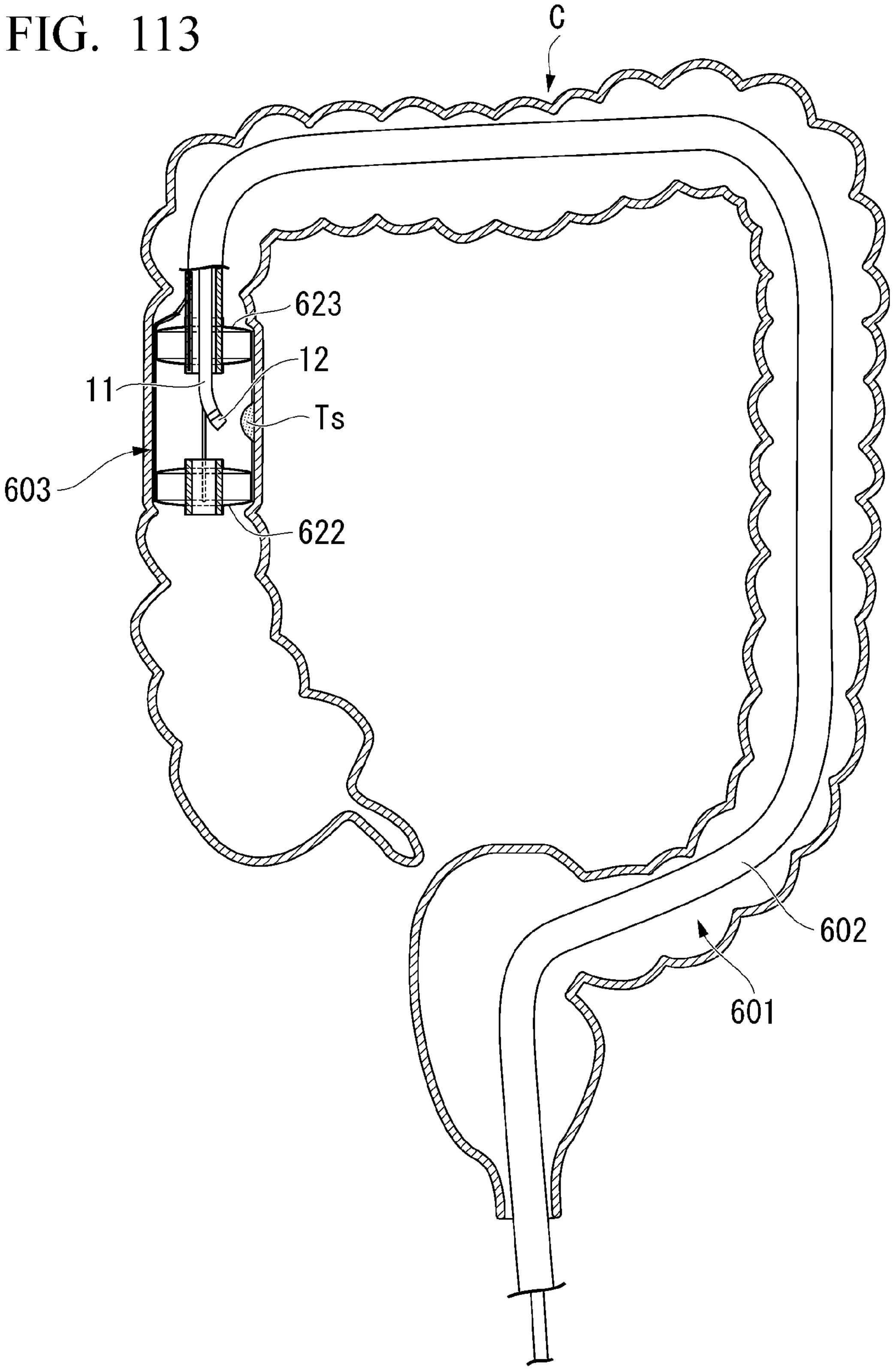
FIG. 113 is a cross-sectional view showing the modified example (the twenty-first modified example) of the method for using the overtube for an endoscope according to the seventh embodiment of the present invention.

FIGS. 111 to 113 are cross-sectional views showing the modified example (the twenty-first modified example) of the method for using the overtube for an endoscope according to the seventh embodiment of the present invention.

This modified example is a modified example regarding a method for inserting the overtube 601.

In the following, differences from the seventh embodiment will be mainly described.

As shown in FIG. 111, in the method of use of this modified example, the overtube 601 is prepared with the endoscope 11 inserted therethrough, with the curved portion 17 and the distal end portion 12 of the endoscope 11 protruding from the tube member 621 of the first fixing portion 617 to the distal side. The distal end fixing portion 603 of the overtube 601 is in the diameter-contracted state, as in the seventh embodiment.

The overtube 601 is inserted into the large intestine C from the anus of the patient together with the endoscope 11 while the amount of protrusion of the endoscope 11 from the tube member 621 is maintained at a constant amount.

After the treatment site Ts appears in the image acquired by the endoscope 11, the operator stops inserting the endoscope 11 and the overtube 601 as shown in FIG. 112. This state is substantially the same as the state in which the overtube 601 is inserted close to the treatment site Ts in the seventh embodiment (refer to a two-dot chain line in FIG. 105).

Then, as in the seventh embodiment, the operator further pushes the overtube 601 to the distal side so that the distal end portion 12 is located between the first fixing portion 617 and the second fixing portion 618.

Then, as shown in FIG. 113, as in the seventh embodiment, the operator fixes the distal end fixing portion 603 to the inner wall of the large intestine C by expanding each of the first balloon 622 and the second balloon 623 of the distal end fixing portion 603.

Then, the operator performs necessary treatment and removal of the endoscope 11 and overtube 601 after the treatment, as in the seventh embodiment.

According to this modified example, only the method for inserting the overtube 601 is different, and thus the treatment after insertion is performed in the same manner as the overtube 601. Therefore, this modified example has the same action as the seventh embodiment.

In particular, according to this modified example, since the overtube 601 is inserted into the lumen to be treated together with the endoscope 11, the lengths of both the endoscope 11 and the overtube 601 may be slightly longer than a length from the insertion port to a position of a treatment target. Therefore, the length of the endoscope 11 can be shorter than when the overtube 601 is inserted as a guide of the endoscope 11 after the endoscope 11 is disposed near the treatment target.

Twenty-Second Modified Example

In the overtube 601 according to the seventh embodiment, a modified example (a twenty-second modified example) of the distal end fixing portion used in place of the distal end fixing portion 603 will be described.

As shown in FIG. 100, a distal end fixing portion 603A of this modified example can be used in place of the distal end fixing portion 603 of the overtube 601.

In the following, differences from the seventh embodiment will be mainly described.

Figure 114:
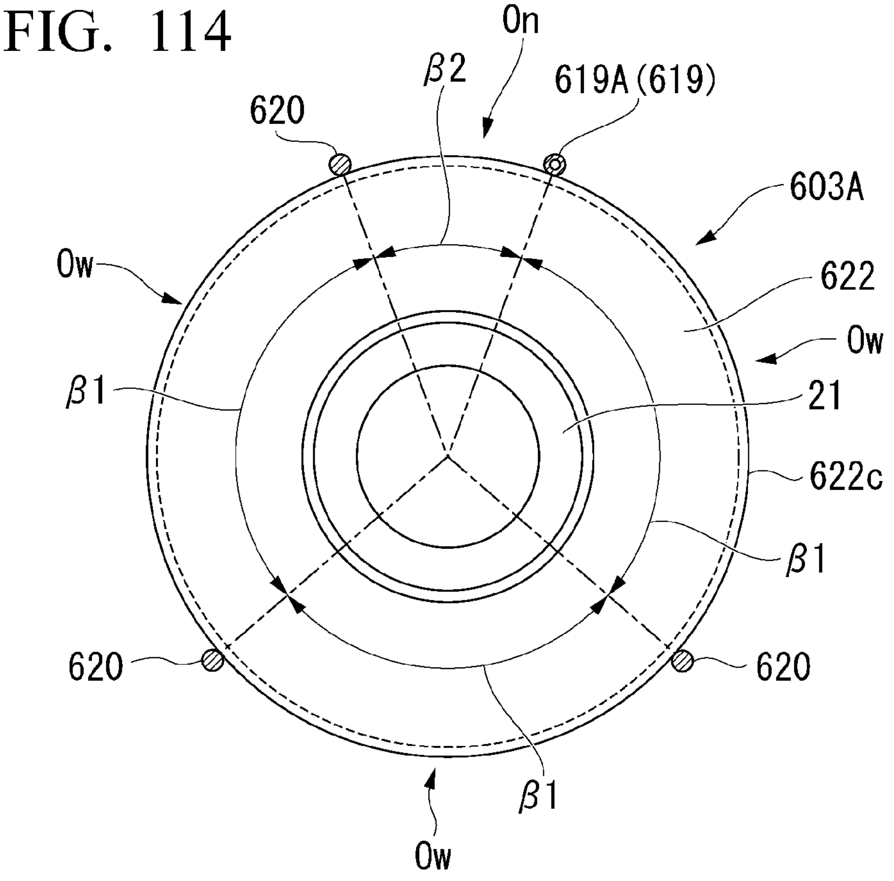
FIG. 114 is a cross-sectional view showing a modified example (a twenty-second modified example) of a distal end fixing portion used in the overtube for an endoscope according to the seventh embodiment of the present invention.
Figure 115:
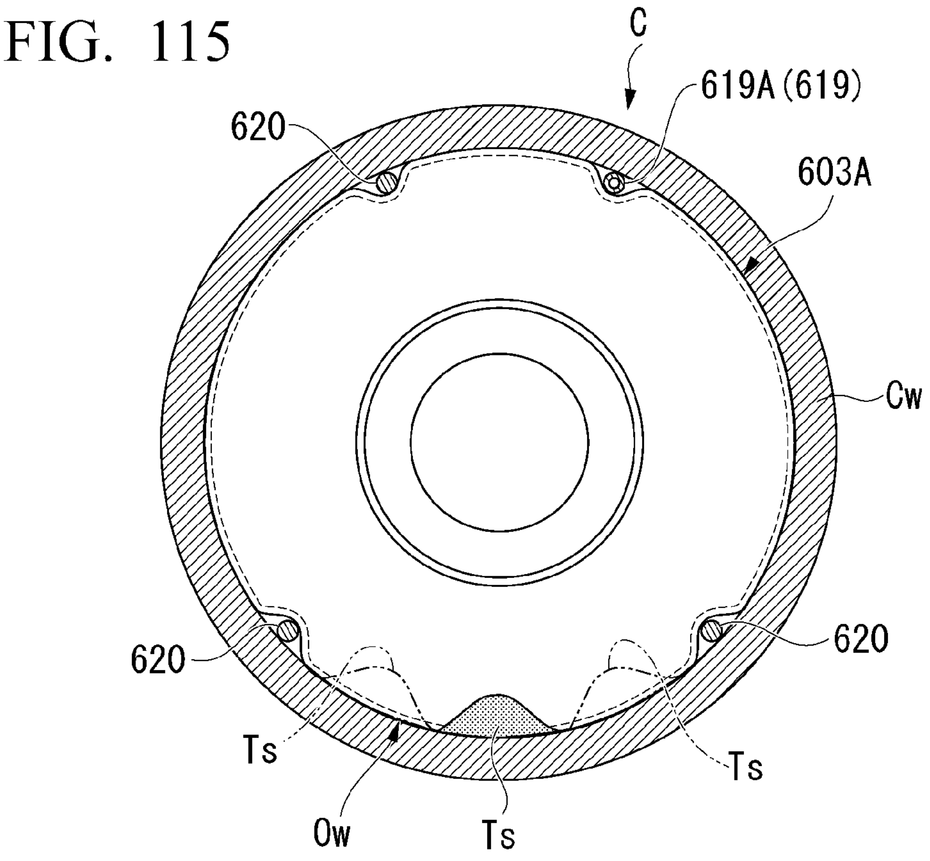
FIG. 115 is a cross-sectional view showing an action of the modified example (the twenty-second modified example) of the distal end fixing portion.

FIG. 114 is a cross-sectional view showing the modified example (the twenty-second modified example) of the distal end fixing portion used in the overtube for an endoscope according to the seventh embodiment of the present invention. FIG. 115 is a cross-sectional view showing the action of the modified example (the twenty-second modified example) of the distal end fixing portion.

As shown in FIG. 114, the distal end fixing portion 603A is the same as the distal end fixing portion 603, except that the first support member 619 and each of the second support members 620 are disposed differently in the circumferential direction.

The first support member 619 and each of the second support members 620 in the distal end fixing portion 603A are disposed at positions that do not equally divide the circumferential direction of the second cylindrical portion 622*c* of the first balloon 622 in the diameter-expanded state. In the example shown in FIG. 114, central angles of the arrangement of the first support member 619 and each of the second support members 620 in the circumferential direction are, for example, $\beta$1, $\beta$1, $\beta$1, and $\beta$2, when measured clockwise from the first support member 619. However, $3\times\beta 1+\beta 2$ is equal to 360°, and $\beta$2 is an acute angle. Thus, $\beta$1 is larger than $\beta$2.

Distances in the circumferential direction between the distal end portion 619A of the first support member 619 and the second support member 620 that are adjacent to each other in the circumferential direction and between the second support members 620 that are adjacent to each other in the circumferential direction are proportional to central angles thereof. Thus, since they are spaced apart by the central angle $\beta$1 in the diameter-expanded state of the distal end fixing portion 603A, wide openings Ow in which the distances in the circumferential direction are wider than a quarter of the circumference are respectively formed between the distal end portion 619A and the second support member 620, and between the second support members 620. On the other hand, an opening On in which the distance in the circumferential direction is narrower than in the wide opening Ow is formed between the distal end portion 619A and the second support member 620 which are spaced apart by the central angle $\beta$2.

According to the distal end fixing portion 603A, when the distal end fixing portion 603A is rotated and adjusted to a position in which the distal end portion 619A of the first support member 619 and the second support member 620 do not straddle the treatment site Ts, the distal end fixing portion 603A is rotated so that the treatment site Ts faces one of the three wide openings Ow. Thus, the distal end fixing portion 603A can be disposed so that it does not exceed a quarter of the inner circumferential surface of the intestinal wall Cw and does not straddle the treatment site Ts.

Furthermore, as shown in FIG. 115, when the treatment site Ts does not exceed a quarter of the inner circumferential surface of the lumen, the degree of freedom in arranging the treatment site Ts within the wide opening Ow is increased, and thus even when rotation accuracy of the distal end fixing portion 603A is low, it is easy to arrange it at a position not straddling the treatment site Ts, as indicated by a two-dot chain line, for example. Therefore, it is possible to reduce a need to redo a fixing operation of the distal end fixing portion 603A.

According to the distal end fixing portion 603A, since the distal end fixing portion 603A can be quickly fixed so as not to straddle various treatment sites Ts, the operator's operation is facilitated.

The distal end fixing portion 603A of this modified example is the same as the distal end fixing portion 603 in the seventh embodiment, except that the distal end portion 619A of the first support member 619 and the distance in the circumferential direction of each of the second support members 620 are different. Therefore, the overtube 601 having the distal end fixing portion 603A has the same action as in the seventh embodiment.

In particular, according to the distal end fixing portion 603A of this modified example, since the distal end fixing portion 603A can be quickly fixed while avoiding the treatment site Ts so that the first support member 619 and each of the second support members 620 do not straddle the various treatment sites Ts, it is easy for the operator to quickly perform the procedure.

Twenty-Third Modified Example

In the overtube 601 according to the seventh embodiment, a modified example (a twenty-third modified example) of the distal end fixing portion used in place of the distal end fixing portion 603 will be described.

As shown in FIG. 100, a distal end fixing portion 603B of this modified example can be used in place of the distal end fixing portion 603 of the overtube 61.

In the following, differences from the seventh embodiment will be mainly described.

Figure 116:
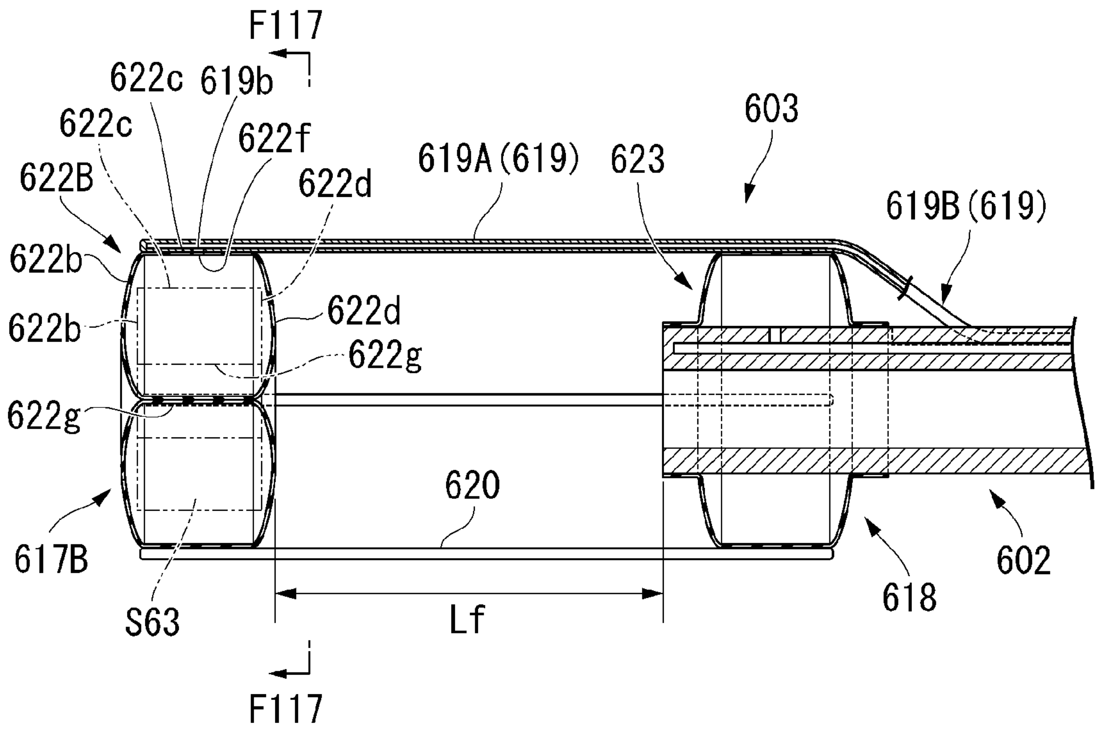
FIG. 116 is a schematic cross-sectional view showing a modified example (a twenty-third modified example) of the distal end fixing portion used in the overtube for an endoscope according to the seventh embodiment of the present invention.
Figure 117:
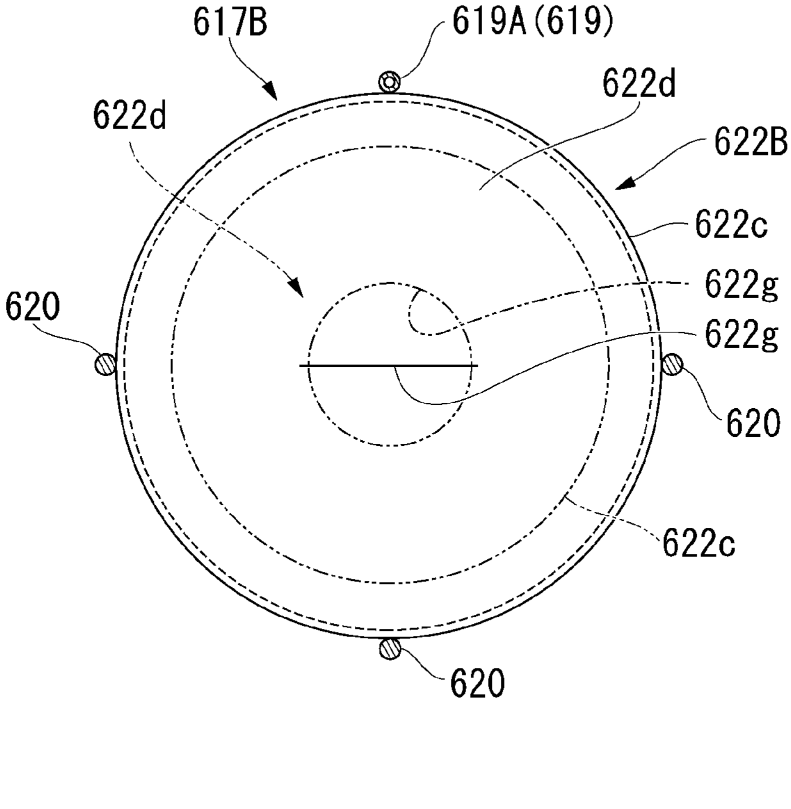
FIG. 117 is a cross-sectional view taken along line F117-F117 in FIG. 116.
Figure 118:
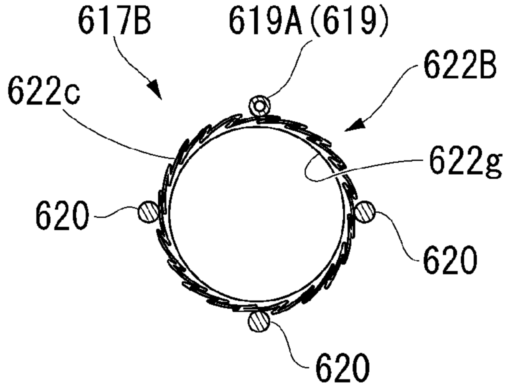
FIG. 118 is a schematic cross-sectional view showing an example of a diameter-contracted state of the modified example (the twenty-third modified example) of the distal end fixing portion.

FIG. 116 is a schematic cross-sectional view showing the modified example (the twenty-third modified example) of the distal end fixing portion used in the overtube for an endoscope according to the seventh embodiment of the present invention. FIG. 117 is a cross-sectional view taken along line F117-F117 in FIG. 116. FIG. 118 is a schematic cross-sectional view showing an example of the diameter-contracted state of the modified example (the twenty-third modified example) of the distal end fixing portion.

As shown in FIG. 116, the distal end fixing portion 603B is the same as the distal end fixing portion 603, except that it includes a first fixing portion 617B instead of the first fixing portion 617 of the distal end fixing portion 603 in the seventh embodiment.

In the following, differences from the seventh embodiment will be mainly described.

The first fixing portion 617B includes a first balloon 622B instead of the first balloon 622 and the tube member 621 in the first fixing portion 617.

The first balloon 622B has a first cylindrical surface portion 622*g*, a second cylindrical portion 622*c*, a distal end surface portion 622*b*, and a proximal end surface portion 622*d*. However, the first balloon 622B shown by a solid line in FIGS. 116 and 117 is in a diameter-expanded state (hereinafter, referred to as a diameter-expanded state when fixing) in which the outer diameter of the first balloon 622B is expanded to a state in which it can be fixed to the lumen in which treatment is performed.

On the other hand, the shape of the first balloon 622B shown by a two-dot chain line in FIGS. 116 and 117 shows a state in which the diameter is expanded in the natural state in which no tension is generated (hereinafter, referred to as a natural diameter-expanded state).

In the natural diameter-expanded state, the first balloon 622B has an annular shape when seen in the axial direction.

Hereinafter, unless otherwise specified, the shape of the first balloon 622B in the natural diameter-expanded state will be described.

As shown by a two-dot chain line in FIG. 116, the first cylindrical surface portion 622*g* has a substantially cylindrical shape extending in the axial direction to the center of the first balloon 622B. An inner diameter of the first cylindrical surface portion 622*g* is the same as the inner circumferential surface 621*a* of the tube member 621. Therefore, the endoscope 11 can be inserted into the inside of the first cylindrical surface portion 622*g*.

The second cylindrical portion 622*c* has the same cylindrical shape as the first balloon 622 in the seventh embodiment, and is disposed coaxially with the first cylindrical surface portion 622*g*. An opening 622*f* similar to that of the first balloon 622 is locked to the second cylindrical portion 622*c*.

An outer diameter of the second cylindrical portion 622*c* is not particularly limited as long as it is larger than the outer diameter of the outer circumferential surface 621*b* and can be expanded beyond the outer diameter that can be fixed to the lumen in which the treatment is performed.

As shown in FIG. 116, the distal end surface portion 622*b* extends in the radial direction and the circumferential direction between the distal ends of the first cylindrical surface portion 622*g* and the second cylindrical portion 622*c*.

The proximal end surface portion 622*d* extends in the radial direction and the circumferential direction between the proximal ends of the first cylindrical surface portion 622*g* and the second cylindrical portion 622*c*.

An annular space S63 in the natural diameter-expanded state is formed inside the first balloon 622B having such a configuration.

The distal end portion 619A of the first support member 619 and three second support members 620 are fixed on the second cylindrical portion 622*c* of the first balloon 622B, as in the first balloon 622.

As in the first balloon 622, the opening 622*f* of the first balloon 622B communicates with the opening 619*b* of the first support member 619 while the surrounding airtight is maintained.

Thus, air can be supplied to the inside of the first balloon 622B from the air supply device 610 through the air supply lumen 619*a* of the first support member 619, and the air can be suctioned using the air supply device 610.

A material that is the same as that of the first balloon 622 may be used as a material of the first balloon 622B.

The first balloon 622B expands and contracts according to the amount of air that is supplied into and suctioned from the inside of the first balloon 622B from the opening 622*f*. For example, when a volume of air at atmospheric pressure equal to a volume of the first balloon 622B is supplied, the first balloon 622B is in the natural diameter-expanded state.

When air is further supplied, the diameter of the first balloon 622B expands to a size that balances with the atmospheric pressure. For example, as shown in FIG. 117, the second cylindrical portion 622*c* expands from a cylinder indicated by an alternated long and short dash line to a substantially cylindrical shape with a larger diameter.

On the other hand, since the first cylindrical surface portion 622*g* expands inward in the radial direction, it deforms such that the inner diameter of the distal end surface portion 622*b* is reduced. When the diameter of the first cylindrical surface portion 622*g* is reduced to some extent, the inner opening of the first cylindrical surface portion 622*g* collapses in the radial direction according to a pressure balance during air supply. Thus, in the diameter-expanded state when fixing, the through hole of the first balloon 622B in the axial direction is closed.

In the example shown by a solid line in FIG. 117, the first cylindrical surface portion 622*g* of the first balloon 622B is collapsed in the up-down direction in the drawing in the diameter-expanded state when fixing and is linearly closed. However, the way that the first cylindrical surface portion 622*g* is collapsed is not limited to a horizontal line as shown in the drawing, and may be, for example, a vertical line, a cross, a radial shape, or the like.

When air is suctioned from the space S63, the folded second cylindrical portion 622*c* comes into close contact with the outer circumference of the first cylindrical surface portion 622*g*, as shown in FIG. 118. The distal end portion 619A and each of the second support members 620 fixed to the second cylindrical portion 622*c* are close to the outer circumferential portion of the first cylindrical surface portion 622*g* together with the second cylindrical portion 622*c*.

Thus, the first fixing portion 617B is contracted into a cylindrical shape having a slightly larger diameter than the inner diameter of the first cylindrical surface portion 622*g* in the natural diameter-expanded state. A through hole extending in the axial direction is formed inside the first cylindrical surface portion 622*g* having a cylindrical shape at the center of the first fixing portion 617B in the diameter-contracted state. The inner diameter of the through hole is equal to the inner diameter of the first cylindrical surface portion 622*g* in the natural diameter-expanded state.

The distal end fixing portion 603B of this modified example is the same as the distal end fixing portion 603, except that it includes the first fixing portion 617B instead of the first fixing portion 617, and thus it has the same action as the seventh embodiment.

In particular, in the diameter-contracted state of the first balloon 622B and the second balloon 623, the distal end fixing portion 603B of this modified example has a cylindrical shape with a slightly larger diameter than the inner diameter of the first cylindrical surface portion 622*g*. Therefore, in the diameter-contracted state, it can be inserted into and removed from the lumen to be treated along or together with the endoscope 11 in the same way as the overtube 601 having the distal end fixing portion 603.

At this time, since the first fixing portion 617B is formed by the first balloon 622B, the first cylindrical portion 3*a* and the third cylindrical portion 3*e* for fixing to the tube member 621 are unnecessary. Furthermore, the tube member 621 for fixing the first cylindrical portion 3*a* and the third cylindrical portion 3*e* is also unnecessary.

Therefore, the first fixing portion 617B can have a smaller thickness in the axial direction than the first fixing portion 617. Thus, even when the width of the second cylindrical portion 622*c* is the same, the thickness of the first fixing portion 617B in the axial direction is smaller than that of the first fixing portion 617.

In this modified example, since the thickness of the first fixing portion 617B in the axial direction can be made thinner than the first fixing portion 617, when a radius of curvature of the bent portion and the curved portion of the endoscope 11 is small, it can move along the endoscope 11 more smoothly, compared to the first fixing portion 617.

Furthermore, since the tube member 621 becomes unnecessary, the number of components can be reduced. Thus, it is possible to reduce the weight of the distal end fixing portion 603B and the component costs.

In this modified example, the through hole of the first fixing portion 617 at the center is closed in the diameter-expanded state when fixing in which the distal end fixing portion 603B is fixed to the lumen to be treated.

Thus, the flow of gas and liquid in the internal space of the lumen on the distal side with respect to the first fixing portion 617B and the internal space of the lumen on the proximal side with respect to the first fixing portion 617B is curbed. As a result, the surgical field between the first fixing portion 617B and the second fixing portion 618 is isolated from the lumen on the distal side, and thus the lumen on the distal side is less likely to be affected by the treatment.

When the overtube 601 having the distal end fixing portion 603B is removed from the lumen, air is suctioned from the space S63 to form the diameter-contracted state. Thus, when the overtube 601 is pulled toward the proximal end side with respect to the distal end portion 12 of the endoscope 11, and the endoscope 11 is inserted through the inside of the first cylindrical surface portion 622*g*, the overtube 601 is removed from the body together with the endoscope 11 in the same manner as during insertion.

The seventh embodiment and each of the modified examples described above may be implemented with various modifications.

For example, the number of second support members 620 is not particularly limited as long as a distance with the other adjacent second support members 620 or the distal end portion 619A of the first support member 619 has a size necessary for the treatment in at least one location in the circumferential direction. For example, four or more second support members 620 may be provided.

For example, in the seventh embodiment and each of the modified examples, the example in which the second support member 620 is a solid rod has been described. However, a shape of the second support member 620 is not particularly limited as long as it has flexibility necessary for the distal end fixing portions 603, 603A, and 603B. For example, the second support member 620 may be a hollow tube closed at both ends. For example, the second support member 620 may be formed of a flat plate that is flat in the radial direction or a plate having a curved surface that is convex to the outside in the radial direction.

For example, in the seventh embodiment and each of the modified examples, the example in which the air flow tube 609 includes two systems of flow paths has been described, but the air flow tube 609 may be formed of two independent tubes. In this case, a connector provided at the distal end of each tube is detachably connected to a first connecting tube and a second connecting tube of the connector 605*c*.

In the seventh embodiment and the twenty-first modified example, the example in which when the distal end portion 12 of the endoscope 11 is disposed between the first balloon 622 and the second balloon 623 in the vicinity of the treatment site Ts, the position of the endoscope 11 is fixed and the overtube 601 is pushed toward the distal side has been described. However, the relative movement between the endoscope 11 and the overtube 601 is not limited to pushing the overtube 601. For example, the endoscope 11 may be pulled toward the proximal side after the position of the overtube 601 is fixed, or the endoscope 11 may be pulled while the overtube 601 is pushed.

In the seventh embodiment, the example in which the endoscope 11 is inserted in advance to the vicinity of the treatment site Ts has been described, and in the twenty-second modified example, the example in which both the endoscope 11 and the overtube 601 are inserted to the vicinity of the treatment site Ts has been described. However, these operations may be combined as appropriate according to the lengths of the endoscope 11 and overtube 601.

For example, the endoscope 11 may be inserted into the lumen to a position away from the treatment site Ts on the proximal side, and then the overtube 601 may be inserted along the endoscope 11 to the vicinity of the distal end portion 12.

Then, after only the endoscope 11 is inserted to the treatment site Ts, the overtube 601 may be inserted to the vicinity of the treatment site Ts, or the overtube 601 may be inserted to the vicinity of the treatment site Ts together with the endoscope 11.

The first balloon 622B in the twenty-third modified example may be used in place of the first balloon 622 in the seventh embodiment and the twenty-second modified example. In this case, the first cylindrical surface portion 622*g* of the first balloon 622B is fixed to the outer circumferential surface 621*b* of the tube member 621. In this case, the length of the tube member 621 in the axial direction may be the same as the length of the first cylindrical surface portion 622*g* in the axial direction. Thus, the length of the first fixing portion 617 in the axial direction can be shortened.

The first balloon 622B in the twenty-third modified example may be used in place of the second balloon 623 in the seventh embodiment, the twenty-second modified example, and the twenty-third modified example. However, in this case, the opening 602*f* is formed in the first cylindrical surface portion 622*g*. The first cylindrical surface portion 622*g* of the first balloon 622B is fixed to the outer circumferential surface 2*d* of the main tube 602 with the opening 602*f* and the opening 2*f* communicating with each other.

In the twenty-second modified example, the example in which the distances in the circumferential direction between the distal end portion 619A of the first support member 619 and the respective second support members 620 correspond to two types of central angles β1 and β2 has been described. However, when the distances in the circumferential direction between the distal end portion 619A of the first support member 619 and the respective second support members 620 are unequal, they are not limited thereto.

As described above, the first balloons 622 and 622B are examples of a distal end side balloon that is disposed on the distal end side with respect to the tube main body and can be expanded and contracted in the radial direction.

The second balloon 623 is an example of a fixing balloon that is provided on the outer circumferential surface of the distal end portion of the tube main body, and is expandable outward of the outer circumferential surface and contractible toward the outer circumferential surface.

The distal end portion 619A of the first support member 619 and the second support member 620 are examples of a plurality of support members that are disposed on the outer circumferential portions of the fixing balloon and the distal end side balloon, extend between the fixing balloon and the distal end side balloon, and can support the inner wall of the lumen.

The first support member 619 has a flow path that communicates with the inside of the distal end side balloon. The first support member 619 is an example of a support member that forms an air supply tube forming a flow path for sending gas to the distal end side balloon.

Eighth Embodiment

An overtube for an endoscope according to an eighth embodiment of the present invention will be described.

Figure 119:
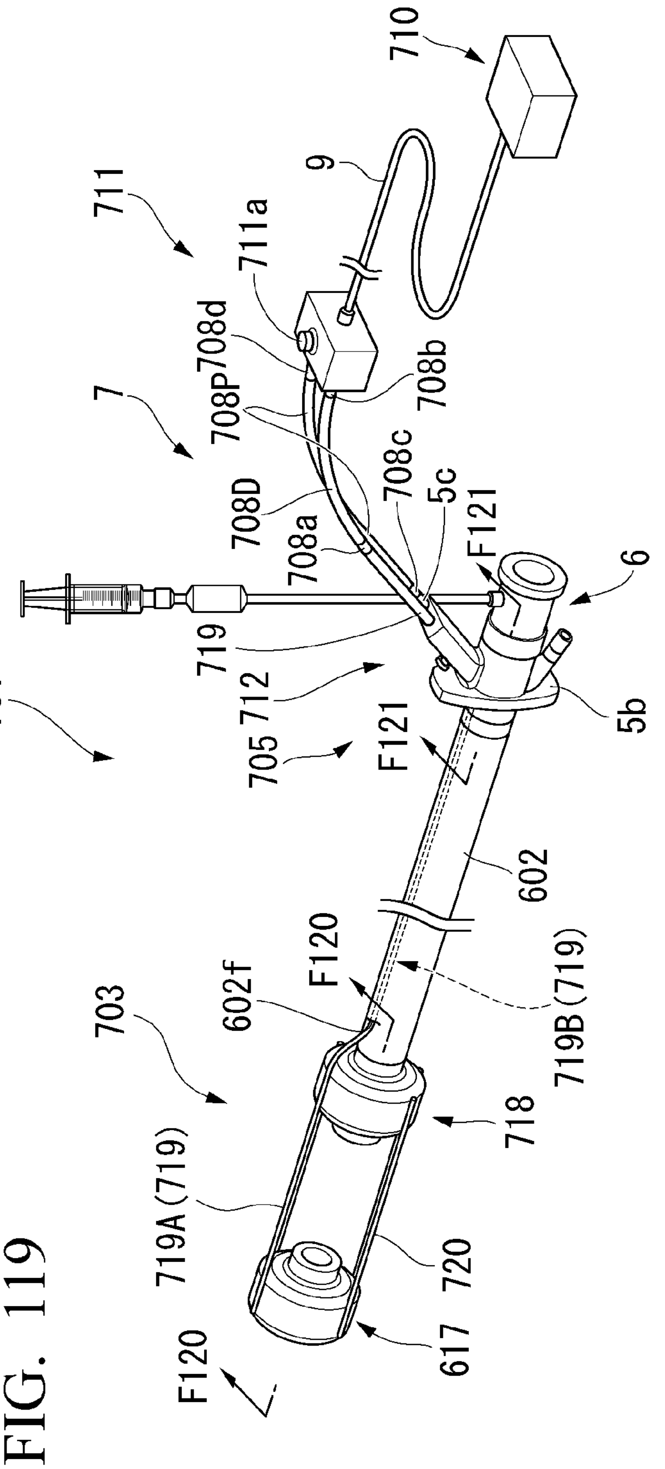
FIG. 119 is a schematic perspective view showing an example of an overtube for an endoscope according to an eighth embodiment of the present invention.
Figure 120:
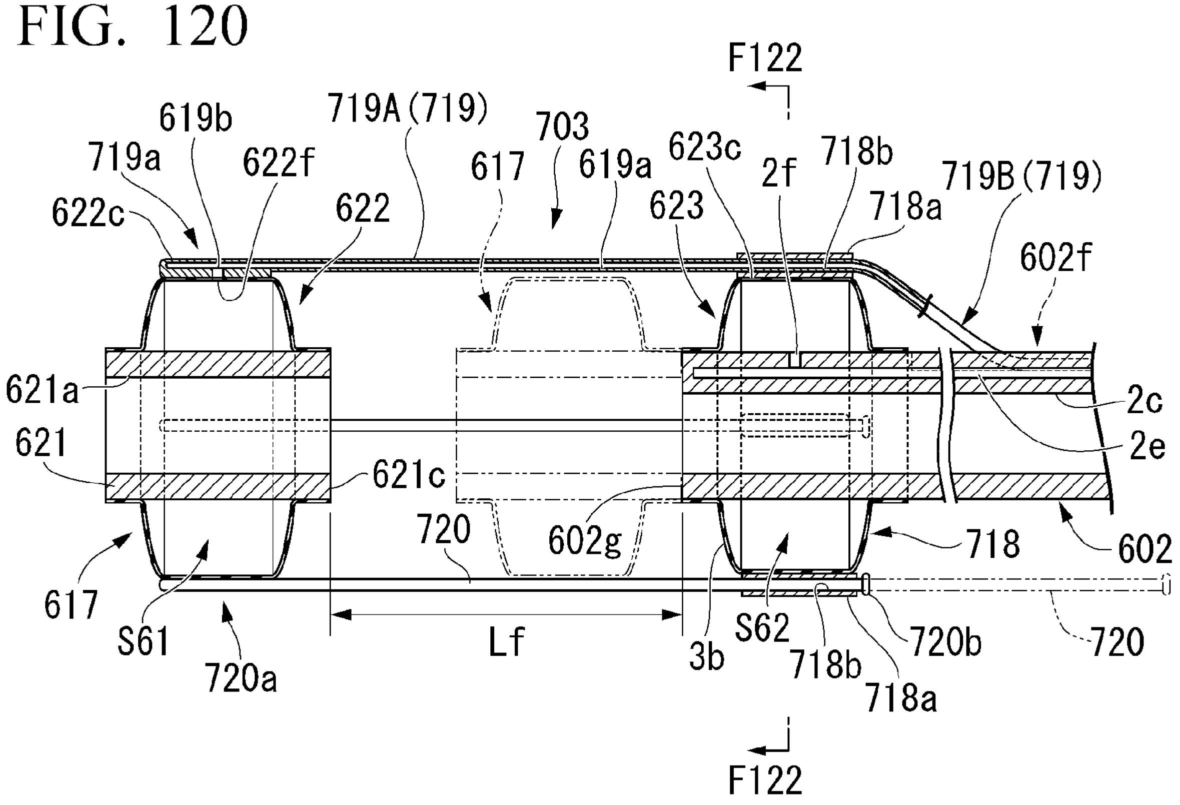
FIG. 120 is a cross-sectional view along line F120-F120 in FIG. 119.
Figure 122:
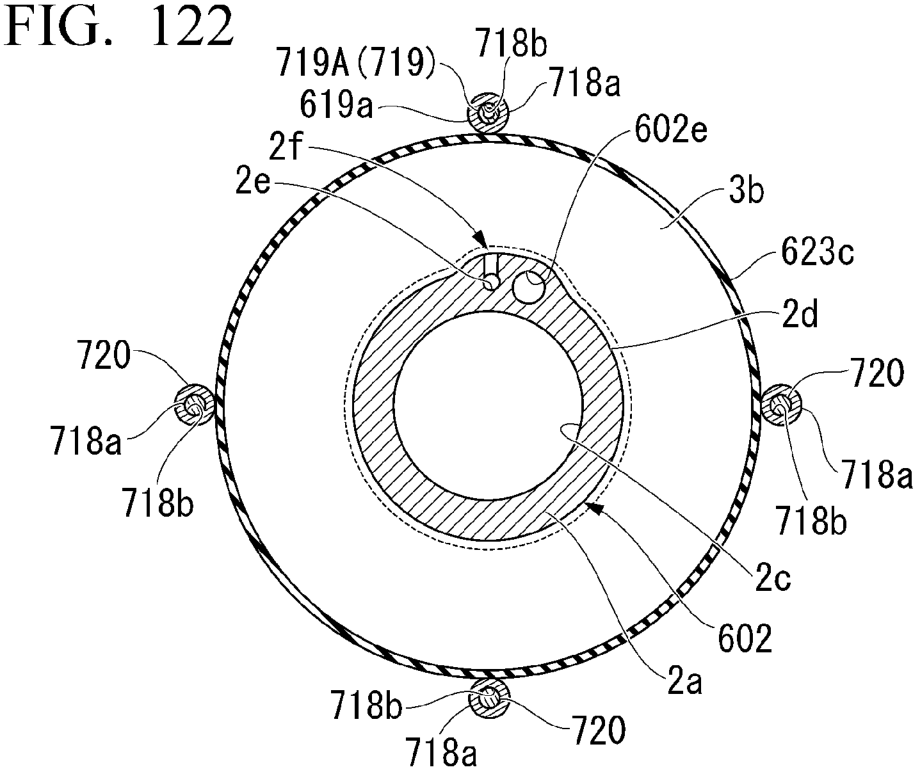
Figure 123:
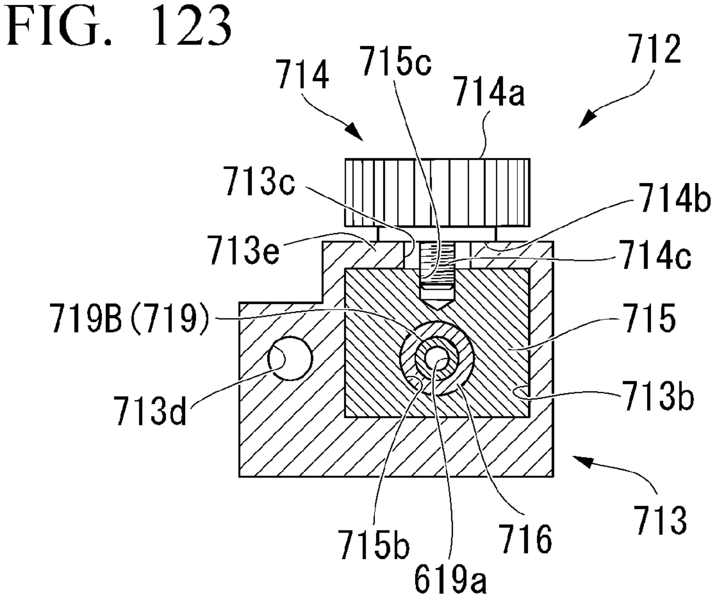

FIG. 119 is a schematic perspective view showing an example of an overtube for an endoscope according to the eighth embodiment of the present invention. FIG. 120 is a cross-sectional view taken along line F120-F120 in FIG. 119. FIG. 122 is a cross-sectional view taken along line F122-F122 in FIG. 120. FIG. 123 is a cross-sectional view taken along line F123-F123 in FIG. 121.

An overtube 701 shown in FIG. 119 is an example of an overtube for an endoscope according to this embodiment.

The overtube 701 includes a distal end fixing portion 703, a grip portion 705, a first connection tube 708D, a second connection tube 708P, an air flow tube 9, and an air supply device 710, instead of the distal end fixing portion 603, the first support member 619, the grip portion 605, the air flow tube 609, and the air supply device 610 of the overtube 601 according to the seventh embodiment. The overtube 701 further includes a flow path switch 711.

Figure 121:
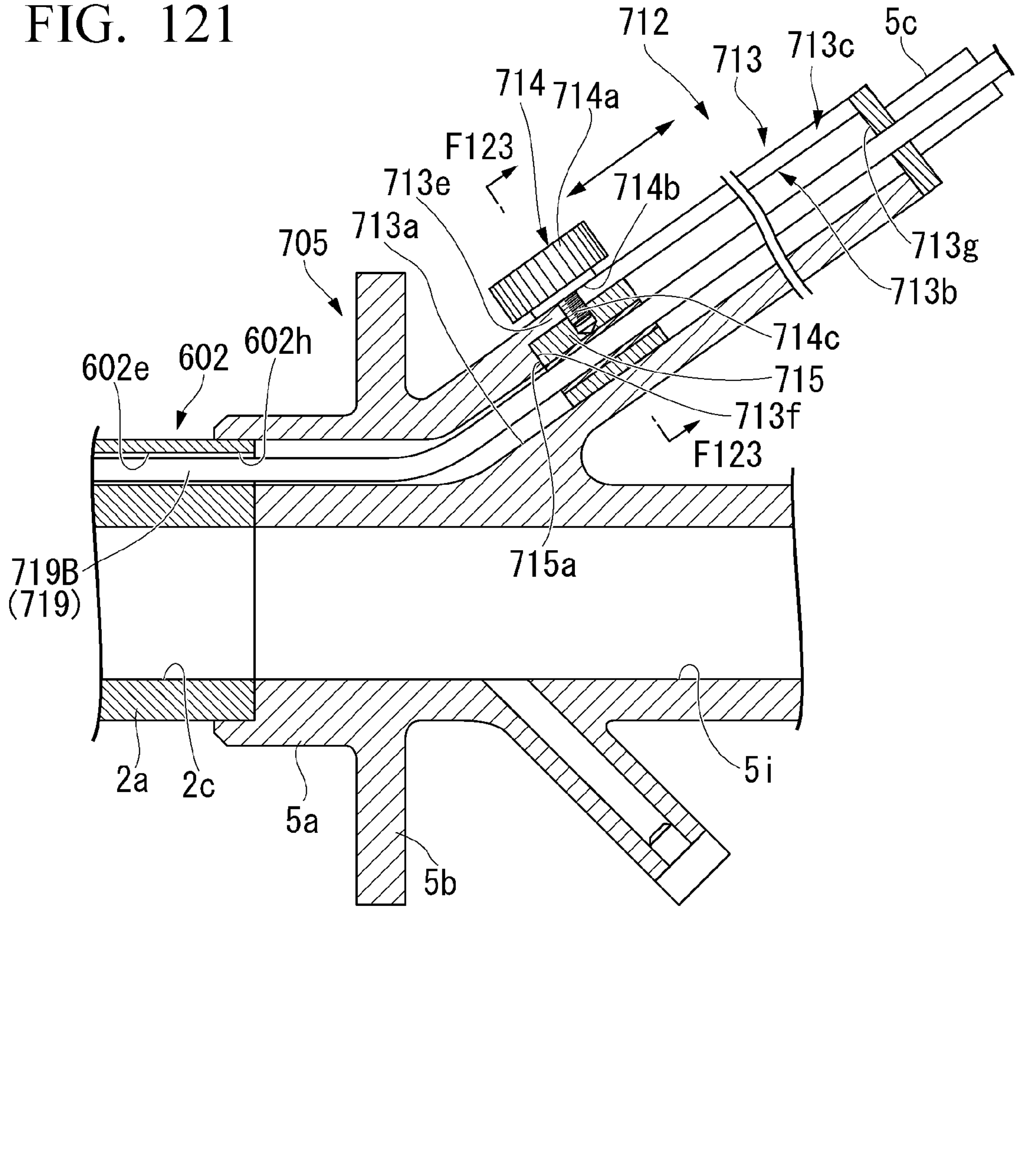

However, as in to the sixth embodiment, FIGS. 119 to 121 show a shape of the distal end fixing portion 703 in the diameter-expanded state.

In the following, differences from the seventh embodiment will be mainly described.

As shown in FIG. 120, the distal end fixing portion 703 in this embodiment includes a first support member 719, a second support member 720 and a second fixing portion 718 instead of the first support member 619, the second support member 620 and the second fixing portion 618 in the seventh embodiment. The distal end fixing portion 703 has a first fixing portion 617 that is the same as the distal end fixing portion 603.

The first support member 719 has a distal end portion 719A and a proximal end portion 719B (an air supply tube, an operating rod) that are the same as the distal end portion 619A and the proximal end portion 619B of the first support member 619.

However, the distal end portion 719A of the first support member 719 is not joined to the second balloon 623, and the proximal end portion 619B passes through the inside of the grip portion 705 which will be described below and is held by a slider 715 (refer to FIG. 122) which will be described below.

Since the first support member 719 is also used as the operating rod for moving the first fixing portion 617 forward and backward in the axial direction, as will be described below, the first support member 719 has such rigidity that it does not undergo buckling deformation even when it receives resistance from the lumen when the first fixing portion 617 is pushing out to the distal side.

As shown in FIG. 120, a distal end region 719*a* of the distal end portion 719A of the first support member 719 is fixed to the second cylindrical portion 622*c* of the first balloon 622, as in the distal end portion 619A of the first support member 619 in the seventh embodiment. However, unlike the first support member 619, the first support member 719 is not fixed to the second balloon 623.

The second support member 720 is the same as the second support member 620, except that a retaining portion 720*b* is formed at the proximal end. The retaining portion 720*b* is a protruding portion that protrudes beyond the exterior of the second support member 720 in a direction orthogonal to the longitudinal direction of the second support member 720.

The second support member 720 has a rod shape with a uniform cross-sectional shape on the distal end side with respect to the retaining portion 720*b*. In the example shown in FIG. 121, the second support member 720 on the distal end side with respect to the retaining portion 720*b* has a cylindrical shape.

As shown in FIG. 120, the distal end portion 720*a* of the second support member 720 is fixed to the second cylindrical portion 622*c* of the first balloon 622, as in the distal end portion of the second support member 620 in the seventh embodiment.

Like the second support member 620, three second support members 720 are provided at positions that divide the second cylindrical portion 622*c* in the diameter-expanded state into four equal portions in the circumferential direction together with the distal end portion 719A of the first support member 719.

The second fixing portion 718 includes the second balloon 623 fixed to the distal end portion of the main tube 602, and a guide tube 718*a*, as in the seventh embodiment.

The guide tube 718*a* has an insertion hole 718*b* that extends in the longitudinal direction at the center thereof.

An inner diameter of the insertion hole 718*b* has a size such that the retaining portion 720*b* cannot be inserted therethrough, and the first support member 719 and the second support member 720 excluding the retaining portion 720*b* can be inserted therethrough.

A shape of the inner circumferential surface forming the insertion hole 718*b* is not particularly limited as long as the second support member 720 excluding the first support member 719 and the retaining portion 720*b* can be inserted smoothly therethrough.

In the example shown in FIG. 121, the inner circumferential surface forming the insertion hole 718*b* is a cylindrical surface corresponding to a cylindrical surface of the outer circumferential portion of the second support member 720 excluding the first support member 719 and the retaining portion 720*b*.

Four guide tubes 718*a* are provided at positions that divide the second cylindrical portion 623*c* of the second balloon 623 into four equal portions in the circumferential direction. Each of the guide tubes 718*a* is fixed to the outer circumferential portion of the second cylindrical portion 623*c*, as in the first support member 619 and each of the second support members 620 in the seventh embodiment.

The distal end portion 719A of the first support member 719 and three second support members 720 are respectively inserted into the guide tubes 718*a* so as to be movable in the axial direction.

The retaining portion 720*b* of each of the second support members 720 protrudes toward the proximal end side of the guide tube 718*a*, and prevents each of the second support members 720 from coming off toward the distal end side.

With such a configuration, the first fixing portion 617 of the distal end fixing portion 703 is movable in the axial direction between a maximum advanced position indicated by a solid line in FIG. 120 and a retracted position indicated by a two-dot chain line in FIG. 120.

Here, the maximum advanced position is a position in which each of the retaining portions 720*b* is locked to the proximal end of each of the guide tubes 718*a* and is farthest from the second fixing portion 718 toward the distal end side. The retracted position is a position in which the proximal end 621*c* of the tube member 621 and the distal end 602*g* of the main tube 602 are in contact with each other.

A distance in the axial direction between the proximal end 621*c* of the tube member 621 and the distal end 602*g* of the main tube 602 at the maximum advanced position is the same distance Lf as in the seventh embodiment.

As shown in FIG. 122, the grip portion 705 has a distal end side balloon moving mechanism 712 instead of the connector 605*c* in the grip portion 605.

The distal end side balloon moving mechanism 712 moves the entire first fixing portion 617 including the first balloon 622 in the axial direction by moving the first support member 619 in the axial direction.

The configuration of the distal end side balloon moving mechanism 712 is not particularly limited as long as it can hold the proximal end side of the proximal end portion 619B of the first support member 619 and can move the first support member 619 in the axial direction.

In the example shown in FIG. 122, the distal end side balloon moving mechanism 712 includes a slide guide portion 713, a slider 715, and a slide operating part 714.

The slide guide portion 713 has a substantially rectangular bar shape that extends from the outer circumferential surface of the grip portion 605 at the proximal end side (the right side in the drawing) of a stopper 5*b* in an inclination direction that goes radially outward toward the proximal end side.

An insertion hole 713*a* and a guide groove 713*b* are disposed in this order inside the slide guide portion 713 and pass therethrough from a surface of the stopper 5*b* on the distal end side (the left side in the drawing) toward the proximal end of the slide guide portion 713.

The first support member 719 extending from the opening 602*h* that opens to the proximal end of the main tube 602 is inserted through the insertion hole 713*a* in an extending direction of the slide guide portion 713. In the example shown in FIG. 122, a cross-sectional shape of the insertion hole 713*a* orthogonal to the extending direction is circular and has a larger diameter than the outer diameter of the first support member 719.

The insertion hole 713*a* passes through the tubular portion 5*a* and communicates with the opening 602*h* of the main tube 602 fixed to the tubular portion 5*a*.

As shown in FIG. 123, the guide groove 713*b* has a substantially rectangular groove shape that guides the rectangular parallelepiped slider 715 in the extending direction. A cross-sectional area of the guide groove 713*b* in a cross-section orthogonal to the extending direction of the slide guide portion 713 is larger than a cross-sectional area of the insertion hole 713*a* in the same cross-section. As shown in FIG. 122, the insertion hole 713*a* opens inside a distal end surface 713*f* formed on the distal end side of the guide groove 713*b*.

The distal end surface 713*f* locks the distal end of the slider 715 when the slider 715 moves to the most distal end side. The distal end surface 713*f* defines a movement position of the slider 715 on the most distal end side.

A proximal end surface 713*g* that prevents the slider 715 from coming off on the proximal end side is formed at the proximal end portion of the slide guide portion 713. The proximal end surface 713*g* defines movement limit of the slider 715 on the most proximal end side. However, since the first fixing portion 617 to which the first support member 719 is connected cannot be retracted to the proximal end side with respect to the retracted position, the proximal end surface 713*g* may be omitted. In this case, the guide groove 713*b* opens to the proximal end of the slide guide portion 713.

As shown in FIG. 123, a slit 713*c* is formed in a side wall 713*e* that is one side wall of the slide guide portion 713 surrounding the guide groove 713*b*.

The side wall 713*e* may be a side wall in any direction as long as it can be operated by the operator. In the example shown in FIG. 122, the side wall 713*e* is a side wall that extends along the inclination of the slide guide portion 713 and is farther from the tubular portion 5*a* in the radial direction.

The slit 713*c* passes through the side wall 713*e* in the thickness direction and extends in an extending direction of the slide guide portion 713. A length of the slit 713*c* is greater than or equal to Lf.

As shown in FIG. 122, an opening width of the slit 713*c* in the transverse direction (the right-left direction in the drawing) is narrower than a groove width of the guide groove 713*b* in the same direction.

With this configuration, the guide groove 713*b* has a C-shaped groove shape with the slit 713*c* opening in the side wall 713*e*.

As shown in FIG. 123, it extends in an extending direction of the slide guide portion 713 next to the guide groove 713*b*. A conduit 713*d* passes through the slide guide portion 713.

Although not shown, the conduit 713*d* passes through the inside of the tubular portion 5*a* and communicates with the second lumen 2*e* of the main tube 602 fixed to the tubular portion 5*a*.

The conduit 713*d* extends to the proximal end of the slide guide portion 713. A first luer connector 5*c* that is the same as in the first embodiment is provided at the proximal end portion of the slide guide portion 713. The first luer connector 5*c* in this embodiment communicates with the inside of the conduit 713*d*.

The slide guide portion 713 may be made of the same material as that of the tubular portion 5*a* and the stopper 5*b*. For example, the slide guide portion 713, the tubular portion 5*a*, and the stopper 5*b* may be formed of resin molded products.

As shown in FIGS. 122 and 123, the slider 715 is fitted into the guide groove 713*b* so as to be slidable in the extending direction of the slide guide portion 713. In the illustrated example, the exterior of the slider 715 is a rectangular parallelepiped.

As shown in FIG. 123, a holding hole 715*b* having a diameter larger than the outer diameter of the first support member 719 passes through the slider 715 in the extending direction of the slide guide portion 713. A proximal end portion 719B of the first support member 719 is inserted through the holding hole 715*b*. The proximal end portion 719B is fixed to the slider 715 inside the holding hole 715*b*. A method for fixing the proximal end portion 719B is not particularly limited. In the example shown in FIG. 123, the proximal end portion 719B is fixed to the holding hole 715*b* with an adhesive 716 interposed.

A female screw portion 715*c* is formed on a side surface of the slider 715 facing the slit 713*c* at a portion that overlaps the inside of the slit 713*c* when seen from the outside.

The material of the slider 715 is not particularly limited as long as it can slide along the guide groove 713*b*. For example, the material of the slider 715 may be a metal or resin.

The slide operating part 714 has a knob portion 714*a*, a fixing portion 714*b*, and a male screw portion 714*c*.

The knob portion 714*a* has a size that can be gripped and rotated by the operator. For example, the knob portion 714*a* is a disc.

The fixing portion 714*b* is a stepped portion that straddles the slit 713*c* and is locked onto the edge portion of the slit 713*c*. For example, the fixing portion 714*b* has a cylindrical shape provided coaxially with the knob portion 714*a*. An outer diameter of the fixing portion 714*b* is larger than a width of the slit 713*c* in the transverse direction.

The male screw portion 714*c* is screwed into the female screw portion 715*c* of the slider 715. The male screw portion 714*c* protrudes from the fixing portion 714*b* so as to be coaxial with the knob portion 714*a*. A length of the male screw portion 714*c* is longer than a thickness of the side wall 713*e*.

The slide operating part 714 is connected to the slider 715 by screwing the male screw portion 714*c* into the female screw portion 715*c* through the slit 713*c*.

An operation of the distal end side balloon moving mechanism 712 will be described.

When the operator rotates the slide operating part 714 in a direction in which the male screw portion 714*c* is screwed, the fixing portion 714*b* comes into contact with a surface of the side wall 713*e*, and the side wall 713*e* at the edge portion of the slit 713*c* is sandwiched between the slider 715 and the fixing portion 714*b*. Thus, the slider 715 and the slide operating part 714 are fixed to the slide guide portion 713.

When the operator rotates the slide operating part 714 in a direction opposite to the direction in which the male screw portion 714*c* is screwed, the side wall 713*e* is released from being sandwiched between the fixing portion 714*b* and the slider 715. Thus, the operator can slide the slider 715 by moving the knob portion 714*a* along the slit 713*c*.

At this time, the first support member 719 fixed to the slider 715 at the proximal end side of the proximal end portion 719B also moves in the same direction. The first fixing portion 617 fixed to the distal end portion 719A of the first support member 719 can be moved in the same way when the first balloon 622 is not fixed to the lumen after being expanded to the diameter-expanded state when fixing.

As described above, according to this embodiment, a position of the first fixing portion 617 within the lumen can be moved in the axial direction without moving the main tube 602 by operating the slide operating part 714. A position after movement can be fixed until the operator loosens the slide operating part 714 by screwing the slide operating part 714.

Furthermore, a distance between the first fixing portion 617 and the distal end of the main tube 602 can also be changed by changing the movement position of the slide operating part 714.

In a movement operation of the first fixing portion 617, the first support member 719 functions as an operating rod that transmits an operating force to the first fixing portion 617.

As shown in FIG. 119, the first connection tube 708D forms a flow path through which air flows between a first end portion 708*a* made of a connector detachably connected to the proximal end of the first support member 719 and a second end portion 708*b* on the proximal end side.

The second end portion 708*b* is provided with an appropriate connector that is detachably connected to the flow path switch 711 which will be described below. The first connection tube 708D is detachably connected to the flow path switch 711 by the connector provided at the second end portion 708*b*.

The second connection tube 708P forms a flow path through which air flows between a first end portion 708*c* configured of a connector that is detachably connected to the first luer connector 5*c* in the distal end side balloon moving mechanism 712 and a second end portion 708*d* on the proximal end side.

A luer connector that is attached on and detached from the first luer connector 5*c* is provided at the first end portion 708*c*. An appropriate connector that is detachably connected to the flow path switch 711 is provided at the second end portion 708*d*. The second connection tube 708P is detachably connected to the flow path switch 711 at the second end portion 708*d*.

The flow path switch 711 selectively switches a flow path formed by the air flow tube 9, as in the first embodiment, between the flow path formed by the first connection tube 708D and the flow path formed by the second connection tube 708P.

The flow path switch 711 has a built-in flow path switching valve, and has a switching operating part 711*a* that operates the flow path switching valve. The switching operating part 711*a* allows a switching operation by the operator.

The air supply device 710 is the same as the air supply device 10 in the first embodiment, except that the air flow tube 9 of the air supply device 710 is connected to the flow path switch 711.

The air supply device 710 may be an electric pump or a manual pump as in the first embodiment. In the case of a manual pump, any air supply device including the manual air supply mechanism 211 in each of the embodiments and modified examples described above may be used as the air supply device 710, for example.

Next, a method for using the overtube 701 will be described focusing on differences from the seventh embodiment. As a treatment, the example of endoscopic full-thickness resection of the large intestine C will be described as in the seventh embodiment.

FIGS. 124 to 128 are cross-sectional views showing an example of the method for using the overtube for an endoscope according to the eighth embodiment of the present invention.

First, the overtube 701 is prepared.

Figure 124:
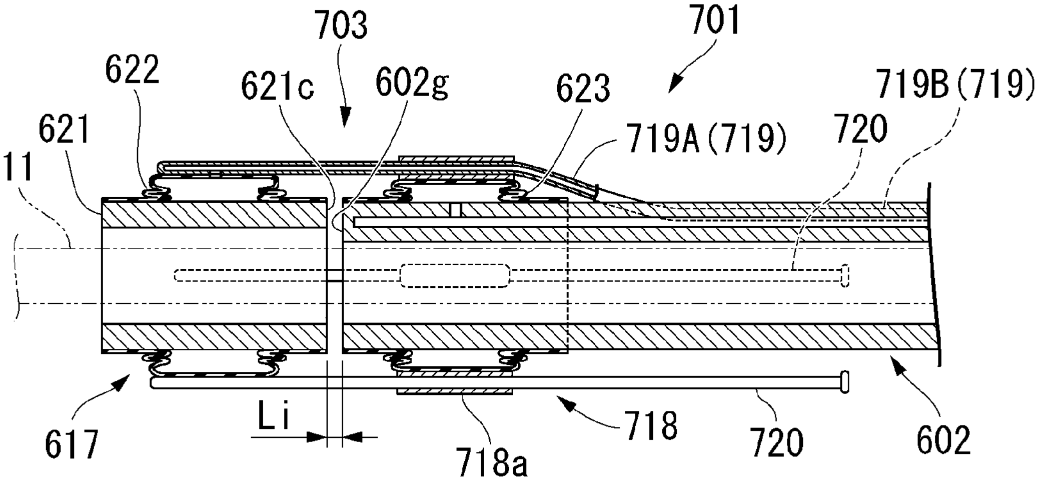

As shown in FIG. 124, the distal end fixing portion 703 of the prepared overtube 701 is in the diameter-contracted state, as in the distal end fixing portion 603 of the overtube 601. Furthermore, in this embodiment, the first support member 719 is pulled to the proximal end side, and thus the first fixing portion 617 retracts to the proximal end side from the maximum advanced position. A distance between the proximal end 621*c* and the distal end 602*g* in the axial direction is Li. The distance Li is 0 or more and less than Lf. The magnitude of Li is determined in consideration of the insertion resistance at the bent or curved portion of the endoscope 11.

For example, when Li is 0, the first fixing portion 617 is in the retracted position. In this case, the tube member 621 and the distal end portion of the main tube 602 are in contact with each other to form an integral cylindrical body. Therefore, the tube member 621 and the main tube 602 are deformed according to the rigidity thereof, and thus the tube member 621 and the main tube 602 are allowed to pass through a bent or curved portion of the endoscope 11. The insertion resistance is reduced as the rigidity of the tube member 621 and the main tube 602 is lower.

On the other hand, when Li is larger than 0, the tube member 621 can rotate within a range of a gap between the proximal end 621*c* and the distal end 602*g*. Thus, the insertion resistance is reduced.

However, as Li approaches Lf, the first support member 719 and second support member 720 between the first fixing portion 617 and the second fixing portion 718 become easier to bend. When the first support member 719 and the second support member 720 are bent along the side surface of the endoscope 11, no particular problem occurs. However, when the radius of curvature of the endoscope 11 is small or when the first fixing portion 617 is caught on the inner wall of the lumen, the external force acting on the first support member 719 or the second support member 720 may increase, and the first support member 719 or the second support member 720 are caused to be bent.

As the Li becomes shorter, the first support member 719 and the second support member 720 are less likely to be bent.

Then, as in the seventh embodiment, the operator can insert the distal end of the endoscope 11 inside the airtight valve unit 6 of the overtube 701 and can extend the insertion portion of the endoscope 1I from the tube member 621, as shown by a two-dot chain line.

In this embodiment, the airtight valve unit 6 may not be provided.

Figure 125:
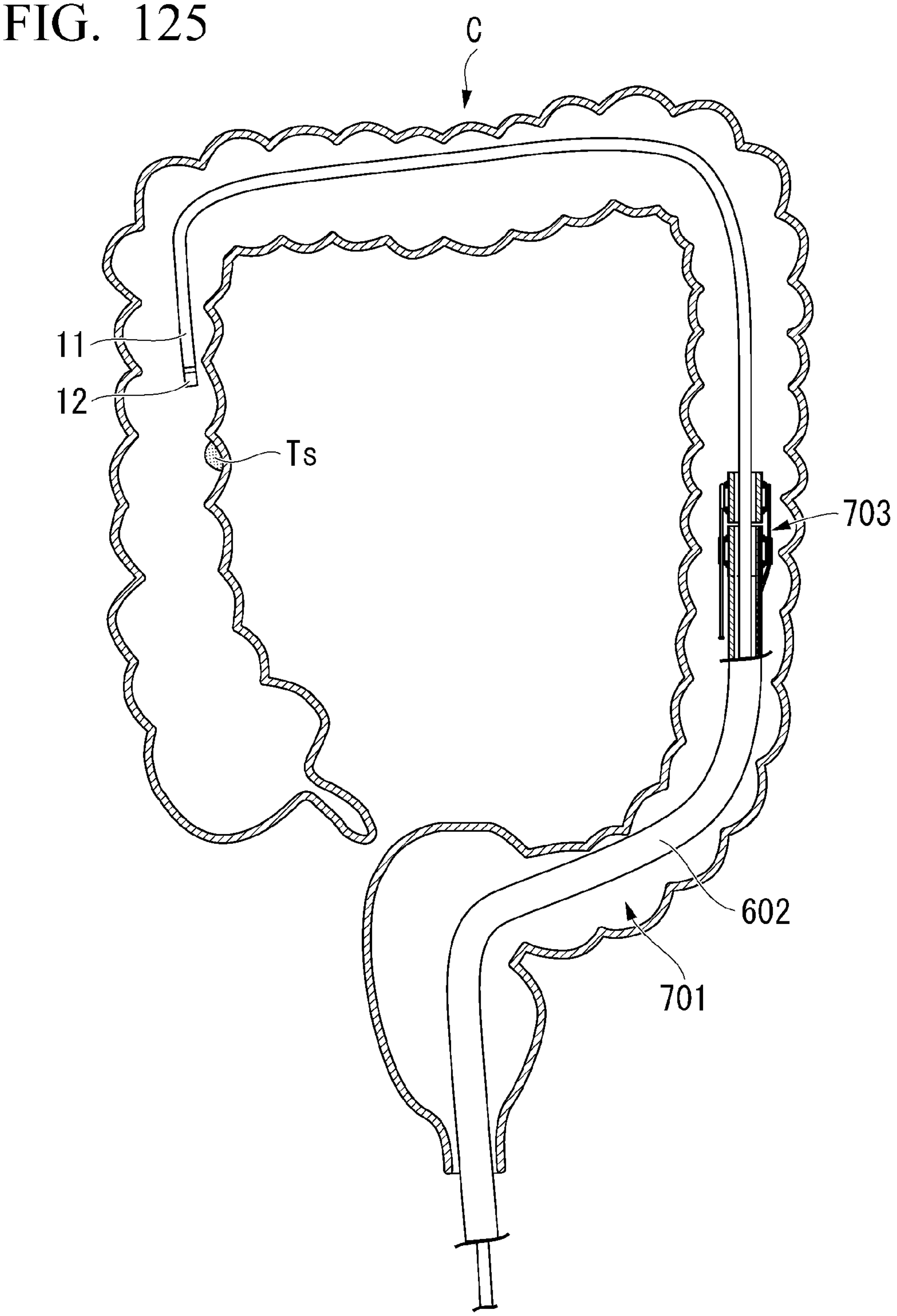

Then, the operator arranges the overtube 701 outside the patient's body, inserts the insertion portion of the endoscope 11 protruding from the overtube 701 into the large intestine C through the anus, as in the seventh embodiment, and moves the distal end portion 12 of the endoscope 11 to a position in which the treatment site Ts can be seen (refer to FIG. 125).

Then, as shown in FIG. 125, the operator inserts the overtube 701 into the large intestine C from the anus along the insertion portion of the endoscope 11, as in the seventh embodiment.

Figure 126:
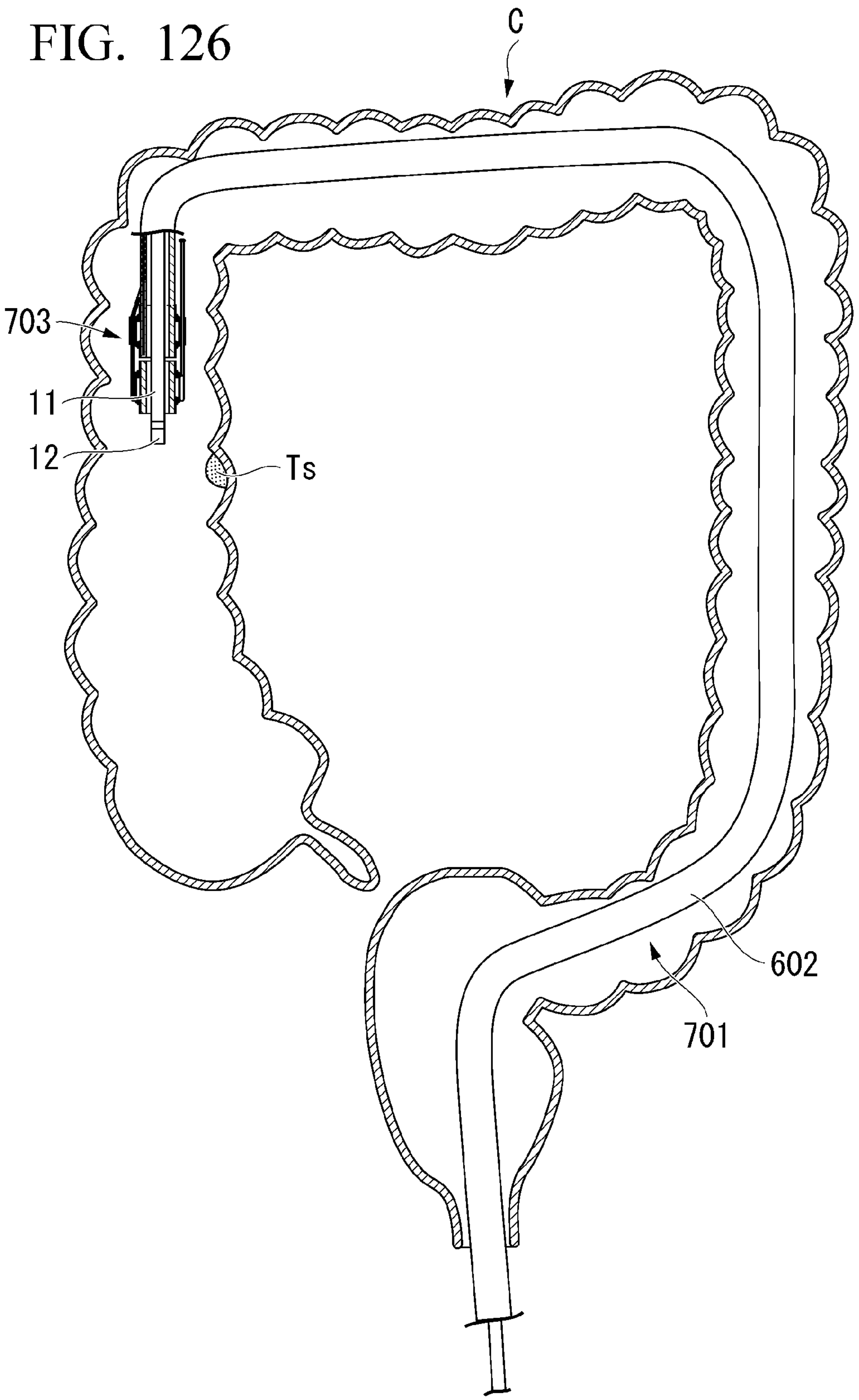

As shown in FIG. 126, the operator inserts the overtube 701 until the distal end fixing portion 703 is located in the vicinity of the proximal end of the distal end portion 12 of the endoscope 11.

Figure 127:
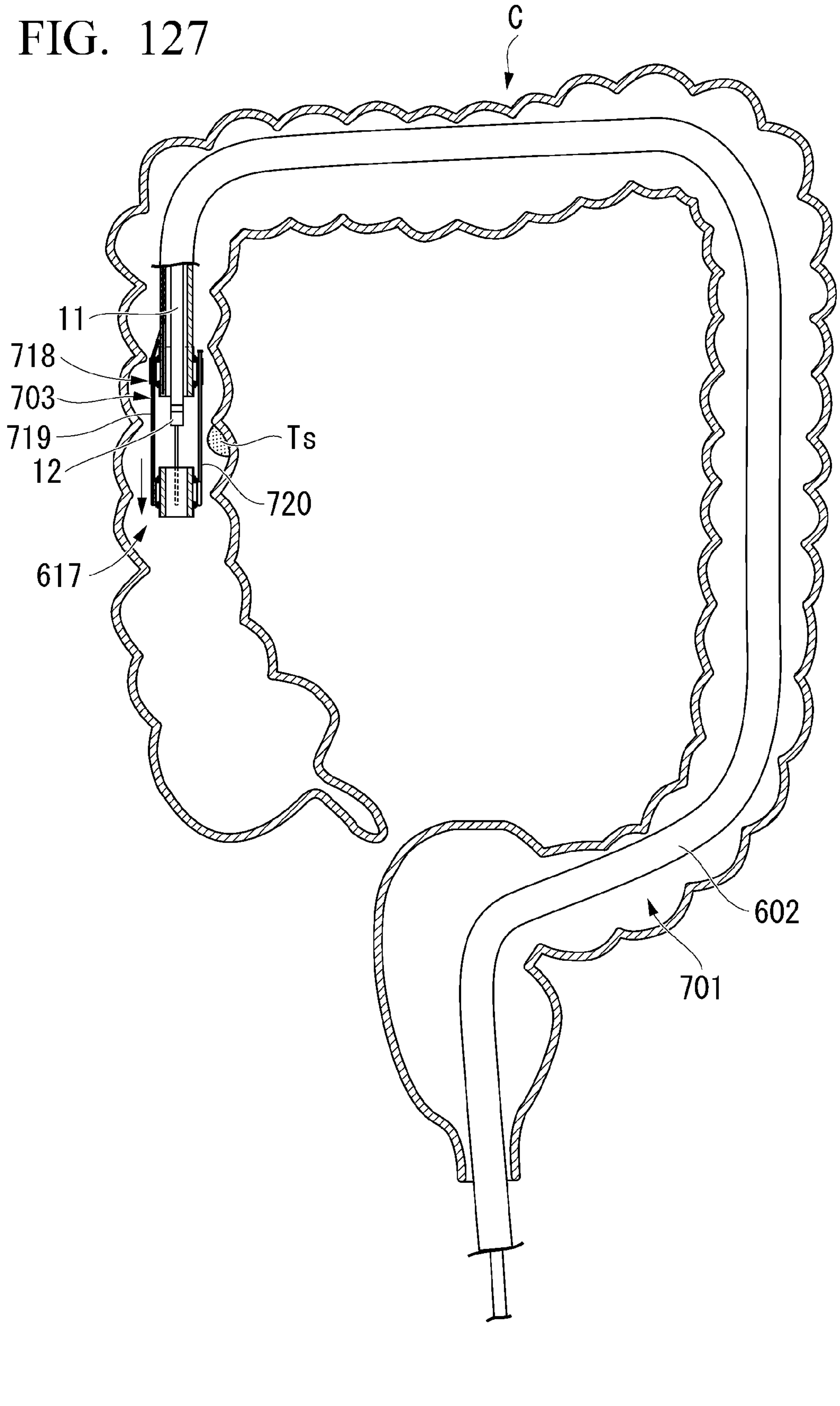

Then, the operator operates the distal end side balloon moving mechanism 712 to advance the first support member 719 to the distal side. Thus, as shown in FIG. 127, the first fixing portion 617 is pushed out further to the distal side than the distal end portion 12.

The operation of pushing out the first fixing portion 617 is performed by the operator simply sliding the unscrewed slide operating part 714 in an extending direction of the slide guide portion 713. The operator does not need to move both the grip portion 705 of the overtube 701, the main tube 602 and the endoscope 11 outside the body during the sliding operation.

For example, when the overtube 601 is pushed and thus the first fixing portion 617 is moved to the distal side as in the seventh embodiment, the overtube 601 slides on the intestinal wall Cw at each portion of the overtube 601 in contact with the intestinal wall Cw in the longitudinal direction. Therefore, the operator needs to operate against the sliding resistance between the overtube 601 and the endoscope 11 and the sliding friction between the overtube 601 and the intestinal wall Cw. In particular, sliding between the overtube 601 and the intestinal wall Cw may be a load on the patient.

However, in this embodiment, the first fixing portion 617 in the diameter-contracted state is pushed out without the main tube 602 being pushed in. Therefore, since the resistance experienced by the operator is the sliding resistance between the first support member 719 having a small diameter and the insertion lumen 602*e*, the resistance experienced by the operator is reduced. Thus, the operator can more easily perform an operation of guiding the first fixing portion 617 to a fixing position. Furthermore, since the first support member 719 does not come into contact with the intestinal wall Cw when pushed out to the distal side, the load on the patient does not occur.

The operator moves the first fixing portion 617 to the maximum advanced position. Thus, the distal end portion 12 is sandwiched between the first fixing portion 617 and the second fixing portion 718 in the axial direction of the large intestine C.

Then, as in the seventh embodiment, the operator confirms whether either the first support member 719 or the second support member 720 is in a position straddling the treatment site Ts. As in the seventh embodiment, the operator rotates the overtube 701 outside the body in the circumferential direction, and shifts the positions of the distal end portion 719A of the first support member 719 and the second support member 720 in the circumferential direction, as necessary.

As necessary, after the position adjustment for the distal end fixing portion 703 in the circumferential direction is completed, the operator operates the air supply device 710 to expand the first balloon 622 and the second balloon 623 to the diameter-expanded state when fixing, as in the seventh embodiment.

However, in this embodiment, since the air supply device 710 has one system of flow path, one of the first balloon 622 and the second balloon 623 is brought into the diameter-expanded state when fixing, and then the other of the first balloon 622 and the second balloon 623 is brought into the diameter-expanded state when fixing.

The overtube 701 may include an air supply device capable of independently supplying air to both the first connection tube 708D and the second connection tube 708P, instead of the air supply device 710. In this case, the first balloon 622 and the second balloon 623 can be brought into the diameter-expanded state when fixing at the same time.

Figure 128:
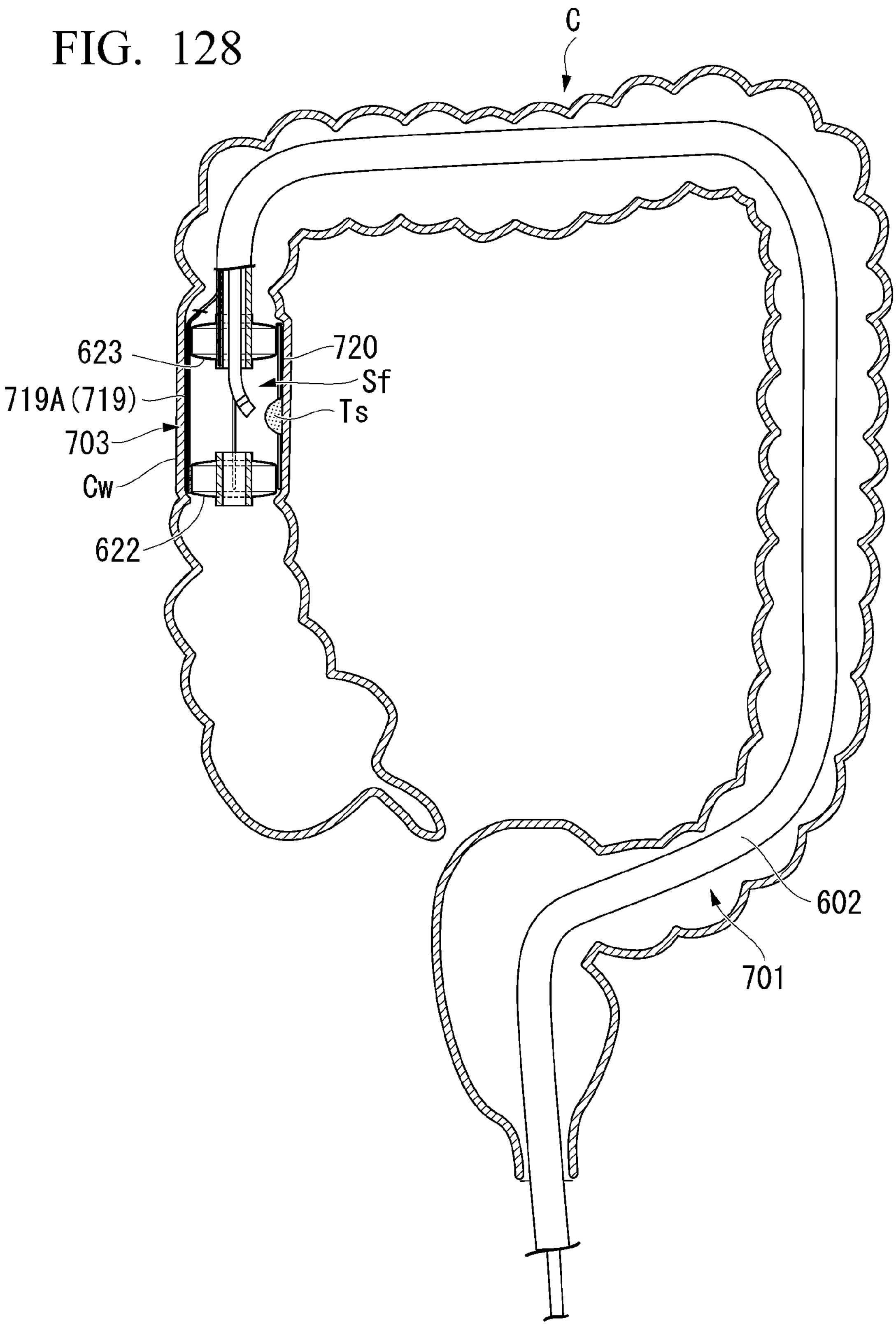

As shown in FIG. 128, when each of the first balloon 622 and the second balloon 623 is brought into the diameter-expanded state when fixing, the distal end fixing portion 703 is fixed inside the intestinal wall Cw. The first support member 719 and each of the second support members 720 are pressed against the inner surface of the intestinal wall Cw and support the intestinal wall Cw from the inside.

Thus, a space Sf in which the endoscope 11 can move is formed between the first balloon 622 and the second balloon 623, as in the seventh embodiment.

Then, the operator can perform endoscopic full-thickness resection inside the space Sf, as in the seventh embodiment. At this time, even when a through hole is formed in the intestinal wall Cw, since the intestinal wall Cw is supported from the inside by the distal end portion 719A of the first support member 719 stretched between the first balloon 622 and the second balloon 623 and each of the second support members 720, a surgical field is secured as in the seventh embodiment.

When all treatments necessary for endoscopic full-thickness resection is completed, the operator operates the air supply device 710 and the flow path switch 711 to suction out the air from the first balloon 622 and the second balloon 623. Thus, the first balloon 622 and the second balloon 623 are brought into the diameter-contracted state.

Then, the operator pulls out the endoscope 11 and the overtube 701 from the anus.

In this way, the endoscopic full-thickness resection using the overtube 701 is completed.

The method for using the overtube 701 has been described above using the example of endoscopic full-thickness resection. However, like the overtube 601 of the seventh embodiment, the overtube 701 may be used for a treatment other than endoscopic full-thickness resection, as long as the treatment is an endoscopic treatment that can be performed using the space Sf as a surgical site.

The overtube 701 according to this embodiment has the same structure as the overtube 601 except that it mainly includes the distal end fixing portion 703 instead of the distal end fixing portion 603, and thus has the same action as in the seventh embodiment. Therefore, according to this embodiment, as in the seventh embodiment, it is possible to provide an overtube for an endoscope that reduces the load on a patient and allows a smooth operation of the endoscope.

Particularly, in this embodiment, the operator can operate and change a distance between the first fixing portion 617 and the second fixing portion 618. Thus, the overtube 701 can be inserted into the lumen while the distal end fixing portion 703 is kept compact, thereby further reducing the load on the patient.

Furthermore, the operator can easily guide the first fixing portion 617 to the fixing position without applying any load to the patient.

The eighth embodiment described above may be implemented with various modifications.

For example, the guide tube 718*a* is not limited to a mode in which a separate member is fixed to the second balloon 623. For example, when the second balloon 623 is molded, a lumen similar to the guide tube 718*a* may be formed on the outer circumferential portion of the second cylindrical portion 623*c*.

For example, the guide tube 718*a* is not limited to a tube member that is long in the axial direction, and may be formed as a ring of which a length is short in the axial direction. In this case, a plurality of rings may be provided spaced apart in the axial direction.

In the eighth embodiment described above, the example in which the proximal end portion 719B of the first support member 719 also serves as an operating rod for moving the first fixing portion 617 forward and backward has been described. However, the operating rod may have a configuration in which the second support member 720 is extended to the proximal end. In this case, in addition to the insertion lumen 602*e* through which the first support member 719 is inserted, an insertion lumen through which the extended second support member is inserted is provided at the main tube 602.

The number of operating rods is not limited to one. As the number of operating rods increases, the first fixing portion 617 can be easily moved.

In the eighth embodiment described above, the example in which the operating rod is inserted into the insertion lumen 602*e* of the main tube 602 has been described. However, the operating rod may be inserted through a sheath fixed to the outer circumferential portion of the overtube 701. In this case, the insertion lumen 602*e* can be eliminated.

As described above, the distal end portion 719A of the first support member 719 and the second support member 720 are examples of a plurality of support members that are disposed on the outer circumferential portion of each of the fixing balloon and the distal end side balloon, extend between the fixing balloon and the distal end side balloon, and can support the inner wall of the lumen.

The first support member 719 has a flow path that communicates with the inside of the distal end side balloon. The first support member 719 is an example of a support member that forms an air supply tube forming a flow path for sending gas to the distal end side balloon.

The proximal end portion 719B of the first support member 719 is an example of an operating rod that extends along a tube main body to a proximal end portion of the tube main body, is provided so as to be interlockable with one of the plurality of support members, and drives a distal end portion of one of the plurality of support members in the axial direction of the tube main body. The operating rod in this embodiment is an example in which it is interlocked with the support member by being formed by the proximal end portion of the support member.

The distal end side balloon moving mechanism 712 is an example of a distal end side balloon moving mechanism that is disposed on the proximal end side with respect to the proximal end portion of the tube main body and moves the operating rod in the axial direction.

Although preferred embodiments and modified examples of the present invention have been described above, the present invention is not limited to these embodiments and modified examples. Additions, omissions, substitutions, and other changes to the configuration are possible without departing from the spirit of the invention.

Moreover, the invention is not limited by the foregoing description, but is limited only by the scope of the appended claims.

What is claimed is:

1. An overtube for an endoscope, comprising:

a multi-lumen tube body having a main lumen through which the endoscope is inserted and an air-supply lumen through which gas flows, each of the main lumen and the air-supply lumen extend parallel to each other and to a longitudinal axis of the multi-lumen tube body;

a fixing balloon provided on an outer peripheral surface of a distal end of the tube body, expandable outward from the outer peripheral surface and contractible toward the outer peripheral surface;

an air supply device configured to send the gas to the air-supply lumen; and an airtight valve unit having a tubular portion communicating with the main lumen at a rear end of the tube body, the airtight valve unit closing a gap between the endoscope inserted through the tubular portion into the main lumen and an inner peripheral surface of the tubular portion;

wherein the airtight valve unit comprises:

an airtight balloon fixed to the inner peripheral surface of the tubular portion and expandable toward inside of the tubular portion;

a volume-variable portion arranged outside the tubular portion so as to communicate with an internal space of the airtight balloon formed between the airtight balloon and the inner peripheral surface, volume of the volume-variable portion changing according to pressure of the gas flowing in from the outside or the internal space, so that at least a height of an outer shape in the radial direction of the tubular portion changes;

a gas supply pipe that communicates with the inside of the volume-variable portion, has a check valve that allows external gas to flow into the volume-variable portion, and prevents outflow of gas to the outside;

a movable mass supported movably in the radial direction of the tubular portion outside the tubular portion, a position of the movable mass in the radial direction changing according to changes in a height of the volume-variable portion;

a probe that is fixed to the movable mass, extends toward the inside of the tubular portion in the radial direction, and has a distal end portion in an extension direction that contacts the outer peripheral portion of the endoscope inserted through the tubular portion; and a biasing material that biases the movable mass toward the tubular portion in the radial direction when the endoscope is inserted through the tubular portion, so that the probe and the outer peripheral portion of the endoscope do not separate.

2. The overtube according to claim 1, wherein the volume-variable portion has an elastic member that changes the volume by elastically deforming, the biasing material comprises a spring that biases the movable mass with an elastic restoring force, and following equations (6e), (6c), (6b), (6f), and (6d) are satisfied, $$P_1 + P_t + P_b < P_S \leq P_C \quad (6e)$$

$$P_S = \frac{V}{(V_S + \pi r_b h)} \cdot p \quad (6c)$$

$$P_t = \frac{E_S(L_{BS} - L_S)}{L_S} \quad (6b)$$

$$P_b = \frac{E_b \Delta L_b}{L_b} \quad (6f)$$

$$P_C = kx \cdot \pi r_c^2 \quad (6d)$$

Here, P1 is an internal pressure on a distal end side of the airtight balloon in the overtube, Pt is a pressure caused by tension generated in the airtight balloon, Pb is a radial pressure generated by the elastic deformation of the volume-variable portion, PS is an internal pressure of the airtight balloon and the volume-variable portion, PC is a pressure corresponding to the biasing force of the spring, V is volume of the gas injected into the volume-variable portion, VS is volume of the internal space of the airtight balloon, rb is an inner diameter of the volume-variable portion in a direction perpendicular to the radial direction, h is a height of the volume-variable portion, p is the atmospheric pressure, the inner diameter of the volume-variable portion is an equivalent diameter in terms of a cylinder, ES is Young's modulus of a material of the airtight balloon, LBS is an outer circumference of the airtight balloon when inflated, LS is an outer circumference length of the airtight balloon before inflation, the outer circumference length of the airtight balloon is a length of the intermediate portion of the airtight balloon in an axial cross section including a central axis of the airtight balloon, Eb is the Young's modulus of a side wall material in a direction orthogonal to the radial direction in the volume-variable portion, Lb is a natural length of the side wall in the radial direction, ΔLb is a change length of the side wall from the natural length, k is a spring constant of the spring, x is a change length of the spring, rC is a radius of the spring, and the change length of the spring is a displacement from the natural length of the spring.

3. The overtube according to claim 2, wherein the inner diameter of the airtight balloon increases as the outer diameter of the outer peripheral portion of the endoscope increases when the endoscope is inserted through the tubular portion, and decreases as the outer diameter decreases.

4. The overtube according to claim 1, wherein the airtight valve unit is separably formed from the multi-lumen tube and is connected to a proximal end of the multi-lumen tube.

5. An overtube for an endoscope, comprising:

a multi-lumen tube body having a main lumen through which the endoscope is inserted and an air-supply lumen through which gas flows, each of the main lumen and the air-supply lumen extend parallel to each other and to a longitudinal axis of the multi-lumen tube body;

a fixing balloon provided on an outer peripheral surface of a distal end of the tube body, expandable outward from the outer peripheral surface and contractible toward the outer peripheral surface;

an air supply device configured to send the gas to the air-supply lumen; and an airtight valve unit having a tubular portion communicating with the main lumen at a rear end of the tube body, the airtight valve unit closing a gap between the endoscope inserted through the tubular portion into the main lumen and an inner peripheral surface of the tubular portion;

wherein the tube body comprises:

a first region including the air-supply lumen, and formed in a thick portion where a thickness defined by a distance between the outer peripheral surface and the inner peripheral surface in the radial direction is greater than a thickness of a constant thickness portion that is constant in a circumferential direction; and a second region adjacent to the first region in the circumferential direction and having lower rigidity than either the constant-thickness portion or the first region.

6. The overtube according to claim 5, wherein, in the second region, a dummy lumen is formed that extends in the axial direction along the extending direction of the air-supply lumen and is a void that cannot supply air to the fixing balloon and cannot inhale air from the fixing balloon.

7. The overtube according to claim 6, wherein, in the thick portion, a minimum thickness in the radial direction of the portion sandwiched between the dummy lumen and the main lumen is thinner than a minimum thickness in the radial direction of the portion sandwiched between the air-supply lumen and the main lumen.

8. The overtube according to claim 7, wherein the air-supply lumen communicates with an air supply tube extending from the air supply device, and the dummy lumen does not communicate with the air supply tube of the air supply device.

9. The overtube according to claim 5, wherein the second region is recessed radially outward from the inner peripheral surface of the main lumen, and is formed with a thickness changing portion where the thickness of the tube body changes.

10. An overtube for an endoscope, comprising:

a tube body having a main lumen through which the endoscope is inserted and an air-supply lumen through which gas flows;

a fixing balloon provided on an outer peripheral surface of a distal end of the tube body, expandable outward from the outer peripheral surface and contractible toward the outer peripheral surface;

an air supply device configured to send the gas to the air-supply lumen; and an airtight valve unit having a tubular portion communicating with the main lumen at a rear end of the tube body, the airtight valve unit closing the gap between the endoscope inserted through the tubular portion into the main lumen and an inner peripheral surface of the tubular portion;

wherein the tube body comprises:

a first region including the air-supply lumen, and formed in a thick portion where a thickness defined by a distance between the outer peripheral surface and the inner peripheral surface in the radial direction is greater than a thickness of a constant thickness portion that is constant in a circumferential direction; and a second region adjacent to the first region in the circumferential direction and having lower rigidity than either the constant-thickness portion or the first region.

11. The overtube according to claim 10, wherein, in the second region, a dummy lumen is formed that extends in the axial direction along the extending direction of the air-supply lumen and is a void that cannot supply air to the fixing balloon and cannot inhale air from the fixing balloon.

12. The overtube according to claim 11, wherein, in the thick portion, a minimum thickness in the radial direction of the portion sandwiched between the dummy lumen and the main lumen is thinner than a minimum thickness in the radial direction of the portion sandwiched between the air-supply lumen and the main lumen.

13. The overtube according to claim 12, wherein the air-supply lumen communicates with an air supply tube extending from the air supply device, and the dummy lumen does not communicate with the air supply tube of the air supply device.

14. The overtube according to claim 10, wherein the second region is recessed radially outward from the inner peripheral surface of the main lumen, and is formed with a thickness changing portion where the thickness of the tube body changes.

15. The overtube according to claim 10, wherein the tube body is a multi-lumen tube body, each of the main lumen and the air-supply lumen extend parallel to each other and to a longitudinal axis of the multi-lumen tube body.

* * * * *